(12) United States Patent
Leonard et al.

(10) Patent No.: US 10,308,962 B1
(45) Date of Patent: Jun. 4, 2019

(54) MICROORGANISMS FOR THE PRODUCTION OF INSECT PHEROMONES AND RELATED COMPOUNDS

(71) Applicant: Provivi, Inc., Santa Monica, CA (US)

(72) Inventors: Effendi Leonard, Santa Monica, CA (US); Peter Meinhold, Topanga, CA (US); Keith Wampler, Santa Monica, CA (US); Pedro Coelho, Santa Monica, CA (US); Micah Sheppard, Santa Monica, CA (US); Thomas Heel, Los Angeles, CA (US)

(73) Assignee: Provivi, Inc., Santa Monica, CA (US)

( * ) Notice: Subject to any disclaimer, the term of this patent is extended or adjusted under 35 U.S.C. 154(b) by 0 days.

(21) Appl. No.: 15/983,706

(22) Filed: May 18, 2018

Related U.S. Application Data

(63) Continuation of application No. PCT/US2016/062852, filed on Nov. 18, 2016.

(60) Provisional application No. 62/351,605, filed on Jun. 17, 2016, provisional application No. 62/257,054, filed on Nov. 18, 2015.

(51) Int. Cl.
  *C12P 7/04* (2006.01)
  *C12N 9/02* (2006.01)
  *A01N 31/02* (2006.01)

(52) U.S. Cl.
  CPC .............. *C12P 7/04* (2013.01); *A01N 31/02* (2013.01); *C12N 9/0008* (2013.01); *C12N 9/0071* (2013.01); *C12Y 102/0105* (2013.01); *C12Y 114/19001* (2013.01); *C12Y 114/19005* (2013.01)

(58) Field of Classification Search
  CPC .............. C12P 7/04; C12Y 114/19005; C12Y 102/0105; C12Y 114/19001; A01N 31/02; C12N 9/0008; C12N 9/0071
  See application file for complete search history.

(56) References Cited

U.S. PATENT DOCUMENTS

| | | | |
|---|---|---|---|
| 4,231,947 A | 11/1980 | Schrock | |
| 4,245,131 A | 1/1981 | Schrock | |
| 4,427,595 A | 1/1984 | Schrock | |
| 4,681,956 A | 7/1987 | Schrock | |
| 4,727,215 A | 2/1988 | Schrock | |
| 5,087,710 A | 2/1992 | Schrock et al. | |
| 5,142,073 A | 8/1992 | Schrock et al. | |
| 5,146,033 A | 9/1992 | Schrock et al. | |
| 6,121,473 A | 9/2000 | Schrock et al. | |
| 6,346,652 B1 | 2/2002 | Schrock et al. | |
| 7,700,833 B2 * | 4/2010 | Renz .................. | C12N 9/0083 800/281 |
| 8,987,531 B2 | 3/2015 | Grubbs et al. | |
| 9,776,179 B2 | 10/2017 | Wampler et al. | |
| 2006/0078973 A1 | 4/2006 | Renz et al. | |
| 2007/0282148 A1 | 12/2007 | Berlin et al. | |
| 2008/0009598 A1 | 1/2008 | Herrmann et al. | |
| 2008/0119678 A1 | 5/2008 | Hock et al. | |
| 2008/0207911 A1 | 8/2008 | Herrmann et al. | |
| 2008/0221345 A1 | 9/2008 | Winde et al. | |
| 2008/0275247 A1 | 11/2008 | Kadyrov et al. | |
| 2010/0087644 A1 | 4/2010 | Mauduit et al. | |
| 2010/0113795 A1 | 5/2010 | Arlt et al. | |
| 2010/0174068 A1 | 7/2010 | Grela et al. | |
| 2010/0199548 A1 | 8/2010 | Del Cardayre et al. | |
| 2011/0015430 A1 | 1/2011 | Schrock et al. | |
| 2011/0282068 A1 | 1/2011 | Herrmann et al. | |
| 2011/0040099 A1 | 2/2011 | Kadyrov et al. | |
| 2011/0065915 A1 | 3/2011 | Malcolmson et al. | |
| 2011/0077421 A1 | 3/2011 | Schrock | |
| 2011/0237815 A1 | 9/2011 | Hock et al. | |
| 2012/0123133 A1 | 5/2012 | Berlin et al. | |

(Continued)

FOREIGN PATENT DOCUMENTS

WO  WO 1991/009825 A1  7/1991
WO  WO 1992/019631 A1  11/1992

(Continued)

OTHER PUBLICATIONS

Broun et al., Catalytic plasticity of fatty acid modification enzymes underlying chemical diversity of plant lipids. Science, 1998, vol. 282: 1315-1317. (Year: 1998).*

Devos et al., Practical limits of function prediction. Proteins: Structure, Function, and Genetics. 2000, vol. 41: 98-107. (Year: 2000).*

Rosenfield et al., Structural and functional conservation and divergence among acyl-CoA desaturases of two noctuid speices, the *Corn earworm, Helicoverpa zea*, and the *Cabbage looper, Trichoplusia ni*. Insect. Biochem. Mol. Biol., 2001, vol. 31: 949-964 (Year: 2001).*

Seffernick et al., Melamine deaminase and Atrazine chlorohydrolase: 98 percent identical but functionally different. J. Bacteriol., 2001, vol. 183 (8): 2405-2410. (Year: 2001).*

(Continued)

*Primary Examiner* — Ganapathirama Raghu
(74) *Attorney, Agent, or Firm* — Cooley LLP

(57) ABSTRACT

The present application relates to recombinant microorganisms useful in the biosynthesis of unsaturated $C_6$-$C_{24}$ fatty alcohols, aldehydes, and acetates which may be useful as insect pheromones, fragrances, flavors, and polymer intermediates. The $C_6$-$C_{24}$ fatty alcohols, aldehydes, and acetates described herein may be used as substrates for metathesis reactions to expand the repertoire of target compounds and pheromones. The application further relates to recombinant microorganisms co-expressing a pheromone pathway and a pathway for the production of a toxic protein, peptide, oligonucleotide, or small molecule suitable for use in an attract-and-kill pest control approach. Also provided are methods of producing unsaturated $C_6$-$C_{24}$ fatty alcohols, aldehydes, and acetates using the recombinant microorganisms, as well as compositions comprising the recombinant microorganisms and/or optionally one or more of the product alcohols, aldehydes, or acetates.

13 Claims, 39 Drawing Sheets

Specification includes a Sequence Listing.

(56) References Cited

U.S. PATENT DOCUMENTS

| | | |
|---|---|---|
| 2012/0302710 A1 | 11/2012 | Hoveyda et al. |
| 2012/0323000 A1 | 12/2012 | Hoveyda et al. |
| 2013/0079515 A1 | 3/2013 | Grela et al. |
| 2013/0116434 A1 | 5/2013 | Schrock et al. |
| 2013/0144060 A1 | 6/2013 | Mauduit et al. |
| 2013/0211096 A1 | 8/2013 | Arlt et al. |
| 2013/0261312 A1 | 10/2013 | Allen et al. |
| 2013/0274482 A1 | 10/2013 | Schrock et al. |
| 2013/0281706 A1 | 10/2013 | Hock et al. |
| 2013/0296511 A1 | 11/2013 | Ung et al. |
| 2014/0171607 A1 | 6/2014 | Grela et al. |
| 2014/0330018 A1 | 11/2014 | Czirok et al. |
| 2014/0378637 A1 | 12/2014 | Schrock et al. |
| 2015/0018557 A1 | 1/2015 | Nolan et al. |
| 2015/0038723 A1 | 2/2015 | Herrmann et al. |
| 2015/0045558 A1 | 2/2015 | Plenio et al. |
| 2015/0125933 A1 | 5/2015 | Groban et al. |
| 2016/0304913 A1 | 10/2016 | Gatter et al. |
| 2018/0162916 A1* | 6/2018 | Borodina ............... C12N 1/16 |

FOREIGN PATENT DOCUMENTS

| | | | |
|---|---|---|---|
| WO | WO 2007/075427 A1 | | 7/2007 |
| WO | WO 2007/140954 A1 | | 12/2007 |
| WO | WO 2008/066754 A1 | | 6/2008 |
| WO | WO 2009/094201 A3 | | 7/2009 |
| WO | WO 2009/126831 A1 | | 10/2009 |
| WO | WO 2010/037550 A1 | | 4/2010 |
| WO | WO 2011/040963 A1 | | 4/2011 |
| WO | WO 2011/069134 A3 | | 6/2011 |
| WO | WO 2011/091980 A1 | | 8/2011 |
| WO | WO 2011/097642 A1 | | 8/2011 |
| WO | WO 2012/167171 A3 | | 12/2012 |
| WO | WO 2012/168183 A1 | | 12/2012 |
| WO | WO 2013/070725 A1 | | 5/2013 |
| WO | WO 2013/135776 A1 | | 9/2013 |
| WO | WO 2014/001291 A1 | | 1/2014 |
| WO | WO 2014/067767 A1 | | 5/2014 |
| WO | WO 2014/134333 A1 | | 9/2014 |
| WO | WO 2014/139679 A3 | | 9/2014 |
| WO | WO 2014/155185 A1 | | 10/2014 |
| WO | WO 2014/169014 A1 | | 10/2014 |
| WO | WO 2014/172534 A1 | | 10/2014 |
| WO | WO 2015/003814 A1 | | 1/2015 |
| WO | WO 2015/003815 A1 | | 1/2015 |
| WO | WO 2015/086684 * | 6/2015 | ............... C12N 9/04 |
| WO | WO 2015/086684 A1 | | 6/2015 |
| WO | WO 2015/171057 A1 | | 11/2015 |
| WO | WO 2016/099568 A1 | | 6/2016 |
| WO | WO 2016/207339 A1 | | 12/2016 |
| WO | WO 2017/087846 A1 | | 5/2017 |
| WO | WO 2018/213554 A1 | | 11/2018 |

OTHER PUBLICATIONS

Whisstock et al., Prediction of protein function from protein sequence. Q. Rev. Biophysics., 2003, vol. 36 (3): 307-340. (Year: 2003).*

Witkowski et al., Conversion of b-ketoacyl synthase to a Malonyl Decarboxylase by replacement of the active cysteine with glutamine. Biochemistry, 1999, vol. 38: 11643-11650. (Year: 1999).*

UniProtKB-O74934 (ACOX_YARL1): 9 (nine) pages down-loaded from https://www.uniprot.org/uniprot/O74934 Oct. 23, 2018 (Year: 2018).*

[Author Unknown] "NP 001037017: (11Z)-hexadec-11-enoyl-CoA conjugase [Bombyx mori]," NCBI Protein, Jul. 5, 2004 (Jul. 5, 2004), pp. 1-4. Retrieved from the Internet: <https://www.ncbi.nlm.nih.gov/protein/162809332> on Jan. 18, 2017 (Jan. 18, 2017). Entire document.

Ayciriex, et al., "YPR139c/LOA1 encodes a novel lysophosphatidic acid acyltransferase associated with lipid droplets and involved in TAG homeostasis." Mol Biol Cell (2012); 23 (2): 233-246.

Baba, et al., "Construction of Escherichia coli K-12 in-frame, single-gene knockout mutants: the Keio collection." Molecular Systems Biology (2006); 2 (1): 1-11.

Beisson, et al., "The acyltransferase GPAT5 is required for the synthesis of suberin in seed coat and root of Arabidopsis." Plant Cell (2007); 19 (1): 351-368.

Benghezal, et al., "SLC1 and SLC4 Encode Partially Redundant Acyl-Coenzyme A 1-Acylglycerol-3-phosphate O-Acyltransferases of Budding Yeast." The Journal of Biological Chemistry (2007); 282 (42): 30845-30855.

Blom, et al., "Sequence and structure-based prediction of eukaryotic protein phosphorylation sites1." J. Mol. Biol. (1999); 294 (5): 1351-1362.

Brown, et al., "Limnanthes douglasii lysophosphatidic acid acyltransferases: immunological quantification, acyl selectivity and functional replacement of the Escherichia coli plsC gene." Biochemical Journal (2002); 364 (3): 795-805.

Chen, et al., "The yeast acylglycerol acyltransferase LCA1 is a key component of Lands cycle for phosphatidylcholine turnover." FEBS Letters (2007); 581 (28): 5511-5516.

Choi, et al., "Regulatory elements that control transcription activation and unsaturated fatty acid-mediated repression of the Saccharomyces cerevisiae OLE1 geneGene" J Biol. Chem. (1996); 271 (7): 3581-3589.

Colby, et al., "Calculating synergistic and antagonistic responses of herbicide combinations." Weeds, (1967); 15 (1): 20-22.

Dahlqvist, et al., "Phospholipid:diacylglycerol acyltransferase: An enzyme that catalyzes the acyl-CoA-independent formation of triacylglycerol in yeast and plants." Proc Natl Acad Sci USA (2000); 97 (12): 6487-6492.

Ding, et al., "Analysis of the Agrotis segetum pheromone gland transcriptome in the light of sex pheromone biosynthesis" BMC Genomics (2015); 16 (711): 1-21.

Endo, et al., "Chelated ruthenium catalysts for Z-selective olefin metathesis" J Am Chem Soc. (2011); 133 (22): 8525-8527.

Flook, et al. "Z-Selective and Syndioselective Ring-Opening Metathesis Polymerization (ROMP) Initiated by MonoAryloxidePyrrolide (MAP) Catalysts" Macromolecules (2010) 43(18):7515-7522.

Goelz and Cronan Jr., "The positional distribution of fatty acids in Escherichia coli phospholipids is not regulated by sn-glycerol 3-phosphate levels." J Bacteriol (1980); 144 (1): 462-464.

Gonzalez, et al., "Fatty acid-responsive control of mRNA stability. Unsaturated fatty acid-induced degradation of the Saccharomyces OLEI transcript" J. Biol. Chem. (1996); 271 (42): 25801-25809.

Greenway and Silbert, "Altered acyltransferase activity in Escherichia coli associated with mutations in acyl coenzyme A synthetase." The Journal of Biological Chemistry (1983); 258 (21): 13034-13042.

Hagstrom, et al., "Semi-selective fatty acyl reductases from four heliothine moths influence the specific pheromone composition" PLoS One (2012); 7 (5): e37230: 1-11.

Halford, B. "Olefin Metathesis for Macrocycles—Organic Synthesis: Tungsten catalysts make macrocyclic olefins with Z-selectivity" Chem. Eng. News (2011); 89 (45): 11.

Hartung, et al., "Highly Z-selective and enantioselective ring-opening/cross-metathesis catalyzed by a resolved stereogenic-at-Ru complex" J Am Chem Soc. (2013); 135 (28): 10183-10185.

Heier, et al., "Identification of Yju3p as functional orthologue of mammalian monoglyceride lipase in the yeast Saccharomyces cerevisiae." Biochimica et Biophysica Acta (2010); 1801 (9): 1063-1071.

Herbert, et al., "Concise syntheses of insect pheromones using Z-selective cross metathesis" Angew Chem Int Ed Engl. (2013); 52 (1): 310-314.

Hobbs, et al., "Cloning of a cDNA encoding diacylglycerol acyltransferase from Arabidopsis thaliana and its functional expression." Febs Lett (1999); 452 (3): 145-149.

Ingrell, et al., "NetPhosYeast: prediction of protein phosphorylation sites in yeast." Bioinformatics (2007); 23 (7): 895-897.

Jain, et al., "Identification of a Novel Lysophospholipid Acyltransferase in Saccharomyces cerevisiae." The Journal of Biological Chemistry (2007); 282 (42): 30562-30569.

Jako, et al., "Seed-Specific Over-Expression of an Arabidopsis cDNA Encoding a Diacylglycerol Acyltransferase Enhances Seed Oil Content and Seed Weight." Plant Physiol (2001); 126 (2): 861-874.

(56) References Cited

OTHER PUBLICATIONS

Jurenka and Rafaeli, "Regulatory Role of PBAN in Sex Pheromone Biosynthesis of Heliothine Moths." Front. Endocrinol. (2011); 2 (46): 1-8.
Kajiwara, et al., "Molecular cloning and characterization of the Δ9 fatty acid desaturase gene and its promoter region from *Saccharomyces kluyveri*" FEMS Yeast. Res. (2002); 2: 333-339.
Kalscheuer and Steinbüchel, "A Novel Bifunctional Wax Ester Synthase/Acyl-CoA:Diacylglycerol Acyltransferase Mediates Wax Ester and Triacylglycerol Biosynthesis in Acinetobacter calcoaceticus ADP1." The Journal of Biological Chemistry (2002); 278 (10): 8075-8082.
Keitz, et al., "Cis-selective ring-opening metathesis polymerization with ruthenium catalysts" J Am Chem Soc. (2012); 134 (4): 2040-2043.
Keitz, et al., "Improved ruthenium catalysts for Z-selective olefin metathesis" J Am Chem Soc. (2012); 134 (1): 693-699.
Kito, et al., "Inhibition of L-Glycerol 3-Phosphate Acyltransferase from *Escherichia coli* by cis-9, 10-Methylenehexadecanoic Acid." The Journal of Biochemistry (1972); 71 (1): 99-105.
Lardizabal, et al., "DGAT2 is a new diacylglycerol acyltransferase gene family: purification, cloning, and expression in insect cells of two polypeptides from Mortierella ramanniana with diacylglycerol acyltransferase activity." The Journal of Biological Chemistry (2001); 276 (42): 38862-38869.
Lassner, et al., "Lysophosphatidic Acid Acyltransferase from Meadowfoam Mediates Insertion of Erucic Acid at the sn-2 Position of Triacylglycerol in Transgenic Rapeseed Oil." Plant Physiol (1995); 109 (4): 1389-1394.
Lee, D. "Organic chemistry: Overcoming catalytic bias" Nature (2011) 471 (7339): 452-453.
Lewin, et al., "Analysis of Amino Acid Motifs Diagnostic for the sn-Glycerol-3-phosphate Acyltransferase Reaction." Biochemistry (1999); 38 (18): 5764-5771.
Li, et al., "Identification of acyltransferases required for cutin biosynthesis and production of cutin with suberin-like monomers." Proc Natl Acad Sci USA (2007); 104 (46): 18339-18344.
Liu, et al., "Functional and Topological Analysis of Yeast Acyl-CoA:Diacylglycerol Acyltransferase 2, an Endoplasmic Reticulum Enzyme Essential for Triacylglycerol Biosynthesis." The Journal of Biological Chemistry (2011); 286 (15): 13115-13126.
Lu, et al., "Acyl-phosphates initiate membrane phospholipid synthesis in Gram-positive pathogens." Mol Cell (2006); 23 (5): 765-772.
Maniatis, et al,. "Regulation of inducible and tissue-specific gene expression" Science (1987); 236 (4806): 1237-1245.
Marx, et al, "Stereoselective access to Z and E macrocycles by ruthenium-catalyzed Z-selective ring-closing metathesis and ethenolysis" J Am Chem Soc. (2013); 135 (1): 94-97.
Mauersberger, et al., "Insertional Mutagenesis in the n-Alkane—Assimilating Yeast *Yarrowia lipolytica*: Generation of Tagged Mutations in Genes Involved in Hydrophobic Substrate Utilization." J. Bacterial. (2001); 183 (17): 5102-5109.
Meek, et al. "Z-selective catalytic olefin cross-metathesis for natural product synthesis" Nature (2011); 471 (7339): 461-466.
Miller, W. T., "Tyrosine kinase signaling and the emergence of multicellularity" Biochimica et Biophysica Acta (BBA)—Molecular Cell Research (2012); 1823 (6): 1053-1057.
Moss, et al. "Determination of cellular fatty acid compositions of various yeasts by gas-liquid chromatography" J Clin Microbiol. (1982); 16 (6): 1073-1079.
Moto, et al., "Involvement of a bifunctional fatty-acyl desaturase in the biosynthesis of the silkmoth, *Bombyx mori*, sex pheromone." PNAS (2004); 101 (23): 8631-8636.
Nagiec, et al., "A suppressor gene that enables *Saccharomyces cerevisiae* to grow without making sphingolipids encodes a protein that resembles an *Escherichia coli* fatty acyltransferase." The Journal of Biological Chemistry (1993); 268 (29): 22156-22163.

Nishida, et al., "The gene and the RNA for the precursor to the plastid-located glycerol-3-phosphate acyltransferase of *Arabidopsis thaliana*." Plant Mol Biol. (1993); 21 (2): 267-277.
Oelkers, et al., "The DGA1 gene determines a second triglyceride synthetic pathway in yeast." The Journal of Biological Chemistry (2002); 277 (11): 8877-8881.
Okuyama and Wakil, "Positional Specificities of Acyl Coenzyme A:Glycerophosphate and Acyl Coenzyme A: Monoacylglycerophosphate Acyltransferases in *Escherichia coli*." The Journal of Biological Chemistry (1973); 248 (14): 5197-5205.
Ondi, et al. "High activity, stabilized formulations, efficient synthesis and industrial use of Mo-and W-based metathesis catalysts" XiMo Technology Updates, 2015: http://www.ximoinc.com/files/ximo/uploads/download/Summary_3.11.15.pdf.
PCT/US2016/062852, International Preliminary Report on Patentability, dated May 22, 2018, 10 pages.
PCT/US2016/062852, International Search Report and Written Opinion, dated Feb. 7, 2017, 13 pages.
PCT/US2016/062852, Third Party Observation filed by Danmarks Tekniske Universitet dated Oct. 5, 2017 with WIPO, 7 pages.
Peryshkov, et al. "B(C6F5)3 Activation of Oxo Tungsten complexes that are relevant to olefin metathesis" Organometallics (2013); 32 (19): 5256-5259.
Peryshkov, et al., "Z-Selective olefin metathesis reactions promoted by tungsten oxo alkylidene complexes" J Am Chem Soc. (2011); 133 (51): 20754-20757.
Riekhof, et al., "Identification and Characterization of the Major Lysophosphatidylethanolamine Acyltransferase in *Saccharomyces cerevisiae*." The Journal of Biological Chemistry (2007); 282 (39): 28344-28352.
Rock, et al., "Phospholipid synthesis in *Escherichia coli*. Characteristics of fatty acid transfer from acyl-acyl carrier protein to sn-glycerol 3-phosphate." The Journal of Biological Chemistry (1981); 256 (2): 736-742.
Sandager, et al., "Storage lipid synthesis is non-essential in yeast." J Biol Chem (2002); 277 (8): 6478-6482.
Schrock, et al. "Z-Selective and syndioselective ring-opening metathesis polymerization (ROMP) Initiated by monoaryloxidepyrrolide (MAP) catalysts" Macromolecules (2010); 43 (18): 7515-7522.
Shi, et al., "Improving Production of Malonyl Coenzyme A-Derived Metabolites by Abolishing Snf1-Dependent Regulation of Acc1." mBio (2014); 5 (3): e01130-14: 1-8.
Sorger and Daum, "Synthesis of Triacylglycerols by the Acyl-Coenzyme A:Diacyl-Glycerol Acyltransferase Dga1p in Lipid Particles of the Yeast *Saccharomyces cerevisiae*." J Bacteriol (2002); 184 (2):519-524.
Ståhl, et al., "Cloning and Functional Characterization of a Phospholipid-:Diacylglycerol Acyltransferase from *Arabidopsis*." Plant Physiology (2004); 135 (3):1324-1335.
Stelinki, et al., "Sprayable microencapsulated sex pheromone formulations for mating disruption of four tortricid species: effects of application height, rate, frequency, and sticker adjuvant" J Econ. Entomol. (2007); 100(4): 1360-9.
Stöveken, et al., "The Wax Ester Synthase/Acyl Coenzyme A:Diacylglycerol Acyltransferase from *Acinetobacter* sp. Strain ADP1: Characterization of a Novel Type of Acyltransferase." J Bacteriol (2005); 187 (4): 1369-1376.
Townsend, et al. "Z-selective metathesis homocoupling of 1,3-dienes by molybdenum and tungsten monoaryloxide pyrrolide (MAP) complexes" J Am Chem Soc. (2012); 134 (28): 11334-11337.
Uthoff, et al., "Thio Wax Ester Biosynthesis Utilizing the Unspecific Bifunctional Wax Ester Synthase/Acyl Coenzyme A:Diacylglycerol Acyltransferase of *Acinetobacter* sp. Strain ADP1." Appl. Environ. Microbiol. (2005); 71 (2): 790-796.
Wahl, et al., "Antagonistic regulation of dgkA and plsB genes of phospholipid synthesis by multiple stress responses in *Escherichia coli*." Molecular Microbiology (2011); 80 (5): 1260-1275.
Wang, et al. "Efficient and selective formation of macrocyclic disubstituted Z alkenes by ring-closing metathesis (RCM) reactions catalyzed by Mo- or W-based monoaryloxide pyrrolide (MAP) complexes: applications to total syntheses of epilachnene, yuzu lactone, ambrettolide, epothilone C, and nakadomarin A" Chemistry (2013); 19 (8): 2726-2740.

(56) References Cited

OTHER PUBLICATIONS

Wang, et al., "Mo-Based Complexes with Two Aryloxides and a Pentafluoroimido Ligand: Catalysts for EfficientZ-Selective Synthesis of a Macrocyclic Trisubstituted Alkene by Ring-Closing Metathesis." Angew Chem Int Ed Engl., (2013); 52 (7): 1939-1943.
Yoshimura, et al., "Involvement of the YneS/YgiH and PlsX proteins in phospholipid biosynthesis in both *Bacillus subtilis* and *Escherichia coli*." BMC Microbiology (2007); 7: 69, 13 pages.
Yousuf, et al., "Microbial conversion of olive oil mill wastewaters into lipids suitable for biodiesel production." J Agric. Food Chem. (2010); 58 (15): 8630-8635.
Yu, et al., "Enol Ethers as Substrates for Efficient Z- and Enantioselective Ring-Opening/Cross-Metathesis Reactions Promoted by Stereogenic-at-Mo Complexes: Utility in Chemical Synthesis and Mechanistic Attributes" J Am. Chem. Soc. (2012); 134(5): 2788-2799.
Yu, et al., "Synthesis of macrocyclic natural products by catalyst-controlled stereoselective ring-closing metathesis" Nature, (2011); 479 (7371): 88-93.
Zhao, et al. "Endo-selective enyne ring-closing metathesis promoted by stereogenic-at-W mono-pyrrolide complexes" Org Lett. (2011); 13 (4): 784-787.
Zheng and Zou, "The initial step of the glycerolipid pathway: identification of glycerol 3-phosphate/dihydroxyacetone phosphate dual substrate acyltransferases in *Saccharomyces cerevisiae*." The Journal of Biological Chemistry (2001); 276 (45): 41710-41716.
Zou, et al., "The *Arabidopsis thaliana* TAG1 mutant has a mutation in a diacylglycerol acyltransferase gene." The Plant Journal (1999); 19 (6): 645-653.
Bredeweg, et al., "A molecular genetic toolbox for Yarrowia lipolytica." Biotechnol Biofuels (2017); 10: 2, pp. 1-22, ePub Jan. 3, 2017.
EBI Accession EAY76846. Oryza sativa triacylglycerol lipase, Dec. 29, 2008 [onlina]. [Retrieved Sep. 21, 2008]. 3 Pages, Retrieved from the internet: <URL: https:/lwww.ebi.ac.uk/ena/data/view/EAY76846&display=text>.
Extended European Search Report for Application No. EP 16867255.8 dated Feb. 5, 2019, 12 pages.
Gatter, et al., "A newly identified fatty alcohol oxidase gene is mainly responsible for the oxidation of long-chain ω-hydroxy fatty acids in *Yarrowia lipolytica*." FEMS Yeast Res. (Sep. 2014); 14(6): 858-872. Epub Jul. 2, 2014.
GenBank Accession AAL49962.1. Diacylglycerol acyltransferase 1 [Bos Taurus], Feb. 11, 2002 [online]. [Retrieved Sep. 21, 2002]. 2 pages, Retrieved from the internet:< URL: https://www.ncbi.nlm.nih.gov/protein/AAL49962.1/>.
GenBank Accession KTA99184.1 Alcohol O-acetyltransferase 2 [Candida] glabrata]. Feb. 9, 2016 [online]. [Retrieved Sep. 21, 2018]. 1 page, Retrieved from the internet:< URL: https://www.ncbi.nlm.nih.gov/protein/KTA99184.1/>.
GenBank Accession AKD01723.1 Alcohol dehydrogenase 12 [Helicoverpa armigera], Apr. 25, 2015 [online]. [retrieved Sep. 21, 2018]. 1 page, Retrieved from the internet:< URL: https://www.ncbi.nlm.nih.gov/protein/AKD01723.1/>.
Groot, et al., "The Genetic Basis of Pheromone Evolution in Moths." Annu Rev Entomol. (2016); 61: 99-117. Epub Nov. 4, 2015.
Hagström, et al., "A moth pheromone brewery: production of (Z)-11-hexadecenol by heterologous co-expression of two biosynthetic genes from a noctuid moth in a yeast cell factory." Microb. Cell Fact. (2013); 12: 125, pp. 1-11.
Iwama, et al., "Alcohol dehydrogenases and an alcohol oxidase involved in the assimilation of exogenous fatty alcohols in Yarrowia lipolytica." FEMS Yeast Research (May 2015); 15(3): fov014, pp. 1-12.
Liénard, et al., "Sex pheromone biosynthetic pathways are conserved between moths and the butterfly Bicyclus anynana." Nature Communications (2014); 5: 3957, pp. 1-12.
PCT/US2018/033151, Invitation to Pay Additional Fees, dated Aug. 14, 2018, 6 pages.
PCT/US2018/033151, International Search Report and Written Opinion, dated Oct. 15, 2018, 22 pages.
Takai et al. "Construction and characterization of a *Yarrowia lipolytica* mutant lacking genes encoding cytochromes P450 subfamily 52." Fungal Genet Biol. (2012); 49 (1): 58-64. Epub Nov. 17, 2011.
Uniprot Accession A0A178WDE4. Acyl-coenzyme A oxidase, Apr. 12, 2017 [online]. [Retrieved on Aug. 10, 2018]. 1 page, Retrieved from the internet: <URL: https://www.uniprot.org/uniproVAOA178WDE4.txt?version=7>.
Uniprot Accession R8XW24. Acinetobacter calcoaceticus—Fatty acyl-CoA reductase, Apr. 13, 2013 [online]. [Retrieved Sep. 21, 2018]. 1 page, Retrieved from the internet: <URL: https://www.uniprot.org/uniprot/R8XW24.txt?version=14>.
Wang, et al., "Exploring fatty alcohol-producing capability of Yarrowia lipolytica." Biotechnology for Biofuels (2016); 9: 107, pp. 1-10.
Xia, et al., "Large number of putative chemoreception and pheromone biosynthesis genes revealed by analyzing transcriptome from ovipositor-pheromone glands of Chilo suppressalis." Scientific Reports (Jan. 2015); 5: 7888. Epub Jan. 20, 2015.

\* cited by examiner

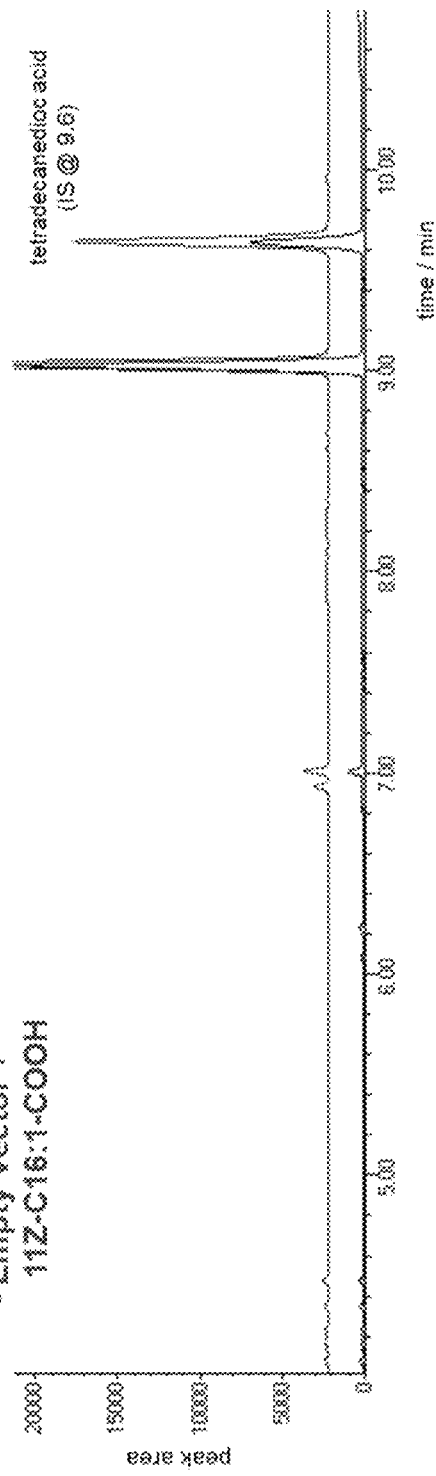
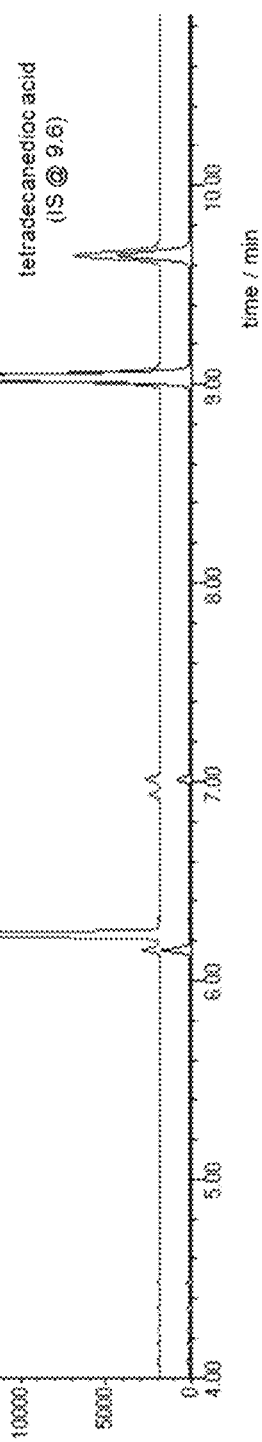
FIG. 6A
- Empty vector
- Empty vector + 11Z-C16:1-COOH
FIG. 6B
- FAR-HA
- FAR-HA + 11Z-C16:1-COOH

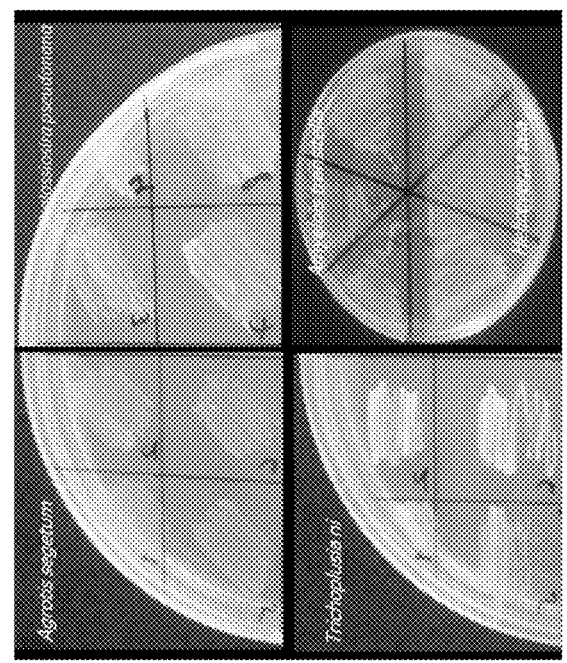
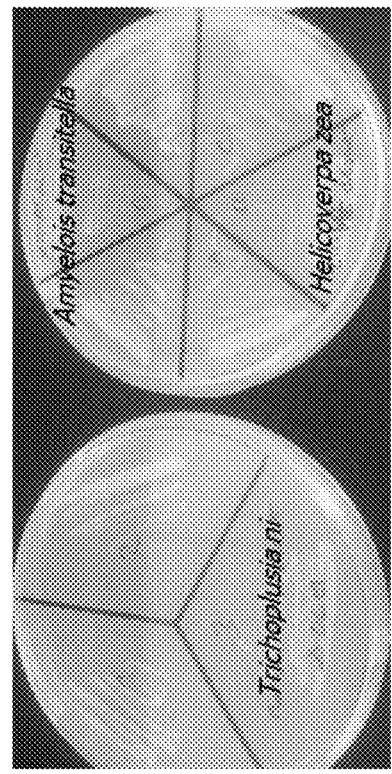
FIG. 12A
FIG. 12B

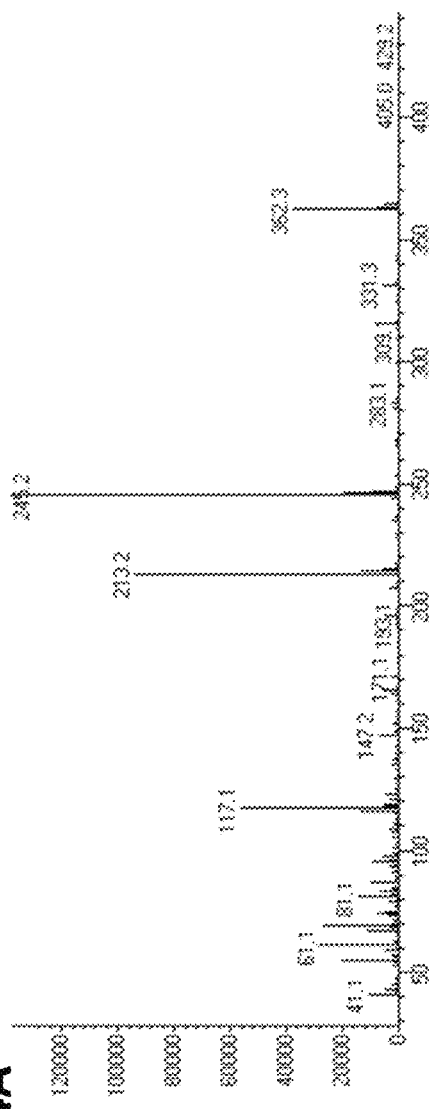
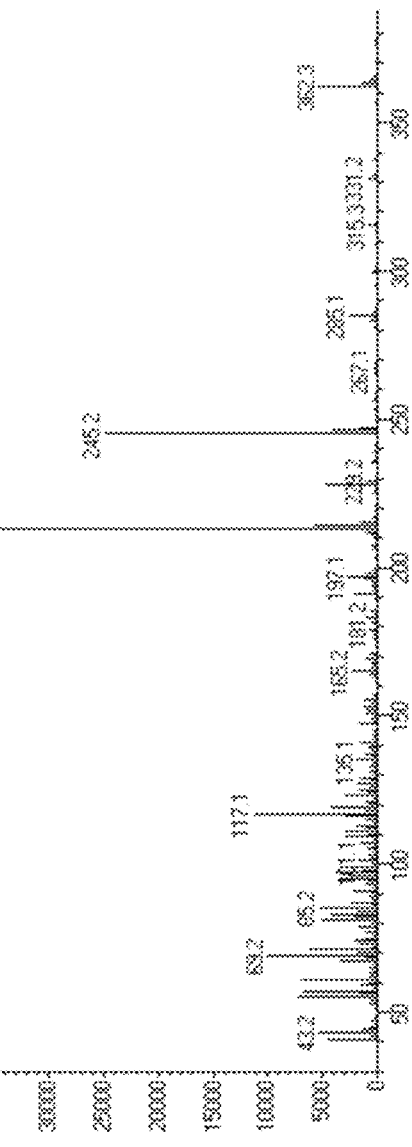
FIG. 14A
FIG. 14B

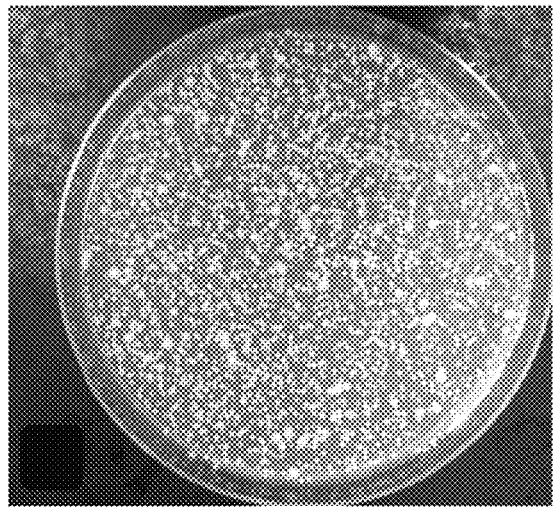
FIG. 21B pPV0137 (mCherry_Ct)
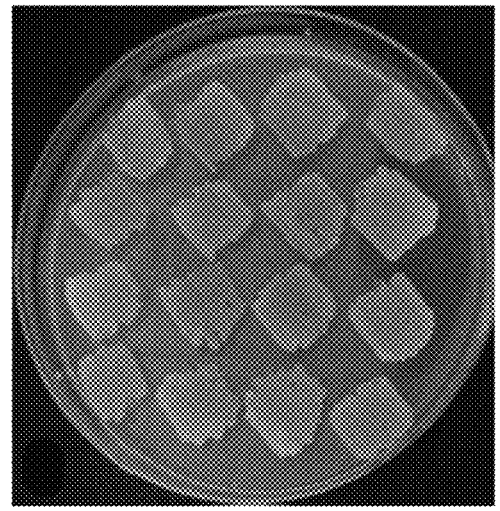
FIG. 21D
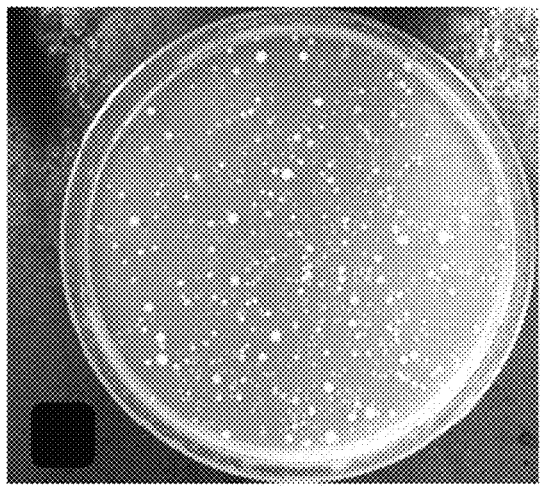
FIG. 21A Negative control (water)
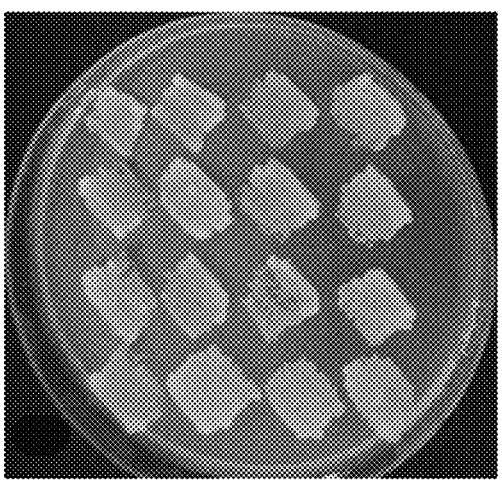
FIG. 21C

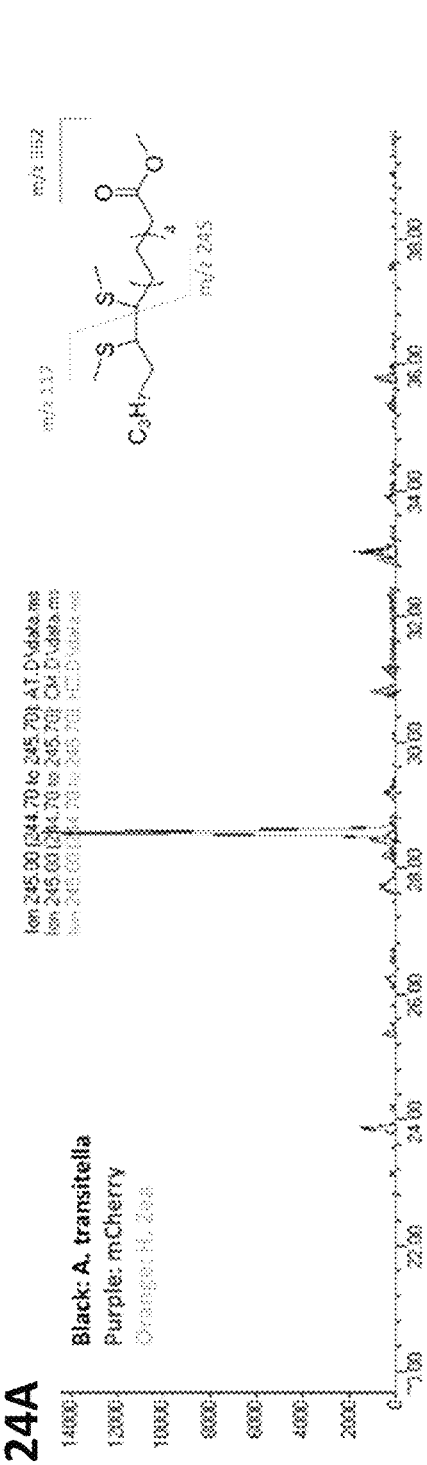
FIG. 24A
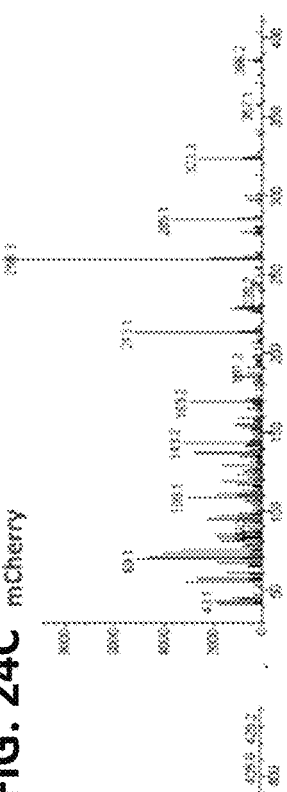
FIG. 24B
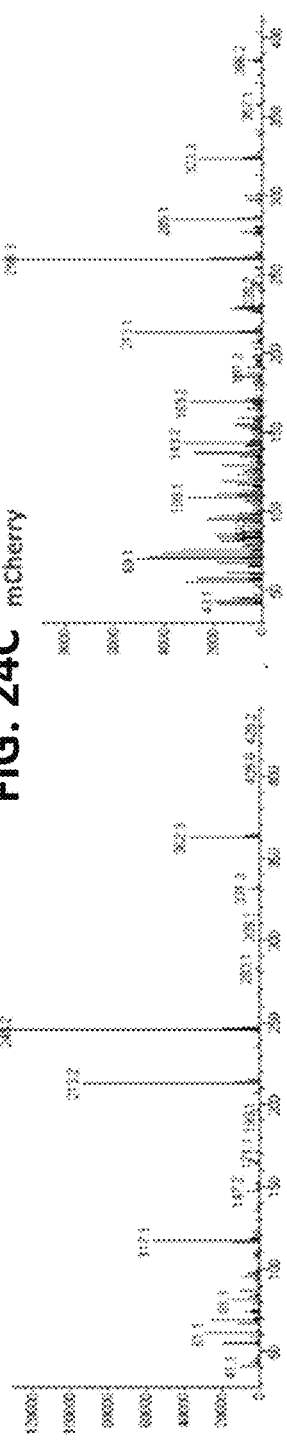
FIG. 24C mCherry
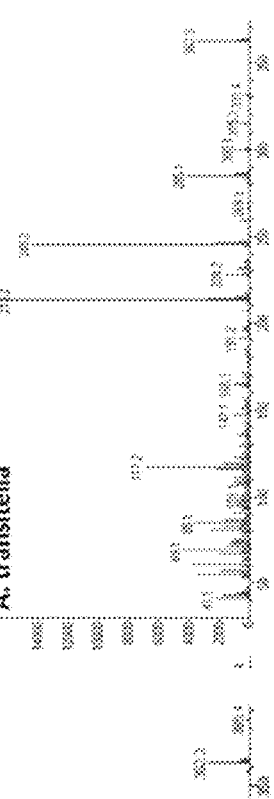
FIG. 24D
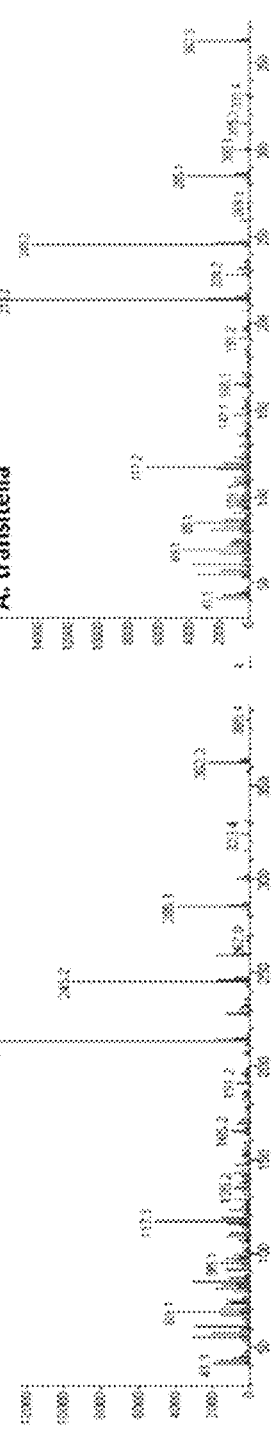
FIG. 24E A. transitella

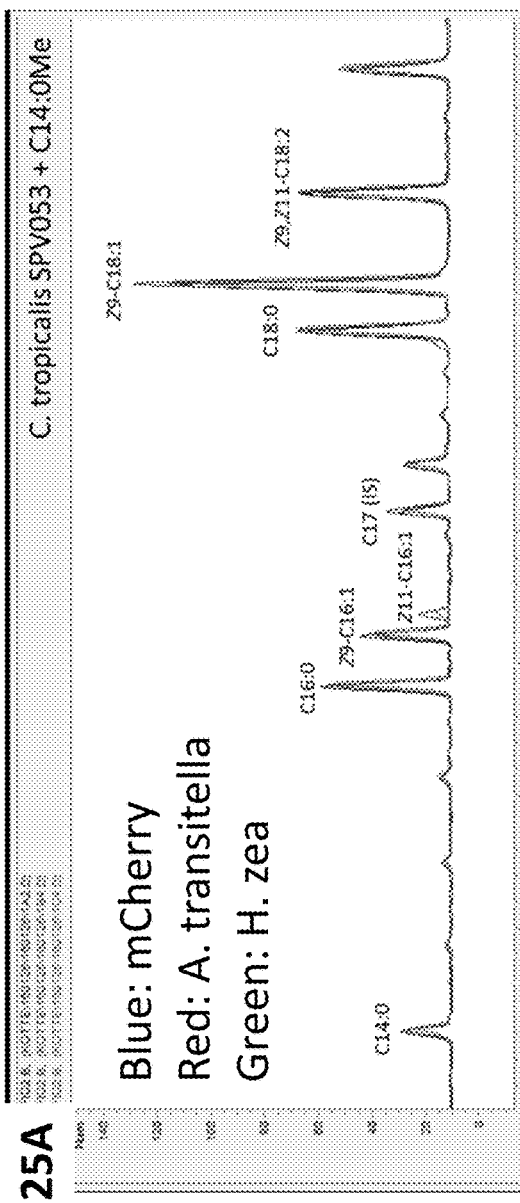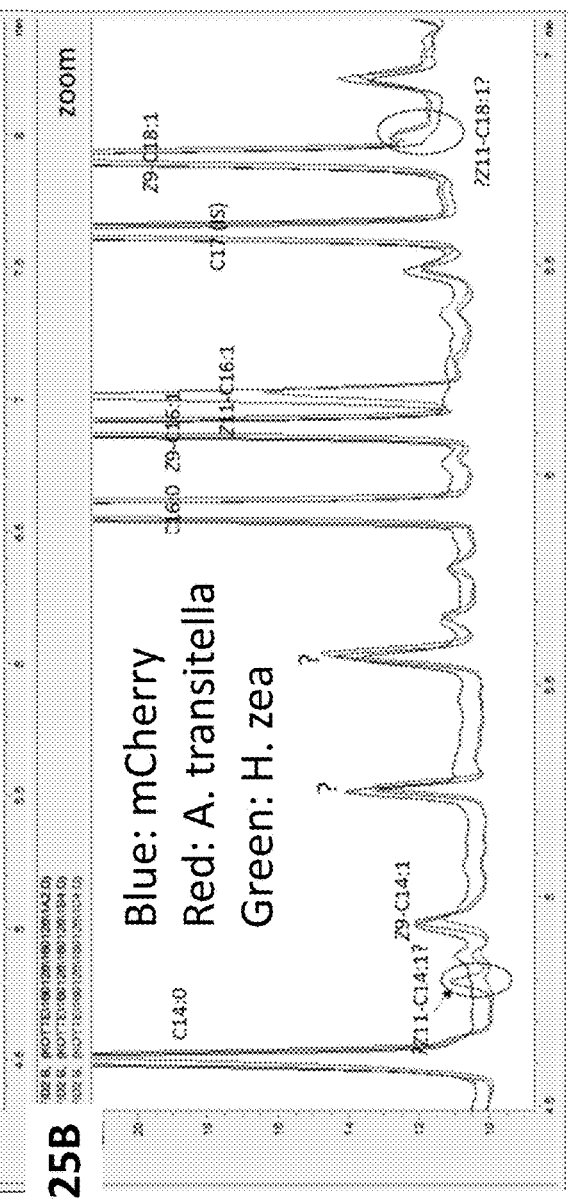
FIG. 25A
FIG. 25B

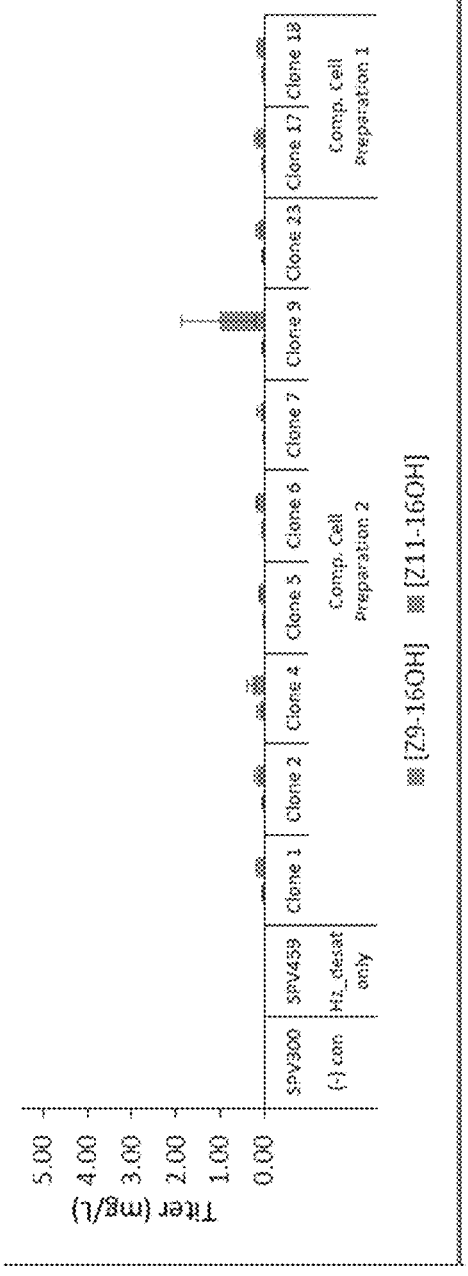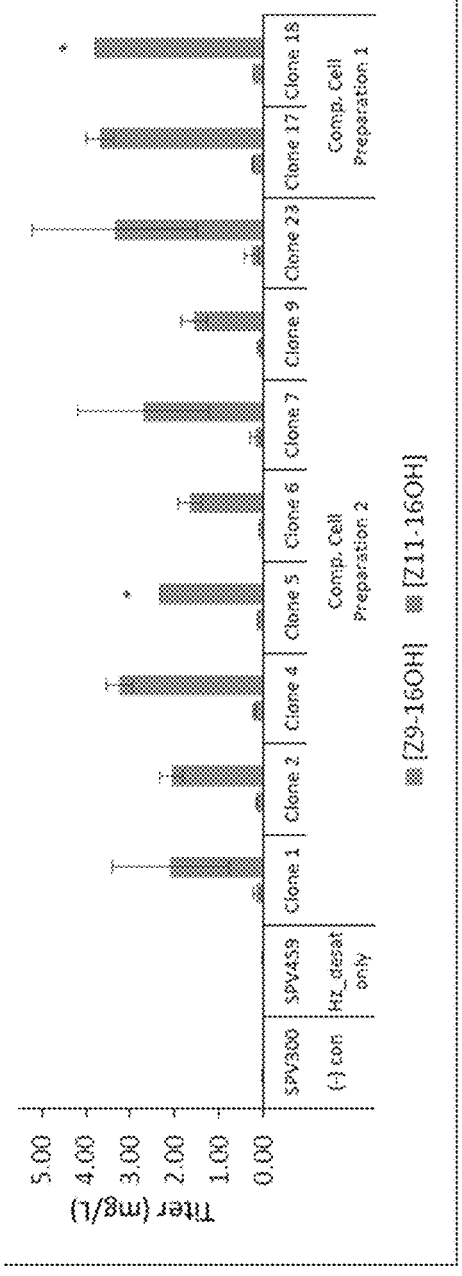
FIG. 32A YPD
FIG. 32B : Semi-Defined C:N=80

SEQUENCE LISTING

```
<160> NUMBER OF SEQ ID NOS: 38

<210> SEQ ID NO 1
<211> LENGTH: 1377
<212> TYPE: DNA
<213> ORGANISM: Agrotis segetum

<400> SEQUENCE: 1
atgccagttt tgacttctag agaagatgaa aagttgtcag ttccagaatt ttacgctggt      60
aaatctatct tcgttacagg tggtactggt ttcttgggta aagtttttat tgaaaagttg     120
ttgtactgtt gtccagatat tgataaaatc tatatgttaa ttagagaaaa gaaaaatttg     180
tctattgatg aaagaatgtc aaagttcttg gatgatccat tattttctag attgaaggaa     240
gaaagacctg gtgacttgga aaagattgtt ttgattccag gtgacattac agctccaaat     300
ttgggtttat cagcagaaaa cgaaagaatt ttgttagaaa aagtttctgt tattattaat     360
tcagctgcaa ctgttaagtt taatgaacca ttgccaatcg cttggaagat taatgttgaa     420
ggtacaagaa tgttgttggc attgtctaga agaatgaaga gaatcgaagt ttttattcat     480
atttctactg cttactcaaa tgcatcttca gatagaatcg ttgttgatga aatcttgtat     540
```

```
ccagctccag cagatatgga tcaagtttac caattggtta agatggtgt tacagaagaa    600 gaaactgaaa gattgttgaa cggtttgcca aacacttaca cttttactaa ggctttgaca    660
gaacatttgg ttgcagaaca tcaaacatac gttccaacta tcatcatcag accatctgtt    720
gttgcttcaa ttaaagatga accaatcaga ggttggttat gtaattggtt tggtgctaca    780
ggtatctctg tttttactgc aaagggtttg aacagagttt tgttgggtaa agcttcaaac    840
atcgttgatg ttatcccagt tgattacgtt gcaaatttgg ttattgttgc tggtgcaaaa    900
tctggtggtc aaaaatcaga tgaattaaag atctataact gttgttcttc agattgtaac    960
ccagttactt tgaagaaaat tattaaagag tttactgaag atactattaa aaataagtct   1020
catattatgc cattgccagg ttggttcgtt tttactaagt acaagtggtt gttgacattg   1080
ttaactatta ttttcaaat gttaccaatg tatttggctg atgtttacag agttttgaca   1140
ggtaaaatcc caagatacat gaagttgcat catttggtta ttcaaacaag attgggtatc   1200
gatttcttta cttctcattc atgggttatg aagacagata gagttagaga attattcggt   1260
tctttgtcat tggcagaaaa gcatatgttt ccatgtgatc catcttcaat cgattggaca   1320
gattatttgc aatcatactg ttacggtgtt agaagatttt tggaaaagaa gaaataa     1377

<210> SEQ ID NO 2
<211> LENGTH: 1365
<212> TYPE: DNA
<213> ORGANISM: Spodoptera littoralis

<400> SEQUENCE: 2
atggttgttt tgacttcaaa ggaaaaatca aacatgtctg ttgctgattt ctacgctggt     60
aaatctgttt ttattacagg tggtactggt ttcttgggta agttttttat tgaaaagttg    120
ttgtactcat gtccagatat tgataaaatc tatatgttga tcagagaaaa gaaaggtcaa    180
tctatcagag aaagattaac taaaattgtt gatgatccat gtttaatag attgaaggat    240 aagagaccag atgatttggg taaaatcgtt ttgatcccag gtgacatcac agttccaggt    300
ttgggtattt ctgaagaaaa cgaaacaatc ttgactgaaa aagttcagt tgttattcat    360 tctgctgcaa ctgttaagtt taatgaacca ttggctactg catggaacgt taacgttgaa    420
ggtacaagaa tgatcatggc attatcaaga agaatgaaga gaatcgaagt ttttattcat    480
atttctactg cttacactaa cacaaacaga gcagttattg atgaagtttt gtatccacca    540
ccagctgata tcaacgatgt tcatcaacat gttaaaaatg gtgttacaga agaagaaact    600
gaaaagattt tgaacggtag accaaacact tacactttta ctaaggcttt gactgaacat    660
ttggttgcag aaaaccaatc atacatgcca acaatcattg ttagaccatc tattgttggt    720
gctattaaag atgatccaat tagaggttgg ttggctaatt ggtatggtgc aacaggtttg    780
tcagttttta ctgcaaaggg tttgaacaga gttatatatg gtcattctaa ccatgttgtt    840
gatttgattc cagttgatta cgttgctaat tggttattg ttgctggtgc aaagacatac    900
cattcaaacg aagttactat ctataactct tgttcttcat cttgtaaccc aatcactatg    960
aagagattgg ttggtttgtt tattgattac acagttaagc ataagtcata cgttatgcca   1020
ttgccaggtt ggtatgttta ctctaactac aagtggttgg ttttcttggt tactgttatt   1080
ttccaagtta ttccagctta cttaggtgac attggtagaa gattgttagg taaaaatcca   1140
agatactaca gttgcaaaaa tttggttgct caaacacaag aagcagttca tttctttaca   1200
tcacatactt gggaaattaa atcaaagaga acttctgaat tgttttcatc tttgtctttg   1260
```

| acagatcaaa gaatgtttcc atgtgatgct aacagaatcg attggacaga ttacatcact | 1320 |
| gattactgtt ctggtgttag acaattttg gaaaagatta aataa | 1365 |

<210> SEQ ID NO 3
<211> LENGTH: 1368
<212> TYPE: DNA
<213> ORGANISM: Helicoverpa armigera

<400> SEQUENCE: 3

| atggttgttt tgacttcaaa ggaaacaaag ccatctgttg ctgaatttta cgctggtaaa | 60 |
| tcagttttta ttacaggtgg tactggtttc ttgggtaaag tttttattga aaagttgttg | 120 |
| tactcttgtc cagatattga aaatatctat atgttgatca gagaaaagaa aggtttgtca | 180 |
| gtttctgaaa gaattaaaca attttttagat gatccattgt ttacaagatt gaaggataag | 240 |
| agaccagctg atttggaaaa gattgttttg atcccaggtg acatcactgc accagatttg | 300 |
| ggtattaatt ctgaaaacga aaagatgttg attgaaaaag tttcagttat tattcattct | 360 |
| gctgcaactg ttaagtttaa tgaaccatta ccaacagctt ggaagattaa tgttgaaggt | 420 |
| actagaatga tgttggcatt gtcaagaaga atgaagagaa tcgaagtttt tattcatatt | 480 |
| tctacagctt acactaacac aaacagagaa gttgttgatg aaatcttgta ccagctcca | 540 |
| gcagatatcg atcaagttca tcaatacgtt aaggatggta tctcagaaga agatactgaa | 600 |
| aagatttttga acggtagacc aaacacttac acttttacta aggctttgac agaacatttg | 660 |
| gttgctgaaa tcaagcata cgttccaact attattgtta gaccatctgt tgttgctgca | 720 |
| attaaagatg aaccattgaa aggttggttg ggtaattggt ttggtgctac aggtttgact | 780 |
| gtttttacag caaagggttt gaacagagtt atatatggtc attcttcata catcgttgat | 840 |
| ttgatcccag ttgattacgt tgctaatttg gttattgctg caggtgcaaa atcttcaaag | 900 |
| tcaacagaat tgaaggttta caactgttgt tcttcatctt gtaacccagt tactatcggt | 960 |
| acattgatgt caatgttcgc tgatgatgca attaaacaaa aatcttacgc tatgccattg | 1020 |
| ccaggttggt acatttttac aaagtacaag tggttggttt tgttgttgac attttttgttc | 1080 |
| caagttattc cagcatacgt tactgatttg tcaagacatt tgatcggtaa atctccaaga | 1140 |
| tacatcaagt tgcaatcatt ggttaaccaa actagatcat ctatcgattt ctttacaaac | 1200 |
| cattcttggg ttatgaaagc tgatagagtt agagaattgt acgcttcatt gtctccagct | 1260 |
| gataagtact tattcccatg tgatccaact gatatcaact ggacacatta catccaagat | 1320 |
| tactgttggg gtgttagaca tttcttggaa aagaaatctt acgaataa | 1368 |

<210> SEQ ID NO 4
<211> LENGTH: 1199
<212> TYPE: DNA
<213> ORGANISM: Artificial Sequence
<220> FEATURE:
<223> OTHER INFORMATION: pOLE1 cassette

<400> SEQUENCE: 4

| cttgctgaaa agatgatgtt ctgaggtatt cgtatcgcta gcttgatacg cttttaacaa | 60 |
| aagtaagctt ttcgtttgca ggtttggtta cttttctgta cgagatgata tcgctaagtt | 120 |
| tatagtcatc tgtgaaattt ctcaaaaacc tcatggtttc tccatcaccc attttcatt | 180 |
| tcatttgccg ggcggaaaaa aaaaggaaa aaaaaaaaa aaaaaaataa atgacacatg | 240 |
| gaaataagtc aaggattagc ggatatgtag ttccagtccg ggttatacca tcacgtgata | 300 |
| ataaatccaa atgagaatga gggtgtcata tctaatcatt atgcacgtca agattctccg | 360 |

```
tgactatggc tctttctga agcattttc gggcgcccgg tggccaaaaa ctaactccga    420
gcccgggcat gtcccggggt tagcgggccc aacaaaggcg cttatctggt gggcttccgt    480
agaagaaaaa aagctgttga gcgagctatt tcgggtatcc cagccttctc tgcagaccgc    540
cccagttggc ttggctctgg tgctgttcgt tagcatcaca tcgcctgtga caggcagagg    600
taataacggc ttaaggttct cttcgcatag tcggcagctt tctttcggac gttgaacact    660
caacaaacct tatctagtgc ccaaccaggt gtgcttctac gagtcttgct cactcagaca    720
cacctatccc tattgttacg gctatgggga tggcacacaa aggtggaaat aatagtagtt    780
aacaatatat gcagcaaatc atcggctcct ggctcatcga gtcttgcaaa tcagcatata    840
catatatata tgggggcaga tcttgattca tttattgttc tatttccatc tttcctactt    900
ctgtttccgt ttatattttg tattacgtag aatagaacat catagtaata gatagttgtg    960
gtgatcatat tataaacagc actaaaacat tacaacaaag aatgccaact tctggaacta    1020
ctattgaatt gattgacgac caatttccaa aggatgactc tgccagcagt ggcattgtcg    1080
acactagtgc ggccgctcac atatgaaagt ataccccgc ttttgtacac tatgtagcta    1140
taattcaatc gtattattgt agctccgcac gaccatgcct tagaaatatc cgcagcgcg    1199
```

<210> SEQ ID NO 5
<211> LENGTH: 655
<212> TYPE: DNA
<213> ORGANISM: Artificial Sequence
<220> FEATURE:
<223> OTHER INFORMATION: OLE1 promoter region

<400> SEQUENCE: 5

```
cttgctgaaa agatgatgtt ctgaggtatt cgtatcgcta gcttgatacg cttttaacaa    60
aagtaagctt ttcgtttgca ggtttggtta cttttctgta cgagatgata tcgctaagtt    120
tatagtcatc tgtgaaattt ctcaaaaacc tcatggtttc tccatcaccc atttttcatt    180
tcatttgccg ggcggaaaaa aaaaggaaa aaaaaaaaa aaaaaaataa atgacacatg    240
gaaataagtc aaggattagc ggatatgtag ttccagtccg ggttatacca tcacgtgata    300
ataaatccaa atgagaatga gggtgtcata tctaatcatt atgcacgtca agattctccg    360
tgactatggc tcttttctga agcattttc gggcgcccgg tggccaaaaa ctaactccga    420
gcccgggcat gtcccggggt tagcgggccc aacaaaggcg cttatctggt gggcttccgt    480
agaagaaaaa aagctgttga gcgagctatt tcgggtatcc cagccttctc tgcagaccgc    540
cccagttggc ttggctctgg tgctgttcgt tagcatcaca tcgcctgtga caggcagagg    600
taataacggc ttaaggttct cttcgcatag tcggcagctt tctttcggac gttga    655
```

<210> SEQ ID NO 6
<211> LENGTH: 346
<212> TYPE: DNA
<213> ORGANISM: Artificial Sequence
<220> FEATURE:
<223> OTHER INFORMATION: OLE1 promoter region

<400> SEQUENCE: 6

```
acactcaaca aaccttatct agtgcccaac caggtgtgct tctacgagtc ttgctcactc    60
agacacacct atccctattg ttacggctat ggggatggca cacaaaggtg gaaataatag    120
tagttaacaa tatatgcagc aaatcatcgg ctcctggctc atcgagtctt gcaaatcagc    180
atatacatat atatatgggg gcagatcttg attcatttat tgttctattt ccatctttcc    240
```

```
tacttctgtt tccgtttata ttttgtatta cgtagaatag aacatcatag taatagatag    300
ttgtggtgat catattataa acagcactaa aacattacaa caaaga                   346

<210> SEQ ID NO 7
<211> LENGTH: 81
<212> TYPE: DNA
<213> ORGANISM: Artificial Sequence
<220> FEATURE:
<223> OTHER INFORMATION: OLE1 27aa leader

<400> SEQUENCE: 7
atgccaactt ctggaactac tattgaattg attgacgacc aatttccaaa ggatgactct    60
gccagcagtg gcattgtcga c                                              81

<210> SEQ ID NO 8
<211> LENGTH: 103
<212> TYPE: DNA
<213> ORGANISM: Artificial Sequence
<220> FEATURE:
<223> OTHER INFORMATION: Vsp13 terminator region

<400> SEQUENCE: 8
tcacatatga agtatatac ccgcttttgt acactatgta gctataattc aatcgtatta     60
ttgtagctcc gcacgaccat gccttagaaa tatccgcagc gcg                     103

<210> SEQ ID NO 9
<211> LENGTH: 1050
<212> TYPE: DNA
<213> ORGANISM: Trichoplusia ni

<400> SEQUENCE: 9
atggctgtga tggctcaaac agtacaagaa acggctacag tgttggaaga ggaagctcgc    60
acagtgactc ttgtggctcc aaagacaacg ccaaggaaat ataaatatat atacaccaac   120
tttcttacat tttcatatgc gcatttagct gcattatacg gactttatt gtgcttcacc   180 tctgcgaaat gggaaacatt gctattctct ttcgtactct tccacatgtc aaatataggc   240
atcaccgcag gggctcaccg actctggact cacaagactt caaagccaa attgcctttg   300 gaaattgtcc tcatgatatt caactcttta gcctttcaaa acacggctat tacatgggct   360
agagaacatc ggctacatca caaatacagc gatactgatg ctgatcccca caatgcgtca   420
agagggttct tctactcgca tgttggctgg ctattagtaa aaaaacatcc cgatgtcctg   480
aaatatggaa aaactataga catgtcggat gtatacaata atcctgtgtt aaaatttcag   540
aaaaagtacg cagtacccct taattggaaca gtttgttttg ctctgccaac tttgattcca   600
gtctactgtt ggggcgaatc gtggaacaac gcttggcaca tagccttatt tcgatacata   660
ttcaatctta acgtgactt cctagtcaac agtgctgcgc atatctgggg gaataagcct   720
tatgataaaa gcatcttgcc cgctcaaaac ctgctggttt ccttcctagc aagtggagaa   780
ggcttccata attaccatca cgtctttcca tgggattacc gcacagcaga attagggaat   840
aacttcctga atttgacgac gctgttcatt gattttgtg cctggtttgg atgggcttat   900
gacttgaagt ctgtatcaga ggatattata aaacagagag ctaaacgaac aggtgacggt   960
tcttcagggg tcatttgggg atgggacgac aaagacatgg accgcgatat aaaatctaaa  1020
gctaacattt tttatgctaa aaaggaatga                                   1050

<210> SEQ ID NO 10
<211> LENGTH: 1011
```

```
<212> TYPE: DNA
<213> ORGANISM: Agrotis segetum

<400> SEQUENCE: 10
atggctcaag gtgtccaaac aactacgata ttgagggagg aggagccgtc attgactttc      60
gtggtacctc aagaaccgag aaagtatcaa atcgtgtacc caaaccttat cacatttggg     120
tactggcata tagctggttt atacgggcta tatttgtgct ttacttcggc aaaatggcaa     180
acaattttat tcagtttcat gctcgttgtg ttagcagagt tgggaataac agccggcgct     240
cacaggttat gggcccacaa aacatataaa gcgaagcttc ccttacaaat tatcctgatg     300
atactgaact ccattgcctt ccaaaattcc gccattgatt gggtgaggga ccaccgtctc     360
catcataagt acagtgacac tgatgcagac cctcacaatg ctactcgtgg tttcttctat     420
tctcatgttg gatggttgct cgtaagaaaa catccagaag tcaagagacg tggaaaggaa     480
cttgacatgt ctgatattta caacaatcca gtgctgagat ttcaaaagaa gtatgctata     540
cccttcatcg gggcaatgtg cttcggatta ccaactttta tccctgttta cttctgggga     600
gaaacctgga gtaatgcttg gcatatcacc atgcttcggt acatcctcaa cctaaacatt     660
actttcctgg tcaacagtgc tgctcatatc tggggataca aaccttatga catcaaaata     720
ttgcctgccc aaaatatagc agtttccata gtaaccggcg gcgaagtttc cataactacc     780
accacgtttt ttccttggga ttatcgtgca gcagaattgg ggaacaatta tcttaatttg     840
acgactaagt tcatagattt cttcgcttgg atcggatggg cttacgatct taagacggtg     900
tccagtgatg ttataaaaag taaggcggaa agaactggtg atgggacgaa tctttggggt     960
ttagaagaca aaggtgaaga agatttttttg aaaatctgga aagacaatta a            1011

<210> SEQ ID NO 11
<211> LENGTH: 1440
<212> TYPE: DNA
<213> ORGANISM: Thalassiosira pseudonana

<400> SEQUENCE: 11
actagtatgg actttctctc cggcgatcct ttccggacac tcgtccttgc agcacttgtt      60
gtcatcggat ttgctgcggc gtggcaatgc ttctacccgc cgagcatcgt cggcaagcct     120
cgtacattaa gcaatggtaa actcaatacc agaatccatg gcaaattgta cgacctctca     180
tcgtttcagc atccaggagg ccccgtggct ctttctcttg ttcaaggtcg cgacggaaca     240
gctctatttg agtcacacca tcccttcata cctcgaaaga atctacttca gatcctctcc     300
aagtacgagg ttccgtcgac tgaagactct gtttccttca tcgccaccct agacgaactc     360
aatggtgaat ctccgtacga ttggaaggac attgaaaatg atgatttcgt atctgaccta     420
cgagctctcg taattgagca cttttctcct ctcgccaagg aaaggggagt ttcactcgtt     480
gagtcgtcga aggcaacacc tcagcggtgg atggtggttc tactgctcct tgcgtcgttc     540
ttcctcagca tcccattata tttgagtggt tcgtggactt tcgttgtcgt cactcccatc     600
ctcgcttggc tggcggttgt caattactgg cacgatgcta ctcactttgc attgagcagc     660
aactggattt tgaatgctgc gctcccatat ctcctccctc tcctatcgag tccgtcaatg     720
tggtatcatc atcacgtcat ggacatcac  gcatacacca acatttccaa aagagatcca     780
gatcttgctc acgctccaca actcatgaga gaacacaaga gtatcaaatg gagaccatct     840
cacttaaatc aaacacagct tccgcgggatt tcttcatct ggtcgattgc agtcggtatt     900
gggttgaact tactgaacga cgtgagagca ctaaccaagc tttcatacaa caacgttgtt     960
```

-continued

| | |
|---|---|
| cgggtggaga agatgtcatc gtcgcgaaca ttactccatt tccttggacg tatgttgcac | 1020 |
| atctttgtga ctacactttg gcccttttg gcgtttccgg tgtggaaggc catcgtttgg | 1080 |
| gcgactgtac cgaatgccat actgagtttg tgcttcatgc tgaatacgca atcaatcac | 1140 |
| ctcatcaaca cgtgtgcaca tgcttccgat aacaactttt acaagcatca agttgtaact | 1200 |
| gctcagaact ttggccgatc aagtgccttt tgcttcatct tctcgggagg tctcaactac | 1260 |
| caaattgaac atcatttgtt gccgacggtg aaccattgcc atttgccagc tttggccccg | 1320 |
| ggtgtagagc gtttgtgtaa aaacacggg gtgacataca actctgttga aggatacaga | 1380 |
| gaggccatca ttgcacactt tgcacatacc aaagatatgt cgacgaagcc tactgattga | 1440 |

<210> SEQ ID NO 12
<211> LENGTH: 981
<212> TYPE: DNA
<213> ORGANISM: Amyelois transitella

<400> SEQUENCE: 12

| | |
|---|---|
| atggtcccta caagggttc cagtgacgtt ttgtctgaac attctgagcc ccagttcact | 60 |
| aaactcatag ctccacaagc agggccgagg aaatacaaga tagtgtatcg aaatttgctc | 120 |
| acattcggct attggcactt atcagctgtt tatgggctct acttgtgctt tacttgtgcg | 180 |
| aaatgggcta ccatcttatt tgcattttc ttatacgtga tcgcggaaat cggtataaca | 240 |
| ggtggcgctc ataggctatg gcacatcgg acttataaag ccaagttgcc tttagagatt | 300 |
| ttgttactca taatgaactc tattgccttc aagacactg ctttcacctg gctcgtgat | 360 |
| caccgccttc atcacaaata ttcggatact gacgctgatc cccacaatgc taccagaggg | 420 |
| tttttctatt cacatgtagg ctggctttg gtgaagaaac ccctgaagt caaagcaaga | 480 |
| ggaaaatact tgtcgttaga tgatcttaag aataatccat tgcttaaatt ccaaaagaaa | 540 |
| tacgctattc tagttatagg cacgttatgc ttccttatgc caacatttgt gcccgtatac | 600 |
| ttctggggcg agggcatcag cacggcctgg aacatcaatc tattgcgata cgtcatgaat | 660 |
| cttaacatga ctttcttagt taacagtgca gcgcatatct ttggcaacaa accatacgat | 720 |
| aagagccatag cctcagtcca aaatatttca gttagcttag ctacttttgg cgaaggattc | 780 |
| cataattacc atcacactta ccctgggat tatcgtgcgg cagaattagg aaataatagg | 840 |
| ctaaatatga ctactgcttt catagatttc ttcgcttgga tcggctgggc ttatgacttg | 900 |
| aagtctgtgc cacaagaggc cattgcaaaa aggtgtgcga aaactggcga tggaacggat | 960 |
| atgtggggtc gaaaaagata a | 981 |

<210> SEQ ID NO 13
<211> LENGTH: 1017
<212> TYPE: DNA
<213> ORGANISM: Helicoverpa zea

<400> SEQUENCE: 13

| | |
|---|---|
| atggcccaaa gctatcaatc aactacggtt ttgagtgagg agaaagaact aacactgcaa | 60 |
| catttggtgc cccaagcatc gcccaggaag tatcaaatag tgtatccgaa cctcattacg | 120 |
| tttggttact ggcacatagc cggactttat ggcctttact tgtgcttcac ttctgctaaa | 180 |
| tgggctacga ttttattcag ctacatcctc ttcgtgttag cagaaatagg aatcacggct | 240 |
| ggcgctcaca gactctgggc ccacaaaact tacaaagcga aactaccatt agaaatactc | 300 |
| ttaatggtat tcaactccat cgcttttcaa aactcagcca ttgactgggt gagggaccac | 360 |
| cgactccacc ataagtatag cgatacagat gctgatcccc acaatgccag ccgagggttc | 420 |

| | |
|---|---|
| tttattccc atgtaggatg gctacttgtg agaaaacatc ctgaagtcaa aaagcgaggg | 480 |
| aaagaactca atatgtccga tatttacaac aatcctgtcc tgcggtttca gaaaaaatac | 540 |
| gccatacct tcattggggc tgtttgtttc gccttaccta caatgatacc tgtttacttc | 600 |
| tggggagaaa cctggtccaa tgcttggcat atcaccatgc ttcgctacat catgaacctc | 660 |
| aatgtcacct ttttggtaaa cagcgctgct catatatggg gaaacaagcc ttatgacgca | 720 |
| aaatattac ctgcacaaaa tgtagctgtg tcggtcgcca ctggtggaga aggtttccat | 780 |
| aattaccacc atgtcttccc ctgggattat cgagcagcgg aactcggtaa caatagcctc | 840 |
| aatctgacga ctaaattcat agatttattc gcagcaatcg gatgggcata tgatctgaag | 900 |
| acggtttcgg aggatatgat aaaacaaagg attaaacgca ctggagatgg aacggatctt | 960 |
| tggggacacg aacaaaactg tgatgaagtg tgggatgtaa agataaaatc aagttaa | 1017 |

<210> SEQ ID NO 14
<211> LENGTH: 711
<212> TYPE: DNA
<213> ORGANISM: Artificial Sequence
<220> FEATURE:
<223> OTHER INFORMATION: mCherry C. tropicalis optimized

<400> SEQUENCE: 14

| | |
|---|---|
| atggtttcta agggtgaaga agacaacatg gcaatcatca aggaatttat gcgttttaag | 60 |
| gtccatatgg aaggctccgt taacggccac gagttcgaga tcgagggaga aggtgagggt | 120 |
| agaccatacg aagtactca aaccgccaag ttgaaagtta caagggtgg tccattgcca | 180 |
| tttgcttggg atatcttgtc cccacaattt atgtacggat caaaggcata tgtcaagcat | 240 |
| cctgccgaca tcccagatta cttgaagtta tcctttccag aaggttttaa gtgggagaga | 300 |
| gttatgaact ttgaagatgg cggagttgtt actgttactc aggactcttc cttgcaagat | 360 |
| ggtgaattta tctataaagt gaaattgaga ggtactaact ttccatccga cggtccagtc | 420 |
| atgcaaaaga agacaatggg ttgggaggct tcttccgaaa gaatgtaccc agaagacggt | 480 |
| gcattgaaag gtgaaatcaa gcaacgttta aagttgaagg acggtggtca ctacgatgcc | 540 |
| gaggtcaaga ccacttataa ggctaagaag ccagtccaat gccaggtgc ttataacgtt | 600 |
| aacatcaagt tagatattac ttcacacaac gaagactaca caatcgttga acaatatgaa | 660 |
| agagccgaag gtagacattc taccggcggc atggacgagt tatataagta g | 711 |

<210> SEQ ID NO 15
<211> LENGTH: 1092
<212> TYPE: DNA
<213> ORGANISM: Agrotis segetum

<400> SEQUENCE: 15

| | |
|---|---|
| atgactacag ttgaacaact tgaaactgtt gatatcacta aattgaatgc cattgctgct | 60 |
| ggtactaata agaaggtgcc aatggctcaa ggtgtccaaa caactacgat attgagggag | 120 |
| gaagagccgt cattgacttt cgtggtacct caagaaccga gaaagtatca atcgtgtac | 180 |
| ccaaaccta tcacatttgg gtactggcat atagctggtt tatacgggct atatttgtgc | 240 |
| tttacttcgg caaaatggca aacaattta ttcagtttca tgctcgttgt gttagcagag | 300 |
| ttgggaataa cagccggcgc tcacaggtta tgggcccaca aacatataa agcgaagctt | 360 |
| cccttacaaa ttatcttaat gatattaaac tccattgcct tccaaaattc cgccattgat | 420 |
| tgggtgaggg accaccgtct ccatcataag tacagtgaca ctgatgcaga ccctcacaat | 480 |

```
gctactcgtg gtttcttcta ttctcatgtt ggatggttgc tcgtaagaaa acatccagaa    540
gtcaagagac gtggaaagga acttgacatg tctgatattt acaacaatcc agtgttaaga    600
tttcaaaaga agtatgctat acccttcatc ggggcaatgt gcttcggatt accaactttt    660
atccctgttt acttctgggg agaaacctgg agtaatgctt ggcatatcac catgcttcgg    720
tacatcctca acctaaacat tactttctta gtcaacagtg ctgctcatat ctggggatac    780
aaaccttatg acatcaaaat attgcctgcc caaaatatag cagtttccat agtaaccggc    840
ggcgaagttt ccataactac caccacgttt tttccttggg attatcgtgc agcagaattg    900
gggaacaatt atcttaattt gacgactaag ttcatagatt tcttcgcttg gatcggatgg    960
gcttacgatc ttaagacggt gtccagtgat gttataaaaa gtaaggcgga agaactggt    1020 gatgggacga atctttgggg tttagaagac aaaggtgaag aagattttt gaaaatctgg    1080 aaagacaatt aa                                                       1092

<210> SEQ ID NO 16
<211> LENGTH: 1011
<212> TYPE: DNA
<213> ORGANISM: Agrotis segetum

<400> SEQUENCE: 16
atggctcaag gtgtccaaac aactacgata ttgagggagg aagagccgtc attgactttc     60
gtggtacctc aagaaccgag aaagtatcaa atcgtgtacc caaaccttat cacatttggg    120
tactggcata tagctggttt atacgggcta tatttgtgct ttacttcggc aaaatggcaa    180
acaattttat tcagtttcat gctcgttgtg ttagcagagt tgggaataac agccggcgct    240
cacaggttat gggcccacaa aacatataaa gcgaagcttc ccttacaaat tatcttaatg    300
atattaaact ccattgcctt ccaaaattcc gccattgatt gggtgaggga ccaccgtctc    360
catcataagt acagtgacac tgatgcagac cctcacaatg ctactcgtgg tttcttctat    420
tctcatgttg gatggttgct cgtaagaaaa catccagaag tcaagagacg tggaaaggaa    480
cttgacatgt ctgatattta caacaatcca gtgttaagat ttcaaaagaa gtatgctata    540
cccttcatcg gggcaatgtg cttcggatta ccaacttttta tccctgttta cttctgggga    600
gaaacctgga gtaatgcttg gcatatcacc atgcttcggt acatcctcaa cctaaacatt    660
actttcttag tcaacagtgc tgctcatatc tggggataca aaccttatga catcaaaata    720
ttgcctgccc aaaatatagc agtttccata gtaaccggcg gcgaagtttc cataactacc    780
accacgtttt tccttgggat tatcgtgcag cagaattggg gaacaattat cttaatttg    840 acgactaagt tcatagattt cttcgcttgg atcggatggg cttacgatct taagacggtg    900
tccagtgatg ttataaaaag taaggcggaa agaactggtg atgggacgaa tctttggggt    960
ttagaagaca aaggtgaaga agatttttg aaaatctgga aagacaatta a             1011

<210> SEQ ID NO 17
<211> LENGTH: 981
<212> TYPE: DNA
<213> ORGANISM: Amyelois transitella

<400> SEQUENCE: 17
atggtcccta caagggttc cagtgacgtt ttgtctgaac attctgagcc ccagttcact     60
aaactcatag ctccacaagc agggccgagg aaatacaaga tagtgtatcg aaatttgctc    120
acattcggct attggcactt atcagctgtt tatgggctct acttgtgctt tacttgtgcg    180
aaatgggcta ccatcttatt tgcattttc ttatacgtga tcgcggaaat cggtataaca    240
```

```
ggtggcgctc ataggctatg ggcacatcgg acttataaag ccaagttgcc tttagagatt      300
ttgttactca taatgaattc tattgccttc caagacactg ctttcacctg gctcgagat       360
caccgccttc atcacaaata ttcggatact gacgctgatc cccacaatgc taccagaggg      420
tttttctatt cacatgtagg ctggcttttg gtgaagaaac accctgaagt caaagcaaga      480
ggaaaatact tgtcgttaga tgatcttaag aataatccat tgcttaaatt ccaaaagaaa      540
tacgctattc tagttatagg cacgttatgc ttccttatgc caacatttgt gcccgtatac      600
ttctggggcg agggcatcag cacggcctgg aacatcaatc tattgcgata cgtcatgaat      660
cttaacatga ctttcttagt taacagtgca gcgcatatct tggcaacaa accatacgat       720
aagagcatag cctcagtcca aatatttca gttagcttag ctactttgg cgaaggattc        780
cataattacc atcacactta cccctgggat tatcgtgcgg cagaattagg aaataatagg      840
ctaaatatga ctactgcttt catagatttc ttcgcttgga tcggctgggc ttatgacttg      900
aagtctgtgc cacaagaggc cattgcaaaa aggtgtgcga aaactggcga tggaacggat      960
atgtggggtc gaaaaagata a                                                981

<210> SEQ ID NO 18
<211> LENGTH: 1050
<212> TYPE: DNA
<213> ORGANISM: Trichoplusia ni

<400> SEQUENCE: 18
atggctgtga tggctcaaac agtacaagaa acggctacag tgttggaaga ggaagctcgc       60
acagtgactc ttgtggctcc aaagacaacg ccaaggaaat ataaatatat atacaccaac      120
tttcttacat tttcatatgc gcatttagct gcattatacg gactttattt gtgcttcacc      180
tctgcgaaat gggaaacatt gctattctct ttcgtactct tccacatgtc aaatataggc      240
atcaccgcag gggctcaccg actctggact cacaagactt tcaaagccaa attgcctttg      300
gaaattgtcc tcatgatatt caactcttta gcctttcaaa acacggctat tacatgggct      360
agagaacatc ggctacatca caaatacagc gatactgatg ctgatcccca caatgcgtca      420
agagggttct tctactcgca tgttggctgg ctattagtaa aaaaacatcc cgatgtctta      480
aaatatggaa aaactataga catgtcggat gtatacaata atcctgtgtt aaaatttcag      540
aaaaagtacg cagtacccct aattggaaca gtttgttttg ctcttccaac tttgattcca      600
gtctactgtt ggggcgaatc gtggaacaac gcttggcaca tagccttatt tcgatacata      660
ttcaatctta acgtgacttt cctagtcaac agtgctgcgc atatctgggg gaataagcct      720
tatgataaaa gcatcttgcc cgctcaaaac ttattagttt ccttcctagc aagtggagaa      780
ggcttccata attaccatca cgtctttcca tgggattacc gcacagcaga attagggaat      840
aacttcttaa atttgacgac gttattcatt gattttgtg cctggtttgg atgggcttat       900
gacttgaagt ctgtatcaga ggatattata aacagagag ctaaacgaac aggtgacggt       960
tcttcagggg tcatttgggg atgggacgac aaagacatgg accgcgatat aaaatctaaa     1020
gctaacattt tttatgctaa aaaggaatga                                      1050

<210> SEQ ID NO 19
<211> LENGTH: 1017
<212> TYPE: DNA
<213> ORGANISM: Helicoverpa zea

<400> SEQUENCE: 19
```

```
atggcccaaa gctatcaatc aactacggtt ttgagtgagg agaaagaact aacattacaa    60
catttggtgc cccaagcatc gcccaggaag tatcaaatag tgtatccgaa cctcattacg   120
tttggttact ggcacatagc cggactttat ggcctttact tgtgcttcac ttctgctaaa   180
tgggctacga ttttattcag ctacatcctc ttcgtgttag cagaaatagg aatcacggct   240
ggcgctcaca gactctgggc ccacaaaact tacaaagcga aactaccatt agaaatactc   300
ttaatggtat tcaactccat cgcttttcaa aactcagcca ttgactgggt gagggaccac   360
cgactccacc ataagtatag cgatacagat gctgatcccc acaatgccag ccgagggttc   420
ttttattccc atgtaggatg gctacttgtg agaaaacatc ctgaagtcaa aaagcgaggg   480
aaagaactca atatgtccga tatttacaac aatcctgtct tacggtttca gaaaaaatac   540
gccatacect tcattgggge tgtttgtttc gccttaccta caatgatacc tgtttacttc   600
tggggagaaa cctggtccaa tgcttggcat atcaccatgc ttcgctacat catgaacctc   660
aatgtcacct tttggtaaa cagcgctgct catatatggg aaacaagcc ttatgacgca    720
aaatattac ctgcacaaaa tgtagctgtg tcggtcgcca ctggtggaga aggtttccat    780
aattaccacc atgtcttccc ctgggattat cgagcagcgg aactcggtaa caatagcctc   840
aatttaacga ctaaattcat agattttattc gcagcaatcg gatgggcata tgatttaaag   900
acggtttcgg aggatatgat aaaacaaagg attaaacgca ctggagatgg aacggatctt   960
tggggacacg aacaaaactg tgatgaagtg tgggatgtaa aagataaatc aagttaa    1017

<210> SEQ ID NO 20
<211> LENGTH: 1068
<212> TYPE: DNA
<213> ORGANISM: Ostrinia furnacalis

<400> SEQUENCE: 20
atggctccta atattaagga cggagctgat ttgaacggag ttttatttga agatgacgct    60
agcaccccg attatgccct tgccacggcc ccagtccaga aagcagacaa ctatcccaga   120
aaactagtgt ggagaaacat catactcttt gcataccttc accttgccgc tgtgtatgga   180
gcataccta tcttatttc agcgaaatgg cagacagata ttttgccta cattctttac     240
gtgatctcag gactcggcat cacagcggga gcccaccgcc tttgggcgca caagtcatac   300
aaggctaagt ggccacttag actcattctt attatcttca acactgtatc attccaggac   360
tctgctctcg actggtcacg tgaccaccgc atgcaccaca atactcggga gaccgacgcc   420
gacccgcaca acgcgactcg agggttcttc ttctctcata tcggctggtt attagtccgc   480
aagcacccgg aattaaagag aaagggcaag ggattagact taagcgactt gtatgctgat   540
cccatcctcc gtttccagaa gaagtactat ttactattaa tgcctcttgg ctgcttcatc   600
atgccgacgg tggtccccggt gtacttctgg ggtgagactt ggactaacgc tttcttcgtc   660
gccgcgctct tccgatacac cttcatcctc aatgtcacct ggttggtcaa ctccgccgcg   720
cacaagtggg gccacaagcc ctatgacagc agcatcaagc cttccgagaa cctctcagtc   780
tccttattcg cgttgggcga aggattccac aactaccacc acacattccc ctgggactac   840
aaaactgccg agctcggcaa caacagactc aatttcacaa caaacttcat caacttcttc   900
gctaaaatcg gatgggctta cgacttgaaa acggtctccg acgagattat tcagaataga   960
gtcaagcgca caggagatgg ctcccaccac ttatggggtt gggcgacaa ggatcaacct   1020
aaagaggagg taaacgcagc cattagaatt aatcctaaag acgagtaa                1068
```

<210> SEQ ID NO 21
<211> LENGTH: 1059
<212> TYPE: DNA
<213> ORGANISM: Lampronia capitella

<400> SEQUENCE: 21

```
atgccgccga acgtgacaga ggcgaacgga gtgttatttg agaatgacgt gcagactcct     60
gacatggggc tagaagtggc ccctgtgcag aaggctgacg agcgtaagat ccagctcgtt    120
tggaggaaca tcatcgcttt tgcatgtctt catttagcag ctgtgtatgg agcttattta    180
ttcttcacct cggctatatg gcagacagac atatttgcat acatccttta cgttatgtct    240
ggattaggaa tcacggcggg agcgcacaga ttatgggctc ataagtcata caaggcgaag    300
tggccgttaa gattaatcct cgtcgcattc aacactttgg cattccagga ttcggcaatc    360
gactgggcgc gcgaccaccg catgcaccac aagtactcgg agacggatgc ggacccacat    420
aacgccactc gcggcttctt cttttcgcac attggttggt tactctgccg aaaacacccg    480
gagctaaagc gcaagggcca gggcctcgac ttaagtgacc tctacgcaga tcctattatt    540
cgcttccaaa agaagtacta cttattgtta atgccgttag cctgctttgt tcttcccacc    600
ataattccgg tctacctctg gggcgagtcc tggaaaaacg cgttcttcgt agctgcaatg    660
ttccgttaca cgttcatcct caacgtaaca tggctcgtca actccgccgc ccacaaatgg    720
ggaggcaagc cctatgataa gaacatccag cccgctcaga acatctctgt agctatcttc    780
gcattaggcg agggcttcca caactaccac cacacgttcc cctgggacta caagaccgct    840
gaattaggaa acaacaggtt aaatttcaca acttcgttta tcaatttctt cgcaagcttc    900
ggatgggcct acgacttaaa gaccgtgtcg gacgagatta tacaacagcg cgttaagagg    960
acgggagatg ggagccatca cttacggggc tggggcgacc aggacatacc ggccgaagaa   1020
gctcaagctg ctttacgcat taaccgtaaa gatgattag                          1059
```

<210> SEQ ID NO 22
<211> LENGTH: 1062
<212> TYPE: DNA
<213> ORGANISM: Helicoverpa zea

<400> SEQUENCE: 22

```
atggctccaa atatatcgga ggatgtgaac ggggtgctct tcgagagtga tgcagcgacg     60
ccggacttag cgttatccac gccgcctgtg cagaaggctg acaacaggcc caagcaatta    120
gtgtggagga acatactatt attcgcgtat cttcacttag cggctcttta cggaggttat    180
ttattcctct tctcagctaa atggcagaca gacatatttg cctacatctt atatgtgatc    240
tccgggcttg gtatcacggc tggagcacat cgcttatggg cccacaagtc ctacaaagct    300
aaatggcctc tccgagttat cttagtcatc tttaacacag tggcattcca ggatgccgct    360
atggactggg cgcgcgacca ccgcatgcat cacaagtact cggaaaccga tgctgatcct    420
cataatgcga cccgaggatt cttcttctct cacattggct ggttacttgt caggaaacat    480
cccgacctta aggagaaggg caagggactc gacatgagcg acttacttgc tgaccccatt    540
ctcaggttcc agaaaaaata ctacttaatc ttaatgccct tggcttgctt cgtgatgcct    600
accgtgattc ctgtgtactt ctggggtgaa acctggacca acgcattctt tgtggcggcc    660
atgttccgct acgcgttcat cctaaatgtg acgtggctcg tcaactctgc cgctcacaag    720
tggggagaca gccctacga caaaagcatt aagccttccg aaaacttgtc ggtcgccatg    780
ttcgctctcg gagaaggatt ccacaactac caccacactt tcccttggga ctacaaaact    840
```

```
gctgagttag gcaacaacaa actcaacttc actaccacct ttattaactt cttcgctaaa      900
attggctggg cttacgactt aaagacagtg tctgatgata tcgtcaagaa cagggtgaag      960
cgcactggtg acggctccca ccacttatgg ggctggggag acgaaaatca atccaaagaa     1020
gaaattgatg ccgctatcag aatcaatcct aaggacgatt aa                        1062
```

<210> SEQ ID NO 23
<211> LENGTH: 1434
<212> TYPE: DNA
<213> ORGANISM: Thalassiosira pseudonana

<400> SEQUENCE: 23

```
atggactttc tctccggcga tcctttccgg acactcgtcc ttgcagcact tgttgtcatc       60
ggatttgctg cggcgtggca atgcttctac ccgccgagca tcgtcggcaa gcctcgtaca      120
ttaagcaatg gtaaactcaa taccagaatc catggcaaat tgtacgacct ctcatcgttt      180
cagcatccag gaggcccgt ggctctttct cttgttcaag gtcgcgacgg aacagctcta      240
tttgagtcac accatccctt catacctcga aagaatctac ttcagatcct ctccaagtac      300
gaggttccgt cgactgaaga ctctgtttcc ttcatcgcca ccctagacga actcaatggt      360
gaatctccgt acgattggaa ggacattgaa atgatgatt cgtatctga cctacgagct       420 ctcgtaattg agcactttc tcctctcgcc aaggaaaggg gagtttcact cgttgagtcg      480
tcgaaggcaa caccctcagcg gtggatggtg gttctattac tccttgcgtc gttcttcctc     540
agcatcccat tatatttgag tggttcgtgg actttcgttg tcgtcactcc catcctcgct      600
tggttagcgg ttgtcaatta ctggcacgat gctactcact ttgcattgag cagcaactgg      660
attttgaatg ctgcgctccc atatctcctc cctctcctat cgagtccgtc aatgtggtat      720
catcatcacg tcattggaca tcacgcatac accaacattt ccaaaagaga tccagatctt      780
gctcacgctc cacaactcat gagagaacac aagagtatca atggagacc atctcactta      840 aatcaaacac agcttccgcg gattctcttc atctggtcga ttgcagtcgg tattgggttg      900
aacttattaa acgacgtgag agcactaacc aagctttcat acaacaacgt tgttcgggtg     960
gagaagatgt catcgtcgcg aacattactc catttccttg gacgtatgtt gcacatctt      1020 gtgactacac tttggcccctt tttggcgttt ccggtgtgga aggccatcgt ttgggcgact    1080
gtaccgaatg ccatattaag tttgtgcttc atgttaaata cgcaaatcaa tcacctcatc   1140
aacacgtgtg cacatgcttc cgataacaac ttttacaagc atcaagttgt aactgctcag    1200
aactttggcc gatcaagtgc ctttttgcttc atcttctcgg gaggtctcaa ctaccaaatt    1260
gaacatcatt tgttgccgac ggtgaaccat tgccatttgc cagctttggc cccgggtgta    1320
gagcgtttgt gtaagaaaca cgggggtgaca tacaactctg ttgaaggata cagagaggcc    1380
atcattgcac actttgcaca taccaaagat atgtcgacga agcctactga ttga          1434
```

<210> SEQ ID NO 24
<211> LENGTH: 1050
<212> TYPE: DNA
<213> ORGANISM: Trichoplusia ni

<400> SEQUENCE: 24

```
atggctgtga tggctcaaac agtacaagaa acggctacag tgttggaaga ggaagctcgc       60
acagtgactc ttgtggctcc aaagacaacg ccaaggaaat ataaatatat atacaccaac      120
tttcttacat tttcatatgc gcatttagct gcattatacg gactttattt gtgcttcacc      180
tctgcgaaat gggaaacatt gctattctct ttcgtactct tccacatgtc aaatataggc      240
```

```
atcaccgcag gggctcaccg actctggact cacaagactt tcaaagccaa attgcctttg      300
gaaattgtcc tcatgatatt caactcttta gcctttcaaa acacggctat tacatgggct      360
agagaacatc ggctacatca caaatacagc gatactgatg ctgatcccca caatgcgtca      420
agagggttct tctactcgca tgttggctgg ctattagtaa aaaaacatcc cgatgtcctg      480
aaatatggaa aaactataga catgtcggat gtatacaata tcctgtgtt aaaatttcag       540 aaaaagtacg cagtacccett aattggaaca gtttgttttg ctctgccaac tttgattcca     600
gtctactgtt ggggcgaatc gtggaacaac gcttggcaca tagccttatt tcgatacata     660
ttcaatctta acgtgacttt cctagtcaac agtgctgcgc atatctgggg gaataagcct     720
tatgataaaa gcatcttgcc cgctcaaaac ctgctggttt ccttcctagc aagtggagaa     780
ggcttccata attaccatca cgtctttcca tgggattacc gcacagcaga attagggaat     840
aacttcctga atttgacgac gctgttcatt gattttgtg cctggtttgg atgggcttat      900
gacttgaagt ctgtatcaga ggatattata aaacagagag ctaaacgaac aggtgacggt     960
tcttcagggg tcatttgggg atgggacgac aaagacatgg accgcgatat aaaatctaaa    1020
gctaacattt tttatgctaa aaaggaatga                                      1050

<210> SEQ ID NO 25
<211> LENGTH: 1017
<212> TYPE: DNA
<213> ORGANISM: Helicoverpa zea

<400> SEQUENCE: 25
atggcccaaa gctatcaatc aactacggtt ttgagtgagg agaaagaact aacactgcaa       60
catttggtgc cccaagcatc gcccaggaag tatcaaatag tgtatccgaa cctcattacg      120
tttggttact ggcacatagc cggactttat ggcctttact tgtgcttcac ttctgctaaa      180
tgggctacga ttttattcag ctacatcctc ttcgtgttag cagaaatagg aatcacggct      240
ggcgctcaca gactctgggc ccacaaaact tacaaagcga aactaccatt agaaatactc      300
ttaatggtat tcaactccat cgcttttcaa aactcagcca ttgactgggt gagggaccac      360
cgactccacc ataagtatag cgatacagat gctgatcccc acaatgccag ccgagggttc      420
ttttattccc atgtaggatg gctacttgtg agaaaacatc ctgaagtcaa aaagcgaggg      480
aaagaactca atatgtccga tatttacaac aatcctgtcc tgcggtttca gaaaaaatac      540 gccatacccct tcattggggc tgtttgtttc gccttaccta caatgatacc tgtttacttc      600
tggggagaaa cctggtccaa tgcttggcat atcaccatgc ttcgctacat catgaacctc      660
aatgtcacct ttttggtaaa cagcgctgct catatatggg aaacaagcc ttatgacgca      720 aaaatattac ctgcacaaaa tgtagctgtg tcggtcgcca ctggtggaga aggtttccat      780
aattaccacc atgtcttccc ctgggattat cgagcagcgg aactcggtaa caatagcctc      840
aatctgacga ctaaattcat agatttattc gcagcaatcg gatgggcata tgatctgaag     900
acggtttcgg aggatatgat aaaacaaagg attaaacgca ctggagatgg aacggatctt    960
tggggacacg aacaaaactg tgatgaagtg tgggatgtaa aagataaatc aagttaa      1017

<210> SEQ ID NO 26
<211> LENGTH: 1050
<212> TYPE: DNA
<213> ORGANISM: Artificial Sequence
<220> FEATURE:
<223> OTHER INFORMATION: Trichoplusia ni Z11 desaturase Homo sapiens
      optimized
```

<400> SEQUENCE: 26

```
atggccgtga tggcccagac cgtgcaggag accgcaacag tgctggagga ggaggcaagg      60
accgtgacac tggtggcacc caagaccaca cctagaaagt acaagtatat ctacaccaac     120
ttcctgacct tcagctacgc acacctggcc gccctgtatg actgtacct gtgctttacc     180
tccgccaagt gggagacact gctgttctct tttgtgctgt tccacatgag caatatcgga    240
atcaccgcag gagcacacag gctgtggacc cacaagacat tcaaggccaa gctgcctctg    300
gagatcgtgc tgatgatctt caactctctg gcctttcaga taccgccat cacatgggcc    360
cgggagcaca gactgcacca agtatagc gacaccgatg cagacccaca caacgcaagc    420
aggggcttct tttactccca cgtgggctgg ctgctggtga agaagcaccc cgacgtgctg   480
aagtatggca agacaatcga catgtccgac gtgtacaaca tcccgtgct gaagtttcag    540
aagaagtatg ccgtgcctct gatcggcacc gtgtgcttcg ccctgccaac actgatcccc   600
gtgtattgtt ggggcgagtc ttggaacaat gcctggcaca cgccctgtt ccggtacatc    660
tttaacctga atgtgacctt tctggtgaac tccgccgccc acatctgggg caataagcct   720
tacgacaagt ctatcctgcc agcccagaac ctgctggtgt ccttcctggc ctctggcgag   780
ggctttcaca attatcacca cgtgttccca tgggactaca ggaccgcaga gctgggcaac   840
aattttctga acctgaccac actgttcatc gattttttgtg cctggttcgg ctgggcctat   900
gacctgaagt ctgtgagcga ggatatcatc aagcagaggg caaagaggac aggcgatggc   960
agctccggcg tgatctgggg atgggacgat aaggatatgg acagagatat caagagcaag  1020
gccaatatct tctacgccaa gaaggagtga                                    1050
```

<210> SEQ ID NO 27
<211> LENGTH: 1017
<212> TYPE: DNA
<213> ORGANISM: Artificial Sequence
<220> FEATURE:
<223> OTHER INFORMATION: Helicoverpa zea Z11 desaturase Homo sapiens
      optimized

<400> SEQUENCE: 27

```
atggcacagt catatcagag cactaccgtc ctgagcgaag agaaggaact gacactgcag      60
cacctggtcc cacaggcatc acctagaaag taccagatcg tgtatccaaa cctgatcacc    120
ttcggctact ggcacatcgc cggcctgtac ggcctgtatc tgtgctttac ctccgccaag    180
tgggccacaa tcctgttctc ttacatcctg tttgtgctgg cagagatcgg aatcaccgca    240
ggagcacaca gactgtgggc acacaagaca tataaggcca agctgcccct ggagatcctg    300
ctgatggtgt tcaacagcat cgccttttcag aattccgcca tcgattgggt gcgggaccac    360
agactgcacc acaagtactc cgacaccgat gccgacccc acaacgcctc tagggggttc    420
tttttatagcc acgtgggatg gctgctggtg cggaagcacc ctgaggtgaa gaagagaggc    480
aaggagctga atatgtctga tatctacaac aatcctgtgc tgcgcttcca gaagaagtat    540
gccatcccat tcatcggcgc cgtgtgcttt gccctgccca ccatgatccc cgtgtacttt    600
tggggcgaga catggagcaa cgcctggcac atcacaatgc tgcggtatat catgaacctg    660
aatgtgacat tcctggtgaa ctccgccgcc cacatctggg gcaataagcc atacgacgcc    720
aagatcctgc ccgcccagaa cgtgccgtg agcgtggcaa ccggaggaga gggcttccac    780
aattaccacc acgtgtttcc ttgggattat cgggccgccg agctgggcaa caattctctg    840
aatctgacca caaagttcat cgacctgttt gccgccatcg gctgggccta tgatctgaag    900
```

```
acagtgagcg aggacatgat caagcagagg atcaagcgca ccggcgatgg cacagacctg    960
tgggggcacg agcagaactg tgatgaagtg tgggatgtga agacaagtc ctcctaa      1017
```

<210> SEQ ID NO 28
<211> LENGTH: 1065
<212> TYPE: DNA
<213> ORGANISM: Artificial Sequence
<220> FEATURE:
<223> OTHER INFORMATION: Yarrowia lipolytica OLE1 leader - Trichoplusia
      ni Z11 desaturase Homo sapiens optimized

<400> SEQUENCE: 28

```
atggtgaaga acgtggacca ggtggatctg tctcaggtgg acaccatcgc aagcggaagg     60
gatgtgaatt ataaggtgaa gtacacatct ggcgtgaaga ccacaccaag aaagtacaag    120
tatatctaca ccaacttcct gacatttttct tacgcccacc tggccgccct gtatggcctg   180
tacctgtgct ttaccagcgc caagtgggag acactgctgt ctcctttgt gctgttccac     240 atgtctaata tcggaatcac cgcaggagca cacaggctgg gaccacaa gacattcaag      300 gccaagctgc ccctggagat cgtgctgatg atcttcaact ccctggcctt tcagaatacc   360
gccatcacat gggcccggga gcacagactg caccacaagt attctgacac cgatgcagac   420
ccacacaacg caagcagggg cttctttttac tcccacgtgg gctggctgct ggtgaagaag   480
caccctgacg tgctgaagta tggcaagaca atcgacatga gcgacgtgta caacaatcct   540
gtgctgaagt ttcagaagaa gtatgccgtg ccactgatcg gcaccgtgtg cttcgccctg   600
cccacactga tccccgtgta ctgttggggc gagtcctgga caatgcctg gcacatcgcc   660 ctgttccggt acatctttaa cctgaatgtg acctttctgg tgaacagcgc cgcccacatc   720
tggggcaata agccatacga caagtccatc ctgcccgccc agaacctgct ggtgtccttc   780
ctggcctctg gcgagggctt tcacaattat caccacgtgt cccttggga ctacaggacc    840 gcagagctgg gcaacaattt tctgaacctg accacactgt tcatcgattt tgtgcctgg    900 ttcggctggg cctatgacct gaagtctgtg agcgaggata tcatcaagca gagggcaaag   960
aggacaggcg atggcagctc cggcgtgatc tggggatggg acgataagga tatggacaga  1020
gatatcaagt ccaaggccaa tatcttctac gccaagaagg agtga                  1065
```

<210> SEQ ID NO 29
<211> LENGTH: 1029
<212> TYPE: DNA
<213> ORGANISM: Artificial Sequence
<220> FEATURE:
<223> OTHER INFORMATION: Yarrowia lipolytica OLE1 leader - Helicoverpa
      zea Z11 desaturase Homo sapiens optimized

<400> SEQUENCE: 29

```
atggtgaaaa acgtggacca agtggatctc tcgcaggtcg acaccattgc ctccggccga    60
gatgtcaact acaaggtcaa gtacacctcc ggcgttcgca agtatcagat cgtgtatcct   120
aacctgatca ccttcggcta ctggcatatc gctggactgt acggactgta tctgtgcttc   180
acttccgcca gtgggccac catcctgttc tcttacatcc tgtttgtgct ggcagagatc   240
ggaatcaccg caggagcaca cagactgtgg gcacacaaga catataaggc caagctgcca  300
ctggagatcc tgctgatggt gttcaacagc atcgcctttc agaattccgc catcgattgg   360
gtgcgggacc acagactgca ccacaagtac tccgacacag atgccgaccc ccacaacgcc   420 tctagggggct tctttttatag ccacgtggga tggctgctgt gcggaagca ccctgaggtg   480
```

```
aagaagagag gcaaggagct gaatatgtct gatatctaca caatcctgt gctgcgcttc    540 cagaagaagt atgccatccc attcatcggc gccgtgtgct ttgccctgcc caccatgatc    600
cccgtgtact tttggggcga gacatggagc aacgcctggc acatcacaat gctgcggtat    660
atcatgaacc tgaatgtgac attcctggtg aactccgccg cccacatctg ggcaataag    720 ccatacgacg ccaagatcct gcccgcccag aacgtggccg tgagcgtggc aaccggagga    780
gagggcttcc acaattacca ccacgtgttt ccatgggatt ataggcagc agagctggga     840 aacaattctc tgaatctgac cacaaagttc atcgacctgt tgccgccat cggctgggcc     900 tatgatctga agacagtgag cgaggacatg atcaagcaga ggatcaagcg caccggcgat    960
ggcacagacc tgtgggggca cgagcagaat tgtgatgaag tgtgggatgt gaaggataaa   1020
agcagttga                                                           1029

<210> SEQ ID NO 30
<211> LENGTH: 981
<212> TYPE: DNA
<213> ORGANISM: Amyelois transitella

<400> SEQUENCE: 30
atggtcccta caagggttc cagtgacgtt ttgtctgaac attctgagcc ccagttcact     60
aaactcatag ctccacaagc agggccgagg aaatacaaga tagtgtatcg aaatttgctc    120
acattcggct attggcactt atcagctgtt tatgggctct acttgtgctt tacttgtgcg    180
aaatgggcta ccatcttatt tgcattttc ttatacgtga tcgcggaaat cggtataaca     240
ggtggcgctc ataggctatg ggcacatcgg acttataaag ccaagttgcc tttagagatt    300
ttgttactca taatgaattc tattgccttc aagacactg ctttcacctg gctcgagat     360 caccgccttc atcacaaata ttcggatact acgctgatc cccacaatgc taccagaggg    420
tttttctatt cacatgtagg ctggcttttg gtgaagaaac accctgaagt caaagcaaga    480
ggaaaatact tgtcgttaga tgatcttaag aataatccat tgcttaaatt ccaaaagaaa    540
tacgctattc tagttatag cacgttatgc ttccttatgc caacatttgt gcccgtatac     600
ttctggggcg aggcatcag cacggcctgg aacatcaatc tattgcgata cgtcatgaat    660
cttaacatga ctttcttagt taacagtgca gcgcatatct ttggcaacaa accatacgat    720
aagagcatag cctcagtcca aaatatttca gttagcttag ctactttgg cgaaggattc    780 cataattacc atcacactta cccctgggat tatcgtgcgg cagaattagg aaataatagg    840
ctaaatatga ctactgcttt catagatttc ttcgcttgga tcggctgggc ttatgacttg    900
aagtctgtgc cacaagaggc cattgcaaaa aggtgtgcga aaactggcga tggaacggat    960
atgtggggtc gaaaaagata a                                              981

<210> SEQ ID NO 31
<211> LENGTH: 1017
<212> TYPE: DNA
<213> ORGANISM: Artificial Sequence
<220> FEATURE:
<223> OTHER INFORMATION: pPV0228 - Z11 Helicoverpa zea desaturase

<400> SEQUENCE: 31
atggcccaaa gctatcaatc aactacggtt ttgagtgagg agaaagaact aacattacaa     60
catttggtgc cccaagcatc gcccaggaag tatcaaatag tgtatccgaa cctcattacg    120
tttggttact ggcacatagc cggactttat ggcctttact gtgcttcac ttctgctaaa     180 tgggctacga ttttattcag ctacatcctc ttcgtgttag cagaaatagg aatcacggct    240
```

```
ggcgctcaca gactctgggc ccacaaaact tacaaagcga aactaccatt agaaatactc    300
ttaatggtat tcaactccat cgcttttcaa aactcagcca ttgactgggt gagggaccac    360
cgactccacc ataagtatag cgatacagat gctgatcccc acaatgccag ccgagggttc    420
ttttattccc atgtaggatg gctacttgtg agaaaacatc ctgaagtcaa aaagcgaggg    480
aaagaactca atatgtccga tatttacaac aatcctgtct tacggtttca gaaaaaatac    540 gccatacccct tcattgggc tgtttgtttc gccttaccta caatgatacc tgtttacttc    600
tggggagaaa cctggtccaa tgcttggcat atcaccatgc ttcgctacat catgaacctc    660
aatgtcacct ttttggtaaa cagcgctgct catatatggg aaacaagcc ttatgacgca    720 aaaatattac ctgcacaaaa tgtagctgtg tcggtcgcca ctggtggaga aggtttccat    780
aattaccacc atgtcttccc ctgggattat cgagcagcgg aactcggtaa caatagcctc    840
aatttaacga ctaaattcat agatttattc gcagcaatcg gatgggcata tgatttaaag    900
acggtttcgg aggatatgat aaaacaaagg attaaacgca ctggagatgg aacggatctt    960
tggggacacg aacaaaactg tgatgaagtg tgggatgtaa agataaaatc aagttaa     1017

<210> SEQ ID NO 32
<211> LENGTH: 1368
<212> TYPE: DNA
<213> ORGANISM: Artificial Sequence
<220> FEATURE:
<223> OTHER INFORMATION: pPV0228 - Helicoverpa armigera reductase codon
      optimized

<400> SEQUENCE: 32
atggtcgttt taacttctaa agagacaaaa ccttcagtag ctgagtttta tgcgggaaaa     60
tctgttttta ttacgggtgg cactggattc cttggaaagg tattcataga gaaactttta    120
tatagctgtc cagatatcga gaatatctac atgctcatac gagagaagaa aggtcttttct    180 gttagcgaaa gaataaaaca gttccttgat gacccgctct ttaccagact aaaagacaaa    240
agaccagctg acttagagaa gattgtatta ataccaggag atattactgc tcctgactta    300
ggcattaatt ctgaaaacga gaagatgctt atagagaagg tatcggtgat tattcattcg    360
gctgctacgg tgaagtttaa tgagcctctc cctacggctt ggaagatcaa cgtggaagga    420
accgaaatga tgttagcttt gagtcgaaga atgaagcgga ttgaggtttt cattcacata    480
tcgacagcat acacgaacac aaacagggaa gtggttgacg agatcttata cccagctcct    540
gctgatatcg accaagttca tcagtatgtc aaagatggaa tctctgagga agacactgag    600
aaaatattaa atggtcgtcc aaatacgtac acgtttacga aagcgttaac tgagcattta    660
gttgctgaga accaagccta cgtacccact attatcgtca ggccgtcagt cgtggcagca    720
ataaaagatg agccattaaa aggttggtta ggcaactggt ttggagcgac tggtctcacc    780
gtgttcaccg ctaagggtct caaccgagtc atctacggtc attctagcta catcgtagac    840
ttaattcctg tggattatgt cgctaattta gtgattgctg ctggggctaa gagtagcaag    900
tcaactgagt tgaaggtata caactgctgc agcagctcct gcaatcccgt cactattggc    960
acgttaatga gcatgtttgc tgacgatgcc atcaaacaga gtcgtatgc tatgccgcta   1020 ccggggtggt acatattcac gaaatataag tggttagttc ttcttttaac atttctcttc   1080
caagttatac cggcgtatgt cacagatctc tccaggcact tgattgggaa gagtccaccgg  1140 tacataaaac tccaatcact agtaaatcaa acgcgctctt caatcgactt cttcacgaat   1200
cactcctggg tgatgaaggc agacagagtg agagagttat atgcgtctct tccccccgca   1260
```

```
gacaagtact tatttccctg tgatcctacg gacattaact ggacacatta catacaagac    1320
tactgttggg gagtccgaca ttttttggag aaaaaaagct acgaataa                 1368

<210> SEQ ID NO 33
<211> LENGTH: 1478
<212> TYPE: DNA
<213> ORGANISM: Artificial Sequence
<220> FEATURE:
<223> OTHER INFORMATION: pPV0228 - ICL promoter

<400> SEQUENCE: 33
tattaggcga agaggcatct agtagtagtg gcagtggtga gaacgtgggc gctgctatag      60
tgaacaatct ccagtcgatg gttaagaaga agagtgacaa accagcagtg aatgacttgt     120
ctgggtccgt gaggaaaaga aagaagcccg acacaaagga cagtaacgtc aagaaaccca     180
agaaataggg gggacctgtt tagatgtata ggaataaaaa ctccgagatg atctcaatgt     240
gtaatggagt tgtaatattg caaagggggga aaatcaagac tcaaacgtgt gtatgagtga    300
gcgtacgtat atctccgaga gtagtatgac ataatgatga ctgtgaatca tcgtaatctc     360
acacaaaaac cccattgtcg gccatatacc acaccaagca acaccacata tcccccggaa     420
aaaaaaacgt gaaaaaaaga aacaatcaaa actacaacct actccttgat cacacagtca     480
ttgatcaagt tacagttcct gctagggaat gaccaaggta caaatcagca ccttaatggt     540
tagcacgctc tcttactctc tctcacagtc ttccggcccc tattcaaaat tctgcacttc     600
catttgaccc cagggttggg aaacagggcc acaaagaaa acccgacgt gaatgaaaaa      660 actaagaaaa gaaaaaaaat tatcacacca gaaatttacc taattgggta attcccatcg     720
gtgtttttcc tggattgtcg cacgcacgca tgctgaaaaa agtgttcgag ttttgctttt     780
gcctcggagt ttcacgcaag ttttttcgatc tcggaaccgg agggcggtcg ccttgttgtt    840
tgtgatgtcg tgctttgggt gttctaatgt gctgttattg tgctcttttt ttttcttctt     900
tttttggtga tcatatgata ttgctcggta gattactttc gtgtgtaggt attcttttag     960
acgtttggtt attgggtaga tatgagagag agagagtggg tggggagga gttggttgta    1020 ggagggaccc ctgggaggaa gtgtagttga gttttccctg acgaatgaaa atacgttttt    1080
gagaagataa tacaggaaag gtgtgtcggt gaatttccat ctatccgagg atatgagtgg    1140
aggagagtcg tgtgcgtgtg gttaattag gatcagtgga acacacaaag taactaagac    1200
agagagacag agagaaaaat ctggggaaga gacaaagagt cagagtgtgt gagttattct    1260
gtattgtgaa atttttttgc ccaactacat aatattgctg aaactaattt tacttaaaaa    1320
gaaaagccaa caacgtcccc agtaaaactt ttctataaat atcagcagtt ttcccttttcc   1380 tccattcctc ttcttgtctt ttttcttact ttcccttttt ataccttttt cattatcatc    1440
ctttataatt gtctaaccaa caactatata tctatcaa                            1478

<210> SEQ ID NO 34
<211> LENGTH: 586
<212> TYPE: DNA
<213> ORGANISM: Artificial Sequence
<220> FEATURE:
<223> OTHER INFORMATION: pPV0228 - TEF Candida tropicalis promoter
      region

<400> SEQUENCE: 34
aggaagacaa ccaaaagaaa gatcaaattg actaaatgtt gaacagacca aaaaaaaga      60 acaacaaata gataaattac aacatattaa tcttttgata tgttgttgaa tattctagta    120
```

```
aatctaatga tctcaatagt ggttatcatt cactctcttc gtcctcctct ctcccctcct      180
cctcttgcag tatattaaaa gcaataaaaa aaaaaaaaa aagaaaatct gccaacacac      240
acaaaaaaaa cttacatagt cgtgtaccag tgtcaatatt tcaccagcgc agagaaaaga     300
agatgaacag aaaaattttc tctttggttt tgtctttggt tttgtattaa tctcattgaa     360
aaattttttc tctctctctc tctctctctc tcactcacac actcactcgc atttcgtttg     420
ggttacagca gaagtcagac agaaaaaaaa aatcgtatat aactctcatc aaatgccta     480 gagaaaaatt tttcttctat cctttttttt ttcttcttct tcttcttttc cttttttctt    540
ttagaagatc tttttgaatt catcaaagat atatatttaa tcaatc                    586

<210> SEQ ID NO 35
<211> LENGTH: 297
<212> TYPE: DNA
<213> ORGANISM: Artificial Sequence
<220> FEATURE:
<223> OTHER INFORMATION: pPV0228 - ICL terminator

<400> SEQUENCE: 35
aagaaaaaag aaaaggtaaa gaacttcatt tgagatgaac ttttgtatat gactttagt      60 ttctacttt tttttattt attgcttaat tttctttatt tcaatccccc atagtttgtg      120
tagaatatat ttattcattc tggtaactca aacacgtagc aagctcgttg catctcgcct    180
cgtcacgggt acagctctgg aaccaaagac aaaaaaaaa gttgatccga accctctcgc     240
tattccttgc tatgctatcc acgagatggg gtttatcagc ccaggcaagt cactaaa       297

<210> SEQ ID NO 36
<211> LENGTH: 217
<212> TYPE: DNA
<213> ORGANISM: Artificial Sequence
<220> FEATURE:
<223> OTHER INFORMATION: pPV0228 - TEF terminator

<400> SEQUENCE: 36
gctgattaat gaataattaa taagtattgt ttttttgtt tttaatatat atatatcttg      60
aaattagtat aaaaaaaatc tttttttttt cttttttatt tattttatca atagtttata   120
tatatatata tataaacttg taagagatta ggtatatcta acagtgatac tactaatagt    180
gcttaatatc tttgttaaac aagaaaataa aataaac                             217

<210> SEQ ID NO 37
<211> LENGTH: 2487
<212> TYPE: DNA
<213> ORGANISM: artificial sequence
<220> FEATURE:
<223> OTHER INFORMATION: SapI-tLIP2-pEXP1-HA_FAR-SapI (insert into
      pPV199 creating pPV247)

<400> SEQUENCE: 37
gcctgaagag cgctatttat cactctttac aacttctacc tcaactatct actttaataa     60
atgaatatcg tttattctct atgattactg tatatgcgtt cctccatggg agtttggcgc    120 ccgtttttc gagccccaca cgtttcggtg agtatgagcg gcggcagatt cgagcgtttc     180
cggtttccgc ggctggacga gagcccatga tgggggctcc caccaccagc aatcagggcc    240
ctgattacac acccacctgt aatgtcatgc tgttcatcgt ggttaatgct gctgtgtgct    300
gtgtgtgtgt gttgtttggc gctcattgtt gcgttatgca gcgtacacca caatattgga   360
agcttattag cctttctatt ttttcgtttg caaggcttaa caacattgct gtggagaggg    420
```

```
atgggatat ggaggccgct ggagggagtc ggagaggcgt tttggagcgg cttggcctgg    480
cgcccagctc gcgaaacgca cctaggaccc tttggcacgc cgaaatgtgc cacttttcag    540
tctagtaacg ccttacctac gtcattccat gcatgcatgt ttgcgccttt tttcccttgc    600
ccttgatcgc cacacagtac agtgcactgt acagtggagg ttttgggggg gtcttagatg    660
ggagctaaaa gcggcctagc ggtacactag tgggattgta tggagtggca tggagcctag    720
gtggagcctg acaggacgca cgaccggcta gcccgtgaca gacgatgggt ggctcctgtt    780
gtccaccgcg tacaaatgtt tgggccaaag tcttgtcagc cttgcttgcg aacctaattc    840
ccaattttgt cacttcgcac ccccattgat cgagccctaa cccctgccca tcaggcaatc    900
caattaagct cgcattgtct gccttgttta gtttggctcc tgcccgtttc ggcgtccact    960
tgcacaaaca caaacaagca ttatatataa ggctcgtctc tccctcccaa ccacactcac   1020
tttttttgccc gtcttccctt gctaacacaa aagtcaagaa cacaaacaac caccccaacc   1080
cccttacaca caagacatat ctacagcaat ggtggtgctg accagcaagg agacaaagcc   1140
ttccgtggcc gagttctacg ccggcaagtc cgtgtttatc acaggcggca ccggcttcct   1200
gggcaaggtg tttatcgaga agctgctgta ctcttgccca gacatcgaga acatctatat   1260
gctgatccgg gagaagaagg gcctgagcgt gtccgagaga atcaagcagt cctggacga   1320
tccccctgttt acacggctga aggacaagag acctgccgat ctggagaaga tcgtgctgat   1380
cccaggcgac atcaccgcac cagatctggg catcaactcc gagaatgaga agatgctgat   1440
cgagaaggtc tccgtgatca tccactctgc cgccaccgtg aagttcaacg agcccctgcc   1500
tacagcctgg aagatcaatg tggagggcac caggatgatg ctggccctga gccggagaat   1560
gaagcgcatc gaggtgttta tccacatctc cacagcctac accaacacaa atcgggaggt   1620
ggtggacgag atcctgtacc cagcccccgc cgacatcgat caggtgcacc agtatgtgaa   1680
ggacggcatc agcgaggagg ataccgagaa gatcctgaac ggccggccaa ataccctacac   1740
attcaccaag gccctgacag agcacctggt ggccgagaac caggcctatg tgcctaccat   1800
catcgtgaga ccatccgtgg tggccgccat caaggatgag cccctgaagg gatggctggg   1860
aaactggttc ggagcaacag gactgaccgt gtttacagcc aagggcctga atagagtgat   1920
ctacggccac agctcctata tcgtggacct gatccccgtg gattacgtgg caaacctggt   1980
catcgcagca ggagccaagt ctagcaagtc taccgagctg aaggtgtata actgctgttc   2040
ctctagctgt aatcctgtga ccatcggcac actgatgtcc atgttcgccg acgatgccat   2100
caagcagaag tcttacgcca tgcctctgcc aggctggtac atctttacaa agtataagtg   2160
gctggtgctg ctgctgacct tcctgtttca ggtcatccca gcctacgtga ccgatctgtc   2220
taggcacctg atcggcaaga gccccgcta tatcaagctg cagtctctgg tgaaccagac   2280
caggtcctct atcgacttct ttacaaatca cagctgggtc atgaaggccg ataggtgcg   2340
cgagctgtac gcctctctga gccctgccga caagtatctg ttcccctgcg accctaccga   2400
tatcaattgg acacactaca tccaggatta ttgttggggc gtgcgccact tcctggagaa   2460
gaagtcctat gagtgagcct gaagagc                                        2487
```

<210> SEQ ID NO 38
<211> LENGTH: 1012
<212> TYPE: DNA
<213> ORGANISM: artificial sequence
<220> FEATURE:
<223> OTHER INFORMATION: NcoI-pTAL-AleI (insert into pPV247 creating pPV248)

```
<400> SEQUENCE: 38
ccatgggtaa gcaggtggct ccgtttgtgt ctttgtgttt ttccoctcct ttttggacca      60 tttgtcagca tgttgcgtag gtctgggtgt ttgactgttc aggtggtgga tgacggatgc     120
atcatctgac ggcagagtgg gtacctggca gtggcaggct cgcagacgag gtagagagat     180
tctgaaagga gccattgaca gatggagaat tggatactcc tggtatgtcc tccgtttcca     240
cttttgacgt tggtgacgtg ctctggaacg actttttct ttttctttaa aacaaaaaaa      300
agaaagaaaa aaaaaacatt tactactacc agtagtacac ctcaacattg ggtccagaac     360
gtcccaactg catgagtcac tggagtcatg ccgaggtcgc taaggtgctg taaaatacaa     420
cgtcaattga gagagacaca ggcgcagcgc gccgagggag aaacgaggca tttatcttct     480
gaccctcctt tttactcgta atctgtatcc cggaaccgcg tcgcatccat gttaattaaa     540
tcaacactta cacttgcttg cttcgtatga tgaagatttc tgactggcaa cccagtcagc     600
agcagattgg ggcagatgta gtaatgaaaa acactgcaag gtgtgacgtt tgagacactc     660
caattggtta gaaagcgaca aagaagacgt cggaaaaata ccggaaaaat cgagtctttt     720
tctttctgcg tattgggccc ttctgcctcc tttgccgccc tttccacgct ctttccacac     780
cctcacactc cctgagcact atgatctcat tgcgcaataa gatatacatg cacgtgcatt     840
tggtgagcac gcagaaccttt gttggggaaa gatgccctaa ccctaagggc gttccatacg     900
gttcgacaga gtaaccttgc tgtcgattat aacgcatata tagccccccc cttcggaccc     960
tccttctgat ttctgtttct gtatcaacat tacacacaaa cacacaatgg tg             1012
```

MICROORGANISMS FOR THE PRODUCTION OF INSECT PHEROMONES AND RELATED COMPOUNDS

CROSS-REFERENCE TO RELATED APPLICATIONS

This application is a Continuation U.S. Utility Application under 35 U.S.C. § 111(a), which claims the benefit of priority to International Application No. PCT/US2016/062852, filed on Nov. 18, 2016, which claims a priority benefit to U.S. Provisional Application Ser. No. 62/257,054, filed Nov. 18, 2015, and claims a priority benefit to U.S. Provisional Application Ser. No. 62/351,605, filed Jun. 17, 2016; each of the aforementioned applications is herein expressly incorporated by reference.

STATEMENT REGARDING THE SEQUENCE LISTING

The Sequence Listing associated with this application is provided in text format in lieu of a paper copy, and is hereby incorporated by reference into the specification. The name of the text file containing the Sequence Listing is PRVI_007_02WO_SeqList_ST25.txt. The text file is about 54 KB, was created on Nov. 15, 2016, and is being submitted electronically via EFS-Web.

TECHNICAL FIELD

This application relates to recombinant microorganisms useful in the biosynthesis of unsaturated $C_6$-$C_{24}$ fatty alcohols, aldehydes, and acetates which may be useful as insect pheromones, fragrances, flavors, and polymer intermediates. The application further relates to methods of producing unsaturated $C_6$-$C_{24}$ fatty alcohols, aldehydes, and acetates using the recombinant microorganisms, as well as compositions comprising one or more of these compounds and/or the recombinant microorganisms.

BACKGROUND

As the global demand for food grows, there is an increasing need for effective pest control. Conventional insecticides are among the most popular chemical control agents because they are readily available, rapid acting, and highly reliable. However, the overuse, misuse, and abuse of these chemicals have led to resistant pests, alteration of the natural ecology, and in some cases, environmental damage.

The use of insect pheromones to control pest populations has gained increasing popularity as a viable, safe, and environmentally-friendly alternative to conventional insecticides. Since their discovery in the late 1950s, these molecules have shown efficacy in reducing insect populations through a variety of methods, including mass trappings, attract and kill, and mating disruption. The latter method in particular represents a non-toxic means of pest control and utilizes the ability of synthetic pheromones to mask naturally occurring pheromones, thereby causing confusion and mating disruption.

Although pheromones have significant potential in agricultural insect control, the cost of synthesizing pheromones using currently available techniques is very high, which prohibits widespread use of this sustainable technology beyond high-value crops. Thus, there is an existing need to develop novel technologies for the cost-efficient production of insect pheromones and related fragrances, flavors, and polymer intermediates. The present inventors address this need with the development of recombinant microorganisms capable of producing a wide-range of unsaturated $C_6$-$C_{24}$ fatty alcohols, aldehydes, and acetates including synthetic insect pheromones from low-cost feedstocks.

SUMMARY OF THE DISCLOSURE

The present application relates to recombinant microorganisms having a biosynthesis pathway for the production of one or more compounds selected from unsaturated $C_6$-$C_{24}$ fatty alcohols, aldehydes, and acetates. The recombinant microorganisms described herein may be used for the production of at least one compound, such as an insect pheromone, a fragrance, or a flavoring agent, selected from unsaturated $C_6$-$C_{24}$ fatty alcohols, aldehydes, and acetates.

In one embodiment, the recombinant microorganism comprises a biosynthesis pathway for the production of an unsaturated $C_6$-$C_{24}$ fatty alcohol. Accordingly, in a first aspect, the application relates to a recombinant microorganism capable of producing an unsaturated $C_6$-$C_{24}$ fatty alcohol from an endogenous or exogenous source of saturated $C_6$-$C_{24}$ fatty acyl-CoA, wherein the recombinant microorganism expresses (a): at least one exogenous nucleic acid molecule encoding a fatty-acyl desaturase that catalyzes the conversion of a saturated $C_6$-$C_{24}$ fatty acyl-CoA to a corresponding mono- or poly-unsaturated $C_6$-$C_{24}$ fatty acyl-CoA; and (b): at least one exogenous nucleic acid molecule encoding a fatty alcohol forming fatty-acyl reductase that catalyzes the conversion of the mono- or poly-unsaturated $C_6$-$C_{24}$ fatty acyl-CoA from (a) into the corresponding mono- or poly-unsaturated $C_6$-$C_{24}$ fatty alcohol. In some embodiments, the mono- or poly-unsaturated $C_6$-$C_{24}$ fatty alcohol is an insect pheromone. In some embodiments, the mono- or poly-unsaturated $C_6$-$C_{24}$ fatty alcohol is a fragrance or flavoring agent. In some embodiments, the recombinant microorganism further comprises at least one endogenous or exogenous nucleic acid molecule encoding an alcohol oxidase or an alcohol dehydrogenase, wherein the alcohol oxidase or alcohol dehydrogenase is capable of catalyzing the conversion of the mono- or poly-unsaturated $C_6$-$C_{24}$ fatty alcohol from (b) into a corresponding mono- or poly-unsaturated $C_6$-$C_{24}$ fatty aldehyde. In some embodiments, the recombinant microorganism further comprises at least one endogenous or exogenous nucleic acid molecule encoding an acetyl transferase capable of catalyzing the conversion of the mono- or poly-unsaturated $C_6$-$C_{24}$ fatty alcohol from (b) into a corresponding mono- or poly-unsaturated $C_6$-$C_{24}$ fatty acetate.

In some embodiments, the fatty-acyl desaturase is a desaturase capable of utilizing a fatty acyl-CoA as a substrate that has a chain length of 6, 7, 8, 9, 10, 11, 12, 13, 14, 15, 16, 17, 18, 19, 20, 21, 22, 23, or 24 carbon atoms.

In some embodiments, the fatty-acyl desaturase is capable of generating a double bond at position C5, C6, C7, C8, C9, C10, C11, C12, or C13 in the fatty acid or its derivatives, such as, for example, fatty acid CoA esters.

In one exemplary embodiment, the fatty-acyl desaturase is a Z11 desaturase. In various embodiments described herein, the Z11 desaturase, or the nucleic acid sequence that encodes it, can be isolated from organisms of the species *Agrotis segetum, Amyelois transitella, Argyrotaenia velutiana, Choristoneura rosaceana, Lampronia capitella, Trichoplusia ni, Helicoverpa zea,* or *Thalassiosira pseudonana*. Further Z11-desaturases, or the nucleic acid sequences encoding them, can be isolated from *Bombyx mori, Manduca sexta, Diatraea grandiosella, Earias insulana, Earias* vittella, *Plutella xylostella*, *Bombyx mori* or *Diaphania nitidalis*. In exemplary embodiments, the Z11 desaturase comprises a sequence selected from GenBank Accession Nos. JX679209, JX964774, AF416738, AF545481, EU152335, AAD03775, AAF81787, and AY493438. In some embodiments, a nucleic acid sequence encoding a Z11 desaturase from organisms of the species *Agrotis segetum*, *Amyelois transitella*, *Argyrotaenia velutiana*, *Choristoneura rosaceana*, *Lampronia capitella*, *Trichoplusia ni*, *Helicoverpa zea*, or *Thalassiosira pseudonana* is codon optimized. In some embodiments, the Z11 desaturase comprises a sequence selected from SEQ ID NOs: 9, 18, 24 and 26 from *Trichoplusia ni*. In other embodiments, the Z11 desaturase comprises a sequence selected from SEQ ID NOs: 10 and 16 from *Agrotis segetum*. In some embodiments, the Z11 desaturase comprises a sequence selected from SEQ ID NOs: 11 and 23 from *Thalassiosira pseudonana*. In certain embodiments, the Z11 desaturase comprises a sequence selected from SEQ ID NOs: 12, 17 and 30 from *Amyelois transitella*. In further embodiments, the Z11 desaturase comprises a sequence selected from SEQ ID NOs: 13, 19, 25, 27 and 31 from *Helicoverpa zea*. In some embodiments, the Z11 desaturase comprises a chimeric polypeptide. In some embodiments, a complete or partial Z11 desaturase is fused to another polypeptide. In certain embodiments, the N-terminal native leader sequence of a Z11 desaturase is replaced by an oleosin leader sequence from another species. In certain embodiments, the Z11 desaturase comprises a sequence selected from SEQ ID NOs: 15, 28 and 29.

In certain embodiments, the Z11 desaturase catalyzes the conversion of a fatty acyl-CoA into a mono- or polyunsaturated product selected from Z11-13:Acyl-CoA, E11-13:Acyl-CoA, (Z,Z)-7,11-13:Acyl-CoA, Z11-14:Acyl-CoA, E11-14:Acyl-CoA, (E,E)-9,11-14:Acyl-CoA, (E,Z)-9,11-14:Acyl-CoA, (Z,E)-9,11-14:Acyl-CoA, (Z,Z)-9,11-14:Acyl-CoA, (E,Z)-9,11-15:Acyl-CoA, (Z,Z)-9,11-15:Acyl-CoA, Z11-16:Acyl-CoA, E11-16:Acyl-CoA, (E,Z)-6,11-16:Acyl-CoA, (E,Z)-7,11-16:Acyl-CoA, (E,Z)-8,11-16:Acyl-CoA, (E,E)-9,11-16:Acyl-CoA, (E,Z)-9,11-16:Acyl-CoA, (Z,E)-9,11-16:Acyl-CoA, (Z,Z)-9,11-16:Acyl-CoA, (E,E)-11,13-16:Acyl-CoA, (E,Z)-11,13-16:Acyl-CoA, (Z,E)-11,13-16:Acyl-CoA, (Z,Z)-11,13-16:Acyl-CoA, (Z,E)-11,14-16:Acyl-CoA, (E,E,Z)-4,6,11-16:Acyl-CoA, (Z,Z,E)-7,11,13-16:Acyl-CoA, (E,E,Z,Z)-4,6,11,13-16:Acyl-CoA, Z11-17:Acyl-CoA, (Z,Z)-8,11-17:Acyl-CoA, Z11-18:Acyl-CoA, E11-18:Acyl-CoA, (Z,Z)-11,13-18:Acyl-CoA, (E,E)-11,14-18:Acyl-CoA, or combinations thereof.

In another exemplary embodiment, the fatty-acyl desaturase is a Z9 desaturase. In various embodiments described herein, the Z9 desaturase, or the nucleic acid sequence that encodes it, can be isolated from organisms of the species *Ostrinia furnacalis*. *Ostrinia nobilalis*, *Choristoneura rosaceana*, *Lampronia capitella*, *Helicoverpa assulta*, or *Helicoverpa zea*. In exemplary embodiments, the Z9 desaturase comprises a sequence selected from GenBank Accession Nos. AY057862, AF243047, AF518017, EU152332, AF482906, and AAF81788. In some embodiments, a nucleic acid sequence encoding a Z9 desaturase is codon optimized. In some embodiments, the Z9 desaturase comprises a sequence set forth in SEQ ID NO: 20 from *Ostrinia furnacalis*. In other embodiments, the Z9 desaturase comprises a sequence set forth in SEQ ID NO: 21 from *Lampronia capitella*. In some embodiments, the Z9 desaturase comprises a sequence set forth in SEQ ID NO: 22 from *Helicoverpa zea*.

In certain embodiments, the Z9 desaturase catalyzes the conversion of a fatty acyl-CoA into a monounsaturated or polyunsaturated product selected from Z9-11:Acyl-CoA, Z9-12:Acyl-CoA, E9-12:Acyl-CoA, (E,E)-7,9-12:Acyl-CoA, (E,Z)-7,9-12:Acyl-CoA, (Z,E)-7,9-12:Acyl-CoA, (Z,Z)-7,9-12:Acyl-CoA, Z9-13:Acyl-CoA, E9-13:Acyl-CoA, (E,Z)-5,9-13:Acyl-CoA, (Z,E)-5,9-13:Acyl-CoA, (Z,Z)-5,9-13:Acyl-CoA, Z9-14:Acyl-CoA, E9-14:Acyl-CoA, (E,Z)-4,9-14:Acyl-CoA, (E,E)-9,11-14:Acyl-CoA, (E,Z)-9,11-14:Acyl-CoA, (Z,E)-9,11-14:Acyl-CoA, (Z,Z)-9,11-14:Acyl-CoA, (E,E)-9,12-14:Acyl-CoA, (Z,E)-9,12-14:Acyl-CoA, (Z,Z)-9,12-14:Acyl-CoA, Z9-15:Acyl-CoA, E9-15:Acyl-CoA, (Z,Z)-6,9-15:Acyl-CoA, Z9-16:Acyl-CoA, E9-16:Acyl-CoA, (E,E)-9,11-16:Acyl-CoA, (E,Z)-9,11-16:Acyl-CoA, (Z,E)-9,11-16:Acyl-CoA, (Z,Z)-9,11-16:Acyl-CoA, Z9-17:Acyl-CoA, E9-18:Acyl-CoA, Z9-18:Acyl-CoA, (E,E)-5,9-18:Acyl-CoA, (E,E)-9,12-18:Acyl-CoA, (Z,Z)-9,12-18:Acyl-CoA, (Z,Z,Z)-3,6,9-18:Acyl-CoA, (E,E,E)-9,12,15-18:Acyl-CoA, (Z,Z,Z)-9,12,15-18:Acyl-CoA, or combinations thereof.

In some embodiments, the recombinant microorganism may express a bifunctional desaturase capable of catalyzing the subsequent desaturation of two double bonds.

In some embodiments, the recombinant microorganism may express more than one exogenous nucleic acid molecule encoding a fatty-acyl desaturase that catalyzes the conversion of a saturated $C_6$-$C_{24}$ fatty acyl-CoA to a corresponding mono- or poly-unsaturated $C_6$-$C_{24}$ fatty acyl-CoA. For instance, the recombinant microorganism may express an exogenous nucleic acid molecule encoding a Z11 desaturase and another exogenous nucleic acid molecule encoding a Z9 desaturase.

In some embodiments, the recombinant microorganism may express a fatty-acyl conjugase that acts independently or together with a fatty-acyl desaturase to catalyze the conversion of a saturated or monounsaturated fatty acyl-CoA to a conjugated polyunsaturated fatty acyl-CoA.

In one embodiment, the disclosure provides a recombinant microorganism capable of producing a polyunsaturated $C_6$-$C_{24}$ fatty alcohol from an endogenous or exogenous source of saturated or monounsaturated $C_6$-$C_{24}$ fatty acyl-CoA, wherein the recombinant microorganism expresses: (a) at least one exogenous nucleic acid molecule encoding a fatty acyl conjugase that catalyzes the conversion of a saturated or monounsaturated $C_6$-$C_{24}$ fatty acyl-CoA to a corresponding polyunsaturated $C_6$-$C_{24}$ fatty acyl-CoA; and (b) at least one exogenous nucleic acid molecule encoding a fatty alcohol forming fatty-acyl reductase that catalyzes the conversion of the polyunsaturated $C_6$-$C_{24}$ fatty acyl-CoA from (a) into the corresponding polyunsaturated $C_6$-$C_{24}$ fatty alcohol.

In another embodiment, the recombinant microorganism expresses at least two exogenous nucleic acid molecules encoding fatty-acyl conjugases that catalyze the conversion of a saturated or monounsaturated $C_6$-$C_{24}$ fatty acyl-CoA to a corresponding polyunsaturated $C_6$-$C_{24}$ fatty acyl-CoA.

In a further embodiment, the disclosure provides a recombinant microorganism capable of producing a polyunsaturated $C_6$-$C_{24}$ fatty alcohol from an endogenous or exogenous source of saturated or monounsaturated $C_6$-$C_{24}$ fatty acyl-CoA, wherein the recombinant microorganism expresses: (a) at least one exogenous nucleic acid molecule encoding a fatty-acyl desaturase and at least one exogenous nucleic acid molecule encoding a fatty acyl conjugase that catalyze the conversion of a saturated or monounsaturated $C_6$-$C_{24}$ fatty acyl-CoA to a corresponding polyunsaturated $C_6$-$C_{24}$ fatty acyl-CoA; and (b) at least one exogenous nucleic acid molecule encoding a fatty alcohol forming fatty-acyl reductase that catalyzes the conversion of the polyunsaturated $C_6$-$C_{24}$ fatty acyl-CoA from (a) into the corresponding polyunsaturated $C_6$-$C_{24}$ fatty alcohol.

In another embodiment, the recombinant microorganism expresses at least two exogenous nucleic acid molecules encoding fatty-acyl desaturases and at least two exogenous nucleic acid molecules encoding fatty-acyl conjugases that catalyze the conversion of a saturated or monounsaturated $C_6$-$C_{24}$ fatty acyl-CoA to a corresponding polyunsaturated $C_6$-$C_{24}$ fatty acyl-CoA.

In yet a further embodiment, the fatty-acyl conjugase is a conjugase capable of utilizing a fatty acyl-CoA as a substrate that has a chain length of 6, 7, 8, 9, 10, 11, 12, 13, 14, 15, 16, 17, 18, 19, 20, 21, 22, 23, or 24 carbon atoms.

In certain embodiments, the conjugase, or the nucleic acid sequence that encodes it, can be isolated from organisms of the species *Cydiapomonella, Cydia nigricana, Lobesia botrana, Myelois cribrella, Plodia interpunctella, Dendrolimus punctatus, Lampronia capitella, Spodoptera litura, Amyelois transitella, Manduca sexta, Bombyx mori, Calendula officinalis, Trichosanthes kirilowii, Punica granatum, Momordica charantia, Impatiens balsamina,* and *Epiphyas postvittana*. In exemplary embodiments, the conjugase comprises a sequence selected from GenBank Accession No. or Uniprot database: A0A059TBF5, A0A0M3L9E8, A0A0M3L9S4, A0A0M3LAH8, A0A0M3LAS8, A0A0M3LAH8, B6CBS4, XP_013183656.1, XP_004923568.2, ALA65425.1, NP_001296494.1, NP_001274330.1, Q4A181, Q75PL7, Q9FPP8, AY178444, AY178446, AF182521, AF182520, Q95UJ3.

In various embodiments described herein, the fatty alcohol forming acyl-CoA reductase, i.e., fatty alcohol forming fatty-acyl reductase, or the nucleic acid sequence that encodes it, can be isolated from organisms of the species *Agrotis segetum, Spodoptera littoralis,* or *Helicoverpa amigera*. In exemplary embodiments, the reductase comprises a sequence selected from GenBank Accession Nos. JX679210 and HG423128, and UniProt Accession No. I3PN86. In some embodiments, a nucleic acid sequence encoding a fatty-acyl reductase from organisms of the species *Agrotis segetum, Spodoptera littoralis,* or *Helicoverpa amigera* is codon optimized. In some embodiments, the reductase comprises a sequence set forth in SEQ ID NO: 1 from *Agrotis segetum*. In other embodiments, the reductase comprises a sequence set forth in SEQ ID NO: 2 from *Spodoptera littoralis*. In some embodiments, the reductase comprises a sequence selected from SEQ ID NOs: 3 and 32 from *Helicoverpa armigera*.

In certain embodiments, the fatty alcohol forming fatty-acyl reductase catalyzes the conversion of a mono- or poly-unsaturated fatty acyl-CoA into a fatty alcohol product selected from (Z)-3-hexenol, (Z)-3-nonenol, (Z)-5-decenol, (E)-5-decenol, (Z)-7-dodecenol, (E)-8-dodecenol, (Z)-8-dodecenol, (Z)-9-dodecenol, (Z)-9-tetradecenol, (Z)-9-hexadecenol, (Z)-11-tetradecenol, (Z)-7-hexadecenol, (Z)-11-hexadecenol, (E)-11-tetradecenol, or (Z,Z)-11,13-hexadecadienol, (11Z,13E)-hexadecadienol, (E,E)-8,10-dodecadienol, (E,Z)-7,9-dodecadienol, (Z)-13-octadecenol, or combinations thereof.

In some embodiments, the recombinant microorganism may express more than one exogenous nucleic acid molecule encoding a fatty alcohol forming fatty-acyl reductase that catalyzes the conversion of a mono- or poly-unsaturated $C_6$-$C_{24}$ fatty acyl-CoA to a corresponding mono- or poly-unsaturated $C_6$-$C_{24}$ fatty alcohol. Such recombinant microorganisms may be advantageously used to produce blends of various insect pheromones.

In addition to the biosynthetic pathway described in the first aspect above, the present application provides an additional biosynthetic pathway for the production of an unsaturated $C_6$-$C_{24}$ fatty alcohol utilizing a saturated $C_6$-$C_{24}$ fatty acyl-ACP intermediate derived from a $C_6$-$C_{24}$ fatty acid. Accordingly, in a second aspect, the application relates to a recombinant microorganism capable of producing an unsaturated $C_6$-$C_{24}$ fatty alcohol from an endogenous or exogenous source of $C_6$-$C_{24}$ fatty acid, wherein the recombinant microorganism expresses (a): at least one exogenous nucleic acid molecule encoding an acyl-ACP synthetase that catalyzes the conversion of a $C_6$-$C_{24}$ fatty acid to a corresponding saturated $C_6$-$C_{24}$ fatty acyl-ACP; (b) at least one exogenous nucleic acid molecule encoding a fatty-acyl-ACP desaturase that catalyzes the conversion of a saturated $C_6$-$C_{24}$ fatty acyl-ACP to a corresponding mono- or poly-unsaturated $C_6$-$C_{24}$ fatty acyl-ACP; (c) one or more endogenous or exogenous nucleic acid molecules encoding a fatty acid synthase complex that catalyzes the conversion of the mono- or poly-unsaturated $C_6$-$C_{24}$ fatty acyl-ACP from (b) to a corresponding mono- or poly-unsaturated $C_6$-$C_{24}$ fatty acyl-ACP with a two carbon elongation relative to the product of (b); (d): at least one exogenous nucleic acid molecule encoding a fatty aldehyde forming fatty-acyl reductase that catalyzes the conversion of the mono- or poly-unsaturated $C_6$-$C_{24}$ fatty acyl-ACP from (c) into a corresponding mono- or poly-unsaturated $C_6$-$C_{24}$ fatty aldehyde; and (e) at least one endogenous or exogenous nucleic acid molecule encoding a dehydrogenase that catalyzes the conversion of the mono- or poly-unsaturated $C_6$-$C_{24}$ fatty aldehyde $C_6$-$C_{24}$ from (d) into a corresponding mono- or poly-unsaturated $C_6$-$C_{24}$ fatty alcohol. In some embodiments, the mono- or poly-unsaturated $C_6$-$C_{24}$ fatty alcohol is an insect pheromone. In some embodiments, the mono- or poly-unsaturated $C_6$-$C_{24}$ fatty alcohol is a fragrance or flavoring agent. In some embodiments, the recombinant microorganism further comprises at least one endogenous or exogenous nucleic acid molecule encoding an alcohol oxidase or an alcohol dehydrogenase, wherein the alcohol oxidase or alcohol dehydrogenase is capable of catalyzing the conversion of the mono- or poly-unsaturated $C_6$-$C_{24}$ fatty alcohol from (e) into a corresponding mono- or poly-unsaturated $C_6$-$C_{24}$ fatty aldehyde. In some embodiments, the recombinant microorganism further comprises at least one endogenous or exogenous nucleic acid molecule encoding an acetyl transferase capable of catalyzing the conversion of the mono- or poly-unsaturated $C_6$-$C_{24}$ fatty alcohol from (e) into a corresponding mono- or poly-unsaturated $C_6$-$C_{24}$ fatty acetate.

In some embodiments, acyl-ACP synthetase is a synthetase capable of utilizing a fatty acid as a substrate that has a chain length of 6, 7, 8, 9, 10, 11, 12, 13, 14, 15, 16, 17, 18, 19, 20, 21, 22, 23, or 24 carbon atoms.

In various embodiments described herein, the acyl-ACP synthetase, or the nucleic acid that encodes it, can be isolated from organisms of the species *Vibrio harveyi, Rhodotorula glutinis,* or *Yarrowia lipolytica*.

In some embodiments, the fatty-acyl-ACP desaturase is a soluble desaturase. In various embodiments described herein, the fatty-acyl-ACP desaturase, or the nucleic acid that encodes it, can be isolated from organisms of the species *Pelargonium hortorum, Asclepias syriaca,* or *Uncaria tomentosa*.

In some embodiments, the recombinant microorganism may express more than one exogenous nucleic acid molecule encoding a fatty-acyl desaturase that catalyzes the conversion of a saturated $C_6$-$C_{24}$ fatty acyl-ACP to a corresponding mono- or poly-unsaturated $C_6$-$C_{24}$ fatty acyl-ACP.

As described above, fatty acid elongation enzymes, i.e., a fatty acid synthase complex, can be utilized to extend the chain length of a mono- or poly-unsaturated $C_6$-$C_{24}$ fatty acyl-ACP by two additional carbons at the alpha carbon. In some embodiments, the two additional carbons are derived from endogenous malonyl-CoA. In one embodiment, the one or more nucleic acid molecules encoding a fatty acid synthase complex are endogenous nucleic acid molecules, i.e., the nucleic acid molecule(s) is/are native to the recombinant microorganism. In another embodiment, the one or more nucleic acid molecules encoding a fatty acid synthase complex are exogenous nucleic acid molecules.

In various embodiments described herein, the fatty aldehyde forming acyl-ACP reductase, i.e., fatty aldehyde forming fatty-acyl reductase, or the nucleic acid sequence that encodes it, can be isolated from organisms of the species can be isolated from organisms of the species *Pelargonium hortorum*, *Asclepias syriaca*, and *Uncaria tomentosa*.

In some embodiments, the recombinant microorganism may express more than one exogenous nucleic acid molecule encoding a fatty aldehyde forming fatty-acyl reductase that catalyzes the conversion of a mono- or poly-unsaturated $C_6$-$C_{24}$ fatty acyl-ACP to a corresponding mono- or poly-unsaturated $C_6$-$C_{24}$ fatty aldehyde. Such recombinant microorganisms may be advantageously used to produce blends of various insect pheromones. An exemplary blend according to the instant invention comprises of (Z)-11-hexadecenal (Z11-16:Ald) and (Z)-9-hexadecenal (Z9-16:Ald). In one embodiment, the ratio of the blend is 90:10, 91:9, 92:8, 93:7, 94:6, 95:5, 96:4, 97:3, 98:2, or 99:1 ratio of (Z)-11-hexadecenal (Z11-16:Ald) to (Z)-9-hexadecenal (Z9-16:Ald). In an exemplary embodiment, the blend is a 97:3 ratio of (Z)-11-hexadecenal (Z11-16:Ald) to (Z)-9-hexadecenal (Z9-16:Ald), corresponding to key components of the *Helicoverpa* female virgin.

As noted above, the recombinant microorganism according to the second aspect comprises at least one endogenous or exogenous nucleic acid molecule encoding a dehydrogenase capable of catalyzing the conversion of the mono- or poly-unsaturated $C_6$-$C_{24}$ fatty aldehyde from (d) into a corresponding mono- or poly-unsaturated $C_6$-$C_{24}$ fatty alcohol. In one embodiment, the dehydrogenase is encoded by an endogenous nucleic acid molecule. In another embodiment, the dehydrogenase is encoded by an exogenous nucleic acid molecule. In exemplary embodiments, the endogenous or exogenous nucleic acid molecule encoding a dehydrogenase is isolated from organisms of the species *Saccharomyces cerevisiae*, *Escherichia coli*, *Yarrowia lipolytica*, or *Candida tropicalis*.

In addition to the biosynthetic pathway described in the first and second aspects above, the present application provides an additional biosynthetic pathway for the production of an unsaturated $C_6$-$C_{24}$ fatty alcohol utilizing a saturated $C_6$-$C_{24}$ fatty acyl-ACP intermediate derived from a $C_6$-$C_{24}$ fatty acid. Accordingly, in a third aspect, the application relates to a recombinant microorganism capable of producing an unsaturated $C_6$-$C_{24}$ fatty alcohol from an endogenous or exogenous source of $C_6$-$C_{24}$ fatty acid, wherein the recombinant microorganism expresses (a): at least one exogenous nucleic acid molecule encoding an acyl-ACP synthetase that catalyzes the conversion of a $C_6$-$C_{24}$ fatty acid to a corresponding saturated $C_6$-$C_{24}$ fatty acyl-ACP; (b) at least one exogenous nucleic acid molecule encoding a fatty-acyl-ACP desaturase that catalyzes the conversion of a saturated $C_6$-$C_{24}$ fatty acyl-ACP to a corresponding mono- or poly-unsaturated $C_6$-$C_{24}$ fatty acyl-ACP; (c) at least one exogenous fatty acyl-ACP thioesterase that catalyzes the conversion of the mono- or poly-unsaturated $C_6$-$C_{24}$ fatty acyl-ACP from (b) to a corresponding mono- or poly-unsaturated $C_6$-$C_{24}$ fatty acid; (d) one or more endogenous or exogenous nucleic acid molecules encoding an elongase that catalyzes the conversion of the mono- or poly-unsaturated $C_6$-$C_{24}$ fatty acyl-CoA derived from CoA activation of the mono- or poly-unsaturated $C_6$-$C_{24}$ fatty acid from (c) to a corresponding mono- or poly-unsaturated $C_6$-$C_{24}$ fatty acyl-CoA with a two carbon or greater elongation relative to the product of (c); and (e): at least one exogenous nucleic acid molecule encoding a fatty alcohol forming fatty-acyl reductase that catalyzes the conversion of the mono- or poly-unsaturated $C_6$-$C_{24}$ fatty acyl-CoA from (d) into a corresponding mono- or poly-unsaturated $C_6$-$C_{24}$ fatty alcohol. In some embodiments, the mono- or poly-unsaturated $C_6$-$C_{24}$ fatty alcohol is an insect pheromone. In some embodiments, the mono- or poly-unsaturated $C_6$-$C_{24}$ fatty alcohol is a fragrance or flavoring agent. In some embodiments, the recombinant microorganism further comprises at least one endogenous or exogenous nucleic acid molecule encoding an alcohol oxidase or an alcohol dehydrogenase, wherein the alcohol oxidase or alcohol dehydrogenase is capable of catalyzing the conversion of the mono- or poly-unsaturated $C_6$-$C_{24}$ fatty alcohol from (e) into a corresponding mono- or poly-unsaturated $C_6$-$C_{24}$ fatty aldehyde. In some embodiments, the recombinant microorganism further comprises at least one endogenous or exogenous nucleic acid molecule encoding an acetyl transferase capable of catalyzing the conversion of the mono- or poly-unsaturated $C_6$-$C_{24}$ fatty alcohol from (e) into a corresponding mono- or poly-unsaturated $C_6$-$C_{24}$ fatty acetate In some embodiments according to this third aspect, a fatty acyl-ACP thioesterase can be utilized to convert a mono- or poly-unsaturated $C_6$-$C_{24}$ fatty acyl-ACP into a corresponding mono- or poly-unsaturated $C_6$-$C_{24}$ fatty acid. In a particular embodiment, soluble fatty acyl-ACP thioesterases can be used to release free fatty acids for reactivation to a CoA thioester. Fatty acyl-ACP thioesterases including Q41635, Q39473, P05521.2, AEM72519, AEM72520, AEM72521, AEM72523, AAC49784, CAB60830, EER87824, EER96252, ABN54268, AAO77182, CAH09236, ACL08376, and homologs thereof may be used. In some embodiments, the mono- or poly-unsaturated $C_6$-$C_{24}$ fatty acyl-CoA may serve as a substrate for an elongase, which can be utilized to extend the chain length of a mono- or poly-unsaturated $C_6$-$C_{24}$ fatty acyl-CoA by two additional carbons at the alpha carbon. In some embodiments, the two additional carbons are derived from endogenous malonyl-CoA.

As described above, in some embodiments, the recombinant microorganism according to the first, second, or third aspect further comprises at least one endogenous or exogenous nucleic acid molecule encoding an alcohol oxidase capable of catalyzing the conversion of a mono- or poly-unsaturated $C_6$-$C_{24}$ fatty alcohol into a corresponding mono- or poly-unsaturated $C_6$-$C_{24}$ fatty aldehyde. In certain embodiments, the alcohol oxidase, or the nucleic acid sequence that encodes it, can be isolated from organisms of the species *Candida boidinii*, *Komagataella pastoris*, *Tanacetum vulgare*, *Simmondsia chinensis*, *Arabidopsis thaliana*, *Lotus japonicas*, or *Candida tropicalis*. In exemplary embodiments, the alcohol oxidase comprises a sequence selected from GenBank Accession Nos. Q00922, F2QY27, Q6QIR6, Q8LDP0, and L7VFV2.

In alternative embodiments, the fatty alcohol may be converted into a fatty aldehyde using chemical methods, including but not limited to, the use of TEMPO-bleach, TEMPO-copper-air, TEMPO-PhI(OAc)$_2$, Swern oxidation, or noble metal-air.

As described above, in some embodiments, the recombinant microorganism according to the first or second aspect further comprises at least one endogenous or exogenous nucleic acid molecule encoding an acetyl transferase capable of catalyzing the conversion of a C$_6$-C$_{24}$ fatty alcohol into a corresponding C$_6$-C$_{24}$ fatty acetate. In certain embodiments, the acetyl transferase, or the nucleic acid sequence that encodes it, can be isolated from organisms of the species *Saccharomyces cerevisiae*, *Danaus plexippus*, *Heliotis virescens*, *Bombyx mori*, *Agrotis ipsilon*, *Agrotis segetum*, *Euonymus alatus*. In exemplary embodiments, the acetyl transferase comprises a sequence selected from GenBank Accession Nos. AY242066, AY242065, AY242064, AY242063, AY242062, EHJ65205, ACX53812, NP_001182381, EHJ65977, EHJ68573, KJ579226, GU594061.

In alternative embodiments, the fatty alcohol may be converted into a fatty acetate using chemical methods, e.g., via chemical catalysis utilizing a chemical agent such as acetyl chloride, acetic anhydride, butyryl chloride, butyric anhydride, propanoyl chloride and propionic anhydride.

In some embodiments, the recombinant microorganism comprising a biosynthesis pathway for the production of an unsaturated C$_6$-C$_{24}$ fatty alcohol, aldehyde, or acetate may further be engineered to express one or more nucleic acids encoding protein or polypeptide which, when expressed, is toxic to an insect. Exemplary toxicant producing genes suitable for the present disclosure can be obtained from entomopathogenic organism, such as *Bacillus thuringiensis*, *Pseudomonas aeruginosa*, *Serratia marcescens*, and members of the genus *Streptomyces*. In an exemplary embodiment, the recombinant microorganism comprising a biosynthesis pathway for the production of an unsaturated C$_6$-C$_{24}$ fatty alcohol, aldehyde, or acetate may further be engineered to express a nucleic acid encoding a *Bacillus thuringiensis* ("Bt") toxin. In additional or alternative embodiments, the recombinant microorganism comprising a biosynthesis pathway for the production of an unsaturated C$_6$-C$_{24}$ fatty alcohol, aldehyde, or acetate may further be engineered to express a nucleic acid encoding other toxic proteins such as spider venom.

In some embodiments, the recombinant microorganism comprising a biosynthesis pathway for the production of an unsaturated C$_6$-C$_{24}$ fatty alcohol, aldehyde, or acetate may further be engineered to express an RNAi molecule which, when expressed, produces an oligonucleotide that is toxic to an insect.

In some embodiments, the recombinant microorganism comprising a biosynthesis pathway for the production of an unsaturated C$_6$-C$_{24}$ fatty alcohol, aldehyde, or acetate may further be engineered to express a metabolic pathway which, when expressed, produces a small molecule that is toxic to an insect. Non-limiting examples of toxic small molecules include azadirachtin, spinosad, avermectin, pyrethrins, and various terpenoids.

In various embodiments described herein, the recombinant microorganism comprising a biosynthesis pathway for the production of an unsaturated C$_6$-C$_{24}$ fatty alcohol, aldehyde, or acetate may be a eukaryotic microorganism, such as a yeast, a filamentous fungi, or an algae, or alternatively, a prokaryotic microorganism, such as a bacterium. For instance, suitable host cells can include cells of a genus selected from the group consisting of *Yarrowia*, *Candida*, *Saccharomyces*, *Pichia*, *Hansenula*, *Clostridium*, *Zymomonas*, *Escherichia*, *Salmonella*, *Rhodococcus*, *Pseudomonas*, *Bacillus*, *Lactobacillus*, *Enterococcus*, *Alcaligenes*, *Klebsiella*, *Paenibacillus*, *Arthrobacter*, *Corynebacterium*, *Brevibacterium*, and *Streptomyces*.

In some embodiments, the recombinant microorganism comprising a biosynthesis pathway for the production of an unsaturated C$_6$-C$_{24}$ fatty alcohol, aldehyde, or acetate is a yeast. Examples of suitable yeasts include yeasts of a genus selected from the group consisting of *Yarrowia*, *Candida*, *Saccharomyces*, *Pichia*, *Hansenula*, *Kluyveromyces*, *Issatchenkia*, *Zygosaccharomyces*, *Debaryomyces*, *Schizosaccharomyces*, *Pachysolen*, *Cryptococcus*, *Trichosporon*, *Rhodotorula*, or *Myxozyma*. In certain embodiments, the yeast is an oleaginous yeast. Exemplary oleaginous yeasts suitable for use in the present disclosure include members of the genera *Yarrowia*, *Candida*, *Rhodotorula*, *Rhodosporidium*, *Cryptococcus*, *Trichosporon*, and *Lipomyces*, including, but not limited to the species of *Yarrowia lipolytica*, *Candida tropicalis*, *Rhodosporidium toruloides*, *Lipomyces starkey*, *L. lipoferus*, *C. revkaufi*, *C. pulcherrima*, *C. utilis*, *Rhodotorula minuta*, *Trichosporon pullans*, *T. cutaneum*, *Cryptococcus curvatus*, *R. glutinis*, and *R. graminis*.

As will be understood in the art, endogenous enzymes can convert critical substrates and/or intermediates upstream of or within the unsaturated C$_6$-C$_{24}$ fatty alcohol, aldehyde, or acetate biosynthesis pathway into unwanted by-products. Accordingly, in some embodiments, the recombinant microorganism is manipulated to delete, disrupt, mutate, and/or reduce the activity of one or more endogenous enzymes that catalyzes a reaction in a pathway that competes with the unsaturated C$_6$-C$_{24}$ fatty alcohol, aldehyde, or acetate biosynthesis pathway.

In one embodiment, the recombinant microorganism is manipulated to delete, disrupt, mutate, and/or reduce the activity of one or more endogenous enzymes that catalyzes the conversion of a fatty acid into a ω-hydroxyfatty acid. In the context of a recombinant yeast microorganism, the recombinant yeast microorganism is engineered to delete, disrupt, mutate, and/or reduce the activity of one or more enzyme selected from XP_504406, XP_504857, XP_504311, XP_500855, XP_500856, XP_500402, XP_500097, XP_501748, XP_500560, XP_501148, XP_501667, XP_500273, BAA02041, CAA39366, CAA39367, BAA02210, BAA02211, BAA02212, BAA02213, BAA02214, AAO73952, AAO73953, AAO73954, AAO73955, AAO73956, AAO73958, AAO73959, AAO73960, AAO73961, AAO73957, XP_002546278, or homologs thereof. In the context of a recombinant bacterial microorganism, the recombinant bacterial microorganism is engineered to delete, disrupt, mutate, and/or reduce the activity of one or more enzyme selected from BAM49649, AAB80867, AAB17462, ADL27534, AAU24352, AAA87602, CAA34612, ABM17701, AAA25760, CAB51047, AAC82967, WP_011027348, or homologs thereof.

In another embodiment, the recombinant microorganism is manipulated to delete, disrupt, mutate, and/or reduce the activity of one or more endogenous enzymes that catalyzes the conversion of a fatty acyl-CoA into α,β-enoyl-CoA. In the context of a recombinant yeast microorganism, the recombinant yeast microorganism is engineered to delete, disrupt, mutate, and/or reduce the activity of one or more enzyme selected from CAA04659, CAA04660, CAA04661, CAA04662, CAA04663, CAG79214, AAA34322, AAA34361, AAA34363, CAA29901, BAA04761, AAA34891, or homologs thereof. In the context of a recombinant bacterial microorganism, the recombinant bacterial microorganism is engineered to delete, disrupt, mutate, and/or reduce the activity of one or more enzyme selected from AAB08643, CAB15271, BAN55749, CAC44516, ADK16968, AEI37634, WP_000973047, WP_025433422, WP_035184107, WP_026484842, CEL80920, WP_026818657, WP_005293707, WP_005883960, or homologs thereof.

In embodiments where the recombinant microorganism is a yeast microorganism, the recombinant microorganism is manipulated to delete, disrupt, mutate, and/or reduce the activity of one or more enzyme involved in peroxisome assembly and/or peroxisome enzyme import. The recombinant yeast microorganism is engineered to delete, disrupt, mutate, and/or reduce the activity of one or more enzyme selected from XP_505754, XP_501986, XP_501311, XP_504845, XP_503326, XP_504029, XP_002549868, XP_002547156, XP_002545227, XP_002547350, XP_002546990, EIW11539, EIW08094, EIW11472, EIW09743, EIW08286, or homologs thereof.

In another embodiment, the recombinant microorganism is manipulated to delete, disrupt, mutate, and/or reduce the activity of one or more endogenous reductase or desaturase enzymes that interferes with the unsaturated $C_6$-$C_{24}$ fatty alcohol, aldehyde, or acetate, i.e., catalyzes the conversion of a pathway substrate or product into an unwanted by-product.

In another embodiment, the recombinant microorganism is manipulated to delete, disrupt, mutate, and/or reduce the activity of one or more endogenous alcohol oxidase or alcohol dehydrogenase enzymes that catalyzes the unwanted conversion of the desired product, e.g., unsaturated $C_6$-$C_{24}$ fatty alcohol into a corresponding unsaturated $C_6$-$C_{24}$ fatty aldehyde.

In another embodiment, the recombinant microorganism is manipulated to delete, disrupt, mutate, and/or reduce the activity of one or more endogenous enzymes that catalyzes a reaction in a pathway that competes with the biosynthesis pathway for one or more unsaturated fatty acyl-CoA intermediates. In one embodiment, the one or more endogenous enzymes comprise one or more diacylglycerol acyltransferases. In the context of a recombinant yeast microorganism, the recombinant yeast microorganism is engineered to delete, disrupt, mutate, and/or reduce the activity of one or more diacylglycerol acyltransferases selected from the group consisting of YALI0E32769g, YALI0D07986g and CTRG_06209, or homolog thereof. In another embodiment, the one or more endogenous enzymes comprise one or more glycerolphospholipid acyltransferases. In the context of a recombinant yeast microorganism, the recombinant yeast microorganism is engineered to delete, disrupt, mutate, and/or reduce the activity of one or more glycerolphospholipid acyltransferases selected from the group consisting of YALI0E16797g and CTG_04390, or homolog thereof. In another embodiment, the one or more endogenous enzymes comprise one or more acyl-CoA/sterol acyltransferases. In the context of a recombinant yeast microorganism, the recombinant yeast microorganism is engineered to delete, disrupt, mutate, and/or reduce the activity of one or more acyl-CoA/sterol acyltransferases selected from the group consisting of YALI0F06578g, CTRG_01764 and CTRG_01765, or homolog thereof.

In another embodiment, the recombinant microorganism is manipulated to delete, disrupt, mutate, and/or reduce the activity of one or more endogenous enzymes that catalyzes a reaction in a pathway that oxidizes fatty aldehyde intermediates. In one embodiment, the one or more endogenous enzymes comprise one or more fatty aldehyde dehydrogenases. In the context of a recombinant yeast microorganism, the recombinant yeast microorganism is engineered to delete, disrupt, mutate, and/or reduce the activity of one or more fatty aldehyde dehydrogenases selected from the group consisting of YALI0A17875g, YALI0E15400g, YALI0B01298g, YALI0F23793g, CTRG_05010 and CTRG_04471, or homolog thereof.

In another embodiment, the recombinant microorganism is manipulated to delete, disrupt, mutate, and/or reduce the activity of one or more endogenous enzymes that catalyzes a reaction in a pathway that consumes fatty acetate products. In one embodiment, the one or more endogenous enzymes comprise one or more sterol esterases. In the context of a recombinant yeast microorganism, the recombinant yeast microorganism is engineered to delete, disrupt, mutate, and/or reduce the activity of one or more sterol esterases selected from the group consisting of YALI0E32035g, YALI0E00528g, CTRG_01138, CTRG_01683 and CTRG_04630, or homolog thereof. In another embodiment, the one or more endogenous enzymes comprise one or more triacylglycerol lipases. In the context of a recombinant yeast microorganism, the recombinant yeast microorganism is engineered to delete, disrupt, mutate, and/or reduce the activity of one or more triacylglycerol lipases selected from the group consisting of YALI0D17534g, YALI0F10010g, CTRG_00057 and CTRG_06185, or homolog thereof. In another embodiment, the one or more endogenous enzymes comprise one or more monoacylglycerol lipases. In the context of a recombinant yeast microorganism, the recombinant yeast microorganism is engineered to delete, disrupt, mutate, and/or reduce the activity of one or more monoacylglycerol lipases selected from the group consisting of YALI0C14520g, CTRG_03360 and CTRG_05049, or homolog thereof. In another embodiment, the one or more endogenous enzymes comprise one or more extracellular lipases. In the context of a recombinant yeast microorganism, the recombinant yeast microorganism is engineered to delete, disrupt, mutate, and/or reduce the activity of one or more extracellular lipases selected from the group consisting of YALI0A20350g, YALI0D19184g, YALI0B09361g, CTRG_05930, CTRG_04188, CTRG_02799, CTRG_03052 and CTRG_03885, or homolog thereof.

In embodiments where the recombinant microorganism is a yeast microorganism, one or more of the exogenous unsaturated $C_6$-$C_{24}$ fatty alcohol, aldehyde, or acetate pathway genes encodes an enzyme that is localized to a yeast compartment selected from the group consisting of the cytosol, the mitochondria, or the endoplasmic reticulum. In an exemplary embodiment, one or more of the exogenous pathway genes encodes an enzyme that is localized to the endoplasmic reticulum. In another embodiment, at least two exogenous pathway genes encode an enzyme that is localized to the endoplasmic reticulum. In yet another embodiment, all exogenous pathway genes encodes an enzyme that is localized to the endoplasmic reticulum.

In a fourth aspect, the present application provides methods of producing an unsaturated $C_6$-$C_{24}$ fatty alcohol, aldehyde, or acetate using a recombinant microorganism as described herein. In one embodiment, the method includes cultivating the recombinant microorganism in a culture medium containing a feedstock providing a carbon source until the unsaturated $C_6$-$C_{24}$ fatty alcohol, aldehyde, or acetate is produced and optionally, recovering the unsaturated $C_6$-$C_{24}$ fatty alcohol, aldehyde, or acetate. Once produced, the unsaturated $C_6$-$C_{24}$ fatty alcohol, aldehyde, or acetate may be isolated from the fermentation medium using various methods known in the art including, but not limited to, distillation, membrane-based separation gas stripping, solvent extraction, and expanded bed adsorption.

In some embodiments, the recombinant microorganism, e.g., a yeast, may be recovered and produced in dry particulate form. In embodiments involving yeast, the yeast may be dried to produce powdered yeast. In some embodiments, the process for producing powdered yeast comprises spray drying a liquid yeast composition in air, optionally followed by further drying. In some embodiments, the recombinant microorganism composition will comprise the unsaturated $C_6$-$C_{24}$ fatty alcohol, aldehyde, or acetate when dried.

As described herein, preferred recombinant microorganisms of the disclosure will have the ability to utilize alkanes and fatty acids as carbon sources. However, as will be understood in the art, a variety of carbon sources may be utilized, including but not limited to, various sugars (e.g., glucose, fructose, or sucrose), glycerol, alcohols (e.g., ethanol), organic acids, lignocellulose, proteins, carbon dioxide, carbon monoxide, as well as the aforementioned alkanes and fatty acids. In an exemplary embodiment, the recombinant microorganism will convert the carbon source to the unsaturated $C_6$-$C_{24}$ fatty alcohol, aldehyde, or acetate under aerobic conditions.

As highlighted above, the present application provides methods of producing one or more unsaturated $C_6$-$C_{24}$ fatty alcohols, aldehydes, or acetates using a recombinant microorganism as described herein. In some embodiments, the product is an insect pheromone. As will be appreciated by the skilled artisan equipped with the instant disclosure, a variety of different exogenous and endogenous enzymes can be expressed in a recombinant host microorganism to produce a desired insect pheromone. Exemplary insect pheromones in the form of fatty alcohols, fatty aldehydes, or fatty acetates capable of being generated using the recombinant microorganisms and methods described herein include, but are not limited to, (Z)-11-hexadecenal, (Z)-11hexadecenyl acetate, (Z)-9-tetradecenyl acetate, (Z,Z)-11,13-hexadecadienal, (9Z,11E)-hexadecadienal, (E,E)-8,10-dodecadien-1-ol, (7E,9Z)-dodecadienyl acetate, (Z)-3-nonen-1-ol, (Z)-5-decen-1-ol, (Z)-5-decenyl acetate, (E)-5-decen-1-ol, (E)-5-decenyl acetate, (Z)-7-dodecen-1-ol, (Z)-7-dodecenyl acetate, (E)-8-dodecen-1-ol, (E)-8-dodecenyl acetate, (Z)-8-dodecen-1-ol, (Z)-8-dodecenyl acetate, (Z)-9-dodecen-1-ol, (Z)-9-dodecenyl acetate, (Z)-9-tetradecen-1-ol, (Z)-11-tetraceden-1-ol, (Z)-11-tetracedenyl acetate, (E)-11-tetradecen-1-ol, (E)-11-tetradecenyl acetate, (Z)-7-hexadecen-1-ol, (Z)-7-hexadecenal, (Z)-9-hexadecen-1-ol, (Z)-9-hexadecenal, (Z)-9-hexadecenyl acetate, (Z)-11-hexadecen-1-ol, (Z)-13-octadecen-1-ol, and (Z)-13-octadecenal.

In a fifth aspect, the present application provides compositions comprising one of more of the insect pheromone-producing recombinant microorganisms described herein. In certain embodiments, the composition may further comprise one or more insect pheromones produced by the recombinant microorganism. In further embodiments, the may additionally comprise one or more toxic proteins or polypeptides produced by the recombinant microorganism.

BRIEF DESCRIPTION OF DRAWINGS

Illustrative embodiments of the disclosure are illustrated in the drawings, in which:

FIG. 6A-FIG. 6B shows sample chromatograms of biotransformation product of Z11-hexadecenoic acid using *S. cerevisiae* expressing either an empty vector (FIG. 6A), or *Helicoverpa armigera* alcohol-forming reductase (FIG. 6B). Black lines: no substrate added. Purple line: Z11-hexadecenoic acid was added as substrate.

FIG. 11A: YPD+palmitoleic acid; FIG. 11B: YPD–palmitoleic acid; FIG. 11C: CM-Ura glucose+palmitoleic acid; FIG. 11D: CM-Ura glucose–palmitoleic acid; FIG. 11E: Map of strains in FIG. 11A-FIG. 11D. Dasher=GFP synthon.

FIG. 12A shows complementation of ΔOLE1 growth without UFA on YPD.

FIG. 12B shows complementation of ΔOLE1 growth without UFA on CM-Ura glucose.

FIG. 14A-FIG. 14B shows a comparison of GC-MS fragmentation pattern of (Z)-11-hexadecenoic acid from an authentic compound (FIG. 14A) and biologically derived (FIG. 14B).

FIG. 19A: Fragmentation pattern of an authentic standard. The m/z 297.3 was used in follow up experiments to selectively detect the alcohol. To also detect the internal standard, the masses 208 and 387.3 were included too. FIG. 19B: In addition to the detection of the specific mass fragment, the retention time was used as second stage confirmation. The retention time is 6.22. FIG. 19C: Comparison of the two different regioisomers 9Z- and 11Z-hexadecenol when detected in SIM mode (297.3) with the same method.

FIG. 21A-FIG. 21D shows mCherry control integration. FIG. 21A: Negative (water-only) control transformation plate. FIG. 21B: pPV0137 mCherry transformation plate. FIG. 21C: Patch plates from negative control clones. FIG. 21D: Patch plates from pPV0137 clones.

FIG. 24A-FIG. 24E shows confirmation of the 11Z-regioisomer. FIG. 24A: The specific peak with an ion fragment of 245 m/z was only observed in *C. tropicalis* SPV053 expressing either the Z11-desaturase from *A. transitella* or *H. zea*. FIG. 24B: The fragmentation patterns of the authentic standard. FIG. 24D: The fragmentation patterns of the newly formed compound in samples with expressed desaturase from *H. zea* match those of the standard. FIG. 24E: The fragmentation patterns of the newly formed compound in samples with expressed desaturase from *A. transitella* match those of the standard. FIG. 24C: The fragmentation patterns of the mCherry control significantly differ from those of FIG. 24B, FIG. 24D and FIG. 24E.

FIG. 25A-FIG. 25B shows a GC-FID chromatogram of different *C. tropicalis* SPV053 strains incubated with methyl tretradecanoate. FIG. 25A: Overall spectrum. The occurrence of the Z11-C16:1 peak is observable for the strains expressing the Z11-desaturases from *A. transitella* and *H. zea*. FIG. 25B: Zoom of the C14 to C18 area. A new peak is visible at 4.8 min, which could correspond to Z11-C14:1. Another peak near Z9-C18:1 is also visible, which could correspond to Z11-C18:1.

FIG. 32A-FIG. 32B shows Z9-16OH and Z11-16OH titers in YPD (FIG. 32A) and Semi-Defined C:N=80 (FIG. 32B) media for pEXP clones. Ten isolates expressing the *H. zea* desaturase under the TEF promoter and *H. armigera* reductase under the EXP promoter from two independent competent cell preparations (Comp. Cell Preparation 1, Comp. Cell Preparation 2) were compared to a parental negative control (SPV300) and a desaturase only negative control (SPV459 Hz_desat only). Error bars represent the SEM (standard error of the mean) measured from technical replicates for each strain and condition (N=2). *One replicate from Clone 5 and Clone 18 under the Semi-Defined C:N=80 condition was lost during sample work-up so the titers for that condition are from a single data point (N=1, Comp. Cell Preparation 1 Clone 18 and Comp. Cell Preparation 2 Clone 5).

SEQUENCES

Figure 1:
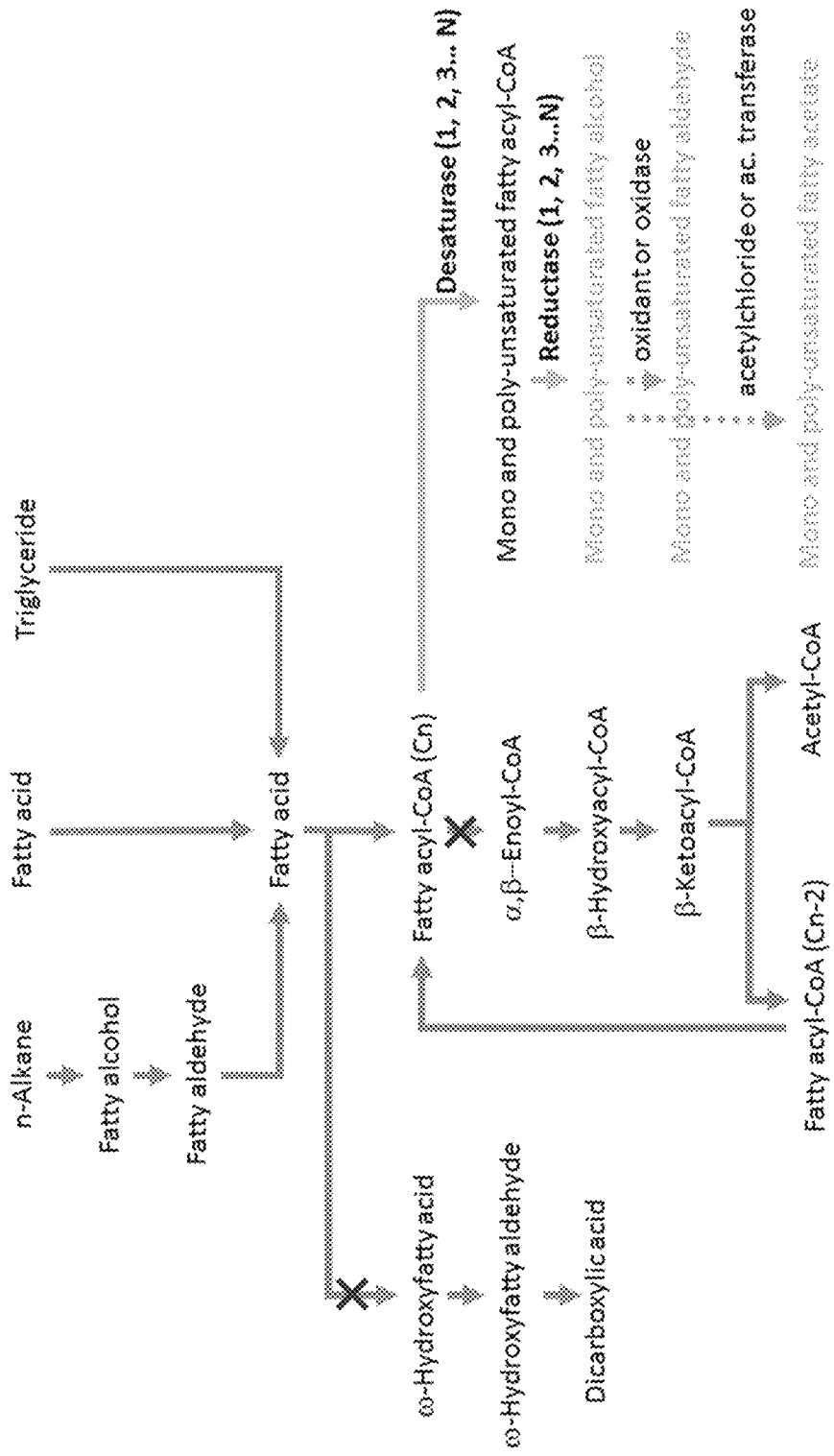
FIG. 1 illustrates the conversion of a saturated fatty acyl-CoA to an unsaturated fatty alcohol.

A sequence listing for SEQ ID NO: 1-SEQ ID NO: 38 is part of this application and is incorporated by reference herein. The sequence listing is provided at the end of this document.

DETAILED DESCRIPTION

Definitions

The following definitions and abbreviations are to be used for the interpretation of the disclosure.

As used herein and in the appended claims, the singular forms "a," "an," and "the" include plural referents unless the context clearly dictates otherwise. Thus, for example, reference to "a pheromone" includes a plurality of such pheromones and reference to "the microorganism" includes reference to one or more microorganisms, and so forth.

As used herein, the terms "comprises," "comprising," "includes," "including," "has," "having," "contains," "containing," or any other variation thereof, are intended to cover a non-exclusive inclusion. A composition, mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive "or" and not to an exclusive "or."

The terms "about" and "around," as used herein to modify a numerical value, indicate a close range surrounding that explicit value. If "X" were the value, "about X" or "around X" would indicate a value from 0.9X to 1.1X, or, in some embodiments, a value from 0.95X to 1.05X. Any reference to "about X" or "around X" specifically indicates at least the values X, 0.95X, 0.96X, 0.97X, 0.98X, 0.99X, 1.01X, 1.02X, 1.03X, 1.04X, and 1.05X. Thus, "about X" and "around X" are intended to teach and provide written description support for a claim limitation of, e.g., "0.98X."

As used herein, the terms "microbial," "microbial organism," and "microorganism" include any organism that exists as a microscopic cell that is included within the domains of archaea, bacteria or eukarya, the latter including yeast and filamentous fungi, protozoa, algae, or higher Protista. Therefore, the term is intended to encompass prokaryotic or eukaryotic cells or organisms having a microscopic size and includes bacteria, archaea, and eubacteria of all species as well as eukaryotic microorganisms such as yeast and fungi. Also included are cell cultures of any species that can be cultured for the production of a chemical.

As described herein, in some embodiments, the recombinant microorganisms are prokaryotic microorganism. In some embodiments, the prokaryotic microorganisms are bacteria. "Bacteria", or "eubacteria", refers to a domain of prokaryotic organisms. Bacteria include at least eleven distinct groups as follows: (1) Gram-positive (gram+) bacteria, of which there are two major subdivisions: (1) high G+C group (Actinomycetes. Mycobacteria. *Micrococcus*, others) (2) low G+C group (*Bacillus, Clostridia, Lactobacillus, Staphylococci, Streptococci, Mycoplasmas*); (2) Proteobacteria, e.g., Purple photosynthetic+non-photosynthetic Gram-negative bacteria (includes most "common" Gram-negative bacteria); (3) Cyanobacteria, e.g., oxygenic phototrophs; (4) Spirochetes and related species; (5) Planctomyces; (6) Bacteroides, Flavobacteria; (7) Chlamydia; (8) Green sulfur bacteria; (9) Green non-sulfur bacteria (also anaerobic phototrophs); (10) Radioresistant micrococci and relatives; (11) Thermotoga and Thermosipho thermophiles.

"Gram-negative bacteria" include cocci, nonenteric rods, and enteric rods. The genera of Gram-negative bacteria include, for example, *Neisseria, Spirillum, Pasteurella, Brucella, Yersinia, Francisella, Haemophilus, Bordetella, Escherichia, Salmonella, Shigella, Klebsiella, Proteus, Vibrio, Pseudomonas, Bacteroides, Acetobacter, Aerobacter,*

*Agrobacterium, Azotobacter, Spirilla, Serratia, Vibrio, Rhizobium, Chlamydia, Rickettsia, Treponema,* and *Fusobacterium*.

"Gram positive bacteria" include cocci, nonsporulating rods, and sporulating rods. The genera of gram positive bacteria include, for example, *Actinomyces, Bacillus, Clostridium, Corynebacterium, Erysipelothrix, Lactobacillus, Listeria, Mycobacterium, Myxococcus, Nocardia, Staphylococcus, Streptococcus*, and *Streptomyces*.

The term "recombinant microorganism" and "recombinant host cell" are used interchangeably herein and refer to microorganisms that have been genetically modified to express or to overexpress endogenous enzymes, to express heterologous enzymes, such as those included in a vector, in an integration construct, or which have an alteration in expression of an endogenous gene. By "alteration" it is meant that the expression of the gene, or level of a RNA molecule or equivalent RNA molecules encoding one or more polypeptides or polypeptide subunits, or activity of one or more polypeptides or polypeptide subunits is up regulated or down regulated, such that expression, level, or activity is greater than or less than that observed in the absence of the alteration. For example, the term "alter" can mean "inhibit," but the use of the word "alter" is not limited to this definition. It is understood that the terms "recombinant microorganism" and "recombinant host cell" refer not only to the particular recombinant microorganism but to the progeny or potential progeny of such a microorganism. Because certain modifications may occur in succeeding generations due to either mutation or environmental influences, such progeny may not, in fact, be identical to the parent cell, but are still included within the scope of the term as used herein.

The term "expression" with respect to a gene sequence refers to transcription of the gene and, as appropriate, translation of the resulting mRNA transcript to a protein. Thus, as will be clear from the context, expression of a protein results from transcription and translation of the open reading frame sequence. The level of expression of a desired product in a host cell may be determined on the basis of either the amount of corresponding mRNA that is present in the cell, or the amount of the desired product encoded by the selected sequence. For example, mRNA transcribed from a selected sequence can be quantitated by qRT-PCR or by Northern hybridization (see Sambrook et al., Molecular Cloning: A Laboratory Manual, Cold Spring Harbor Laboratory Press (1989)). Protein encoded by a selected sequence can be quantitated by various methods, e.g., by ELISA, by assaying for the biological activity of the protein, or by employing assays that are independent of such activity, such as western blotting or radioimmunoassay, using antibodies that recognize and bind the protein. See Sambrook et al., 1989, supra.

The term "polynucleotide" is used herein interchangeably with the term "nucleic acid" and refers to an organic polymer composed of two or more monomers including nucleotides, nucleosides or analogs thereof, including but not limited to single stranded or double stranded, sense or antisense deoxyribonucleic acid (DNA) of any length and, where appropriate, single stranded or double stranded, sense or antisense ribonucleic acid (RNA) of any length, including siRNA. The term "nucleotide" refers to any of several compounds that consist of a ribose or deoxyribose sugar joined to a purine or a pyrimidine base and to a phosphate group, and that are the basic structural units of nucleic acids. The term "nucleoside" refers to a compound (as guanosine or adenosine) that consists of a purine or pyrimidine base combined with deoxyribose or ribose and is found especially in nucleic acids. The term "nucleotide analog" or "nucleoside analog" refers, respectively, to a nucleotide or nucleoside in which one or more individual atoms have been replaced with a different atom or with a different functional group. Accordingly, the term polynucleotide includes nucleic acids of any length, DNA, RNA, analogs and fragments thereof. A polynucleotide of three or more nucleotides is also called nucleotidic oligomer or oligonucleotide.

It is understood that the polynucleotides described herein include "genes" and that the nucleic acid molecules described herein include "vectors" or "plasmids." Accordingly, the term "gene", also called a "structural gene" refers to a polynucleotide that codes for a particular sequence of amino acids, which comprise all or part of one or more proteins or enzymes, and may include regulatory (non-transcribed) DNA sequences, such as promoter sequences, which determine for example the conditions under which the gene is expressed. The transcribed region of the gene may include untranslated regions, including introns, 5'-untranslated region (UTR), and 3'-UTR, as well as the coding sequence.

The term "enzyme" as used herein refers to any substance that catalyzes or promotes one or more chemical or biochemical reactions, which usually includes enzymes totally or partially composed of a polypeptide or polypeptides, but can include enzymes composed of a different molecule including polynucleotides.

As used herein, the term "non-naturally occurring," when used in reference to a microorganism organism or enzyme activity of the disclosure, is intended to mean that the microorganism organism or enzyme has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microorganism's genetic material. Such modifications include, for example, coding regions and functional fragments thereof, for heterologous, homologous, or both heterologous and homologous polypeptides for the referenced species. Additional modifications include, for example, non-coding regulatory regions in which the modifications alter expression of a gene or operon. Exemplary non-naturally occurring microorganism or enzyme activity includes the hydroxylation activity described above.

The term "exogenous" as used herein with reference to various molecules, e.g., polynucleotides, polypeptides, enzymes, etc., refers to molecules that are not normally or naturally found in and/or produced by a given yeast, bacterium, organism, microorganism, or cell in nature.

On the other hand, the term "endogenous" or "native" as used herein with reference to various molecules, e.g., polynucleotides, polypeptides, enzymes, etc., refers to molecules that are normally or naturally found in and/or produced by a given yeast, bacterium, organism, microorganism, or cell in nature.

The term "heterologous" as used herein in the context of a modified host cell refers to various molecules, e.g., polynucleotides, polypeptides, enzymes, etc., wherein at least one of the following is true: (a) the molecule(s) is/are foreign ("exogenous") to (i.e., not naturally found in) the host cell; (b) the molecule(s) is/are naturally found in (e.g., is "endogenous to") a given host microorganism or host cell but is either produced in an unnatural location or in an unnatural amount in the cell; and/or (c) the molecule(s) differ(s) in nucleotide or amino acid sequence from the endogenous nucleotide or amino acid sequence(s) such that the molecule differing in nucleotide or amino acid sequence from the endogenous nucleotide or amino acid as found endogenously is produced in an unnatural (e.g., greater than naturally found) amount in the cell.

The term "homolog," as used herein with respect to an original enzyme or gene of a first family or species, refers to distinct enzymes or genes of a second family or species which are determined by functional, structural, or genomic analyses to be an enzyme or gene of the second family or species which corresponds to the original enzyme or gene of the first family or species. Homologs most often have functional, structural, or genomic similarities. Techniques are known by which homologs of an enzyme or gene can readily be cloned using genetic probes and PCR. Identity of cloned sequences as homologs can be confirmed using functional assays and/or by genomic mapping of the genes.

A protein has "homology" or is "homologous" to a second protein if the amino acid sequence encoded by a gene has a similar amino acid sequence to that of the second gene. Alternatively, a protein has homology to a second protein if the two proteins have "similar" amino acid sequences. Thus, the term "homologous proteins" is intended to mean that the two proteins have similar amino acid sequences. In certain instances, the homology between two proteins is indicative of its shared ancestry, related by evolution.

The term "fatty acid" as used herein refers to a compound of structure R—COOH, wherein R is a $C_6$ to $C_{24}$ saturated, unsaturated, linear, branched or cyclic hydrocarbon and the carboxyl group is at position 1. In a particular embodiment, R is a $C_6$ to $C_{24}$ saturated or unsaturated linear hydrocarbon and the carboxyl group is at position 1.

The term "fatty alcohol" as used herein refers to an aliphatic alcohol having the formula R—OH, wherein R is a $C_6$ to $C_{24}$ saturated, unsaturated, linear, branched or cyclic hydrocarbon. In a particular embodiment, R is a $C_6$ to $C_{24}$ saturated or unsaturated linear hydrocarbon.

The term "fatty acyl-CoA" refers to a compound having the structure R—(CO)—S—$R_1$, wherein $R_1$ is Coenzyme A, and the term "fatty acyl-ACP" refers to a compound having the structure R—(CO)—S—$R_1$, wherein $R_1$ is an acyl carrier protein ACP.

INTRODUCTION

The present disclosure addresses the need for novel technologies for the cost-efficient production of valuable products from low-cost feedstocks. Specifically, the present inventors have addressed this need with the development of recombinant microorganisms capable of producing a wide-range of unsaturated $C_6$-$C_{24}$ fatty alcohols, aldehydes, and acetates including synthetic insect pheromones, fragrances, flavors, and polymer intermediates from low-cost feedstocks. Thus, aspects of the disclosure are based on the inventors' discovery that recombinant microorganisms can be engineered in order to produce valuable products from low-cost feedstocks, which circumvents conventional synthetic methodologies to produce valuable products.

As discussed above, recombinant microorganisms can be engineered to synthesize mono- or poly-unsaturated $C_6$-$C_{24}$ fatty alcohols. Mono- or poly-unsaturated $C_6$-$C_{24}$ fatty alcohols synthesized as described herein can be further converted into the corresponding aldehydes or acetates. Thus, various embodiments of the present disclosure can be used to synthesize a variety of insect pheromones selected from fatty alcohols, aldehydes, and acetates. Additionally, embodiments described herein can also be used for the synthesis of fragrances, flavors, and polymer intermediates.

Pheromones

As described above, embodiments of the disclosure provide for the synthesis of one or more insect pheromones using a recombinant microorganism. A pheromone is a volatile chemical compound that is secreted by a particular insect for the function of chemical communication within the species. That is, a pheromone is secreted or excreted chemical factor that triggers a social response in members of the same species. There are, inter alia, alarm pheromones, food trail pheromones, sex pheromones, aggregation pheromones, epideictic pheromones, releaser pheromones, primer pheromones, and territorial pheromones, that affect behavior or physiology.

Non-limiting examples of insect pheromones which can be synthesized using the recombinant microorganisms and methods disclosed herein include linear alcohols, aldehydes, and acetates listed in Table 1.

TABLE 1

| $C_6$-$C_{20}$ Linear Pheromones | |
| --- | --- |
| Name | Name |
| (E)-2-Decen-1-ol | (E,E)-10,12-Tetradecadien-1-ol |
| (E)-2-Decenyl acetate | (E,E)-10,12-Tetradecadienyl acetate |
| (E)-2-Decenal | (E,E)-10,12-Tetradecadienal |
| (Z)-2-Decen-1-ol | (E,Z)-10,12-Tetradecadienyl acetate |
| (Z)-2-Decenyl acetate | (Z,E)-10,12-Tetradecadienyl acetate |
| (Z)-2-Decenal | (Z,Z)-10,12-Tetradecadien-1-ol |
| (E)-3-Decen-1-ol | (Z,Z)-10,12-Tetradecadienyl acetate |
| (Z)-3-Decenyl acetate | (E,Z,Z)-3,8,11-Tetradecatrienyl acetate |
| (Z)-3-Decen-1-ol | (E)-8-Pentadecen-1-ol |
| (Z)-4-Decen-1-ol | (E)-8-Pentadecenyl acetate |
| (E)-4-Decenyl acetate | (Z)-8-Pentadecen-1-ol |
| (Z)-4-Decenyl acetate | (Z)-8-Pentadecenyl acetate |
| (Z)-4-Decenal | (Z)-9-Pentadecenyl acetate |
| (E)-5-Decen-1-ol | (E)-9-Pentadecenyl acetate |
| (E)-5-Decenyl acetate | (Z)-10-Pentadecenyl acetate |
| (Z)-5-Decen-1-ol | (Z)-10-Pentadecenal |
| (Z)-5-Decenyl acetate | (E)-12-Pentadecenyl acetate |
| (Z)-5-Decenal | (Z)-12-Pentadecenyl acetate |
| (E)-7-Decenyl acetate | (Z,Z)-6,9-Pentadecadien-1-ol |
| (Z)-7-Decenyl acetate | (Z,Z)-6,9-Pentadecadienyl acetate |
| (E)-8-Decen-1-ol | (Z,Z)-6,9-Pentadecadienal |
| (E,E)-2,4-Decadienal | (E,E)-8,10-Pentadecadienyl acetate |
| (E,Z)-2,4-Decadienal | (E,Z)-8,10-Pentadecadien-1-ol |
| (Z,Z)-2,4-Decadienal | (E,Z)-8,10-Pentadecadienyl acetate |
| (E,E)-3,5-Decadienyl acetate | (Z,E)-8,10-Pentadecadienyl acetate |
| (Z,E)-3,5-Decadienyl acetate | (Z,Z)-8,10-Pentadecadienyl acetate |
| (Z,Z)-4,7-Decadien-1-ol | (E,Z)-9,11-Pentadecadienal |
| (Z,Z)-4,7-Decadienyl acetate | (Z,Z)-9,11-Pentadecadienal |
| (E)-2-Undecenyl acetate | (Z)-3-Hexadecenyl acetate |
| (E)-2-Undecenal | (E)-5-Hexadecen-1-ol |
| (Z)-5-Undecenyl acetate | (E)-5-Hexadecenyl acetate |
| (Z)-7-Undecenyl acetate | (Z)-5-Hexadecen-1-ol |
| (Z)-8-Undecenyl acetate | (Z)-5-Hexadecenyl acetate |
| (Z)-9-Undecenyl acetate | (E)-6-Hexadecenyl acetate |
| (E)-2-Dodecenal | (E)-7-Hexadecen-1-ol |
| (Z)-3-Dodecen-1-ol | (E)-7-Hexadecenyl acetate |
| (E)-3-Dodecenyl acetate | (E)-7-Hexadecenal |
| (Z)-3-Dodecenyl acetate | (Z)-7-Hexadecen-1-ol |
| (E)-4-Dodecenyl acetate | (Z)-7-Hexadecenyl acetate |
| (E)-5-Dodecen-1-ol | (Z)-7-Hexadecenal |
| (E)-5-Dodecenyl acetate | (E)-8-Hexadecenyl acetate |
| (Z)-5-Dodecen-1-ol | (E)-9-Hexadecen-1-ol |
| (Z)-5-Dodecenyl acetate | (E)-9-Hexadecenyl acetate |
| (Z)-5-Dodecenal | (E)-9-Hexadecenal |
| (E)-6-Dodecen-1-ol | (Z)-9-Hexadecen-1-ol |
| (Z)-6-Dodecenyl acetate | (Z)-9-Hexadecenyl acetate |
| (E)-6-Dodecenal | (Z)-9-Hexadecenal |
| (E)-7-Dodecen-1-ol | (E)-10-Hexadecen-1-ol |
| (E)-7-Dodecenyl acetate | (E)-10-Hexadecenal |
| (E)-7-Dodecenal | (Z)-10-Hexadecenyl acetate |
| (Z)-7-Dodecen-1-ol | (Z)-10-Hexadecenal |

TABLE 1-continued

C$_6$-C$_{20}$ Linear Pheromones

| Name | Name |
|---|---|
| (Z)-7-Dodecenyl acetate | (E)-11-Hexadecen-1-ol |
| (Z)-7-Dodecenal | (E)-11-Hexadecenyl acetate |
| (E)-8-Dodecen-1-ol | (E)-11-Hexadecenal |
| (E)-8-Dodecenyl acetate | (Z)-11-Hexadecen-1-ol |
| (E)-8-Dodecenal | (Z)-11-Hexadecenyl acetate |
| (Z)-8-Dodecen-1-ol | (Z)-11-Hexadecenal |
| (Z)-8-Dodecenyl acetate | (Z)-12-Hexadecenyl acetate |
| (E)-9-Dodecen-1-ol | (Z)-12-Hexadecenal |
| (E)-9-Dodecenyl acetate | (E)-14-Hexadecenal |
| (E)-9-Dodecenal | (Z)-14-Hexadecenyl acetate |
| (Z)-9-Dodecen-1-ol | (E,E)-1,3-Hexadecadien-1-ol |
| (Z)-9-Dodecenyl acetate | (E,E)-4,6-Hexadecadien-1-ol |
| (Z)-9-Dodecenal | (E,Z)-4,6-Hexadecadienyl acetate |
| (E)-10-Dodecen-1-ol | (E,Z)-4,6-Hexadecadienal |
| (E)-10-Dodecenyl acetate | (E,Z)-6,11-Hexadecadienyl acetate |
| (E)-10-Dodecenal | (E,Z)-6,11-Hexadecadienal |
| (Z)-10-Dodecen-1-ol | (Z,Z)-7,10-Hexadecadien-1-ol |
| (Z)-10-Dodecenyl acetate | (Z,Z)-7,10-Hexadecadienyl acetate |
| (E,Z)-3,5-Dodecadienyl acetate | (Z,E)-7,11-Hexadecadien-1-ol |
| (Z,E)-3,5-Dodecadienyl acetate | (Z,E)-7,11-Hexadecadienyl acetate |
| (Z,Z)-3,6-Dodecadien-1-ol | (Z,E)-7,11-Hexadecadienal |
| (E,E)-4,10-Dodecadienyl acetate | (Z,Z)-7,11-Hexadecadien-1-ol |
| (E,E)-5,7-Dodecadien-1-ol | (Z,Z)-7,11-Hexadecadienyl acetate |
| (E,E)-5,7-Dodecadienyl acetate | (Z,Z)-7,11-Hexadecadienal |
| (E,Z)-5,7-Dodecadien-1-ol | (Z,Z)-8,10-Hexadecadienyl acetate |
| (E,Z)-5,7-Dodecadienyl acetate | (E,Z)-8,11-Hexadecadienal |
| (E,Z)-5,7-Dodecadienal | (E,E)-9,11-Hexadecadienal |
| (Z,E)-5,7-Dodecadien-1-ol | (E,Z)-9,11-Hexadecadienyl acetate |
| (Z,E)-5,7-Dodecadienyl acetate | (E,Z)-9,11-Hexadecadienal |
| (Z,E)-5,7-Dodecadienal | (Z,E)-9,11-Hexadecadienal |
| (Z,Z)-5,7-Dodecadienyl acetate | (Z,Z)-9,11-Hexadecadienal |
| (Z,Z)-5,7-Dodecadienal | (E,E)-10,12-Hexadecadien-1-ol |
| (E,E)-7,9-Dodecadienyl acetate | (E,E)-10,12-Hexadecadienyl acetate |
| (E,Z)-7,9-Dodecadien-1-ol | (E,E)-10,12-Hexadecadienal |
| (E,Z)-7,9-Dodecadienyl acetate | (E,Z)-10,12-Hexadecadien-1-ol |
| (E,Z)-7,9-Dodecadienal | (E,Z)-10,12-Hexadecadienyl acetate |
| (Z,E)-7,9-Dodecadien-1-ol | (E,Z)-10,12-Hexadecadienal |
| (Z,E)-7,9-Dodecadienyl acetate | (Z,E)-10,12-Hexadecadienyl acetate |
| (Z,Z)-7,9-Dodecadien-1-ol | (Z,E)-10,12-Hexadecadienal |
| (Z,Z)-7,9-Dodecadienyl acetate | (Z,Z)-10,12-Hexadecadienal |
| (E,E)-8,10-Dodecadien-1-ol | (E,E)-11,13-Hexadecadien-1-ol |
| (E,E)-8,10-Dodecadienyl acetate | (E,E)-11,13-Hexadecadienyl acetate |
| (E,E)-8,10-Dodecadienal | (E,E)-11,13-Hexadecadienal |
| (E,Z)-8,10-Dodecadien-1-ol | (E,Z)-11,13-Hexadecadien-1-ol |
| (E,Z)-8,10-Dodecadienyl acetate | (E,Z)-11,13-Hexadecadienyl acetate |
| (E,Z)-8,10-Dodecadienal | (E,Z)-11,13-Hexadecadienal |
| (Z,E)-8,10-Dodecadien-1-ol | (Z,E)-11,13-Hexadecadien-1-ol |
| (Z,E)-8,10-Dodecadienyl acetate | (Z,E)-11,13-Hexadecadienyl acetate |
| (Z,E)-8,10-Dodecadienal | (Z,E)-11,13-Hexadecadienal |
| (Z,Z)-8,10-Dodecadien-1-ol | (Z,Z)-11,13-Hexadecadien-1-ol |
| (Z,Z)-8,10-Dodecadienyl acetate | (Z,Z)-11,13-Hexadecadienyl acetate |
| (Z,E,E)-3,6,8-Dodecatrien-1-ol | (Z,Z)-11,13-Hexadecadienal |
| (Z,Z,E)-3,6,8-Dodecatrien-1-ol | (E,E)-10,14-Hexadecadienal |
| (E)-2-Tridecenyl acetate | (Z,E)-11,14-Hexadecadienyl acetate |
| (Z)-2-Tridecenyl acetate | (E,E,Z)-4,6,10-Hexadecatrien-1-ol |
| (E)-3-Tridecenyl acetate | (E,E,Z)-4,6,10-Hexadecatrienyl acetate |
| (E)-4-Tridecenyl acetate | (E,Z,Z)-4,6,10-Hexadecatrien-1-ol |
| (Z)-4-Tridecenyl acetate | (E,Z,Z)-4,6,10-Hexadecatrienyl acetate |
| (Z)-4-Tridecenal | (E,E,Z)-4,6,11-Hexadecatrienyl acetate |
| (E)-6-Tridecenyl acetate | (E,E,Z)-4,6,11-Hexadecatrienal |
| (E)-7-Tridecenyl acetate | (Z,Z,E)-7,11,13-Hexadecatrienal |
| (E)-8-Tridecenyl acetate | (E,E,E)-10,12,14-Hexadecatrienyl acetate |
| (Z)-8-Tridecenyl acetate | (E,E,E)-10,12,14-Hexadecatrienal |
| (E)-9-Tridecenyl acetate | (E,E,Z)-10,12,14-Hexadecatrienyl acetate |
| (Z)-9-Tridecenyl acetate | (E,E,Z)-10,12,14-Hexadecatrienal |
| (Z)-10-Tridecenyl acetate | (E,E,Z,Z)-4,6,11,13-Hexadecatetraenal |
| (E)-11-Tridecenyl acetate | (E)-2-Heptadecenal |
| (Z)-11-Tridecenyl acetate | (Z)-2-Heptadecenal |
| (E,Z)-4,7-Tridecadienyl acetate | (E)-8-Heptadecen-1-ol |
| (Z,Z)-4,7-Tridecadien-1-ol | (E)-8-Heptadecenyl acetate |
| (E,Z)-4,7-Tridecadienyl acetate | (Z)-8-Heptadecen-1-ol |
| (E,Z)-5,9-Tridecadienyl acetate | (Z)-9-Heptadecenal |
| (Z,E)-5,9-Tridecadienyl acetate | (E)-10-Heptadecenyl acetate |
| (Z,Z)-5,9-Tridecadienyl acetate | (Z)-11-Heptadecen-1-ol |
| (Z,Z)-7,11-Tridecadienyl acetate | (Z)-11-Heptadecenyl acetate |
| (E,Z,Z)-4,7,10-Tridecatrienyl acetate | (E,E)-4,8-Heptadecadienyl acetate |
| (E)-3-Tetradecen-1-ol | (Z,Z)-8,10-Heptadecadien-1-ol |
| (E)-3-Tetradecenyl acetate | (Z,Z)-8,11-Heptadecadienyl acetate |
| (Z)-3-Tetradecen-1-ol | (E)-2-Octadecenyl acetate |
| (Z)-3-Tetradecenyl acetate | (E)-2-Octadecenal |
| (E)-5-Tetradecen-1-ol | (Z)-2-Octadecenyl acetate |
| (E)-5-Tetradecenyl acetate | (Z)-2-Octadecenal |
| (E)-5-Tetradecenal | (E)-9-Octadecen-1-ol |
| (Z)-5-Tetradecen-1-ol | (E)-9-Octadecenyl acetate |
| (Z)-5-Tetradecenyl acetate | (E)-9-Octadecenal |
| (Z)-5-Tetradecenal | (Z)-9-Octadecen-1-ol |
| (E)-6-Tetradecenyl acetate | (Z)-9-Octadecenyl acetate |
| (Z)-6-Tetradecenyl acetate | (Z)-9-Octadecenal |
| (E)-7-Tetradecen-1-ol | (E)-11-Octadecen-1-ol |
| (E)-7-Tetradecenyl acetate | (E)-11-Octadecenal |
| (Z)-7-Tetradecen-1-ol | (Z)-11-Octadecen-1-ol |
| (Z)-7-Tetradecenyl acetate | (Z)-11-Octadecenyl acetate |
| (Z)-7-Tetradecenal | (Z)-11-Octadecenal |
| (E)-8-Tetradecen-1-ol | (E)-13-Octadecenyl acetate |
| (Z)-8-Tetradecen-1-ol | (E)-13-Octadecenal |
| (Z)-8-Tetradecenyl acetate | (Z)-13-Octadecen-1-ol |
| (Z)-8-Tetradecenal | (Z)-13-Octadecenyl acetate |
| (E)-9-Tetradecen-1-ol | (Z)-13-Octadecenal |
| (E)-9-Tetradecenyl acetate | (E)-14-Octadecenal |
| (Z)-9-Tetradecen-1-ol | (E,Z)-2,13-Octadecadien-1-ol |
| (Z)-9-Tetradecenyl acetate | (E,Z)-2,13-Octadecadienyl acetate |
| (Z)-9-Tetradecenal | (E,Z)-2,13-Octadecadienal |
| (E)-10-Tetradecenyl acetate | (Z,E)-2,13-Octadecadienyl acetate |
| (Z)-10-Tetradecenyl acetate | (Z,Z)-2,13-Octadecadien-1-ol |
| (E)-11-Tetradecen-1-ol | (Z,Z)-2,13-Octadecadienyl acetate |
| (E)-11-Tetradecenyl acetate | (E,E)-3,13-Octadecadienyl acetate |
| (E)-11-Tetradecenal | (E,Z)-3,13-Octadecadienyl acetate |
| (Z)-11-Tetradecen-1-ol | (E,Z)-3,13-Octadecadienal |
| (Z)-11-Tetradecenyl acetate | (Z,E)-3,13-Octadecadienyl acetate |
| (Z)-11-Tetradecenal | (Z,Z)-3,13-Octadecadienyl acetate |
| (E)-12-Tetradecenyl acetate | (Z,Z)-3,13-Octadecadienal |
| (Z)-12-Tetradecenyl acetate | (E,E)-5,9-Octadecadien-1-ol |
| (E,E)-2,4-Tetradecadienal | (E,E)-5,9-Octadecadienyl acetate |
| (E,E)-3,5-Tetradecadienyl acetate | (E,E)-9,12-Octadecadien-1-ol |
| (E,Z)-3,5-Tetradecadienyl acetate | (Z,Z)-9,12-Octadecadienyl acetate |
| (Z,E)-3,5-Tetradecadienyl acetate | (Z,Z)-9,12-Octadecadienal |
| (E,Z)-3,7-Tetradecadienyl acetate | (Z,Z)-11,13-Octadecadienal |
| (E,Z)-3,8-Tetradecadienyl acetate | (E,E)-11,14-Octadecadienal |
| (E,Z)-4,9-Tetradecadienyl acetate | (Z,Z)-13,15-Octadecadienal |
| (E,Z)-4,9-Tetradecadienal | (Z,Z,Z)-3,6,9-Octadecatrienyl acetate |
| (E,Z)-4,10-Tetradecadienyl acetate | (E,E,E)-9, 12, 15-Octadecatrien-1-ol |
| (E,E)-5,8-Tetradecadienal | (Z,Z,Z)-9, 12, 15-Octadecatrienyl acetate |
| (Z,Z)-5,8-Tetradecadien-1-ol | (Z,Z,Z)-9, 12, 15-Octadecatrienal |
| (Z,Z)-5,8-Tetradecadienyl acetate | |
| (Z,Z)-5,8-Tetradecadienal | |
| (E,E)-8,10-Tetradecadien-1-ol | |
| (E,E)-8,10-Tetradecadienyl acetate | |
| (E,E)-8,10-Tetradecadienal | |
| (E,Z)-8,10-Tetradecadienyl acetate | |
| (E,Z)-8,10-Tetradecadienal | |
| (Z,E)-8,10-Tetradecadien-1-ol | |
| (Z,E)-8,10-Tetradecadienyl acetate | |
| (Z,Z)-8,10-Tetradecadienal | |
| (E,E)-9,11-Tetradecadienyl acetate | |
| (E,Z)-9,11-Tetradecadienyl acetate | |
| (Z,E)-9,11-Tetradecadien-1-ol | |
| (Z,E)-9,11-Tetradecadienyl acetate | |
| (Z,E)-9,11-Tetradecadienal | |
| (Z,Z)-9,11-Tetradecadien-1-ol | |
| (Z,Z)-9,11-Tetradecadienyl acetate | |
| (Z,Z)-9,11-Tetradecadienal | |
| (E,E)-9,12-Tetradecadienyl acetate | |
| (Z,E)-9,12-Tetradecadien-1-ol | |
| (Z,E)-9,12-Tetradecadienyl acetate | |
| (Z,E)-9,12-Tetradecadienal | |
| (Z,Z)-9,12-Tetradecadien-1-ol | |
| (Z,Z)-9,12-Tetradecadienyl acetate | |

In some aspects, the pheromones synthesized as taught in this disclosure include at least one pheromone listed in Table 2a to modulate the behavior of an insect listed in Table 2a. In other aspects, non-limiting examples of insect pheromones which can be synthesized using the recombinant microorganisms and methods disclosed herein include alcohols, aldehydes, and acetates listed in Table 2a. However, the microorganisms described herein are not limited to the synthesis of $C_6$-$C_{20}$ pheromones listed in Table 1 and Table 2a. Rather, the disclosed microorganisms can also be utilized in the synthesis of various $C_6$-$C_{24}$ mono- or poly-unsaturated fatty alcohols, aldehydes, and acetates, including fragrances, flavors, and polymer intermediates.

TABLE 2a

Exemplary pheromones that can be synthesized according to methods described in the present disclosure.

| Name | Structure | Example of Biological importance |
|---|---|---|
| (Z)-3-hexen-1-ol | 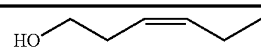 | See, Sugimoto et al. (2014) |
| (Z)-3-nonen-1-ol | 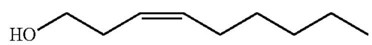 | West Indian Fruity Fly male sex pheromone |
| (Z)-5-decen-1-ol | 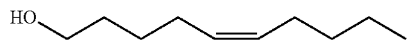 | |
| (Z)-5-decenyl acetate | 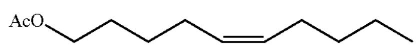 | *Agrotis segetum* sex pheromone component |
| (E)-5-decen-1-ol | 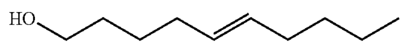 | *Anarsia lineatella* sex pheromone component |
| (E)-5-decenyl acetate | 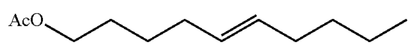 | *Anarsia lineatella* sex pheromone component |
| (Z)-7-dodecen-1-ol | 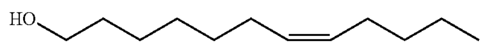 | |
| (Z)-7-dodecenyl acetate | 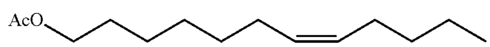 | *Pseudoplusia includens* sex pheromone<br>*Agrotis segetum* sex pheromone component |
| (E)-8-dodecen-1-ol | 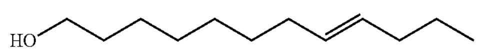 | Citrus Fruit Moth sex pheromone |
| (E)-8-dodecenyl acetate | 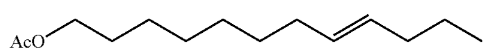 [SMILES: CCC/C=C/CCCCCCCOC(C)=O] | *Grapholitha molesta*, *Ecdytolopha aurantiana* sex pheromone component |
| (Z)-8-dodecen-1-ol | 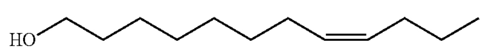 | *Grapholitha molesta*, *Ecdytolopha aurantiana* sex pheromone component |
| (Z)-8-dodecenyl acetate | 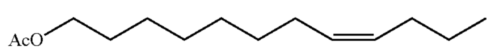 | *Grapholitha molesta* sex pheromone component |
| (Z)-9-dodecen-1-ol | 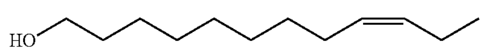 | |
| (Z)-9-dodecenyl acetate | 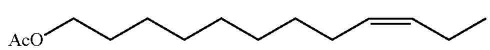 | *Eupoecilia ambiguella* sex pheromone |
| (E,E)-8,10-dodecadien-1-ol | 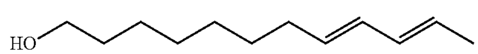 | *Cydia pomonella* |
| (7E,9Z)-dodecadienyl acetate | 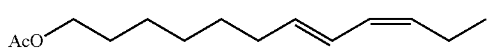 | *Lobesia botrana* |
| (Z)-9-tetradecen-1-ol | 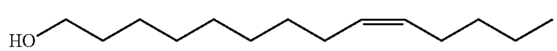 | |
| (Z)-9-tetradecenyl acetate | 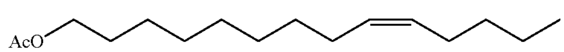 [SMILES: CCCC/C=C\CCCCCCCCOC(C)=O] | *Pandemis pyrusana, Naranga aenescens, Agrotis segetum* sex pheromone component |
| (Z)-11-tetradecen-1-ol | 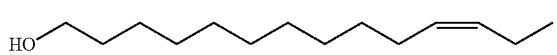 | |
| (Z)-11-tetradecenyl acetate | 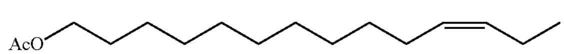 [SMILES: CC/C=C\CCCCCCCCCCOC(C)=O] | *Pandemis pyrusana, Choristoneura roseceana* sex pheromone component |
| (E)-11-tetradecen-1-ol | 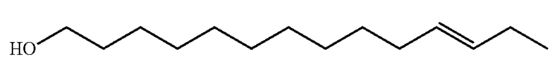 | |

TABLE 2a-continued

Exemplary pheromones that can be synthesized according to methods described in the present disclosure.

| Name | Structure | Example of Biological importance |
|---|---|---|
| (E)-11-tetradecenyl acetate | 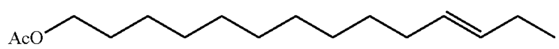 [SMILES: CC/C=C/CCCCCCCCCCOC(C)=O] | *Choristoneura roseceana, Crocidolomia pavonana* sex pheromone component |
| (Z)-7-hexadecen-1-ol | 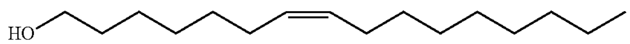 | |
| (Z)-7-hexadecenal | 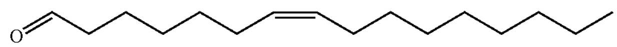 | *Diatraea considerata* sex pheromone component |
| (Z)-9-hexadecen-1-ol | 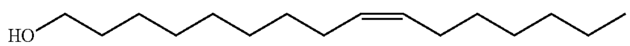 [SMILES: CCCCCC/C=C\CCCCCCCCO] | |
| (Z)-9-hexadecenal | 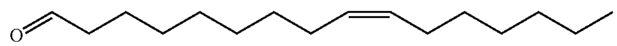 [SMILES: CCCCCC/C=C\CCCCCCCC=O] | *Helicoverpa zea, Helicoverpa armigera, Heliothis virescens* sex pheromone component |
| (Z)-9-hexadecenyl acetate | 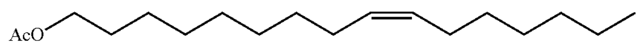 [SMILES: CCCCCC/C=C\CCCCCCCCOC(C)=O] | *Naranga aenescens* sex pheromone component |
| (Z)-11-hexadecen-1-ol | 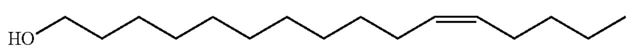 [SMILES: CCCC/C=C\CCCCCCCCCCO] | |
| (Z)-11-hexadecenal | 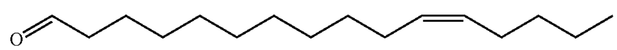 [SMILES: CCCC/C=C\CCCCCCCCCC=O] | *Platyptila carduidectyle, Heliothis virescens* sex pheromone *Helicoverpa zea, Helicoverpa armigera, Plutella xylostella, Diatraea considerate, Diatraea grandiosella, Diatraea saccharalis, Acrolepiopsis assectella* sex pheromone component |
| (Z)-11-hexadecenyl acetate | 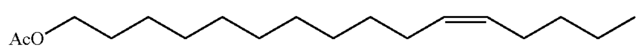 [SMILES: CCCC/C=C\CCCCCCCCCCOC(C)=O] | *Discestra trifolii* sex pheromone *Heliothis virescens, Plutella xylostella, Acrolepiopsis assectella, Crocidolomia pavonana, Naranga aenescens* sex pheromone component |
| (Z,Z)-11,13-hexadecadienal | 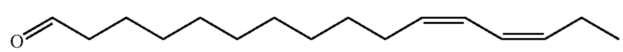 | *Amyelosis transitella* |
| (Z,Z)-11,13-hexadecadien-1-ol | 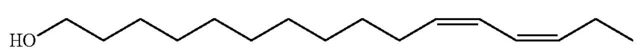 [SMILES: CC/C=C\C=C/CCCCCCCCCCO] | *Amyelosis transitella* |
| (11Z,13E)-hexadecadien-1-ol | 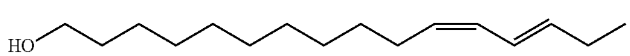 | *Amyelosis transitella* |
| (9Z,11E)-hexadecadienal | 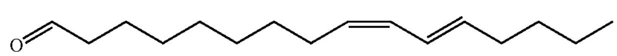 [SMILES: CCCC/C=C/C=C\CCCCCCCC=O] | |
| (Z)-13-octadecen-1-ol | 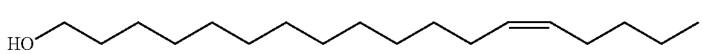 [SMILES: CCCC/C=C\CCCCCCCCCCCCO] | |
| (Z)-13-octadecenal | 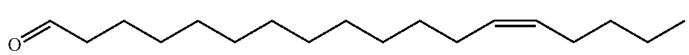 [SMILES: CCCC/C=C\CCCCCCCCCCCC=O] | *Diatraea considerata, Diatraea grandiosella* sex pheromone component |
| (Z,Z,Z,Z,Z)-3,6,9,12,15-tricosapentaene | 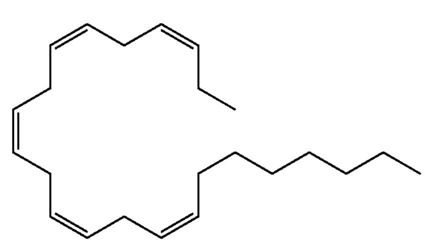 [SMILES: CC/C=C\C/C=C\C/C=C\C/C=C\C/C=C\CCCCCCC] | *Amyelosis transitella* |

Most pheromones comprise a hydrocarbon skeleton with the terminal hydrogen substituted by a functional group (Ryan M F (2002). Insect Chemoreception. Fundamental and Applied. Kluwer Academic Publishers). Table 2b shows some common functional groups, along with their formulas, prefixes and suffixes. The presence of one or more double bonds, generated by the loss of hydrogens from adjacent carbons, determines the degree of unsaturation of the molecule and alters the designation of a hydrocarbon from -ane (no multiple bonds) to -ene. The presence of two and three double bonds is indicated by ending the name with -diene and -triene, respectively. The position of each double bond is represented by a numeral corresponding to that of the carbon from which it begins, with each carbon numbered from that attached to the functional group. The carbon to which the functional group is attached is designated -1-. Pheromones may have, but are not limited to, hydrocarbon chain lengths numbering 10 (deca-), 12 (dodeca-), 14 (tetradeca-), 16 (hexadeca-), or 18 (octadeca-) carbons long. The presence of a double bond has another effect. It precludes rotation of the molecule by fixing it in one of two possible configurations, each representing geometric isomers that are different molecules. These are designated either E (from the German word Entgegen, opposite) or Z (Zusammen, together), when the carbon chains are connected on the opposite (trans) or same (cis) side, respectively, of the double bond.

TABLE 2b

Prefixes and suffixes for common functional groups

| Functional group | Formula | Prefix | Suffix |
| --- | --- | --- | --- |
| Alcohol | —OH | Hydroxy- | -ol |
| Aldehyde | —CH=O | Formyl- | -al |
| Amine | —NH$_2$ | Amino- | -amine |
| Carboxylic acid | —COOH | Carboxy- | -oic acid |
| Ester | —COOR | R-oxycarbonyl- | -R-oate |
| Ketone | >C=O | Oxo- | -one |

From Howse, PE, Stevens, IDR and Jones, OT (1998). Insect pheromones and their use in pest management. London: Chapman and Hall.

Pheromones described herein can be referred to using IUPAC nomenclature or various abbreviations or variations known to one skilled in the art. For example, (11Z)-hexadecen-1-al, can also be written as Z-11-hexadecen-1-al, Z-11-hexadecenal, or Z-x-y:Ald, wherein x represents the position of the double bond and y represents the number of carbons in the hydrocarbon skeleton. Abbreviations used herein and known to those skilled in the art to identify functional groups on the hydrocarbon skeleton include "Ald," indicating an aldehyde, "OH," indicating an alcohol, and "Ac," indicating an acetyl. Also, the number of carbons in the chain can be indicated using numerals rather than using the written name. Thus, as used herein, an unsaturated carbon chain comprised of sixteen carbons can be written as hexadecene or 16.

Similar abbreviation and derivations are used herein to describe pheromone precursors. For example, the fatty acyl-CoA precursors of (11Z)-hexadecen-1-al can be identified as (11Z)-hexadecenyl-CoA or Z-11-16:Acyl-CoA.

The present disclosure relates to the synthesis of mono- or poly-unsaturated $C_6$-$C_{24}$ fatty alcohols, aldehydes, and acetates using a recombinant microorganism comprised of one or more heterologous enzymes, which catalyze substrate to product conversions for one or more steps in the synthesis process.

Desaturase

The present disclosure describes enzymes that desaturate fatty acyl substrates to corresponding unsaturated fatty acyl substrates.

In some embodiments, a desaturase is used to catalyze the conversion of a fatty acyl-CoA or acyl-ACP to a corresponding unsaturated fatty acyl-CoA or acyl-ACP. A desaturase is an enzyme that catalyzes the formation of a carbon-carbon double bond in a saturated fatty acid or fatty acid derivative, e.g., fatty acyl-CoA or fatty acyl-ACP (collectively referred to herein as "fatty acyl"), by removing at least two hydrogen atoms to produce a corresponding unsaturated fatty acid/acyl. Desaturases are classified with respect to the ability of the enzyme to selectively catalyze double bond formation at a subterminal carbon relative to the methyl end of the fatty acid/acyl or a subterminal carbon relative to the carbonyl end of the fatty acid/acyl. Omega (ω) desaturases catalyze the formation of a carbon-carbon double bond at a fixed subterminal carbon relative to the methyl end of a fatty acid/acyl. For example, an $\omega^3$ desaturase catalyzes the formation of a double bond between the third and fourth carbon relative the methyl end of a fatty acid/acyl. Delta (Δ) desaturases catalyze the formation of a carbon-carbon double bond at a specific position relative to the carboxyl group of a fatty acid or the carbonyl group of a fatty acyl CoA. For example, a $\Delta^9$ desaturase catalyzes the formation of a double bond between the $C_9$ and $C_{10}$ carbons with respect to the carboxyl end of the fatty acid or the carbonyl group of a fatty acyl CoA.

As used herein, a desaturase can be described with reference to the location in which the desaturase catalyzes the formation of a double bond and the resultant geometric configuration (i.e., E/Z) of the unsaturated hydrocarbon. Accordingly, as used herein, a Z9 desaturase refers to a Δ desaturase that catalyzes the formation of a double bond between the $C_9$ and $C_{10}$ carbons with respect to the carbonyl end of a fatty acid/acyl, thereby orienting two hydrocarbons on opposing sides of the carbon-carbon double bonds in the cis or Z configuration. Similarly, as used herein, a Z11 desaturase refers to a Δ desaturase that catalyzes the formation of a double bond between the $C_{11}$ and $C_{12}$ carbons with respect to the carbonyl end of a fatty acid/acyl.

Desaturases have a conserved structural motif. This sequence motif of transmembrane desaturases is characterized by [HX3-4HX7-41(3 non-His)HX2-3(1 nonHis) HHX61-189(40 non-His)HX2-3(1 non-His)HH]. The sequence motif of soluble desaturases is characterized by two occurrences of [D/EEXXH].

In some embodiments, the desaturase is a fatty acyl-CoA desaturase that catalyzes the formation of a double bond in a fatty acyl-CoA. In some such embodiments, the fatty acyl-CoA desaturase described herein is capable of utilizing a fatty acyl-CoA as a substrate that has a chain length of 6, 7, 8, 9, 10, 11, 12, 13, 14, 15, 16, 17, 18, 19, 20, 21, 22, 23, or 24 carbon atoms. Thus, the desaturase used in the recombinant microorganism can be selected based on the chain length of the substrate.

In some embodiments, the fatty acyl desaturase described herein is capable of catalyzing the formation of a double bond at a desired carbon relative to the terminal CoA on the unsaturated fatty acyl-CoA. Thus, in some embodiments, a desaturase can be selected for use in the recombinant microorganism which catalyzes double bond insertion at the 3, 4, 5, 6, 7, 8, 9, 10, 11, 12, or 13 position with respect to the carbonyl group on a fatty acyl-CoA.

In some embodiments, the fatty acyl desaturase described herein is capable of catalyzing the formation of a double bond in a saturated fatty acyl-CoA such that the resultant unsaturated fatty acyl-CoA has a cis or trans (i.e., Z or E) geometric configuration.

In some embodiments, the desaturase is a fatty acyl-ACP desaturase that catalyzes the formation of a double bond in a fatty acyl-ACP. In some embodiments, the fatty acyl-ACP desaturase described herein is capable of utilizing a fatty acyl-CoA as a substrate that has a chain length of 6, 7, 8, 9, 10, 11, 12, 13, 14, 15, 16, 17, 18, 19, 20, 21, 22, 23, or 24 carbon atoms. Thus, the desaturase used in the recombinant microorganism can be selected based on the chain length of the substrate.

In some embodiments, the fatty acyl-ACP desaturase described herein is capable of catalyzing the formation of a double bond at a desired carbon relative to the terminal carbonyl on the unsaturated fatty acyl-ACP. Thus, in some embodiments, a desaturase can be selected for use in the recombinant microorganism which catalyzes double bond insertion at the 3, 4, 5, 6, 7, 8, 9, 10, 11, 12, or 13 position with respect to the carbonyl group on a fatty acyl-ACP.

In some embodiments, the fatty acyl desaturase described herein is capable of catalyzing the formation of a double bond in a saturated fatty acyl-CoA such that the resultant unsaturated fatty acyl-ACP has a cis or trans (i.e., Z or E) geometric configuration.

In one embodiment, the fatty acyl desaturase is a Z11 desaturase. In some embodiments, a nucleic acid sequence encoding a Z11 desaturase from organisms of the species *Agrotis segetum, Amyelois transitella, Argyrotaenia velutiana, Choristoneura rosaceana, Lampronia capitella, Trichoplusia ni, Helicoverpa zea,* or *Thalassiosira pseudonana* is codon optimized. In some embodiments, the Z11 desaturase comprises a sequence selected from SEQ ID NOs: 9, 18, 24 and 26 from *Trichoplusia ni.* In other embodiments, the Z11 desaturase comprises a sequence selected from SEQ ID NOs: 10 and 16 from *Agrotis segetum.* In some embodiments, the Z11 desaturase comprises a sequence selected from SEQ ID NOs: 11 and 23 from *Thalassiosira pseudonana.* In certain embodiments, the Z11 desaturase comprises a sequence selected from SEQ ID NOs: 12, 17 and 30 from *Amyelois transitella.* In further embodiments, the Z11 desaturase comprises a sequence selected from SEQ ID NOs: 13, 19, 25, 27 and 31 from *Helicoverpa zea.* In some embodiments, the Z11 desaturase comprises a chimeric polypeptide. In some embodiments, a complete or partial Z11 desaturase is fused to another polypeptide. In certain embodiments, the N-terminal native leader sequence of a Z11 desaturase is replaced by an oleosin leader sequence from another species. In certain embodiments, the Z11 desaturase comprises a sequence selected from SEQ ID NOs: 15, 28 and 29.

In one embodiment, the fatty acyl desaturase is a Z9 desaturase. In some embodiments, a nucleic acid sequence encoding a Z9 desaturase is codon optimized. In some embodiments, the Z9 desaturase comprises a sequence set forth in SEQ ID NO: 20 from *Ostrinia furnacalis.* In other embodiments, the Z9 desaturase comprises a sequence set forth in SEQ ID NO: 21 from *Lampronia capitella.* In some embodiments, the Z9 desaturase comprises a sequence set forth in SEQ ID NO: 22 from *Helicoverpa zea.*

Fatty Acyl Reductase

The present disclosure describes enzymes that reduce fatty acyl substrates to corresponding fatty alcohols or aldehydes.

In some embodiments, a fatty alcohol forming fatty acyl-reductase is used to catalyze the conversion of a fatty acyl-CoA to a corresponding fatty alcohol. In some embodiments, a fatty aldehyde forming fatty acyl-reductase is used to catalyze the conversion of a fatty acyl-ACP to a corresponding fatty aldehyde. A fatty acyl reductase is an enzyme that catalyzes the reduction of a fatty acyl-CoA to a corresponding fatty alcohol or the reduction of a fatty acyl-ACP to a corresponding fatty aldehyde. A fatty acyl-CoA and fatty acyl-ACP has a structure of R—(CO)—S—$R_1$, wherein R is a $C_6$ to $C_{24}$ saturated, unsaturated, linear, branched or cyclic hydrocarbon, and $R_1$ represents CoA or ACP. In a particular embodiment, R is a $C_6$ to $C_{24}$ saturated or unsaturated linear hydrocarbon. "CoA" is a non-protein acyl carrier group involved in the synthesis and oxidation of fatty acids. "ACP" is an acyl carrier protein, i.e., a polypeptide or protein subunit, of fatty acid synthase used in the synthesis of fatty acids.

Thus, in some embodiments, the disclosure provides for a fatty alcohol forming fatty acyl-reductase which catalyzes the reduction of a fatty acyl-CoA to the corresponding fatty alcohol. For example, R—(CO)—S-CoA is converted to R—$CH_2OH$ and CoA-SH when two molecules of NAD(P)H are oxidized to NAD(P)$^+$. Accordingly, in some such embodiments, a recombinant microorganism described herein can include a heterologous fatty alcohol forming fatty acyl-reductase, which catalyzes the reduction a fatty acyl-CoA to the corresponding fatty alcohol. In an exemplary embodiment, a recombinant microorganism disclosed herein includes at least one exogenous nucleic acid molecule encoding a fatty alcohol forming fatty-acyl reductase which catalyzes the conversion of a mono- or poly-unsaturated $C_6$-$C_{24}$ fatty acyl-CoA into the corresponding mono- or poly-unsaturated $C_6$-$C_{24}$ fatty alcohol.

In other embodiments, the disclosure provides for a fatty aldehyde forming fatty acyl-reductase which catalyzes the reduction of a fatty acyl-ACP to the corresponding fatty aldehyde. For example, R—(CO)—S-ACP is converted to R—(CO)—H and ACP-SH when one molecule of NAD(P)H is oxidized to NAD(P)$^+$. In some such embodiments, a recombinant microorganism described herein can include a heterologous fatty aldehyde forming fatty acyl-reductase, which catalyzes the reduction a fatty acyl-ACP to the corresponding fatty aldehyde. In an exemplary embodiment, a recombinant microorganism disclosed herein includes at least one exogenous nucleic acid molecule encoding a fatty aldehyde forming fatty-acyl reductase which catalyzes the conversion of a mono- or poly-unsaturated $C_6$-$C_{24}$ fatty acyl-ACP into the corresponding mono- or poly-unsaturated $C_6$-$C_{24}$ fatty aldehyde.

In some embodiments, a nucleic acid sequence encoding a fatty-acyl reductase from organisms of the species *Agrotis segetum, Spodoptera littoralis,* or *Helicoverpa amigera* is codon optimized. In some embodiments, the fatty acyl reductase comprises a sequence set forth in SEQ ID NO: 1 from *Agrotis segetum.* In other embodiments, the fatty acyl reductase comprises a sequence set forth in SEQ ID NO: 2 from *Spodoptera littoralis.* In some embodiments, the fatty acyl reductase comprises a sequence selected from SEQ ID NOs: 3 and 32 from *Helicoverpa armigera.*

Acyl-ACP Synthetase

The present disclosure describes enzymes that ligate a fatty acid to the corresponding fatty acyl-ACP.

In some embodiments, an acyl-ACP synthetase is used to catalyze the conversion of a fatty acid to a corresponding fatty acyl-ACP. An acyl-ACP synthetase is an enzyme capable of ligating a fatty acid to ACP to produce a fatty acid acyl-ACP. In some embodiments, an acyl-ACP synthetase can be used to catalyze the conversion of a fatty acid to a corresponding fatty acyl-ACP. In some embodiments, the acyl-ACP synthetase is a synthetase capable of utilizing a fatty acid as a substrate that has a chain length of 6, 7, 8, 9, 10, 11, 12, 13, 14, 15, 16, 17, 18, 19, 20, 21, 22, 23, or 24 carbon atoms. In one such embodiment, a recombinant microorganism described herein can include a heterologous acyl-ACP synthetase, which catalyzes the conversion of a fatty acid to a corresponding fatty acyl-ACP. In an exemplary embodiment, a recombinant microorganism disclosed herein includes at least one exogenous nucleic acid molecule which encodes an acyl-ACP synthetase that catalyzes the conversion of a saturated $C_6$-$C_{24}$ fatty acid to a corresponding saturated $C_6$-$C_{24}$ fatty acyl-ACP.

Fatty Acid Synthase Complex

The present disclosure describes enzymes that catalyze the elongation of a carbon chain in fatty acid.

In some embodiments, a fatty acid synthase complex is used to catalyze initiation and elongation of a carbon chain in a fatty acid. A "fatty acid synthase complex" refers to a group of enzymes that catalyzes the initiation and elongation of a carbon chain on a fatty acid. The ACP along with the enzymes in the fatty acid synthase (FAS) pathway control the length, degree of saturation, and branching of the fatty acids produced. The steps in this pathway are catalyzed by enzymes of the fatty acid biosynthesis (fab) and acetyl-CoA carboxylase (acc) gene families. Depending upon the desired product, one or more of these genes can be attenuated, expressed or over-expressed. In exemplary embodiments, one or more of these genes is over-expressed.

There are two principal classes of fatty acid synthases. Type I (FAS I) systems utilize a single large, multifunctional polypeptide and are common to both mammals and fungi (although the structural arrangement of fungal and mammalian synthases differ). The Type I FAS system is also found in the CMN group of bacteria (corynebacteria, mycobacteria, and nocardia). The Type II FAS (FAS II) is characterized by the use of discrete, monofunctional enzymes for fatty acid synthesis, and is found in archaea and bacteria.

The mechanism of FAS I and FAS II elongation and reduction is the substantially similar, as the domains of the FAS I multienzyme polypeptides and FAS II enzymes are largely conserved.

Fatty acids are synthesized by a series of decarboxylative Claisen condensation reactions from acetyl-CoA and malonyl-CoA. The steps in this pathway are catalyzed by enzymes of the fatty acid biosynthesis (fab) and acetyl-CoA carboxylase (acc) gene families. For a description of this pathway, see, e.g., Heath et al., *Prog. Lipid Res.* 40:467, 2001, which is herein incorporated by reference in its entirety. Without being limited by theory, in bacteria, acetyl-CoA is carboxylated by acetyl-CoA carboxylase (Acc, a multi-subunit enzyme encoded by four separate genes, accABCD), to form malonyl-CoA. In yeast, acetyl-CoA is carboxylated by the yeast equivalents of the acetyl-CoA carboxylase, encoded by ACC1 and ACC2. In bacteria, the malonate group is transferred to ACP by malonyl-CoA:ACP transacylase (FabD) to form malonyl-ACP. In yeast, a malonyl-palmityl tranferase domain adds malonyl from malonyl-CoA to the ACP domain of the FAS complex. A condensation reaction then occurs, where malonyl-ACP merges with acyl-CoA, resulting in β-ketoacyl-ACP. In this manner, the hydrocarbon substrate is elongated by 2 carbons.

Following elongation, the β-keto group is reduced to the fully saturated carbon chain by the sequential action of a keto-reductase (KR), dehydratase (DH), and enol reductase (ER). The elongated fatty acid chain is carried between these active sites while attached covalently to the phosphopantetheine prosthetic group of ACP. First, the β-ketoacyl-ACP is reduced by NADPH to form β-hydroxyacyl-ACP. In bacteria, this step is catalyzed by β-ketoacyl-ACP reductase (FabG). The equivalent yeast reaction is catalyzed by the ketoreductase (KR) domain of FAS. β-hydroxyacyl-ACP is then dehydrated to form trans-2-enoyl-ACP, which is catalyzed by either β-hydroxyacyl-ACP dehydratase/isomerase (FabA) or β-hydroxyacyl-ACP dehydratase (FabZ) in bacteria or the dehydratase (DH) domain of FAS in yeast. NADPH-dependent trans-2-enoyl-ACP reductase I, II, or III (FabI, FabK, and FabL, respectively) in bacteria and the enol reductase (ER) domain of FAS in yeast reduces trans-2-enoyl-ACP to form acyl-ACP. Subsequent cycles are started by the condensation of malonyl-ACP with acyl-ACP by β-ketoacyl-ACP synthase I or β-ketoacyl-ACP synthase II (FabB and FabF, respectively, in bacteria or the beta-ketoacyl synthase (KS) domain in yeast).

In some embodiments, a fatty acid synthase complex can be used to catalyze elongation of a fatty acyl-ACP to a corresponding fatty acyl-ACP with a two carbon elongation relative to the substrate.

Dehydrogenase

The present disclosure describes enzymes that catalyze the conversion of a fatty aldehyde to a fatty alcohol. In some embodiments, an alcohol dehydrogenase (ADH, Table 3) is used to catalyze the conversion of a fatty aldehyde to a fatty alcohol. A number of ADHs identified from alkanotrophic organisms, *Pseudomonas fluorescens* NRRL B-1244 (Hou et al. 1983), *Pseudomonas butanovora* ATCC 43655 (Vangnai and Arp 2001), and *Acinetobacter* sp. strain M-1 (Tani et al. 2000), have shown to be active on short to medium-chain alkyl alcohols ($C_2$ to $C_{14}$). Additionally, commercially available ADHs from Sigma, Horse liver ADH and Baker's yeast ADH have detectable activity for substrates with length $C_{10}$ and greater. The reported activities for the longer fatty alcohols may be impacted by the difficulties in solubilizing the substrates. For the yeast ADH from Sigma, little to no activity is observed for $C_{12}$ to $C_{14}$ aldehydes by (Tani et al. 2000), however, activity for $C_{12}$ and $C_{16}$ hydroxy-ω-fatty acids has been observed (Lu et al. 2010). Recently, two ADHs were characterized from *Geobacillus thermodenitrificans* NG80-2, an organism that degrades $C_{15}$ to $C_{36}$ alkanes using the LadA hydroxylase. Activity was detected from methanol to 1-triacontanol ($C_{30}$) for both ADHs, with 1-octanol being the preferred substrate for ADH2 and ethanol for ADH1 (Liu et al. 2009).

The use of ADHs in whole-cell bioconversions has been mostly focused on the production of chiral alcohols from ketones (Ernst et al. 2005) (Schroer et al. 2007). Using the ADH from *Lactobacillus brevis* and coupled cofactor regeneration with isopropanol, Schroer et al. reported the production of 797 g of (R)-methyl-3 hydroxybutanoate from methyl acetoacetate, with a space time yield of 29 g/L/h (Schroer et al. 2007). Examples of aliphatic alcohol oxidation in whole-cell transformations have been reported with commercially obtained *S. cerevisiae* for the conversion of hexanol to hexanal (Presecki et al. 2012) and 2-heptanol to 2-heptanone (Cappaert and Larroche 2004).

TABLE 3

Exemplary alcohol dehydrogenase enzymes.

| Organism | Gene Name | Accession No. |
|---|---|---|
| *Bactrocera oleae* (Olive fruit fly) (*Dacus oleae*) | ADH | Q9NAR7 |

TABLE 3-continued

Exemplary alcohol dehydrogenase enzymes.

| Organism | Gene Name | Accession No. |
|---|---|---|
| *Cupriavidus necator* (*Alcaligenes eutrophus*) (*Ralstonia eutropha*) | adh | P14940 |
| *Drosophila adiastola* (Fruit fly) (*Idiomyia adiastola*) | Adh | Q00669 |
| *Drosophila affinidisjuncta* (Fruit fly) (*Idiomyia affinidisjuncta*) | Adh | P21518 |
| *Drosophila ambigua* (Fruit fly) | Adh | P25139 |
| *Drosophila borealis* (Fruit fly) | Adh | P48584 |
| *Drosophila differens* (Fruit fly) | Adh | P22245 |
| *Drosophila equinoxialis* (Fruit fly) | Adh | Q9NG42 |
| *Drosophila flavomontana* (Fruit fly) | Adh | P48585 |
| *Drosophila guanche* (Fruit fly) | Adh | Q09009 |
| *Drosophila hawaiiensis* (Fruit fly) | Adh | P51549 |
| *Drosophila heteroneura* (Fruit fly) | Adh | P21898 |
| *Drosophila immigrans* (Fruit fly) | Adh | Q07588 |
| *Drosophila insularis* (Fruit fly) | Adh | Q9NG40 |
| *Drosophila lebanonensis* (Fruit fly) (*Scaptodrosophila lebanonensis*) | Adh | P10807 |
| *Drosophila mauritiana* (Fruit fly) | Adh | P07162 |
| *Drosophila madeirensis* (Fruit fly) | Adh | Q09010 |
| *Drosophila mimica* (Fruit fly) (*Idiomyia mimica*) | Adh | Q00671 |
| *Drosophila nigra* (Fruit fly) (*Idiomyia nigra*) | Adh | Q00672 |
| *Drosophila orena* (Fruit fly) | Adh | P07159 |
| *Drosophila pseudoobscura bogotana* (Fruit fly) | Adh | P84328 |
| *Drosophila picticornis* (Fruit fly) (*Idiomyia picticornis*) | Adh | P23361 |
| *Drosophila planitibia* (Fruit fly) | Adh | P23277 |
| *Drosophila paulistorum* (Fruit fly) | Adh | Q9U8S9 |
| *Drosophila silvestris* (Fruit fly) | Adh | P23278 |
| *Drosophila subobscura* (Fruit fly) | Adh | Q03384 |
| *Drosophila teissieri* (Fruit fly) | Adh | P28484 |
| *Drosophila tsacasi* (Fruit fly) | Adh | P51550 |
| *Fragaria ananassa* (Strawberry) | ADH | P17648 |
| *Malus domestica* (Apple) (*Pyrus malus*) | ADH | P48977 |
| *Scaptomyza albovittata* (Fruit fly) | Adh | P25988 |
| *Scaptomyza crassifemur* (Fruit fly) (*Drosophila crassifemur*) | Adh | Q00670 |
| *Sulfolobus sp.* (strain RC3) | adh | P50381 |
| *Zaprionus tuberculatus* (Vinegar fly) | Adh | P51552 |
| *Geobacillus stearothermophilus* (*Bacillus stearothermophilus*) | adh | P42327 |
| *Drosophila mayaguana* (Fruit fly) | Adh, Adh2 | P25721 |
| *Drosophila melanogaster* (Fruit fly) | Adh, CG3481 | P00334 |
| *Drosophila pseudoobscura pseudoobscura* (Fruit fly) | Adh, GA17214 | Q6LCE4 |
| *Drosophila simulans* (Fruit fly) | Adh, GD23968 | Q24641 |
| *Drosophila yakuba* (Fruit fly) | Adh, GE19037 | P26719 |
| *Drosophila ananassae* (Fruit fly) | Adh, GF14888 | Q50L96 |
| *Drosophila erecta* (Fruit fly) | Adh, GG25120 | P28483 |
| *Drosophila grimshawi* (Fruit fly) (*Idiomyia grimshawi*) | Adh, GH13025 | P51551 |
| *Drosophila willistoni* (Fruit fly) | Adh, GK18290 | Q05114 |
| *Drosophila persimilis* (Fruit fly) | Adh, GL25993 | P37473 |
| *Drosophila sechellia* (Fruit fly) | Adh, GM15656 | Q9GN94 |
| *Cupriavidus necator* (strain ATCC 17699/H16/DSM 428/Stanier 337) (*Ralstonia eutropha*) | adh, H16_A0757 | Q0KDL6 |
| *Mycobacterium tuberculosis* (strain CDC 1551/Oshkosh) | adh, MT1581 | P9WQC2 |
| *Staphylococcus aureus* (strain MW2) | adh, MW0568 | Q8NXU1 |
| *Mycobacterium tuberculosis* (strain ATCC 25618/H37Rv) | adh, Rv1530 | P9WQC3 |
| *Staphylococcus aureus* (strain N315) | adh, SA0562 | Q7A742 |
| *Staphylococcus aureus* (strain bovine RF122/ET3-1) | adh, SAB0557 | Q2YSX0 |
| *Sulfolobus acidocaldarius* (strain ATCC 33909/DSM 639/JCM 8929/NBRC 15157/NCIMB 11770) | adh, Saci_2057 | Q4J781 |
| *Staphylococcus aureus* (strain COL) | adh, SACOL0660 | Q5HI63 |
| *Staphylococcus aureus* (strain NCTC 8325) | adh, SAOUHSC_00608 | Q2G0G1 |
| *Staphylococcus aureus* (strain MRSA252) | adh, SAR0613 | Q6GJ63 |
| *Staphylococcus aureus* (strain MSSA476) | adh, SAS0573 | Q6GBM4 |
| *Staphylococcus aureus* (strain USA300) | adh, SAUSA300_0594 | Q2FJ31 |
| *Staphylococcus aureus* (strain Mu50/ATCC 700699) | adh, SAV0605 | Q99W07 |
| *Staphylococcus epidermidis* (strain ATCC 12228) | adh, SE_0375 | Q8CQ56 |
| *Staphylococcus epidermidis* (strain ATCC 35984/RP62A) | adh, SERP0257 | Q5HRD6 |
| *Sulfolobus solfataricus* (strain ATCC 35092/DSM 1617/JCM 11322/P2) | adh, SSO2536 | P39462 |
| *Sulfolobus tokodaii* (strain DSM 16993/JCM 10545/NBRC 100140/7) | adh, STK_25770 | Q96XE0 |
| *Anas platyrhynchos* (Domestic duck) (*Anas boschas*) | ADH1 | P30350 |
| *Apteryx australis* (Brown kiwi) | ADH1 | P49645 |
| *Ceratitis capitata* (Mediterranean fruit fly) (*Tephritis capitata*) | ADH1 | P48814 |
| *Ceratitis cosyra* (Mango fruit fly) (*Trypeta cosyra*) | ADH1 | Q70UN9 |
| *Gallus gallus* (Chicken) | ADH1 | P23991 |
| *Columba livia* (Domestic pigeon) | ADH1 | P86883 |
| *Coturnix coturnix japonica* (Japanese quail) (*Coturnix japonica*) | ADH1 | P19631 |
| *Drosophila hydei* (Fruit fly) | Adh1 | P23236 |
| *Drosophila montana* (Fruit fly) | Adh1 | P48586 |
| *Drosophila mettleri* (Fruit fly) | Adh1 | P22246 |
| *Drosophila mulleri* (Fruit fly) | Adh1 | P07161 |
| *Drosophila navojoa* (Fruit fly) | Adh1 | P12854 |
| *Geomys attwateri* (Attwater's pocket gopher) (*Geomys bursarius attwateri*) | ADH1 | Q9Z2M2 |
| *Geomys bursarius* (Plains pocket gopher) | ADH1 | Q64413 |
| *Geomys knoxjonesi* (Knox Jones's pocket gopher) | ADH1 | Q64415 |
| *Hordeum vulgare* (Barley) | ADH1 | P05336 |
| *Kluyveromyces marxianus* (Yeast) (*Candida kefyr*) | ADH1 | Q07288 |
| *Zea mays* (Maize) | ADH1 | P00333 |
| *Mesocricetus auratus* (Golden hamster) | ADH1 | P86885 |
| *Pennisetum americanum* (Pearl millet) (*Pennisetum glaucum*) | ADH1 | P14219 |
| *Petunia hybrida* (Petunia) | ADH1 | P25141 |
| *Oryctolagus cuniculus* (Rabbit) | ADH1 | Q03505 |
| *Solanum tuberosum* (Potato) | ADH1 | P14673 |
| *Struthio camelus* (Ostrich) | ADH1 | P80338 |
| *Trifolium repens* (Creeping white clover) | ADH1 | P13603 |
| *Zea luxurians* (Guatemalan teosinte) (*Euchlaena luxurians*) | ADH1 | Q07264 |
| *Saccharomyces cerevisiae* (strain ATCC 204508/S288c) (Baker's yeast) | ADH1, ADC1, YOL086C, O0947 | P00330 |
| *Arabidopsis thaliana* (Mouse-ear cress) | ADH1, ADH, At1g77120, F22K20.19 | P06525 |
| *Schizosaccharomyces pombe* (strain 972/ATCC 24843) (Fission yeast) | adh1, adh, SPCC13B11.01 | P00332 |
| *Drosophila lacicola* (Fruit fly) | Adh1, Adh-1 | Q27404 |
| *Mus musculus* (Mouse) | Adh1, Adh-1 | P00329 |
| *Peromyscus maniculatus* (North American deer mouse) | ADH1, ADH-1 | P41680 |
| *Rattus norvegicus* (Rat) | Adh1, Adh-1 | P06757 |
| *Drosophila virilis* (Fruit fly) | Adh1, Adh-1, GJ18208 | B4M8Y0 |
| *Scheffersomyces stipitis* (strain ATCC 58785/CBS 6054/NBRC 10063/NRRL Y-11545) (Yeast) (*Pichia stipitis*) | ADH1, ADH2, PICST_68558 | O00097 |
| *Aspergillus flavus* (strain ATCC 200026/FGSC A1120/NRRL 3357/JCM 12722/SRRC 167) | adh1, AFLA_048690 | P41747 |
| *Neurospora crassa* (strain ATCC 24698/74-OR23-1A/CBS 708.71/DSM | adh-1, B17C10.210, | Q9P6C8 |

TABLE 3-continued

Exemplary alcohol dehydrogenase enzymes.

| Organism | Gene Name | Accession No. |
|---|---|---|
| 1257/FGSC 987) | NCU01754 | |
| *Candida albicans* (Yeast) | ADH1, CAD | P43067 |
| *Oryza sativa* subsp. *japonica* (Rice) | ADH1, DUPR11.3, Os11g0210300, LOC_Os11g10480, OsJ_032001 | Q2R8Z5 |
| *Drosophila mojavensis* (Fruit fly) | Adh1, GI17644 | P09370 |
| *Kluyveromyces lactis* (strain ATCC 8585/CBS 2359/DSM 70799/NBRC 1267/NRRL Y-1140/WM37) (Yeast) (*Candida sphaerica*) | ADH1, KLLA0F21010g | P20369 |
| *Oryza sativa* subsp. *indica* (Rice) | ADH1, OsI_034290 | Q75ZX4 |
| *Pongo abelii* (Sumatran orangutan) (*Pongo pygmaeus abelii*) | ADH1A | Q5RBP7 |
| *Homo sapiens* (Human) | ADH1A, ADH1 | P07327 |
| *Macaca mulatta* (Rhesus macaque) | ADH1A, ADH1 | P28469 |
| *Pan troglodytes* (Chimpanzee) | ADH1B | Q5R1W2 |
| *Papio hamadryas* (Hamadryas baboon) | ADH1B | P14139 |
| *Homo sapiens* (Human) | ADH1B, ADH2 | P00325 |
| *Homo sapiens* (Human) | ADH1C, ADH3 | P00326 |
| *Papio hamadryas* (Hamadryas baboon) | ADH1C, ADH3 | O97959 |
| *Ceratitis capitata* (Mediterranean fruit fly) (*Tephritis capitata*) | ADH2 | P48815 |
| *Ceratitis cosyra* (Mango fruit fly) (*Trypeta cosyra*) | ADH2 | Q70UP5 |
| *Ceratitis rosa* (Natal fruit fly) (*Pterandrus rosa*) | ADH2 | Q70UP6 |
| *Drosophila arizonae* (Fruit fly) | Adh2 | P27581 |
| *Drosophila buzzatii* (Fruit fly) | Adh2 | P25720 |
| *Drosophila hydei* (Fruit fly) | Adh2 | P23237 |
| *Drosophila montana* (Fruit fly) | Adh2 | P48587 |
| *Drosophila mulleri* (Fruit fly) | Adh2 | P07160 |
| *Drosophila wheeleri* (Fruit fly) | Adh2 | P24267 |
| *Entamoeba histolytica* | ADH2 | Q24803 |
| *Hordeum vulgare* (Barley) | ADH2 | P10847 |
| *Kluyveromyces marxianus* (Yeast) (*Candida kefyr*) | ADH2 | Q9P4C2 |
| *Zea mays* (Maize) | ADH2 | P04707 |
| *Oryza sativa* subsp. *indica* (Rice) | ADH2 | Q4R1E8 |
| *Solanum lycopersicum* (Tomato) (*Lycopersicon esculentum*) | ADH2 | P28032 |
| *Solanum tuberosum* (Potato) | ADH2 | P14674 |
| *Scheffersomyces stipitis* (strain ATCC 58785/CBS 6054/NBRC 10063/NRRL Y-11545) (Yeast) (*Pichia stipitis*) | ADH2, ADH1, PICST_27980 | O13309 |
| *Arabidopsis thaliana* (Mouse-ear cress) | ADH2, ADHIII, FDH1, At5g43940, MRH10.4 | Q96533 |
| *Saccharomyces cerevisiae* (strain ATCC 204508/S288c) (Baker's yeast) | ADH2, ADR2, YMR303C, YM9952.05C | P00331 |
| *Candida albicans* (strain SC5314/ATCC MYA-2876) (Yeast) | ADH2, Ca41C10.04, CaO19.12579, CaO19.5113 | O94038 |
| *Oryza sativa* subsp. *japonica* (Rice) | ADH2, DUPR11.1, Os11g0210500, LOC_Os11g10510 | Q0ITW7 |
| *Drosophila mojavensis* (Fruit fly) | Adh2, GI17643 | P09369 |
| *Kluyveromyces lactis* (strain ATCC 8585/CBS 2359/DSM 70799/NBRC 1267/NRRL Y-1140/WM37) (Yeast) (*Candida sphaerica*) | ADH2, KLLA0F18260g | P49383 |
| *Oryctolagus cuniculus* (Rabbit) | ADH2-1 | O46649 |
| *Oryctolagus cuniculus* (Rabbit) | ADH2-2 | O46650 |
| *Hordeum vulgare* (Barley) | ADH3 | P10848 |
| *Solanum tuberosum* (Potato) | ADH3 | P14675 |
| *Kluyveromyces lactis* (strain ATCC 8585/CBS 2359/DSM 70799/NBRC 1267/NRRL Y-1140/WM37) (Yeast) (*Candida sphaerica*) | ADH3, KLLA0B09064g | P49384 |
| *Saccharomyces cerevisiae* (strain ATCC 204508/5288c) (Baker's yeast) | ADH3, YMR083W, YM9582.08 | P07246 |
| *Homo sapiens* (Human) | ADH4 | P08319 |
| *Mus musculus* (Mouse) | Adh4 | Q9QYY9 |
| *Rattus norvegicus* (Rat) | Adh4 | Q64563 |
| *Struthio camelus* (Ostrich) | ADH4 | P80468 |
| *Kluyveromyces lactis* (strain ATCC 8585/CBS 2359/DSM 70799/NBRC 1267/NRRL Y-1140/WM37) (Yeast) (*Candida sphaerica*) | ADH4, KLLA0F13530g | P49385 |
| *Schizosaccharomyces pombe* (strain 972/ATCC 24843) (Fission yeast) | adh4, SPAC5H10.06c | Q09669 |
| *Saccharomyces cerevisiae* (strain YJM789) (Baker's yeast) | ADH4, ZRG5, SCY_1818 | A6ZTT5 |
| *Saccharomyces cerevisiae* (strain ATCC 204508/5288c) (Baker's yeast) | ADH4, ZRG5, YGL256W, NRC465 | P10127 |
| *Saccharomyces pastorianus* (Lager yeast) (*Saccharomyces cerevisiae* x *Saccharomyces eubayanus*) | ADH5 | Q6XQ67 |
| *Bos taurus* (Bovine) | ADH5 | Q3ZC42 |
| *Equus caballus* (Horse) | ADH5 | P19854 |
| *Mus musculus* (Mouse) | Adh5, Adh-2, Adh2 | P28474 |
| *Rattus norvegicus* (Rat) | Adh5, Adh-2, Adh2 | P12711 |
| *Oryctolagus cuniculus* (Rabbit) | ADH5, ADH3 | O19053 |
| *Homo sapiens* (Human) | ADH5, ADHX, FDH | P11766 |
| *Dictyostelium discoideum* (Slime mold) | adh5, DDB_G0281865 | Q54TC2 |
| *Saccharomyces cerevisiae* (strain ATCC 204508/S288c) (Baker's yeast) | ADH5, YBR145W, YBR1122 | P38113 |
| *Homo sapiens* (Human) | ADH6 | P28332 |
| *Peromyscus maniculatus* (North American deer mouse) | ADH6 | P41681 |
| *Pongo abelii* (Sumatran orangutan) (*Pongo pygmaeus abelii*) | ADH6 | Q5R7Z8 |
| *Rattus norvegicus* (Rat) | Adh6 | Q5XI95 |
| *Homo sapiens* (Human) | ADH7 | P40394 |
| *Rattus norvegicus* (Rat) | Adh7 | P41682 |
| *Mus musculus* (Mouse) | Adh7, Adh-3, Adh3 | Q64437 |
| *Mycobacterium tuberculosis* (strain CDC 1551/Oshkosh) | adhA, MT1911 | P9WQC0 |
| *Rhizobium meliloti* (strain 1021) (*Ensifer meliloti*) (*Sinorhizobium meliloti*) | adhA, RA0704, SMa1296 | O31186 |
| *Mycobacterium tuberculosis* (strain ATCC 25618/H37Rv) | adhA, Rv1862 | P9WQC1 |
| *Zymomonas mobilis* subsp. *mobilis* (strain ATCC 31821/ZM4/CP4) | adhA, ZMO1236 | P20368 |
| *Mycobacterium bovis* (strain ATCC BAA-935/AF2122/97) | adhB, Mb0784c | Q7U1B9 |
| *Mycobacterium tuberculosis* (strain CDC 1551/Oshkosh) | adhB, MT0786 | P9WQC6 |
| *Mycobacterium tuberculosis* (strain ATCC 25618/H37Rv) | adhB, Rv0761c, MTCY369.06c | P9WQC7 |
| *Zymomonas mobilis* subsp. *mobilis* (strain ATCC 31821/ZM4/CP4) | adhB, ZMO1596 | P0DJA2 |
| *Zymomonas mobilis* subsp. *mobilis* (strain ATCC 10988/DSM 424/LMG 404/NCIMB 8938/NRRL B-806/ZM1) | adhB, Zmob_1541 | F8DVL8 |
| *Mycobacterium tuberculosis* (strain CDC 1551/Oshkosh) | adhD, MT3171 | P9WQB8 |
| *Mycobacterium tuberculosis* (strain ATCC 25618/H37Rv) | adhD, Rv3086 | P9WQB9 |
| *Clostridium acetobutylicum* (strain ATCC 824/DSM 792/JCM 1419/LMG 5710/VKM B-1787) | adhE, aad, CA_P0162 | P33744 |
| *Escherichia coli* (strain K12) | adhE, ana, b1241, JW1228 | P0A9Q7 |

TABLE 3-continued

Exemplary alcohol dehydrogenase enzymes.

| Organism | Gene Name | Accession No. |
|---|---|---|
| *Escherichia coli* O157:H7 | adhE, Z2016, ECs1741 | P0A9Q8 |
| *Rhodobacter sphaeroides* (strain ATCC 17023/2.4.1/NCIB 8253/DSM 158) | adhI, RHOS4_11650, RSP_2576 | P72324 |
| *Oryza sativa* subsp. *indica* (Rice) | ADHIII, OsI_009236 | A2XAZ3 |
| *Escherichia coli* (strain K12) | adhP, yddN, b1478, JW1474 | P39451 |
| *Geobacillus stearothermophilus* (*Bacillus stearothermophilus*) | adhT | P12311 |
| *Emericella nidulans* (strain FGSC A4/ATCC 38163/CBS 112.46/ NRRL 194/M139) (*Aspergillus nidulans*) | alcA, AN8979 | P08843 |
| *Emericella nidulans* (strain FGSC A4/ATCC 38163/CBS 112.46/ NRRL 194/M139) (*Aspergillus nidulans*) | alc, AN3741 | P54202 |
| *Emericella nidulans* (strain FGSC A4/ATCC 38163/CBS 112.46/NRRL 194/M139) (*Aspergillus nidulans*) | alcC, adh3, AN2286 | P07754 |
| *Arabidopsis thaliana* (Mouse-ear cress) | At1g22430, F12K8.22 | Q9SK86 |
| *Arabidopsis thaliana* (Mouse-ear cress) | At1g22440, F12K8.21 | Q9SK87 |
| *Arabidopsis thaliana* (Mouse-ear cress) | At1g32780, F6N18.16 | A1L4Y2 |
| *Arabidopsis thaliana* (Mouse-ear cress) | At1g64710, F13O11.3 | Q8VZ49 |
| *Arabidopsis thaliana* (Mouse-ear cress) | At4g22110, F1N20.210 | Q0V7W6 |
| *Arabidopsis thaliana* (Mouse-ear cress) | At5g24760, T4C12_30 | Q8LEB2 |
| *Arabidopsis thaliana* (Mouse-ear cress) | At5g42250, K5J14.5 | Q9FH04 |
| *Zea mays* (Maize) | FDH | P93629 |
| *Drosophila melanogaster* (Fruit fly) | Fdh, gfd, ODH, CG6598 | P46415 |
| *Bacillus subtilis* (strain 168) | gbsB, BSU31050 | P71017 |
| *Caenorhabditis elegans* | H24K24.3 | Q17335 |
| *Oryza sativa* subsp. *japonica* (Rice) | Os02g0815500, LOC_Os02g57040, OsJ_008550, P0643F09.4 | Q0DWH1 |
| *Mycobacterium tuberculosis* (strain ATCC 25618/H37Rv) | Rv1895 | O07737 |
| *Caenorhabditis elegans* | sodh-1, K12G11.3 | Q17334 |
| *Caenorhabditis elegans* | sodh-2, K12G11.4 | O45687 |
| *Pseudomonas* sp. | terPD | P33010 |
| *Escherichia coli* (strain K12) | yiaY, b3589, JW5648 | P37686 |
| *Moraxella* sp. (strain TAE123) | | P81786 |
| *Alligator mississippiensis* (American alligator) | | P80222 |
| *Catharanthus roseus* (Madagascar periwinkle) (*Vinca rosea*) | | P85440 |
| *Gadus morhua* subsp. *callarias* (Baltic cod) (*Gadus callarias*) | | P26325 |
| *Naja naja* (Indian cobra) | | P80512 |
| *Pisum sativum* (Garden pea) | | P12886 |
| *Pelophylax perezi* (Perez's frog) (*Rana perezi*) | | P22797 |
| *Saara hardwickii* (Indian spiny-tailed lizard) (*Uromastyx hardwickii*) | | P25405 |
| *Saara hardwickii* (Indian spiny-tailed lizard) (*Uromastyx hardwickii*) | | P25406 |
| *Equus caballus* (Horse) | | P00327 |
| *Equus caballus* (Horse) | | P00328 |
| *Geobacillus stearothermophilus* (*Bacillus stearothermophilus*) | | P42328 |
| *Gadus morhua* (Atlantic cod) | | P81600 |
| *Gadus morhua* (Atlantic cod) | | P81601 |
| *Myxine glutinosa* (Atlantic hagfish) | | P80360 |
| *Octopus vulgaris* (Common octopus) | | P81431 |
| *Pisum sativum* (Garden pea) | | P80572 |
| *Saara hardwickii* (Indian spiny-tailed lizard) (*Uromastyx hardwickii*) | | P80467 |
| *Scyliorhinus canicula* (Small-spotted catshark) (*Squalus canicula*) | | P86884 |
| *Sparus aurata* (Gilthead sea bream) | | P79896 |

Alcohol Oxidase

The present disclosure describes enzymes that oxidize fatty alcohols to fatty aldehydes.

In some embodiments, an alcohol oxidase (AOX) is used to catalyze the conversion of a fatty alcohol to a fatty aldehyde. Alcohol oxidases catalyze the conversion of alcohols into corresponding aldehydes (or ketones) with electron transfer via the use of molecular oxygen to form hydrogen peroxide as a by-product. AOX enzymes utilize flavin adenine dinucleotide (FAD) as an essential cofactor and regenerate with the help of oxygen in the reaction medium. Catalase enzymes may be coupled with the AOX to avoid accumulation of the hydrogen peroxide via catalytic conversion into water and oxygen.

Based on the substrate specificities, AOXs may be categorized into four groups: (a) short chain alcohol oxidase, (b) long chain alcohol oxidase, (c) aromatic alcohol oxidase, and (d) secondary alcohol oxidase (Goswami et al. 2013). Depending on the chain length of the desired substrate, some members of these four groups are better suited than others as candidates for evaluation.

Short chain alcohol oxidases (including but not limited to those currently classified as EC 1.1.3.13, Table 4) catalyze the oxidation of lower chain length alcohol substrates in the range of C1-C8 carbons (van der Klei et al. 1991) (Ozimek et al. 2005). Aliphatic alcohol oxidases from methylotrophic yeasts such as *Candida boidinii* and *Komagataella pastoris* (formerly *Pichia pastoris*) catalyze the oxidation of primary alkanols to the corresponding aldehydes with a preference for unbranched short-chain aliphatic alcohols. The most broad substrate specificity is found for alcohol oxidase from the *Pichia pastoris* including propargyl alcohol, 2-chloroethanol, 2-cyanoethanol (Dienys et al. 2003). The major challenge encountered in alcohol oxidation is the high reactivity of the aldehyde product. Utilization of a two liquid phase system (water/solvent) can provide in-situ removal of the aldehyde product from the reaction phase before it is further converted to the acid. For example, hexanal production from hexanol using *Pichia pastoris* alcohol oxidase coupled with bovine liver catalase was achieved in a biphasic system by taking advantage of the presence of a stable alcohol oxidase in aqueous phase (Karra-Chaabouni et al. 2003). For example, alcohol oxidase from *Pichia pastoris* was able to oxidize aliphatic alcohols of C6 to C11 when used biphasic organic reaction system (Murray and Duff 1990). Methods for using alcohol oxidases in a biphasic system according to (Karra-Chaabouni et al. 2003) and (Murray and Duff 1990) are incorporated by reference in their entirety.

Long chain alcohol oxidases (including but not limited to those currently classified as EC 1.1.3.20; Table 5) include fatty alcohol oxidases, long chain fatty acid oxidases, and long chain fatty alcohol oxidases that oxidize alcohol substrates with carbon chain length of greater than six (Goswami et al. 2013). Banthorpe et al. reported a long chain alcohol oxidase purified from the leaves of *Tanacetum vulgare* that was able to oxidize saturated and unsaturated long chain alcohol substrates including hex-trans-2-en-1-ol and octan-1-ol (Banthorpe 1976) (Cardemil 1978). Other plant species, including *Simmondsia chinensis* (Moreau, R. A., Huang 1979), *Arabidopsis thaliana* (Cheng et al. 2004), and *Lotus japonicas* (Zhao et al. 2008) have also been reported as sources of long chain alcohol oxidases. Fatty alcohol oxidases are mostly reported from yeast species (Hommel and Ratledge 1990) (Vanhanen et al. 2000) (Hommel et al. 1994) (Kemp et al. 1990) and these enzymes play an important role in long chain fatty acid metabolism (Cheng et al. 2005). Fatty alcohol oxidases from yeast species that degrade and grow on long chain alkanes and fatty acid catalyze the oxidation of fatty alcohols. Fatty alcohol oxidase from *Candida tropicalis* has been isolated as microsomal cell fractions and characterized for a range of substrates (Eirich et al. 2004) (Kemp et al. 1988) (Kemp et al. 1991) (Mauersberger et al. 1992). Significant activity is observed for primary alcohols of length $C_8$ to $C_{16}$ with reported $K_M$ in the 10-50 μM range (Eirich et al. 2004). Alcohol oxidases described may be used for the conversion of medium chain aliphatic alcohols to aldehydes as described, for example, for whole-cells *Candida boidinii* (Gabelman and Luzio 1997), and *Pichia pastoris* (Duff and Murray 1988) (Murray and Duff 1990). Long chain alcohol oxidases from filamentous fungi were produced during growth on hydrocarbon substrates (Kumar and Goswami 2006) (Savitha and Ratledge 1991). The long chain fatty alcohol oxidase (LjFAO1) from *Lotus japonicas* has been heterologously expressed in *E. coli* and exhibited broad substrate specificity for alcohol oxidation including 1-dodecanol and 1-hexadecanol (Zhao et al. 2008).

TABLE 4

Alcohol oxidase enzymes capable of oxidizing short chain alcohols (EC 1.1.3.13)

| Organism | Gene names | Accession No. |
|---|---|---|
| *Komagataella pastoris* (strain ATCC 76273/CBS 7435/CECT 11047/NRRL Y-11430/Wegner 21-1) (Yeast) (*Pichia pastoris*) | AOX1 PP7435_Chr4-0130 | F2QY27 |
| *Komagataella pastoris* (strain GS115/ ATCC 20864) (Yeast) (*Pichia pastoris*) | AOX1 PAS_chr4_0821 | P04842 |
| *Komagataella pastoris* (strain ATCC 76273/CBS 7435/CECT 11047/NRRL Y-11430/Wegner 21-1) (Yeast) (*Pichia pastoris*) | AOX2 PP7435_Chr4-0863 | F2R038 |
| *Komagataella pastoris* (strain GS115/ ATCC 20864) (Yeast) (*Pichia pastoris*) | AOX2 PAS_chr4_0152 | C4R702 |
| *Candida boidinii* (Yeast) | AOD1 | Q00922 |
| *Pichia angusta* (Yeast) (*Hansenula polymorpha*) | MOX | P04841 |
| *Thanatephorus cucumeris* (strain AG1-IB/isolate 7/3/14) (Lettuce bottom rot fungus) (*Rhizoctonia solani*) | AOD1 BN14_10802 | M5CC52 |
| *Thanatephorus cucumeris* (strain AG1-IB/isolate 7/3/14) (Lettuce bottom rot fungus) (*Rhizoctonia solani*) | MOX BN14_12214 | M5CF32 |
| *Thanatephorus cucumeris* (strain AG1-IB/isolate 7/3/14) (Lettuce bottom rot fungus) (*Rhizoctonia solani*) | AOD1 BN14_10691 | M5CAV1 |
| *Thanatephorus cucumeris* (strain AG1-IB/isolate 7/3/14) (Lettuce bottom rot fungus) (*Rhizoctonia solani*) | AOD1 BN14_09479 | M5C7F4 |
| *Thanatephorus cucumeris* (strain AG1-IB/isolate 7/3/14) (Lettuce bottom rot fungus) (*Rhizoctonia solani*) | AOD1 BN14_10803 | M5CB66 |
| *Thanatephorus cucumeris* (strain AG1-IB/isolate 7/3/14) (Lettuce bottom rot fungus) (*Rhizoctonia solani*) | AOD1 BN14_09900 | M5C9N9 |
| *Thanatephorus cucumeris* (strain AG1-IB/isolate 7/3/14) (Lettuce bottom rot fungus) (*Rhizoctonia solani*) | AOD1 BN14_08302 | M5C2L8 |
| *Thanatephorus cucumeris* (strain AG1-IB/isolate 7/3/14) (Lettuce bottom rot fungus) (*Rhizoctonia solani*) | MOX BN14_09408 | M5C784 |
| *Thanatephorus cucumeris* (strain AG1-IB/isolate 7/3/14) (Lettuce bottom rot fungus) (*Rhizoctonia solani*) | MOX BN14_09478 | M5C8F8 |
| *Thanatephorus cucumeris* (strain AG1-IB/isolate 7/3/14) (Lettuce bottom rot fungus) (*Rhizoctonia solani*) | AOD1 BN14_11356 | M5CH40 |
| *Ogataea henricii* | AOD1 | A5LGF0 |
| *Candida methanosorbosa* | AOD1 | A5LGE5 |
| *Candida methanolovescens* | AOD1 | A5LGE4 |
| *Candida succiphila* | AOD1 | A5LGE6 |
| *Aspergillus niger* (strain CBS 513.88/ FGSC A1513) | An15g02200 | A2R501 |
| *Aspergillus niger* (strain CBS 513.88/ FGSC A1513) | An18g05480 | A2RB46 |
| *Moniliophthora perniciosa* (Witches'-broom disease fungus) (*Marasmius perniciosus*) | | I7CMK2 |
| *Candida cariosilignicola* | AOD1 | A5LGE3 |
| *Candida pignaliae* | AOD1 | A5LGE1 |
| *Candida pignaliae* | AOD2 | A5LGE2 |
| *Candida sonorensis* | AOD1 | A5LGD9 |
| *Candida sonorensis* | AOD2 | A5LGE0 |
| *Pichia naganishii* | AOD1 | A5LGF2 |
| *Ogataea minuta* | AOD1 | A5LGF1 |
| *Ogataea philodendra* | AOD1 | A5LGF3 |
| *Ogataea wickerhamii* | AOD1 | A5LGE8 |
| *Kuraishia capsulate* | AOD1 | A5LGE7 |
| *Talaromyces stipitatus* (strain ATCC 10500/CBS 375.48/QM 6759/NRRL 1006) (*Penicillium stipitatum*) | TSTA_021940 | B8MHF8 |
| *Talaromyces stipitatus* (strain ATCC 10500/CBS 375.48/QM 6759/NRRL 1006) (*Penicillium stipitatum*) | TSTA_065150 | B8LTH7 |
| *Talaromyces stipitatus* (strain ATCC 10500/CBS 375.48/QM 6759/NRRL 1006) (*Penicillium stipitatum*) | TSTA_065150 | B8LTH8 |
| *Talaromyces stipitatus* (strain ATCC 10500/CBS 375.48/QM 6759/NRRL 1006) (*Penicillium stipitatum*) | TSTA_000410 | B8MSB1 |
| *Ogataea glucozyma* | AOD1 | A5LGE9 |
| *Ogataea parapolymorpha* (strain DL-1/ATCC 26012/NRRL Y-7560) (Yeast) (*Hansenula polymorpha*) | HPODL_03886 | W1QCJ3 |
| *Gloeophyllum trabeum* (Brown rot fungus) | AOX | A8DPS4 |
| *Pichia angusta* (Yeast) (*Hansenula polymorpha*) | mox1 | A6PZG8 |
| *Pichia trehalophila* | AOD1 | A5LGF4 |
| *Pichia angusta* (Yeast) (*Hansenula polymorpha*) | mox1 | A6PZG9 |
| *Pichia angusta* (Yeast) (*Hansenula polymorpha*) | mox1 | A6PZG7 |
| *Ixodes scapularis* (Black-legged tick) (Deer tick) | IscW_ISCW017898 | B7PIZ7 |

TABLE 5

Alcohol oxidase enzymes capable of oxidizing long chain alcohols including fatty alcohols (EC 1.1.3.20)

| Organism | Gene names | Accession No. |
| --- | --- | --- |
| *Lotus japonicus* (*Lotus comiculatus* var. *japonicus*) | FAO1 | B5WWZ8 |
| *Arabidopsis thaliana* (Mouse-ear cress) | FAO1 At1g03990 F21M11.7 | Q9ZWB9 |
| *Lotus japonicus* (*Lotus comiculatus* var. *japonicus*) | FAO2 | B5WWZ9 |
| *Arabidopsis thaliana* (Mouse-ear cress) | FAO3 At3g23410 MLM24.14 MLM24.23 | Q9LW56 |
| *Arabidopsis thaliana* (Mouse-ear cress) | FAO4A At4g19380 T5K18.160 | O65709 |
| *Arabidopsis thaliana* (Mouse-ear cress) | FAO4B At4g28570 T5F17.20 | Q94BP3 |
| *Microbotryum violaceum* (strain p1A1 Lamole) (Anther smut fungus) (*Ustilago violacea*) | MVLG_06864 | U5HIL4 |
| *Ajellomyces dermatitidis* ATCC 26199 | BDFG_03507 | T5BNQ0 |
| *Gibberella zeae* (strain PH-1/ATCC MYA-4620/FGSC 9075/NRRL 31084) (Wheat head blight fungus) (*Fusarium graminearum*) | FG06918.1 FGSG_06918 | I1RS14 |
| *Pichia sorbitophila* (strain ATCC MYA-4447/BCRC 22081/CBS 7064/NBRC 10061/NRRL Y-12695) (Hybrid yeast) | Piso0_004410 GNLVRS01_PISO0K16268g GNLVRS01_PISO0L16269g | G8Y5E1 |
| *Emericella nidulans* (strain FGSC A4/ATCC 38163/CBS 112.46/NRRL 194/M139) (*Aspergillus nidulans*) | AN0623.2 ANIA_00623 | Q5BFQ7 |
| *Pyrenophora tritici-repentis* (strain Pt-1C-BFP) (Wheat tan spot fungus) (*Drechslera tritici-repentis*) | PTRG_10154 | B2WJW5 |
| *Paracoccidioides lutzii* (strain ATCC MYA-826/Pb01) (*Paracoccidioides brasiliensis*) | PAAG_09117 | C1HEC6 |
| *Candida parapsilosis* (strain CDC 317/ATCC MYA-4646) (Yeast) (*Monilia parapsilosis*) | CPAR2_204420 | G8BG15 |
| *Pseudozyma brasiliensis* (strain GHG001) (Yeast) | PSEUBRA_SCAF2g03010 | V5GPS6 |
| *Candida parapsilosis* (strain CDC 317/ATCC MYA-4646) (Yeast) (*Monilia parapsilosis*) | CPAR2_204430 | G8BG16 |
| *Sclerotinia borealis* F-4157 | SBOR_5750 | W9CDE2 |
| *Sordaria macrospora* (strain ATCC MYA-333/DSM 997/K(L3346)/K-hell) | SMAC_06361 | F7W6K4 |
| *Sordaria macrospora* (strain ATCC MYA-333/DSM 997/K(L3346)/K-hell) | SMAC_01933 | F7VSA1 |
| *Meyerozyma guilliermondii* (strain ATCC 6260/CBS 566/DSM 6381/JCM 1539/NBRC 10279/NRRL Y-324) (Yeast) (*Candida guilliermondii*) | PGUG_03467 | A5DJL6 |
| Trichophyton rubrum CBS 202.88 | H107_00669 | A0A023ATC5 |
| Arthrobotrys oligospora (strain ATCC 24927/CBS 115.81/DSM 1491) (Nematode-trapping fungus) (*Didymozoophaga oligospora*) | AOL_s00097g516 | G1XJI9 |
| *Scheffersomyces stipitis* (strain ATCC 58785/CBS 6054/NBRC 10063/NRRL Y-11545) (Yeast) (*Pichia stipitis*) | FAO1 PICST_90828 | A3LYX9 |
| *Scheffersomyces stipitis* (strain ATCC 58785/CBS 6054/NBRC 10063/NRRL Y-11545) (Yeast) (*Pichia stipitis*) | FAO2 PICST_32359 | A3LW61 |
| *Aspergillus oryzae* (strain 3.042) (Yellow koji mold) | Ao3042_09114 | I8TL25 |
| *Fusarium oxysporum* (strain Fo5176) (*Fusarium* vascular wilt) | FOXB_17532 | F9GFU8 |
| *Rhizopus delemar* (strain RA 99-880/ATCC MYA-4621/FGSC 9543/NRRL 43880) (Mucormycosis agent) (*Rhizopus arrhizus* var. *delemar*) | RO3G_08271 | I10536 |
| *Rhizopus delemar* (strain RA 99-880/ATCC MYA-4621/FGSC 9543/NRRL 43880) (Mucormycosis agent) (*Rhizopus arrhizus* var. *delemar*) | RO3G_00154 | I1BGX0 |
| *Fusarium oxysporum* (strain Fo5176) (*Fusarium* vascular wilt) | FOXB_07532 | F9FMA2 |

TABLE 5-continued

Alcohol oxidase enzymes capable of oxidizing long chain
alcohols including fatty alcohols (EC 1.1.3.20)

| Organism | Gene names | Accession No. |
|---|---|---|
| *Penicillium roqueforti* | PROQFM164_S02g001772 | W6QPY1 |
| *Aspergillus clavatus* (strain ATCC 1007/ CBS 513.65/DSM 816/NCTC 3887/ NRRL 1) | ACLA_018400 | A1CNB5 |
| *Arthroderma otae* (strain ATCC MYA-4605/CBS 113480) (*Microsporum canis*) | MCYG_08732 | C5G1B0 |
| *Trichophyton tonsurans* (strain CBS 112818) (Scalp ringworm fungus) | TESG_07214 | F2S8I2 |
| *Colletotrichum higginsianum* (strain IMI 349063) (*Crucifer anthracnose* fungus) | CH063_13441 | H1VUE7 |
| *Ajellomyces capsulatus* (strain H143) (Darling's disease fungus) (*Histoplasma capsulatum*) | HCDG_07658 | C6HN77 |
| *Trichophyton rubrum* (strain ATCC MYA-4607/CBS 118892) (Athlete's foot fungus) | TERG_08235 | F2T096 |
| *Cochliobolus heterostrophus* (strain C5/ ATCC 48332/race O) (Southern corn leaf blight fungus) (*Bipolaris maydis*) | COCHEDRAFT_1201414 | M2UMT9 |
| *Candida orthopsilosis* (strain 90-125) (Yeast) | CORT_0D04510 | H8X643 |
| *Candida orthopsilosis* (strain 90-125) (Yeast) | CORT_0D04520 | H8X644 |
| *Candida orthopsilosis* (strain 90-125) (Yeast) | CORT_0D04530 | H8X645 |
| *Pseudozyma aphidis* DSM 70725 | PaG_03027 | W3VP49 |
| *Coccidioides posadasii* (strain C735) (Valley fever fungus) | CPC735_000380 | C5P005 |
| *Magnaporthe oryzae* (strain P131) (Rice blast fungus) (*Pyricularia oryzae*) | OOW_P131scaffold01214g15 | L7IZ92 |
| *Neurospora tetrasperma* (strain FGSC 2508/ATCC MYA-4615/P0657) | NEUTE1DRAFT_82541 | F8MKD1 |
| *Hypocrea virens* (strain Gv29-8/FGSC 10586) (*Gliocladium virens*) (*Trichoderma virens*) | TRIVIDRAFT_54537 | G9MMY7 |
| *Hypocrea virens* (strain Gv29-8/FGSC 10586) (*Gliocladium virens*) (*Trichoderma virens*) | TRIVIDRAFT_53801 | G9MT89 |
| *Aspergillus niger* (strain CBS 513.88/ FGSC A1513) | An01g09620 | A2Q9Z3 |
| *Verticillium dahliae* (strain VdLs.17/ ATCC MYA-4575/FGSC 10137) (*Verticillium* wilt) | VDAG_05780 | G2X6J8 |
| *Ustilago maydis* (strain 521/FGSC 9021) (Corn smut fungus) | UM02023.1 | Q4PCZ0 |
| *Fusarium oxysporum* f. sp. *lycopersici* MN25 | FOWG_13006 | W9LNI9 |
| *Fusarium oxysporum* f. sp. *lycopersici* MN25 | FOWG_02542 | W9N9Z1 |
| *Candida tropicalis* (Yeast) | FAO1 | Q6QIR6 |
| *Magnaporthe oryzae* (strain 70-15/ ATCC MYA-4617/FGSC 8958) (Rice blast fungus) (*Pyricularia oryzae*) | MGG_11317 | G4MVK1 |
| *Candida tropicalis* (Yeast) | faot | Q9P8D9 |
| *Candida tropicalis* (Yeast) | FAO2a | Q6QIR5 |
| *Phaeosphaeria nodorum* (strain SN15/ ATCC MYA-4574/FGSC 10173) (Glume blotch fungus) (*Septoria nodorum*) | SNOG_02371 | Q0V0U3 |
| *Candida tropicalis* (Yeast) | FAO2b | Q6QIR4 |
| *Pestalotiopsis fici* W106-1 | PFICI_11209 | W3WU04 |
| *Magnaporthe oryzae* (strain Y34) (Rice blast fungus) (*Pyricularia oryzae*) | OOU_Y34scaffold00240g57 | L7IFT5 |
| *Pseudogymnoascus destructans* (strain ATCC MYA-4855/20631-21) (Bat white-nose syndrome fungus) (*Geomyces destructans*) | GMDG_01756 | L8G0G6 |
| *Pseudogymnoascus destructans* (strain ATCC MYA-4855/20631-21) (Bat white-nose syndrome fungus) (*Geomyces destructans*) | GMDG_04950 | L8GCY2 |
| *Mycosphaerella fijiensis* (strain CIRAD86) (Black leaf streak disease fungus) (*Pseudocercospora fijiensis*) | MYCFIDRAFT_52380 | M2Z831 |

TABLE 5-continued

Alcohol oxidase enzymes capable of oxidizing long chain alcohols including fatty alcohols (EC 1.1.3.20)

| Organism | Gene names | Accession No. |
| --- | --- | --- |
| *Bipolaris oryzae* ATCC 44560 | COCMIDRAFT_84580 | W7A0I8 |
| *Cladophialophora psammophila* CBS 110553 | A1O5_08147 | W9WTM9 |
| *Fusarium oxysporum* f. sp. *melonis* 26406 | FOMG_05173 | X0AEE6 |
| *Fusarium oxysporum* f. sp. *melonis* 26406 | FOMG_17829 | W9ZBB7 |
| *Cyphellophora europaea* CBS 101466 | HMPREF1541_02174 | W2S2S5 |
| *Aspergillus kawachii* (strain NBRC 4308) (White koji mold) (*Aspergillus awamori* var. *kawachi*) | AKAW_00147 | G7X626 |
| *Aspergillus terreus* (strain NIH 2624/FGSC A1156) | ATEG_05086 | Q0CMJ8 |
| *Coccidioides immitis* (strain RS) (Valley fever fungus) | CIMG_02987 | J3KAI8 |
| *Ajellomyces dermatitidis* (strain ER-3/ATCC MYA-2586) (*Blastomyces dermatitidis*) | BDCG_04701 | C5GLS5 |
| *Fusarium oxysporum* f. sp. *cubense* (strain race 1) (Panama disease fungus) | FOC1_g10013865 | N4U732 |
| *Rhodotorula glutinis* (strain ATCC 204091/IIP 30/MTCC 1151) (Yeast) | RTG_00643 | G0SVU8 |
| *Aspergillus niger* (strain ATCC 1015/CBS 113.46/FGSC A1144/LSHB Ac4/NCTC 3858a/NRRL 328/USDA 3528.7) | ASPNIDRAFT_35778 | G3XTM6 |
| *Candida cloacae* | fao1 | Q9P8D8 |
| *Candida cloacae* | fao2 | Q9P8D7 |
| *Fusarium oxysporum* f. sp. *cubense* (strain race 1) (Panama disease fungus) | FOC1_g10006358 | N4TUH3 |
| *Candida albicans* (strain SC5314/ATCC MYA-2876) (Yeast) | FAO1 CaO19.13562 orf19.13562 | Q59RS8 |
| *Candida albicans* (strain SC5314/ATCC MYA-2876) (Yeast) | FAO1 CaO19.6143 orf19.6143 | Q59RP0 |
| *Chaetomium thermophilum* (strain DSM 1495/CBS 144.50/IMI 039719) | CTHT_0018560 | G0S2U9 |
| *Mucor circinelloides* f. *circinelloides* (strain 1006PhL) (*Mucormycosis agent*) (*Calyptromyces circinelloides*) | HMPREF1544_05296 | S2JDN0 |
| *Mucor circinelloides* f. *circinelloides* (strain 1006PhL) (Mucormycosis agent) (*Calyptromyces circinelloides*) | HMPREF1544_05295 | S2JYP5 |
| *Mucor circinelloides* f. *circinelloides* (strain 1006PhL) (Mucormycosis agent) (*Calyptromyces circinelloides*) | HMPREF1544_06348 | S2JVK9 |
| *Botryotinia fuckeliana* (strain BcDW1) (Noble rot fungus) (*Botrytis cinerea*) | BcDW1_6807 | M7UD26 |
| *Podospora anserina* (strain S/ATCC MYA-4624/DSM 980/FGSC 10383) (*Pleurage anserina*) | PODANS_5_13040 | B2AFD8 |
| *Neosartorya fumigata* (strain ATCC MYA-4609/Af293/CBS 101355/FGSC A1100) (*Aspergillus fumigatus*) | AFUA_1G17110 | Q4WR91 |
| *Fusarium oxysporum* f. sp. *vasinfectum* 25433 | FOTG_00686 | X0MEE6 |
| Fusarium oxysporum f. sp. *vasinfectum* 25433 | FOTG_12485 | X0LE98 |
| Trichophyton interdigitale H6 | H101_06625 | A0A022U717 |
| *Beauveria bassiana* (strain ARSEF 2860) (White muscardine disease fungus) (*Tritirachium shiotae*) | BBA_04100 | J4UNY3 |
| *Fusarium oxysporum* f. sp. *radicis-lycopersici* 26381 | FOCG_00843 | X0GQ62 |
| *Fusarium oxysporum* f. sp. *radicis-lycopersici* 26381 | FOCG_15170 | X0F4T1 |
| *Neurospora tetrasperma* (strain FGSC 2509/P0656) | NEUTE2DRAFT_88670 | G4UNN6 |
| *Pseudozyma hubeiensis* (strain SY62) (Yeast) | PHSY_000086 | R9NVU1 |
| *Lodderomyces elongisporus* (strain ATCC 11503/CBS 2605/JCM 1781/NBRC 1676/NRRL YB-4239) (Yeast) (*Saccharomyces elongisporus*) | LELG_03289 | A5E102 |

TABLE 5-continued

Alcohol oxidase enzymes capable of oxidizing long chain alcohols including fatty alcohols (EC 1.1.3.20)

| Organism | Gene names | Accession No. |
|---|---|---|
| *Malassezia globosa* (strain ATCC MYA-4612/CBS 7966) (Dandruff-associated fungus) | MGL_3855 | A8QAY8 |
| *Byssochlamys spectabilis* (strain No. 5/NBRC 109023) (*Paecilomyces variotii*) | PVAR5_7014 | V5GBL6 |
| *Ajellomyces capsulatus* (strain H88) (Darling's disease fungus) (*Histoplasma capsulatum*) | HCEG_03274 | F0UF47 |
| *Trichosporon asahii* var. *asahii* (strain ATCC 90039/CBS 2479/JCM 2466/KCTC 7840/NCYC 2677/UAMH 7654) (Yeast) | A1Q1_03669 | J6FBP4 |
| *Penicillium oxalicum* (strain 114-2/CGMCC 5302) (*Penicillium decumbens*) | PDE_00027 | S7Z8U8 |
| *Fusarium oxysporum* f. sp. *conglutinans* race 2 54008 | FOPG_02304 | X0IBE3 |
| *Fusarium oxysporum* f. sp. *conglutinans* race 2 54008 | FOPG_13066 | X0H540 |
| *Fusarium oxysporum* f. sp. *raphani* 54005 | FOQG_00704 | X0D1G8 |
| *Fusarium oxysporum* f. sp. *raphani* 54005 | FOQG_10402 | X0C482 |
| *Metarhizium acridum* (strain CQMa 102) | MAC_03115 | E9DZR7 |
| *Arthroderma benhamiae* (strain ATCC MYA-4681/CBS 112371) (*Trichophyton mentagrophytes*) | ARB_02250 | D4B1C1 |
| *Fusarium oxysporum* f. sp. *cubense* tropical race 4 54006 | FOIG_12161 | X0JFI6 |
| *Fusarium oxysporum* f. sp. *cubense* tropical race 4 54006 | FOIG_12751 | X0JDU5 |
| *Cochliobolus heterostrophus* (strain C4/ATCC 48331/race T) (Southern corn leaf blight fungus) (*Bipolaris maydis*) | COCC4DRAFT_52836 | N4WZZ0 |
| *Trichosporon asahii* var. *asahii* (strain CBS 8904) (Yeast) | A1Q2_00631 | K1VZW1 |
| *Mycosphaerella graminicola* (strain CBS 115943/IPO323) (Speckled leaf blotch fungus) (*Septoria tritici*) | MYCGRDRAFT_37086 | F9X375 |
| *Botryotinia fuckeliana* (strain T4) (Noble rot fungus) (*Botrytis cinerea*) | BofuT4_P072020.1 | G2XQ18 |
| *Metarhizium anisopliae* (strain ARSEF 23/ATCC MYA-3075) | MAA_05783 | E9F0I4 |
| *Cladophialophora carrionii* CBS 160.54 | G647_05801 | V9DAR1 |
| *Coccidioides posadasii* (strain RMSCC 757/Silveira) (Valley fever fungus) | CPSG_09174 | E9DH75 |
| *Rhodosporidium toruloides* (strain NP11) (Yeast) (*Rhodotorula gracilis*) | RHTO_06879 | M7X159 |
| *Puccinia graminis* f. sp. *tritici* (strain CRL 75-36-700-3/race SCCL) (Black stem rust fungus) | PGTG_10521 | E3KIL8 |
| *Trichophyton rubrum* CBS 288.86 | H103_00624 | A0A022WG28 |
| *Colletotrichum fioriniae* PJ7 | CFIO01_08202 | A0A010RKZ4 |
| *Trichophyton rubrum* CBS 289.86 | H104_00611 | A0A022XB46 |
| *Cladophialophora yegresii* CBS 114405 | A1O7_02579 | W9WC55 |
| *Colletotrichum orbiculare* (strain 104-T/ATCC 96160/CBS 514.97/LARS 414/MAFF 240422) (Cucumber anthracnose fungus) (*Colletotrichum lagenarium*) | Cob_10151 | N4VFP3 |
| *Drechslerella stenobrocha* 248 | DRE_03459 | W7IDL6 |
| Neosartorya fumigata (strain CEA10/CBS 144.89/FGSC A1163) (*Aspergillus fumigatus*) | AFUB_016500 | B0XP90 |
| *Thielavia terrestris* (strain ATCC 38088/NRRL 8126) (*Acremonium alabamense*) | THITE_2117674 | G2R8H9 |
| *Gibberella fujikuroi* (strain CBS 195.34/IMI 58289/NRRL A-6831) (Bakanae and foot rot disease fungus) (*Fusarium fujikuroi*) | FFUJ_02948 | S0DZP7 |
| *Gibberella fujikuroi* (strain CBS 195.34/IMI 58289/NRRL A-6831) (Bakanae | FFUJ_12030 | S0EMC6 |

TABLE 5-continued

Alcohol oxidase enzymes capable of oxidizing long chain alcohols including fatty alcohols (EC 1.1.3.20)

| Organism | Gene names | Accession No. |
|---|---|---|
| and foot rot disease fungus) (*Fusarium fujikuroi*) | | |
| *Aspergillus flavus* (strain ATCC 200026/ FGSC A1120/NRRL 3357/JCM 12722/SRRC 167) | AFLA_109870 | B8N941 |
| *Togninia minima* (strain UCR-PA7) (Esca disease fungus) (*Phaeoacremonium aleophilum*) | UCRPA7_1719 | R8BTZ6 |
| *Ajellomyces dermatitidis* (strain ATCC 18188/CBS 674.68) (*Blastomyces dermatitidis*) | BDDG_09783 | F2TUC0 |
| *Macrophomina phaseolina* (strain MS6) (Charcoal rot fungus) | MPH_10582 | K2RHA5 |
| *Neurospora crassa* (strain ATCC 24698/ 74-OR23-1A/CBS 708.71/DSM 1257/ FGSC 987) | NCU08977 | Q7S2Z2 |
| *Neosartorya fischeri* (strain ATCC 1020/ DSM 3700/FGSC A1164/NRRL 181) (*Aspergillus fischerianus*) | NFIA_008260 | A1D156 |
| *Fusarium pseudograminearum* (strain CS3096) (Wheat and barley crown-rot fungus) | FPSE_11742 | K3U9J5 |
| *Spathaspora passalidarum* (strain NRRL Y-27907/11-Y1) | SPAPADRAFT_54193 | G3AJP0 |
| *Spathaspora passalidarum* (strain NRRL Y-27907/11-Y1) | SPAPADRAFT_67198 | G3ANX7 |
| *Trichophyton verrucosum* (strain HKI 0517) | TRV_07960 | D4DL86 |
| *Arthroderma gypseum* (strain ATCC MYA-4604/CBS 118893) (*Microsporum gypseum*) | MGYG_07264 | E4V2J0 |
| *Hypocrea jecorina* (strain QM6a) (*Trichoderma reesei*) | TRIREDRAFT_43893 | G0R7P8 |
| *Trichophyton rubrum* MR1448 | H110_00629 | A0A022Z1G4 |
| *Aspergillus ruber* CBS 135680 | EURHEDRAFT_512125 | A0A017SPR0 |
| *Glarea lozoyensis* (strain ATCC 20868/ MF5171) | GLAREA_04397 | S3D6C1 |
| *Setosphaeria turcica* (strain 28A) (Northern leaf blight fungus) (*Exserohilum turcicum*) | SETTUDRAFT_20639 | R0K6H8 |
| *Paracoccidioides brasiliensis* (strain Pb18) | PADG_06552 | C1GH16 |
| *Fusarium oxysporum* Fo47 | FOZG_13577 | W9JPG9 |
| *Fusarium oxysporum* Fo47 | FOZG_05344 | W9KPH3 |
| *Trichophyton rubrum* MR1459 | H113_00628 | A0A022ZY09 |
| *Penicillium marneffei* (strain ATCC 18224/CBS 334.59/QM 7333) | PMAA_075740 | B6QBY3 |
| *Sphaerulina musiva* (strain SO2202) (Poplar stem canker fungus) (*Septoria musiva*) | SEPMUDRAFT_154026 | M3DAK6 |
| *Gibberella moniliformis* (strain M3125/ FGSC 7600) (Maize ear and stalk rot fungus) (*Fusarium verticillioides*) | FVEG_10526 | W7N4P8 |
| *Gibberella moniliformis* (strain M3125/ FGSC 7600) (Maize ear and stalk rot fungus) (*Fusarium verticillioides*) | FVEG_08281 | W7MVR9 |
| *Pseudozyma antarctica* (strain T-34) (Yeast) (*Candida antarctica*) | PANT_22d00298 | M9MGF2 |
| *Paracoccidioides brasiliensis* (strain Pb03) | PABG_07795 | C0SJD4 |
| *Rhizophagus irregularis* (strain DAOM 181602/DAOM 197198/MUCL 43194) (*Arbuscular mycorrhizal* fungus) (*Glomus intraradices*) | GLOINDRAFT_82554 | U9TF61 |
| *Penicillium chrysogenum* (strain ATCC 28089/DSM 1075/Wisconsin 54- 1255) (*Penicillium notatum*) | Pc21g23700 PCH_Pc21g23700 | B6HJ58 |
| *Baudoinia compniacensis* (strain UAMH 10762) (Angels' share fungus) | BAUCODRAFT_274597 | M2M6Z5 |
| *Hypocrea atroviridis* (strain ATCC 20476/IMI 206040) (*Trichoderma atroviride*) | TRIATDRAFT_280929 | G9NJ32 |
| *Colletotrichum gloeosporioides* (strain Cg-14) (Anthracnose fungus) (*Glomerella cingulata*) | CGLO_06642 | T0LPH0 |

TABLE 5-continued

Alcohol oxidase enzymes capable of oxidizing long chain
alcohols including fatty alcohols (EC 1.1.3.20)

| Organism | Gene names | Accession No. |
|---|---|---|
| *Cordyceps militaris* (strain CM01) (Caterpillar fungus) | CCM_02665 | G3JB34 |
| *Pyronema omphalodes* (strain CBS 100304) (*Pyronema confluens*) | PCON_13062 | U4LKE9 |
| *Colletotrichum graminicola* (strain M1.001/M2/FGSC 10212) (Maize anthracnose fungus) (*Glomerella graminicola*) | GLRG_08499 | E3QR67 |
| *Glarea lozoyensis* (strain ATCC 74030/ MF5533) | M7I_2117 | H0EHX4 |
| *Fusarium oxysporum* f. sp. *cubense* (strain race 4) (Panama disease fungus) | FOC4_g10002493 | N1S969 |
| *Fusarium oxysporum* f. sp. *cubense* (strain race 4) (Panama disease fungus) | FOC4_g10011461 | N1RT80 |
| *Cochliobolus sativus* (strain ND90Pr/ ATCC 201652) (Common root rot and spot blotch fungus) (*Bipolaris sorokiniana*) | COCSADRAFT_295770 | M2TBE4 |
| *Mixia osmundae* (strain CBS 9802/ IAM 14324/JCM 22182/KY 12970) | Mo05571 E5Q_05571 | G7E7S3 |
| *Mycosphaerella pini* (strain NZE10/ CBS 128990) (Red band needle blight fungus) (*Dothistroma septosporum*) | DOTSEDRAFT_69651 | N1PXR0 |
| *Grosmannia clavigera* (strain kw1407/ UAMH 11150) (Blue stain fungus) (*Graphiocladiella clavigera*) | CMQ_1113 | F0XC64 |
| *Fusarium oxysporum* FOSC 3-a | FOYG_03004 | W9IUE5 |
| *Fusarium oxysporum* FOSC 3-a | FOYG_16040 | W9HNP0 |
| *Fusarium oxysporum* FOSC 3-a | FOYG_17058 | W9HB31 |
| *Nectria haematococca* (strain 77-13-4/ ATCC MYA-4622/FGSC 9596/ MPVI) (*Fusarium solani* subsp. *pisi*) | NECHADRAFT_37686 | C7YQL1 |
| *Nectria haematococca* (strain 77-13-4/ ATCC MYA-4622/FGSC 9596/ MPVI) (*Fusarium solani* subsp. *pisi*) | NECHADRAFT_77262 | C7ZJI0 |
| *Tuber melanosporum* (strain Mel28) (Perigord black truffle) | GSTUM_00010376001 | D5GLS0 |
| *Ajellomyces dermatitidis* (strain SLH14081) (*Blastomyces dermatitidis*) | BDBG_07633 | C5JYI9 |
| *Chaetomium globosum* (strain ATCC 6205/CBS 148.51/DSM 1962/NBRC 6347/NRRL 1970) (Soil fungus) | CHGG_09885 | Q2GQ69 |
| *Candida tenuis* (strain ATCC 10573/ BCRC 21748/CBS 615/JCM 9827/ NBRC 10315/NRRL Y-1498/VKM Y-70) (Yeast) | CANTEDRAFT_108652 | G3B9Z1 |
| *Trichophyton rubrum* CBS 100081 | H102_00622 | A0A022VKY4 |
| *Pyrenophora teres* f. *teres* (strain 0-1) (Barley net blotch fungus) (*Drechslera teres* f. *teres*) | PTT_09421 | E3RLZ3 |
| *Colletotrichum gloeosporioides* (strain Nara gc5) (Anthracnose fungus) (*Glomerella cingulata*) | CGGC5_4608 | L2GB29 |
| *Gibberella zeae* (Wheat head blight fungus) (*Fusarium graminearum*) | FG05_06918 | A0A016PCS4 |
| *Trichophyton soudanense* CBS 452.61 | H105_00612 | A0A022Y6A6 |
| *Sclerotinia sclerotiorum* (strain ATCC 18683/1980/Ss-1) (White mold) (*Whetzelinia sclerotiorum*) | SS1G_07437 | A7EQ37 |
| *Fusarium oxysporum* f. sp. *pisi* HDV247 | FOVG_14401 | W9NWU8 |
| *Fusarium oxysporum* f. sp. *pisi* HDV247 | FOVG_02874 | W9Q5V3 |
| *Ustilago hordei* (strain Uh4875-4) (Barley covered smut fungus) | UHOR_03009 | I2G1Z4 |
| *Sporisorium reilianum* (strain SRZ2) (Maize head smut fungus) | sr12985 | E6ZYF7 |
| *Bipolaris zeicola* 26-R-13 | COCCADRAFT_81154 | W6YIP8 |
| *Melampsora larici-populina* (strain 98AG31/pathotype 3-4-7) (Poplar leaf rust fungus) | MELLADRAFT_78490 | F4RUZ8 |
| *Fusarium oxysporum* f. sp. *lycopersici* (strain 4287/CBS 123668/FGSC 9935/ NRRL 34936) (*Fusarium* vascular wilt of tomato) | FOXG_01901 | J9MG95 |
| *Fusarium oxysporum* f. sp. *lycopersici* (strain 4287/CBS 123668/FGSC 9935/ | FOXG_11941 | J9N9S4 |

TABLE 5-continued

Alcohol oxidase enzymes capable of oxidizing long chain alcohols including fatty alcohols (EC 1.1.3.20)

| Organism | Gene names | Accession No. |
| --- | --- | --- |
| NRRL 34936) (*Fusarium* vascular wilt of tomato) | | |
| *Bipolaris victoriae* FI3 | COCVIDRAFT_39053 | W7EMJ8 |
| *Debaryomyces hansenii* (strain ATCC 36239/CBS 767/JCM 1990/NBRC 0083/IGC 2968) (Yeast) (*Torulaspora hansenii*) | DEHA2E04268g | Q6BQL4 |
| *Clavispora lusitaniae* (strain ATCC 42720) (Yeast) (*Candida lusitaniae*) | CLUG_01505 | C4XZX3 |
| *Candida albicans* (strain WO-1) (Yeast) | CAWG_02023 | C4YME4 |
| *Trichophyton rubrum* MR850 | H100_00625 | A0A022U0Q2 |
| *Candida dubliniensis* (strain CD36/ATCC MYA-646/CBS 7987/NCPF 3949/NRRL Y-17841) (Yeast) | CD36_32890 | B9WMC7 |
| *Starmerella bombicola* | AOX1 | A0A024FB95 |
| *Thielavia heterothallica* (strain ATCC 42464/BCRC 31852/DSM 1799) (*Myceliophthora thermophila*) | MYCTH_103590 | G2QJL7 |
| *Claviceps purpurea* (strain 20.1) (Ergot fungus) (*Sphacelia segetum*) | CPUR_07614 | M1WFI4 |
| *Aspergillus oryzae* (strain ATCC 42149/RIB 40) (Yellow koji mold) | AO090023000571 | Q2UH61 |
| *Dictyostelium discoideum* (Slime mold) | DDB_0184181 DDB_G0292042 | Q54DT6 |
| *Triticum urartu* (Red wild einkorn) (*Crithodium urartu*) | TRIUR3_22733 | M7YME5 |
| *Solanum tuberosum* (Potato) | PGSC0003DMG400017211 | M1BG07 |
| *Oryza sativa* subsp. *japonica* (Rice) | OSJNBb0044B19.5 LOC_Os10g33540 | Q8W5P8 |
| *Oryza sativa* subsp. *japonica* (Rice) | OJ1234_B11.20 Os02g0621800 | Q6K9N5 |
| *Oryza sativa* subsp. *japonica* (Rice) | OSJNBa0001K12.5 LOC_Os10g33520 | Q8W5P3 |
| *Zea mays* (Maize) | ZEAMMB73_809149 | C0P3J6 |
| *Citrus clementina* | CICLE_v10011111mg | V4S9P4 |
| *Citrus clementina* | CICLE_v10018992mg | V4U4C9 |
| *Citrus clementina* | CICLE_v10004405mg | V4S9D3 |
| *Citrus clementina* | CICLE_v10004403mg | V4RZZ6 |
| *Morus notabilis* | L484_011703 | W9RIK0 |
| *Morus notabilis* | L484_005930 | W9RET7 |
| *Medicago truncatula* (Barrel medic) (*Medicago tribuloides*) | MTR_1g075650 | G7I4U3 |
| *Arabidopsis thaliana* (Mouse-ear cress) | | Q8LDP0 |
| *Medicago truncatula* (Barrel medic) (*Medicago tribuloides*) | MTR_4g081080 | G7JF07 |
| *Simmondsia chinensis* (Jojoba) (*Buxus chinensis*) | | L7VFV2 |
| *Prunus persica* (Peach) (*Amygdalus persica*) | PRUPE_ppa018458mg | M5VXL1 |
| *Aphanomyces astaci* | H257_07411 | W4GI89 |
| *Aphanomyces astaci* | H257_07412 | W4GI44 |
| *Aphanomyces astaci* | H257_07411 | W4GKE3 |
| *Aphanomyces astaci* | H257_07411 | W4GK29 |
| *Aphanomyces astaci* | H257_07411 | W4GJ79 |
| *Aphanomyces astaci* | H257_07411 | W4GI38 |
| *Phaeodactylum tricornutum* (strain CCAP 1055/1) | PHATRDRAFT_48204 | B7G6C1 |
| *Hordeum vulgare* var. *distichum* (Two-rowed barley) | | F2E4R4 |
| *Hordeum vulgare* var. *distichum* (Two-rowed barley) | | F2DZG1 |
| *Hordeum vulgare* var. *distichum* (Two-rowed barley) | | M0YPG7 |
| *Hordeum vulgare* var. *distichum* (Two-rowed barley) | | M0YPG6 |
| *Hordeum vulgare* var. *distichum* (Two-rowed barley) | | F2CUY4 |
| *Ricinus communis* (Castor bean) | RCOM_0867830 | B9S1S3 |
| *Brassica rapa* subsp. *pekinensis* (Chinese cabbage) (*Brassica pekinensis*) | BRA014947 | M4DEM5 |
| *Ricinus communis* (Castor bean) | RCOM_0258730 | B9SV13 |
| *Brassica rapa* subsp. *pekinensis* (Chinese cabbage) (*Brassica pekinensis*) | BRA001912 | M4CCI2 |
| *Brassica rapa* subsp. *pekinensis* (Chinese cabbage) (*Brassica pekinensis*) | BRA012548 | M4D7T8 |

TABLE 5-continued

Alcohol oxidase enzymes capable of oxidizing long chain alcohols including fatty alcohols (EC 1.1.3.20)

| Organism | Gene names | Accession No. |
|---|---|---|
| Brassica rapa subsp. pekinensis (Chinese cabbage) (Brassica pekinensis) | BRA024190 | M4E5Y6 |
| Brassica rapa subsp. pekinensis (Chinese cabbage) (Brassica pekinensis) | BRA015283 | M4DFL0 |
| Ricinus communis (Castor bean) | RCOM_1168730 | B9SS54 |
| Zea mays (Maize) | | C4J691 |
| Oryza glaberrima (African rice) | | I1P2B7 |
| Zea mays (Maize) | | B6SXM3 |
| Zea mays (Maize) | | C0HFU4 |
| Aegilops tauschii (Tausch's goatgrass) (Aegilops squarrosa) | F775_19577 | R7W4J3 |
| Solanum habrochaites (Wild tomato) (Lycopersicon hirsutum) | | R9R6T0 |
| Physcomitrella patens subsp. patens (Moss) | PHYPADRAFT_124285 | A9S535 |
| Physcomitrella patens subsp. patens (Moss) | PHYPADRAFT_113581 | A9RG13 |
| Physcomitrella patens subsp. patens (Moss) | PHYPADRAFT_182504 | A9S9A5 |
| Solanum pennellii (Tomato) (Lycopersicon pennellii) | | R9R6Q1 |
| Vitis vinifera (Grape) | VIT_02s0087g00630 | F6HJ27 |
| Vitis vinifera (Grape) | VIT_07s0005g03780 | F6HZM3 |
| Vitis vinifera (Grape) | VIT_05s0049g01400 | F6H8T4 |
| Vitis vinifera (Grape) | VITISV_019349 | A5AH38 |
| Capsella rubella | CARUB_v10013046mg | R0HIT3 |
| Capsella rubella | CARUB_v10004212mg | R0GUX4 |
| Capsella rubella | CARUB_v10004208mg | R0F3X6 |
| Capsella rubella | CARUB_v10012453mg | R0ILD0 |
| Capsella rubella | CARUB_v10004208mg | R0GUX1 |
| Eutrema salsugineum (Saltwater cress) (Sisymbrium salsugineum) | EUTSA_v10024496mg | V4MD54 |
| Eutrema salsugineum (Saltwater cress) (Sisymbrium salsugineum) | EUTSA_v10020141mg | V4NM59 |
| Eutrema salsugineum (Saltwater cress) (Sisymbrium salsugineum) | EUTSA_v10024496mg | V4LUR9 |
| Eutrema salsugineum (Saltwater cress) (Sisymbrium salsugineum) | EUTSA_v10024528mg | V4P767 |
| Eutrema salsugineum (Saltwater cress) (Sisymbrium salsugineum) | EUTSA_v10006882mg | V4L2P6 |
| Selaginella moellendorffii (Spikemoss) | SELMODRAFT_87684 | D8R6Z6 |
| Selaginella moellendorffii (Spikemoss) | SELMODRAFT_87621 | D8R6Z5 |
| Selaginella moellendorffii (Spikemoss) | SELMODRAFT_74601 | D8QN81 |
| Selaginella moellendorffii (Spikemoss) | SELMODRAFT_73531 | D8QN82 |
| Sorghum bicolor (Sorghum) (Sorghum vulgare) | Sb04g026390 SORBIDRAFT_04g026390 | C5XXS4 |
| Sorghum bicolor (Sorghum) (Sorghum vulgare) | Sb04g026370 SORBIDRAFT_04g026370 | C5XXS1 |
| Sorghum bicolor (Sorghum) (Sorghum vulgare) | Sb01g019470 SORBIDRAFT_01g019470 | C5WYH6 |
| Sorghum bicolor (Sorghum) (Sorghum vulgare) | Sb01g019480 SORBIDRAFT_01g019480 | C5WYH7 |
| Sorghum bicolor (Sorghum) (Sorghum vulgare) | Sb01g019460 SORBIDRAFT_01g019460 | C5WYH5 |
| Solanum pimpinellifolium (Currant tomato) (Lycopersicon pimpinellifolium) | | R9R6J2 |
| Phaseolus vulgaris (Kidney bean) (French bean) | PHAVU_007G124200g | V7BGM7 |
| Phaseolus vulgaris (Kidney bean) (French bean) | PHAVU_011G136600g | V7AI35 |
| Phaseolus vulgaris (Kidney bean) (French bean) | PHAVU_001G162800g | V7D063 |
| Solanum tuberosum (Potato) | PGSC0003DMG400024294 | M1C923 |
| Solanum tuberosum (Potato) | PGSC0003DMG400018458 | M1BKV4 |
| Solanum tuberosum (Potato) | PGSC0003DMG400018458 | M1BKV3 |
| Glycine max (Soybean) (Glycine hispida) | | K7LK61 |
| Glycine max (Soybean) (Glycine hispida) | | K7KXQ9 |
| Populus trichocarpa (Western balsam poplar) (Populus balsamifera subsp. trichocarpa) | POPTR_0008s16920g | B9HKS3 |
| Picea sitchensis (Sitka spruce) (Pinus sitchensis) | | B8LQ84 |
| Populus trichocarpa (Western balsam poplar) (Populus balsamifera subsp. trichocarpa) | POPTR_0004s24310g | U5GKQ5 |

TABLE 5-continued

Alcohol oxidase enzymes capable of oxidizing long chain
alcohols including fatty alcohols (EC 1.1.3.20)

| Organism | Gene names | Accession No. |
|---|---|---|
| *Populus trichocarpa* (Western balsam poplar) (*Populus balsamifera* subsp. *trichocarpa*) | POPTR_0010s07980g | B9HSG9 |
| *Glycine max* (Soybean) (*Glycine hispida*) | | I1N9S7 |
| *Glycine max* (Soybean) (*Glycine hispida*) | | I1LSK5 |
| *Setaria italica* (Foxtail millet) (*Panicum italicum*) | Si034362m.g | K4A658 |
| *Solanum lycopersicum* (Tomato) (*Lycopersicon esculentum*) | Solyc09g072610.2 | K4CUT7 |
| *Setaria italica* (Foxtail millet) (*Panicum italicum*) | Si016380m.g | K3YQ38 |
| *Solanum lycopersicum* (Tomato) (*Lycopersicon esculentum*) | | R9R6I9 |
| *Solanum lycopersicum* (Tomato) (*Lycopersicon esculentum*) | Solyc09g090350.2 | K4CW61 |
| *Solanum lycopersicum* (Tomato) (*Lycopersicon esculentum*) | Solyc08g005630.2 | K4CI54 |
| *Solanum lycopersicum* (Tomato) (*Lycopersicon esculentum*) | Solyc08g075240.2 | K4CMP1 |
| *Setaria italica* (Foxtail millet) (*Panicum italicum*) | Si034359m.g | K4A655 |
| *Setaria italica* (Foxtail millet) (*Panicum italicum*) | Si034354m.g | K4A650 |
| *Mimulus guttatus* (Spotted monkey flower) (Yellow monkey flower) | MIMGU_mgv1a001896mg | A0A022PU07 |
| *Mimulus guttatus* (Spotted monkey flower) (Yellow monkey flower) | MIMGU_mgv1a022390mg | A0A022RAV4 |
| *Mimulus guttatus* (Spotted monkey flower) (Yellow monkey flower) | MIMGU_mgv1a001868mg | A0A022S2E6 |
| *Mimulus guttatus* (Spotted monkey flower) (Yellow monkey flower) | MIMGU_mgv1a001883mg | A0A022S275 |
| *Mimulus guttatus* (Spotted monkey flower) (Yellow monkey flower) | MIMGU_mgv1a001761mg | A0A022QNF0 |
| *Musa acuminata* subsp. *malaccensis* (Wild banana) (*Musa malaccensis*) | | M0SNA8 |
| *Musa acuminata* subsp. *malaccensis* (Wild banana) (*Musa malaccensis*) | | M0RUT7 |
| *Musa acuminata* subsp. *malaccensis* (Wild banana) (*Musa malaccensis*) | | M0RUK3 |
| *Saprolegnia diclina* VS20 | SDRG_10901 | T0RG89 |
| *Brachypodium distachyon* (Purple false brome) (*Trachynia distachya*) | BRADI3G49085 | I1IBP7 |
| *Brachypodium distachyon* (Purple false brome) (*Trachynia distachya*) | BRADI3G28677 | I1I4N2 |
| *Brachypodium distachyon* (Purple false brome) (*Trachynia distachya*) | BRADI3G28657 | I1I4N0 |
| *Oryza sativa* subsp. *indica* (Rice) | OsI_34012 | B8BHG0 |
| *Oryza sativa* subsp. *indica* (Rice) | OsI_08118 | B8AFT8 |
| *Oryza sativa* subsp. *indica* (Rice) | OsI_34008 | A2Z8H1 |
| *Oryza sativa* subsp. *indica* (Rice) | OsI_34014 | B8BHG1 |
| *Oryza sativa* subsp. *japonica* (Rice) | LOC_Os10g33460 | Q7XDG3 |
| *Oryza sativa* subsp. *japonica* (Rice) | Os10g0474800 | Q0IX12 |
| *Oryza sativa* subsp. *japonica* (Rice) | Os10g0474966 | C7J7R1 |
| *Oryza sativa* subsp. *japonica* (Rice) | OSJNBa0001K12.13 | Q8W5N7 |
| *Oryza sativa* subsp. *japonica* (Rice) | OsJ_31873 | B9G683 |
| *Oryza sativa* subsp. *japonica* (Rice) | OsJ_31875 | B9G684 |
| *Oryza sativa* subsp. *japonica* (Rice) | OSJNBa0001K12.3 | Q8W5P5 |
| *Arabidopsis lyrata* subsp. *lyrata* (Lyre-leaved rock-cress) | ARALYDRAFT_470376 | D7KDA3 |
| *Arabidopsis lyrata* subsp. *lyrata* (Lyre-leaved rock-cress) | ARALYDRAFT_479855 | D7L3B6 |
| *Arabidopsis lyrata* subsp. *lyrata* (Lyre-leaved rock-cress) | ARALYDRAFT_491906 | D7MDA9 |
| *Arabidopsis lyrata* subsp. *lyrata* (Lyre-leaved rock-cress) | ARALYDRAFT_914728 | D7MGS9 |

Acetyl Transferase

The present disclosure describes enzymes that convert alcohols to fatty acetates.

In some embodiments, an acetyl transferase is used to catalyze the conversion of a fatty alcohol to a fatty acetate. An acetyl transferase is an enzyme that has the ability to produce an acetate ester by transferring the acetyl group from acetyl-CoA to an alcohol. In some embodiments, the acetyl transferase may have an EC number of 2.3.1.84.

The acetyl transferase, or the nucleic acid sequence that encodes it, can be isolated from various organisms, including but not limited to, organisms of the species *Saccharomyces cerevisiae*, *Danaus plexippus*, *Heliotis virescens*, *Bombyx mori*, *Agrotis ipsilon*, *Agrotis segetum*, *Euonymus*

*alatus*. In exemplary embodiments, the acetyl transferase comprises a sequence selected from GenBank Accession Nos. AY242066, AY242065, AY242064, AY242063, AY242062, EHJ65205, ACX53812, NP_001182381, EHJ65977, EHJ68573, KJ579226, GU594061. Additional exemplary acetyl transferase peptides may be found in US2010/0199548, which is herein incorporated by reference.

Fatty Acyl-ACP Thioesterase

Acyl-ACP thioesterase releases free fatty acids from Acyl-ACPs, synthesized from de novo fatty acid biosynthesis. The reaction terminates fatty acid biosynthesis. In plants, fatty acid biosynthesis occurs in the plastid and thus requires plastid-localized acyl-ACP thioesterases. The main products of acyl-ACP thioesterase are oleate (C18:0) and to a lesser extent palmitate (C16:0) in the vegetative tissues of all plants. The released free fatty acids are re-esterified to coenzyme A in the plastid envelope and exported out of plastid.

There are two isoforms of acyl-ACP thioesterase, FatA and FatB. Substrate specificity of these isoforms determines the chain length and level of saturated fatty acids in plants. The highest activity of FatA is with C18:1-ACP. FatA has very low activities towards other acyl-ACPs when compared with C18:1-ACP. FatB has highest activity with C16:0-ACP. It also has significant high activity with C18:1-ACP, followed by C18:0-ACP and C16:1-ACP. Kinetics studies of FatA and FatB indicate that their substrate specificities with different acyl-ACPs came from the Kcat values, rather than from Km. Km values of the two isoforms with different substrates are similar, in the micromolar order. Domain swapping of FatA and FatB indicates the N-terminus of the isoforms determines their substrate specificities (Salas J J and Ohlrogge J B (2002) Characterization of substrate specificity of plant FatA and FatB acyl-ACP thioesterases. Arch Biochem Biophys 403(1): 25-34). For those plants which predominantly accumulate medium-chain length saturated fatty acids in seeds, they evolved with specialized FatB and/or FatA thioesterases (Voelker T and Kinney A J (2001) Variations in the biosynthesis of seed-storage lipids. Annu Rev Plant Physiol Plant Mol Biol 52: 335-361). For example, laurate (12:0) is the predominant seed oil in coconut. Correspondingly, the medium-chain specific acyl-ACP thioesterase activity was detected in coconut seeds.

In one embodiment, one or more fatty acyl-ACP thioesterases are selected from the group consisting of Q41635, Q39473, P05521.2, AEM72519, AEM72520, AEM72521, AEM72523, AAC49784, CAB60830, EER87824, EER96252, ABN54268, AAO77182, CAH09236, ACL08376, and homologs thereof.

Expression of Toxic Proteins or Polypeptides

The present disclosure describes a toxic protein, peptide, or small molecule that can be encoded by a recombinant microorganism. In some embodiments, the toxic protein, peptide, or small molecule is biosynthetically produced along with an insect pheromone.

In some embodiments, the recombinant microorganism expresses one or more nucleic acid molecules encoding a protein or polypeptide which is toxic to an insect. In some embodiments, the toxic protein or polypeptide is from an entomopathogenic organism. In some embodiments, the entomopathogenic organism is selected from *Bacillus thuringiensis*, *Pseudomonas aeruginosa*, and *Serratia marcescens*. In a particular embodiment, the nucleic acid molecule encodes a *Bacillus thuringiensis* toxin.

In some embodiments, a recombinant microorganism is engineered to express a metabolic pathway which, when expressed, produces a small molecule that is toxic to an insect.

In exemplary embodiments, an insect pheromone produced by a recombinant microorganism described herein may be used to attract a pest insect, and subsequently, the pest insect is eradicated with a toxic substance, such as a toxic protein, peptide, or small molecule, which has been co-produced by a recombinant microorganism described herein.

Biosynthesis of Pheromones Using a Recombinant Microorganism

As discussed above, in a first aspect, the present disclosure relates to a recombinant microorganism capable of producing a mono- or poly-unsaturated $C_6$-$C_{24}$ fatty alcohol from an endogenous or exogenous source of saturated $C_6$-$C_{24}$ fatty acyl-CoA. An illustrative embodiment of the first aspect is shown in FIG. 1. The blue lines designate biochemical pathways used to produce a saturated acyl-CoA, which acts as a substrate for unsaturated fatty-acyl CoA conversion. The substrate to unsaturated fatty acyl-CoA conversion can be performed by endogenous or exogenous enzymes in a host. Green lines indicate conversions catalyzed by an exogenous nucleic acid molecule encoding for an enzyme. Accordingly, in some embodiments, the conversion of a saturated fatty acyl-CoA to a mono- or poly-unsaturated fatty acyl-CoA is catalyzed by at least one desaturase, which is encoded by an exogenous nucleic acid molecule. In further embodiments, the conversion of the mono- or poly-unsaturated fatty acyl-CoA to a mono- or poly-unsaturated fatty alcohol is catalyzed by at least one reductase, which is encoded by an exogenous nucleic acid molecule. The dashed grey lines indicate downstream steps for the synthesis of pheromones, fragrances, flavors, and polymer intermediates, such as using an alcohol oxidase or oxidant to produce a mono- or poly-unsaturated fatty aldehyde, and an acetyl transferase or a chemical such as acetylchloride to produce a mono- or poly-unsaturated fatty acetate. The red crosses indicate deleted or down regulated pathways native to the host, which increase flux towards the engineered pathway.

Accordingly, in one embodiment, the recombinant microorganism expresses: (a) at least one exogenous nucleic acid molecule encoding a fatty acyl desaturase that catalyzes the conversion of a saturated $C_6$-$C_{24}$ fatty acyl-CoA to a corresponding mono- or poly-unsaturated $C_6$-$C_{24}$ fatty acyl-CoA; and (b) at least one exogenous nucleic acid molecule encoding a fatty alcohol forming fatty-acyl reductase that catalyzes the conversion of the mono- or poly-unsaturated $C_6$-$C_{24}$ fatty acyl-CoA from (a) into the corresponding mono- or poly-unsaturated $C_6$-$C_{24}$ fatty alcohol. In some embodiments, the saturated $C_6$-$C_{24}$ fatty acyl-CoA can be produced using endogenous enzymes in the host microorganism. In other embodiments, the saturated $C_6$-$C_{24}$ fatty acyl-CoA can be produced using one or more exogenous enzymes in the host microorganism.

As described above, a fatty acyl desaturase catalyzes the desaturation of the hydrocarbon chain on, e.g., a saturated fatty acyl-CoA molecule to generate a corresponding unsaturated fatty acyl CoA molecule. In some embodiments, an exogenous fatty acyl desaturase can be selected and expressed in a recombinant microorganism to catalyze the formation of at least one double bond in fatty acyl-CoA molecule having from 6 to 24 carbons in the hydrocarbon chain. Accordingly, in some embodiments, the fatty-acyl desaturase is a desaturase capable of utilizing a fatty acyl- CoA as a substrate that has a chain length of 6, 7, 8, 9, 10, 11, 12, 13, 14, 15, 16, 17, 18, 19, 20, 21, 22, 23, or 24 carbon atoms.

An exogenous fatty acyl desaturase described herein can be selected to catalyze the desaturation at a desired position on the hydrocarbon chain. Accordingly, in some embodiments, the fatty-acyl desaturase is capable of generating a double bond at position C5, C6, C7, C8, C9, C10, C11, C12, or C13, in the fatty acid or its derivatives, such as, for example, fatty acid CoA esters.

One or more than one fatty acyl-CoA desaturase can be expressed in the host to catalyze desaturation at multiple positions on the hydrocarbon chain. In some embodiments, the fatty acyl-CoA desaturase is heterologous to the host microorganism. Accordingly, various embodiments provide for recombinant microorganism comprised of at least one exogenous nucleic acid molecule, which encodes a fatty acyl desaturase that catalyzes the conversion of a saturated $C_6$-$C_{24}$ fatty acyl-CoA to a corresponding mono- or poly-unsaturated $C_6$-$C_{24}$ fatty acyl-CoA.

In one exemplary embodiment, the fatty-acyl desaturase is a Z11 desaturase. The Z11 fatty-acyl desaturase catalyze double bond formation between the $11^{th}$ and $12^{th}$ carbons in the substrate relative to the carbonyl group. In various embodiments described herein, the Z11 desaturase, or the nucleic acid sequence that encodes it, can be isolated from organisms of the species *Agrotis segetum, Amyelois transitella, Argyrotaenia velutiana, Choristoneura rosaceana, Lampronia capitella, Trichoplusia ni, Helicoverpa zea,* or *Thalassiosira pseudonana*. Further Z11-desaturases, or the nucleic acid sequences encoding them, can be isolated from *Bombyx mori, Manduca sexta, Diatraea grandiosella, Earias insulana, Earias vittella, Plutella xylostella, Bombyx mori* or *Diaphania nitdalis*. In exemplary embodiments, the Z11 desaturase comprises a sequence selected from GenBank Accession Nos. JX679209, JX964774, AF416738, AF545481, EU152335, AAD03775, AAF81787, and AY493438. In some embodiments, a nucleic acid sequence encoding a Z11 desaturase from organisms of the species *Agrotis segetum, Amyelois transitella, Argyrotaenia velutiana, Choristoneura rosaceana, Lampronia capitella, Trichoplusia ni, Helicoverpa zea,* or *Thalassiosira pseudonana* is codon optimized. In some embodiments, the Z11 desaturase comprises a sequence selected from SEQ ID NOs: 9, 18, 24 and 26 from *Trichoplusia ni*. In other embodiments, the Z11 desaturase comprises a sequence selected from SEQ ID NOs: 10 and 16 from *Agrotis segetum*. In some embodiments, the Z11 desaturase comprises a sequence selected from SEQ ID NOs: 11 and 23 from *Thalassiosira pseudonana*. In certain embodiments, the Z11 desaturase comprises a sequence selected from SEQ ID NOs: 12, 17 and 30 from *Amyelois transitella*. In further embodiments, the Z11 desaturase comprises a sequence selected from SEQ ID NOs: 13, 19, 25, 27 and 31 from *Helicoverpa zea*. In some embodiments, the Z11 desaturase comprises a chimeric polypeptide. In some embodiments, a complete or partial Z11 desaturase is fused to another polypeptide. In certain embodiments, the N-terminal native leader sequence of a Z11 desaturase is replaced by an oleosin leader sequence from another species. In certain embodiments, the Z11 desaturase comprises a sequence selected from SEQ ID NOs: 15, 28 and 29.

In certain embodiments, the Z11 desaturase catalyzes the conversion of a fatty acyl-CoA into a mono- or poly-unsaturated product selected from Z11-13:Acyl-CoA, E11-13:Acyl-CoA, (Z,Z)-7,11-13:Acyl-CoA, Z11-14:Acyl-CoA, E11-14:Acyl-CoA, (E,E)-9,11-14:Acyl-CoA, (E,Z)-9,11-14: Acyl-CoA, (Z,E)-9,11-14:Acyl-CoA, (Z,Z)-9,11-14:Acyl-CoA, (E,Z)-9,11-15:Acyl-CoA, (Z,Z)-9,11-15:Acyl-CoA, Z11-16:Acyl-CoA, E11-16:Acyl-CoA, (E,Z)-6,11-16:Acyl-CoA, (E,Z)-7,11-16:Acyl-CoA, (E,Z)-8,11-16:Acyl-CoA, (E,E)-9,11-16:Acyl-CoA, (E,Z)-9,11-16:Acyl-CoA, (Z,E)-9,11-16:Acyl-CoA, (Z,Z)-9,11-16:Acyl-CoA, (E,E)-11,13-16:Acyl-CoA, (E,Z)-11,13-16:Acyl-CoA, (Z,E)-11,13-16:Acyl-CoA, (Z,Z)-11,13-16:Acyl-CoA, (Z,E)-11,14-16:Acyl-CoA, (E,E,Z)-4,6,11-16:Acyl-CoA, (Z,Z,E)-7,11,13-16:Acyl-CoA, (E,E,Z,Z)-4,6,11,13-16:Acyl-CoA, Z11-17:Acyl-CoA, (Z,Z)-8,11-17:Acyl-CoA, Z11-18:Acyl-CoA, E11-18:Acyl-CoA, (Z,Z)-11,13-18:Acyl-CoA, (E,E)-11,14-18:Acyl-CoA, or combinations thereof.

In another exemplary embodiment, the fatty-acyl desaturase is a Z9 desaturase. The Z9 fatty-acyl desaturase catalyze double bond formation between the $9^{th}$ and $10^{th}$ carbons in the substrate relative to the carbonyl group. In various embodiments described herein, the Z9 desaturase, or the nucleic acid sequence that encodes it, can be isolated from organisms of the species *Ostrinia furnacalis, Ostrinia nobilalis, Choristoneura rosaceana, Lampronia capitella, Helicoverpa assulta,* or *Helicoverpa zea*. In exemplary embodiments, the Z9 desaturase comprises a sequence selected from GenBank Accession Nos. AY057862, AF243047, AF518017, EU152332, AF482906, and AAF81788. In some embodiments, a nucleic acid sequence encoding a Z9 desaturase is codon optimized. In some embodiments, the Z9 desaturase comprises a sequence set forth in SEQ ID NO: 20 from *Ostrinia furnacalis*. In other embodiments, the Z9 desaturase comprises a sequence set forth in SEQ ID NO: 21 from *Lampronia capitella*. In some embodiments, the Z9 desaturase comprises a sequence set forth in SEQ ID NO: 22 from *Helicoverpa zea*.

In certain embodiments, the Z9 desaturase catalyzes the conversion of a fatty acyl-CoA into a monounsaturated or polyunsaturated product selected from Z9-11:Acyl-CoA, Z9-12:Acyl-CoA, E9-12:Acyl-CoA, (E,E)-7,9-12:Acyl-CoA, (E,Z)-7,9-12:Acyl-CoA, (Z,E)-7,9-12:Acyl-CoA, (Z,Z)-7,9-12:Acyl-CoA, Z9-13:Acyl-CoA, E9-13:Acyl-CoA, (E,Z)-5,9-13:Acyl-CoA, (Z,E)-5,9-13:Acyl-CoA, (Z,Z)-5,9-13:Acyl-CoA, Z9-14:Acyl-CoA, E9-14:Acyl-CoA, (E,Z)-4,9-14:Acyl-CoA, (E,E)-9,11-14:Acyl-CoA, (E,Z)-9,11-14:Acyl-CoA, (Z,E)-9,11-14:Acyl-CoA, (Z,Z)-9,11-14:Acyl-CoA, (E,E)-9,12-14:Acyl-CoA, (Z,E)-9,12-14:Acyl-CoA, (Z,Z)-9,12-14:Acyl-CoA, Z9-15:Acyl-CoA, E9-15:Acyl-CoA, (Z,Z)-6,9-15:Acyl-CoA, Z9-16:Acyl-CoA, E9-16:Acyl-CoA, (E,E)-9,11-16:Acyl-CoA, (E,Z)-9,11-16:Acyl-CoA, (Z,E)-9,11-16:Acyl-CoA, (Z,Z)-9,11-16:Acyl-CoA, Z9-17:Acyl-CoA, E9-18:Acyl-CoA, Z9-18:Acyl-CoA, (E,E)-5,9-18:Acyl-CoA, (E,E)-9,12-18:Acyl-CoA, (Z,Z)-9,12-18:Acyl-CoA, (Z,Z,Z)-3,6,9-18:Acyl-CoA, (E,E,E)-9,12,15-18:Acyl-CoA, (Z,Z,Z)-9,12,15-18:Acyl-CoA, or combinations thereof.

Desaturation of a saturated $C_6$-$C_{24}$ fatty acyl-CoA can proceed through a plurality of reactions to produce a polyunsaturated $C_6$-$C_{24}$ fatty acyl-CoA. In some embodiments, the recombinant microorganism may express a bifunctional desaturase capable of catalyzing the formation at least two double bonds. In some embodiments, the recombinant microorganism may express more than one exogenous nucleic acid molecule encoding more than one fatty-acyl desaturase that catalyzes the conversion of a saturated $C_6$-$C_{24}$ fatty acyl-CoA to a corresponding poly-unsaturated $C_6$-$C_{24}$ fatty acyl-CoA. For example, the recombinant microorganism may express an exogenous nucleic acid molecule encoding a Z11 desaturase and another exogenous nucleic acid molecule encoding a Z9 desaturase. Thus, the resultant poly-unsaturated fatty acyl-CoA would have a double bond between the $9^{th}$ and $10^{th}$ carbon and another double bond between the $11^{th}$ and $12^{th}$ carbon.

In some embodiments, the recombinant microorganism may express a fatty-acyl conjugate that acts independently or together with a fatty-acyl desaturase to catalyze the conversion of a saturated or monounsaturated fatty acyl-CoA to a conjugated polyunsaturated fatty acyl-CoA.

In one embodiment, the disclosure provides a recombinant microorganism capable of producing a polyunsaturated $C_6$-$C_{24}$ fatty alcohol from an endogenous or exogenous source of saturated or monounsaturated $C_6$-$C_{24}$ fatty acyl-CoA, wherein the recombinant microorganism expresses: (a) at least one exogenous nucleic acid molecule encoding a fatty acyl conjugase that catalyzes the conversion of a saturated or monounsaturated $C_6$-$C_{24}$ fatty acyl-CoA to a corresponding polyunsaturated $C_6$-$C_{24}$ fatty acyl-CoA; and (b) at least one exogenous nucleic acid molecule encoding a fatty alcohol forming fatty-acyl reductase that catalyzes the conversion of the polyunsaturated $C_6$-$C_{24}$ fatty acyl-CoA from (a) into the corresponding polyunsaturated $C_6$-$C_{24}$ fatty alcohol.

In another embodiment, the recombinant microorganism expresses at least two exogenous nucleic acid molecules encoding fatty-acyl conjugases that catalyze the conversion of a saturated or monounsaturated $C_6$-$C_{24}$ fatty acyl-CoA to a corresponding polyunsaturated $C_6$-$C_{24}$ fatty acyl-CoA.

In a further embodiment, the disclosure provides a recombinant microorganism capable of producing a polyunsaturated $C_6$-$C_{24}$ fatty alcohol from an endogenous or exogenous source of saturated or monounsaturated $C_6$-$C_{24}$ fatty acyl-CoA, wherein the recombinant microorganism expresses: (a) at least one exogenous nucleic acid molecule encoding a fatty-acyl desaturase and at least one exogenous nucleic acid molecule encoding a fatty acyl conjugase that catalyze the conversion of a saturated or monounsaturated $C_6$-$C_{24}$ fatty acyl-CoA to a corresponding polyunsaturated $C_6$-$C_{24}$ fatty acyl-CoA; and (b) at least one exogenous nucleic acid molecule encoding a fatty alcohol forming fatty-acyl reductase that catalyzes the conversion of the polyunsaturated $C_6$-$C_{24}$ fatty acyl-CoA from (a) into the corresponding polyunsaturated $C_6$-$C_{24}$ fatty alcohol.

In another embodiment, the recombinant microorganism expresses at least two exogenous nucleic acid molecules encoding fatty-acyl desaturases and at least two exogenous nucleic acid molecules encoding fatty-acyl conjugases that catalyze the conversion of a saturated or monounsaturated $C_6$-$C_{24}$ fatty acyl-CoA to a corresponding polyunsaturated $C_6$-$C_{24}$ fatty acyl-CoA.

In yet a further embodiment, the fatty-acyl conjugase is a conjugase capable of utilizing a fatty acyl-CoA as a substrate that has a chain length of 6, 7, 8, 9, 10, 11, 12, 13, 14, 15, 16, 17, 18, 19, 20, 21, 22, 23, or 24 carbon atoms.

In certain embodiments, the conjugase, or the nucleic acid sequence that encodes it, can be isolated from organisms of the species *Cydiapomonella, Cydia nigricana, Lobesia botrana, Myelois cribrella, Plodia interpunctella, Dendrolimus punctatus, Lampronia capitella, Spodoptera litura, Amyelois transitella, Manduca sexta, Bombyrx mori, Calendula officinalis, Trichosanthes kirilowii, Punica granatum, Momordica charantia, Impatiens balsamina,* and *Epiphyas postvittana*. In exemplary embodiments, the conjugase comprises a sequence selected from GenBank Accession No. or Uniprot database: A0A059TBF5, A0A0M3L9E8, A0A0M3L9S4, A0A0M3LAH8, A0A0M3LAS8, A0A0M3LAH8, B6CBS4, XP_013183656.1, XP_004923568.2, ALA65425.1, NP_001296494.1, NP_001274330.1, Q4A181, Q75PL7, Q9FPP8, AY178444, AY178446, AF182521, AF182520, Q95UJ3.

As described above, a fatty acyl reductase catalyzes the reduction of a carbonyl group, e.g., on an unsaturated fatty acyl-CoA molecule to generate a corresponding unsaturated fatty acid molecule. In some embodiments, the fatty alcohol forming fatty acyl CoA reductase is heterologous to the microorganism. Accordingly, various embodiments provide for recombinant microorganism comprised of at least one exogenous nucleic acid molecule, which encodes a fatty alcohol forming fatty acyl reductase that catalyzes the reduction of a carbonyl group on an unsaturated fatty acyl-CoA molecule to generate a corresponding unsaturated fatty acid molecule.

In some embodiments, the fatty acyl reductase is from an organism of the species *Agrotis segetum, Spodoptera littoralis,* or *Helicoverpa amigera*. In some embodiments, a nucleic acid sequence encoding a fatty-acyl reductase is codon optimized. In some embodiments, the fatty acyl reductase comprises a sequence set forth in SEQ ID NO: 1 from *Agrotis segetum*. In other embodiments, the fatty acyl reductase comprises a sequence set forth in SEQ ID NO: 2 from *Spodoptera littoralis*. In some embodiments, the fatty acyl reductase comprises a sequence selected from SEQ ID NOs: 3 and 32 from *Helicoverpa armigera*.

In exemplary embodiments, the fatty-acyl reductase catalyzes the conversion of a mono- or poly-unsaturated fatty acyl-CoA into a fatty alcohol product selected from (Z)-3-hexenol, (Z)-3-nonenol, (Z)-5-decenol, (E)-5-decenol, (Z)-7-dodecenol, (E)-8-dodecenol, (Z)-8-dodecenol, (Z)-9-dodecenol, (Z)-9-tetradecenol, (Z)-9-hexadecenol, (Z)-11-tetradecenol, (Z)-7-hexadecenol, (Z)-11-hexadecenol, (E)-11-tetradecenol, or (Z,Z)-11,13-hexadecadienol, (11Z,13E)-hexadecadienol, (E,E)-8,10-dodecadienol, (E,Z)-7,9-dodecadienol, (Z)-13-octadecenol, or combinations thereof.

In some embodiments, a recombinant microorganism described herein can include a plurality of fatty acyl reductases. Accordingly, in such embodiments, the recombinant microorganism expresses at least two exogenous nucleic acid molecules, which encode fatty-acyl reductases that catalyze the conversion of the mono- or poly-unsaturated $C_6$-$C_{24}$ fatty acyl-CoA into the corresponding mono- or poly-unsaturated $C_6$-$C_{24}$ fatty alcohol.

Figure 2:
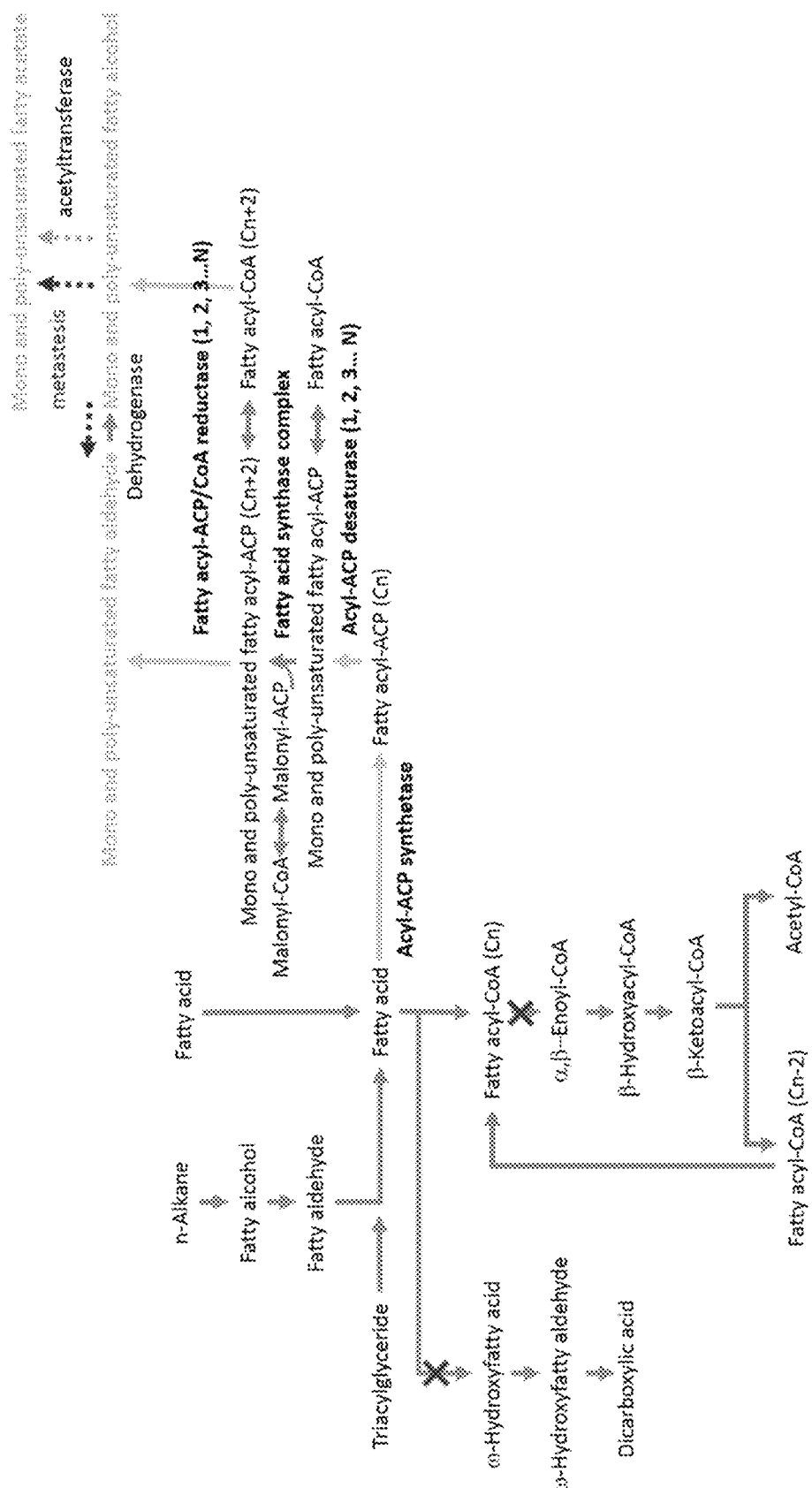
FIG. 2 illustrates the conversion of a saturated fatty acid to a mono- or poly-unsaturated fatty aldehyde, alcohol, or acetate.

As discussed above, in a second aspect, the application relates to a recombinant microorganism capable of producing an unsaturated $C_6$-$C_{24}$ fatty alcohol from an endogenous or exogenous source of $C_6$-$C_{24}$ fatty acid. An illustrative embodiment of the second aspect is shown in FIG. 2. The blue lines designate biochemical pathways endogenous to the host, e.g., pathways for converting an n-alkane, fatty alcohol, or fatty aldehyde to a fatty acid, or the conversion of a fatty acid to fatty-acyl-CoA, acetyl-CoA, or dicarboxylic acid. The substrate to unsaturated fatty acid conversion can be performed by endogenous or exogenous enzymes in a host. Yellow lines indicate conversions catalyzed by an exogenous nucleic acid molecule encoding for an enzyme. Accordingly, in some embodiments, the conversion of a saturated fatty acid to a saturated fatty acyl-ACP can be catalyzed by at least one saturated fatty acyl-ACP synthetase, wherein the fatty acyl-ACP synthetase is encoded by an exogenous nucleic acid molecule. In further embodiments, the conversion of the saturated fatty acyl-ACP to a mono- or poly-unsaturated fatty acyl-ACP can be catalyzed by at least one fatty acyl-ACP desaturase, wherein the fatty acyl-ACP desaturase is encoded by an exogenous nucleic acid molecule. In still further embodiments, the mono- or poly-unsaturated fatty acyl-ACP can be elongated by at least 2 carbons relative using a fatty acid synthase complex and a carbon source, e.g., malonyl-ACP. In one such embodiment, the conversion of the mono- or poly-unsaturated fatty acyl-ACP to a corresponding two carbon elongated mono- or poly-unsaturated fatty acyl-ACP can be catalyzed by at least one fatty acid synthase complex, wherein the fatty acid synthase complex is encoded by one or more exogenous nucleic acid molecules. In yet further embodiments, the conversion of the elongated mono- or poly-unsaturated fatty acyl-ACP to a mono- or poly-unsaturated fatty aldehyde can be catalyzed by a fatty aldehyde forming fatty acyl reductase, wherein the fatty aldehyde forming fatty acyl reductase is encoded by an exogenous nucleic acid molecule. In some embodiments, the mono- or poly-unsaturated fatty aldehyde can be converted to a corresponding mono- or poly-unsaturated fatty alcohol, wherein the substrate to product conversion is catalyzed by a dehydrogenase, wherein the dehydrogenase is encoded by an endogenous or exogenous nucleic acid molecule. The dashed lines indicate downstream steps of the disclosure, such as utilizing an acetyl transferase or metathesis, or subsequent chemical transformations to produce functionalized pheromones. The red crosses indicate deleted or down regulated pathways native to the host, which increase flux towards the engineered pathway.

In one embodiment, the recombinant microorganism expresses (a): at least one exogenous nucleic acid molecule encoding an acyl-ACP synthetase that catalyzes the conversion of a $C_6$-$C_{24}$ fatty acid to a corresponding saturated $C_6$-$C_{24}$ fatty acyl-ACP; (b) at least one exogenous nucleic acid molecule encoding a fatty-acyl-ACP desaturase that catalyzes the conversion of a saturated $C_6$-$C_{24}$ fatty acyl-ACP to a corresponding mono- or poly-unsaturated $C_6$-$C_{24}$ fatty acyl-ACP; (c) one or more endogenous or exogenous nucleic acid molecules encoding a fatty acid synthase complex that catalyzes the conversion of the mono- or poly-unsaturated $C_6$-$C_{24}$ fatty acyl-ACP from (b) to a corresponding mono- or poly-unsaturated $C_6$-$C_{24}$ fatty acyl-ACP with a two carbon elongation relative to the product of (b); (d): at least one exogenous nucleic acid molecule encoding a fatty aldehyde forming fatty-acyl reductase that catalyzes the conversion of the mono- or poly-unsaturated $C_6$-$C_{24}$ fatty acyl-ACP from (c) into a corresponding mono- or poly-unsaturated $C_6$-$C_{24}$ fatty aldehyde; and (e) at least one endogenous or exogenous nucleic acid molecule encoding a dehydrogenase that catalyzes the conversion of the mono- or poly-unsaturated $C_6$-$C_{24}$ fatty aldehyde $C_6$-$C_{24}$ from (d) into a corresponding mono- or poly-unsaturated $C_6$-$C_{24}$ fatty alcohol. In some embodiments, the $C_6$-$C_{24}$ fatty acid can be produced using endogenous enzymes in the host microorganism. In other embodiments, the saturated $C_6$-$C_{24}$ fatty acid can be produced by one or more exogenous enzymes in the host microorganism.

In some embodiments, the recombinant microorganism disclosed herein includes an acyl-ACP synthetase to catalyze the conversion of a $C_6$-$C_{24}$ fatty acid to a corresponding saturated $C_6$-$C_{24}$ fatty acyl-ACP. In some embodiments the acyl-ACP synthetase is a synthetase capable of utilizing a fatty acid as a substrate that has a chain length of 6, 7, 8, 9, 10, 11, 12, 13, 14, 15, 16, 17, 18, 19, 20, 21, 22, 23, or 24 carbon atoms. In exemplary embodiments, the recombinant microorganism can include a heterologous the acyl-ACP synthetase from an organism of the species *Vibrio harveyi*, *Rhodotorula glutinis*, or *Yarrowia lipolytica*.

In some embodiments, the recombinant microorganism includes a fatty acyl-ACP desaturase. In some embodiments, the fatty acyl-ACP desaturase is a soluble desaturase. In other embodiments, the fatty-acyl-ACP desaturase is from an organism of the species *Pelargonium hortorum*, *Asclepias syriaca*, or *Uncaria tomentosa*.

In some embodiments, the recombinant microorganism includes a fatty acid synthase complex. In some embodiments, the one or more nucleic acid molecules encoding the fatty acid synthase complex are endogenous nucleic acid molecules. In other embodiments, the one or more nucleic acid molecules encoding a fatty acid synthase complex are exogenous nucleic acid molecules.

In some embodiments, the recombinant microorganism disclosed herein includes a fatty aldehyde forming fatty-acyl reductase which catalyzes the conversion of a $C_6$-$C_{24}$ fatty acyl-ACP to the corresponding $C_6$-$C_{24}$ fatty aldehyde. In exemplary embodiments, the fatty aldehyde forming fatty-acyl reductase is from an organism of the species *Pelargonium hortorum*, *Asclepias syriaca*, and *Uncaria tomentosa*. In some embodiments, the recombinant microorganism includes a dehydrogenase to convert the unsaturated fatty aldehyde to a corresponding unsaturated fatty alcohol. In some embodiments, the nucleic acid molecule encoding the dehydrogenase is endogenous to the recombinant microorganism. In other embodiments, the nucleic acid molecule encoding a dehydrogenase is exogenous to the recombinant microorganism. In exemplary embodiments, the endogenous or exogenous nucleic acid molecule encoding a dehydrogenase is isolated from organisms of the species *Saccharomyces cerevisiae*, *Escherichia coli*, *Yarrowia lipolytica*, or *Candida tropicalis*.

Figure 3:
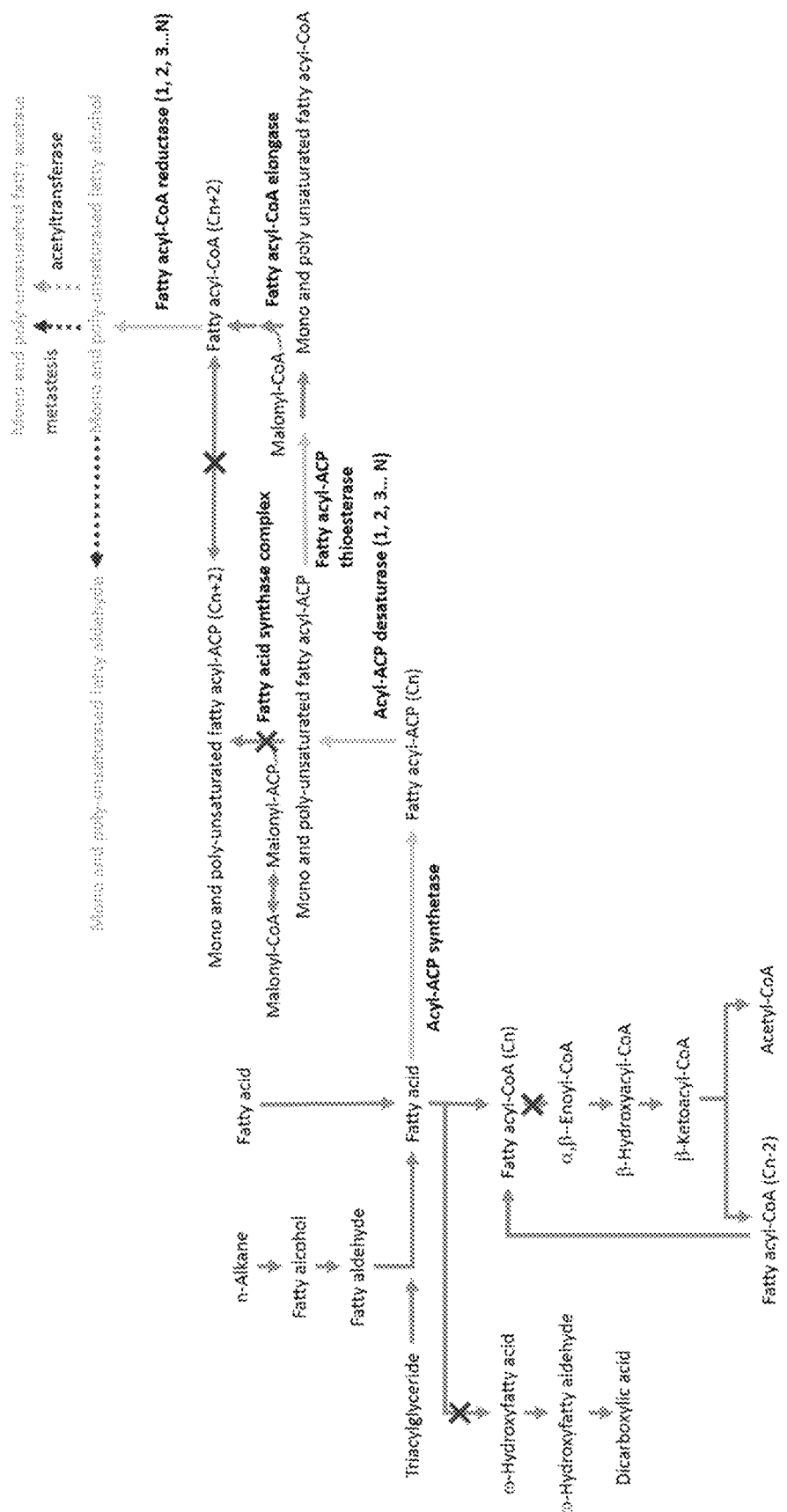
FIG. 3 illustrates an additional pathway for the conversion of a saturated fatty acid to a mono- or poly-unsaturated fatty aldehyde, alcohol, or acetate
Figure 4:
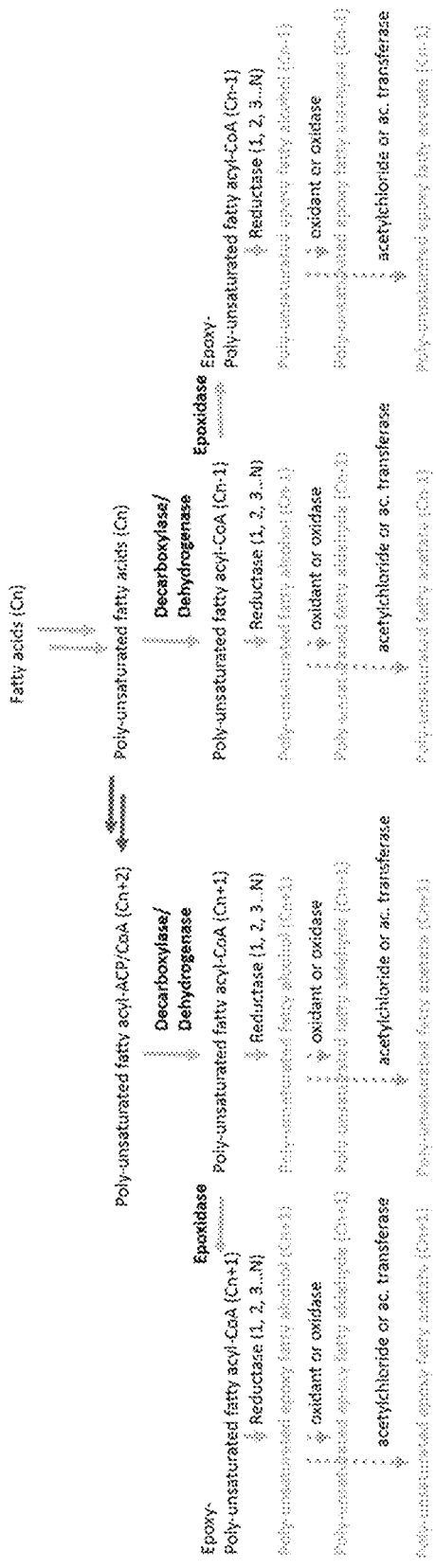
FIG. 4 illustrates a pathway for the conversion of a saturated fatty acid to various trienes, dienes, epoxides, and odd-numbered pheromones.

As discussed above, in a third aspect, the application relates to a recombinant microorganism capable of producing an unsaturated $C_6$-$C_{24}$ fatty alcohol from an endogenous or exogenous source of $C_6$-$C_{24}$ fatty acid. An illustrative embodiment of the second aspect is shown in FIG. 3. The blue lines designate biochemical pathways endogenous to the host, e.g., pathways for converting an n-alkane, fatty alcohol, or fatty aldehyde to a fatty acid, or the conversion of a fatty acid to fatty-acyl-CoA, acetyl-CoA, or dicarboxylic acid. The substrate to unsaturated fatty acid conversion can be performed by endogenous or exogenous enzymes in a host. Yellow lines indicate conversions catalyzed by an exogenous nucleic acid molecule encoding for an enzyme. Accordingly, in some embodiments, the conversion of a saturated fatty acid to a saturated fatty acyl-ACP can be catalyzed by at least one saturated fatty acyl-ACP synthetase, wherein the fatty acyl-ACP synthetase is encoded by an exogenous nucleic acid molecule. The non-native saturated fatty acyl-ACP thioesters create a substrate suitable for desaturation and distinct from CoA-thioesters used for beta-oxidation or fatty acid elongation. In further embodiments, the conversion of the saturated fatty acyl-ACP to a mono- or poly-unsaturated fatty acyl-ACP can be catalyzed by at least one fatty acyl-ACP desaturase, wherein the fatty acyl-ACP desaturase is encoded by an exogenous nucleic acid molecule. In still further embodiments, the mono- or poly-unsaturated fatty acyl-ACP can be converted to a corresponding mono- or poly-unsaturated fatty acid by a fatty-acyl-ACP thioesterase. In a particular embodiment, soluble fatty acyl-ACP thioesterases can be used to release free fatty acids for reactivation to a CoA thioester. Fatty acyl-ACP thioesterases including Q41635, Q39473, P05521.2, AEM72519, AEM72520, AEM72521, AEM72523, AAC49784, CAB60830, EER87824, EER96252, ABN54268, AAO77182, CAH09236, ACL08376, and homologs thereof may be used. In an additional embodiment, the mono- or poly-unsaturated fatty acyl-CoA can be elongated by at least 2 carbons relative using an elongase and a carbon source, e.g., malonyl-ACP. In yet further embodiments, the conversion of the elongated mono- or poly-unsaturated fatty acyl-CoA to a mono- or poly-unsaturated fatty alcohol can be catalyzed by a fatty alcohol forming fatty acyl reductase, wherein the fatty alcohol forming fatty acyl reductase is encoded by an exogenous nucleic acid molecule. The dashed lines indicate downstream steps of the disclosure, such as utilizing an acetyl transferase or metathesis, or subsequent chemical transformations to produce functionalized pheromones. The red crosses indicate deleted or down regulated pathways native to the host, which increase flux towards the engineered pathway.

The fatty alcohols produced as taught herein can be further converted to produce downstream products such as insect pheromones, fragrances, flavors, and polymer intermediates, which utilize aldehydes or acetate functional groups. Thus, in some embodiments, the recombinant microorganism further comprises at least one endogenous or exogenous nucleic acid molecule encoding an alcohol oxidase or an alcohol dehydrogenase, wherein the alcohol oxidase or alcohol dehydrogenase is capable of catalyzing the conversion of a $C_6$-$C_{24}$ fatty alcohol into a corresponding $C_6$-$C_{24}$ fatty aldehyde. In other embodiments, the recombinant microorganism can further comprise at least one endogenous or exogenous nucleic acid molecule encoding an acetyl transferase capable of catalyzing the conversion of a $C_6$-$C_{24}$ fatty alcohol into a corresponding $C_6$-$C_{24}$ fatty acetate. In certain embodiments, the acetyl transferase, or the nucleic acid sequence that encodes it, can be isolated from organisms of the species *Saccharomyces cerevisiae, Danaus plexippus, Heliotis virescens, Bombyx mori, Agrotis ipsilon, Agrotis segetum, Euonymus alatus*. In exemplary embodiments, the acetyl transferase comprises a sequence selected from GenBank Accession Nos. AY242066, AY242065, AY242064, AY242063, AY242062, EHJ65205, ACX53812, NP_001182381, EHJ65977, EHJ68573, KJ579226, GU594061.

Recombinant Microorganism

The disclosure provides microorganisms that can be engineered to express various exogenous enzymes.

In various embodiments described herein, the recombinant microorganism is a eukaryotic microorganism. In some embodiments, the eukaryotic microorganism is a yeast. In exemplary embodiments, the yeast is a member of a genus selected from the group consisting of *Yarrowia, Candida, Saccharomyces, Pichia, Hansenula, Kluyveromyces, Issatchenkia, Zygosaccharomyces, Debaryomyces, Schizosaccharomyces, Pachysolen, Cryptococcus, Trichosporon, Rhodotorula*, and *Myxozyma*.

The present inventors have discovered that oleaginous yeast, such as *Candida* and *Yarrowia*, have a surprisingly high tolerance to the $C_6$-$C_{24}$ fatty alcohol substrates and products. Accordingly, in one such exemplary embodiment, the recombinant microorganism of the invention is an oleaginous yeast. In further embodiments, the oleaginous yeast is a member of a genus selected from the group consisting of *Yarrowia, Candida, Rhodotorula, Rhodosporidium, Cryptococcus, Trichosporon*, and *Lipomyces*. In even further embodiments, the oleaginous yeast is a member of a species selected from *Yarrowia lipolytica, Candida tropicalis, Rhodosporidium toruloides, Lipomyces starkey, L. lipoferus, C. revkaufi, C. pulcherrima, C. utilis, Rhodotorula minuta, Trichosporon pullans, T. cutaneum, Cryptococcus curvatus, R. glutinis*, and *R. graminis*.

In some embodiments, the recombinant microorganism is a prokaryotic microorganism. In exemplary embodiments, the prokaryotic microorganism is a member of a genus selected from the group consisting of *Escherichia, Clostridium, Zymomonas, Salmonella, Rhodococcus, Pseudomonas, Bacillus, Lactobacillus, Enterococcus, Alcaligenes, Klebsiella, Paenibacillus, Arthrobacter, Corynebacterium*, and *Brevibacterium*.

In some embodiments, the recombinant microorganism is used to produce a mono- or poly-unsaturated $C_6$-$C_{24}$ fatty alcohol, aldehyde, or acetate disclosed herein.

Accordingly, in another aspect, the present inventions provide a method of producing a mono- or poly-unsaturated $C_6$-$C_{24}$ fatty alcohol, aldehyde, or acetate using a recombinant microorganism described herein. In one embodiment, the method comprises cultivating the recombinant microorganism in a culture medium containing a feedstock providing a carbon source until the mono- or poly-unsaturated $C_6$-$C_{24}$ fatty alcohol, aldehyde, or acetate is produced. In a further embodiment, the mono- or poly-unsaturated $C_6$-$C_{24}$ fatty alcohol, aldehyde, or acetate is recovered. Recovery can be by methods known in the art, such as distillation, membrane-based separation gas stripping, solvent extraction, and expanded bed adsorption.

In some embodiments, the feedstock comprises a carbon source. In various embodiments described herein, the carbon source may be selected from sugars, glycerol, alcohols, organic acids, alkanes, fatty acids, lignocellulose, proteins, carbon dioxide, and carbon monoxide. In a further embodiment, the sugar is selected from the group consisting of glucose, fructose, and sucrose.

Enzyme Engineering

The enzymes in the recombinant microorganism can be engineered to improve one or more aspects of the substrate to product conversion. Non-limiting examples of enzymes that can be further engineered for use in methods of the disclosure include a desaturase (e.g., a fatty acyl-CoA desaturase or fatty acyl-ACP desaturase), an acyl-ACP synthetase, a fatty acid synthetase, a fatty acid synthase complex, an acetyl transferase, dehydrogenase, and an alcohol oxidase, and combinations thereof. These enzymes can be engineered for improved catalytic activity, improved selectivity, improved stability, improved tolerance to various fermentations conditions (temperature, pH, etc.), or improved tolerance to various metabolic substrates, products, by-products, intermediates, etc.

Desaturase enzymes can be engineered for improved catalytic activity in the desaturation of an unsaturated substrate, for improved hydrocarbon selectivity, for improved selectivity of a Z product over an E product, or an E product over a Z product. For example, the Z9 fatty-acyl desaturase can be engineered to improve the yield in the substrate to product conversion of a saturated fatty acyl-CoA to the corresponding unsaturated fatty acyl-CoA, and, in addition or in the alternative, to improve selectivity of the desaturation at the 9 position to produce a corresponding Z-9 fatty acyl-CoA. In further non-limiting examples, the fatty acyl-ACP synthetase can be engineered for improved ACP ligation activity; a fatty acid synthase complex enzyme can be engineered for improved catalytic activity of elongation of a fatty acid substrate; a fatty alcohol forming fatty acyl-reductase can be engineered for improved catalytic activity in the reduction of a fatty acyl-CoA to a corresponding fatty alcohol; a fatty aldehyde forming fatty acyl-reductase can be engineered for improved catalytic activity in the reduction of a fatty acyl-ACP to a corresponding fatty aldehyde; a dehydrogenase can be engineered for improved catalytic activity in the conversion of a fatty acyl-ACP to a corresponding fatty alcohol; an alcohol oxidase can be engineered for improved catalytic activity in the conversion of a fatty alcohol into a corresponding fatty aldehyde; and an acetyl transferase can be engineered for improved catalytic activity in the conversion of a fatty alcohol into a corresponding fatty acetate.

The term "improved catalytic activity" as used herein with respect to a particular enzymatic activity refers to a higher level of enzymatic activity than that measured relative to a comparable non-engineered enzyme, such as a non-engineered desaturase (e.g. fatty acyl-CoA desaturase or fatty acyl-ACP desaturase), fatty alcohol or aldehyde forming fatty-acyl reductase, acyl-ACP synthetase, fatty acid synthetase, fatty acid synthase complex, acyl transferase, dehydrogenase, or an alcohol oxidase enzyme. For example, overexpression of a specific enzyme can lead to an increased level of activity in the cells for that enzyme. Mutations can be introduced into a desaturase (e.g. fatty acyl-CoA desaturase or fatty acyl-ACP desaturase), a fatty alcohol or aldehyde forming fatty-acyl reductase, a acyl-ACP synthetase, a fatty acid synthetase, a fatty acid synthase complex, a acyl transferase, a dehydrogenase, or an alcohol oxidase enzyme resulting in engineered enzymes with improved catalytic activity. Methods to increase enzymatic activity are known to those skilled in the art. Such techniques can include increasing the expression of the enzyme by increasing plasmid copy number and/or use of a stronger promoter and/or use of activating riboswitches, introduction of mutations to relieve negative regulation of the enzyme, introduction of specific mutations to increase specific activity and/or decrease the $K_M$ for the substrate, or by directed evolution. See. e.g., *Methods in Molecular Biology* (vol. 231), ed. Arnold and Georgiou, Humana Press (2003).

Metabolic Engineering—Enzyme Overexpression and gene deletion/downregulation for Increased Pathway Flux In various embodiments described herein, the exogenous and endogenous enzymes in the recombinant microorganism participating in the biosynthesis pathways described herein may be overexpressed.

The terms "overexpressed" or "overexpression" refers to an elevated level (e.g., aberrant level) of mRNAs encoding for a protein(s), and/or to elevated levels of protein(s) in cells as compared to similar corresponding unmodified cells expressing basal levels of mRNAs or having basal levels of proteins. In particular embodiments, mRNA(s) or protein(s) may be overexpressed by at least 2-fold, 3-fold, 4-fold, 5-fold, 6-fold, 8-fold, 10-fold, 12-fold, 15-fold or more in microorganisms engineered to exhibit increased gene mRNA, protein, and/or activity.

In some embodiments, a recombinant microorganism of the disclosure is generated from a host that contains the enzymatic capability to synthesize a substrate fatty acid. In this specific embodiment it can be useful to increase the synthesis or accumulation of a fatty acid to, for example, increase the amount of fatty acid available to an engineered fatty alcohol production pathway.

In some embodiments, it may be useful to increase the expression of endogenous or exogenous enzymes involved in the fatty alcohol, aldehyde, or acetate production pathway to increase flux from the fatty acid to the fatty alcohol, aldehyde, or acetate, thereby resulting in increased synthesis or accumulation of the fatty alcohol, aldehyde, or acetate.

In some embodiments, it may be useful to increase the expression of endogenous or exogenous enzymes to increase intracellular levels of a coenzyme. In one embodiment, the coenzyme is NADH. In another embodiment, the coenzyme is NADPH. In one embodiment, the expression of proteins in the pentose phosphate pathway is increased to increase the intracellular levels of NADPH. The pentose phosphate pathway is an important catabolic pathway for supplying reduction equivalents and an important anabolic pathway for biosynthesis reactions. In one embodiment, a glucose-6-phosphate dehydrogenase that converts glucose-6-phosphate to 6-phospho D-glucono-1,5-lactone is overexpressed. In some embodiments, the glucose-6-phosphate dehydrogenase is ZWF1 from yeast. In another embodiment, the glucose-6-phosphate dehydrogenase is ZWF1 (YNL241C) from *Saccharomyces cerevisiae*. In one embodiment, a glucose-6-phosphate-1-dehydrogenase that converts D-glucopyranose-6-phosphate to 6-phospho D-glucono-1,5-lactone is overexpressed. In another embodiment, the glucose-6-phosphate-1-dehydrogenase is zwf from bacteria. In certain embodiments, the glucose-6-phosphate-1-dehydrogenase is zwf (NP_416366) from *E. coli*. In one embodiment, a 6-phosphogluconolactonase that converts 6-phospho D-glucono-1,5-lactone to D-gluconate 6-phosphate is overexpressed. In some embodiments, the 6-phosphogluconolactonase is SOL3 of yeast. In certain embodiments, the 6-phosphogluconolactonase is SOL3 (NP_012033) of *Saccharomyces cerevisiae*. In some embodiments, the 6-phosphogluconolactonase is SOL4 of yeast. In certain embodiments, the 6-phosphogluconolactonase is SOL4 (NP_011764) of *Saccharomyces cerevisiae*. In some embodiments, the 6-phosphogluconolactonase is pgl of bacteria. In certain embodiments, the 6-phosphogluconolactonase is pgl (NP_415288) of *E. coli*. In one embodiment, a 6-phosphogluconate dehydrogenase that converts D-gluconate 6-phosphate to D-ribulose 5-phosphate is overexpressed. In some embodiments, the 6-phosphogluconate dehydrogenase is GND1 from yeast. In certain embodiments, the 6-phosphogluconate dehydrogenase is GND1 (YHR183W) from *Saccharomyces cerevisiae*. In some embodiments, the 6-phosphogluconate dehydrogenase is GND2 from yeast. In certain embodiments, the 6-phosphogluconate dehydrogenase is GND2 (YGR256W) from *Saccharomyces cerevisiae*. In some embodiments, the 6-phosphogluconate dehydrogenase is gnd from bacteria. In certain embodiments, the 6-phosphogluconate dehydrogenase is gnd (NP_416533) from *E. coli*. In one embodiment, a transaldolase that interconverts D-glyceraldehyde 3-phosphate and D-sedoheptulose 7-phosphate to β-D-fructofuranose 6-phosphate and D-erythrose 4-phosphate is overexpressed. In some embodiments, the transaldolase is TAL1 of yeast. In certain embodiments, the transaldolase is TAL1 (NP_013458) of *Saccharomyces cerevisiae*. In some embodiments, the transaldolase is NQM1 of yeast. In certain embodiments, the transaldolase is NQM1 (NP_011557) of *Saccharomyces cerevisiae*. In some embodiments, the transaldolase is tal of bacteria. In certain embodiments, the transaldolase is talB (NP_414549) of *E. coli*. In certain embodiments, the transaldolase is talA (NP_416959) of *E. coli*. In one embodiment, a transketolase that interconverts D-erythrose 4-phosphate and D-xylulose 5-phosphate to β-D-fructofuranose 6-phosphate and D-glyceraldehyde 3-phosphate and/or interconverts D-sedoheptulose 7-phosphate and D-glyceraldehyde 3-phosphate to D-ribose 5-phosphate and D-xylulose 5-phosphate is overexpressed. In some embodiments, the transketolase is TKL1 of yeast. In certain embodiments, the transketolase is TKL1 (NP_015399) of *Saccharomyces cerevisiae*. In some embodiments, the transketolase is TKL2 of yeast. In some embodiments, the transketolase is TKL2 (NP_009675) of *Saccharomyces cerevisiae*. In some embodiments, the transketolase is tkt of bacteria. In certain embodiments, the transketolase is tktA (YP_026188) of *E. coli*. In certain embodiments, the transketolase is tktB (NP_416960) of *E. coli*. In one embodiment, a ribose-5- phosphate ketol-isomerase that interconverts D-ribose 5-phosphate and D-ribulose 5-phosphate is overexpressed. In some embodiments, the ribose-5-phosphate ketol-isomerase is RKI1 of yeast. In certain embodiments, the ribose-5-phosphate ketol-isomerase is RKI1 (NP_014738) of *Saccharomyces cerevisiae*. In some embodiments, the ribose-5-phosphate isomerase is rpi of bacteria. In certain embodiments, the ribose-5-phosphate isomerase is rpiA (NP_417389) of *E. coli*. In certain embodiments, the ribose-5-phosphate isomerase is rpiB (NP_418514) of *E. coli*. In one embodiment, a D-ribulose-5-phosphate 3-epimerase that interconverts D-ribulose 5-phosphate and D-xylulose 5-phosphate is overexpressed. In some embodiments, the D-ribulose-5-phosphate 3-epimerase is RPE1 of yeast. In certain embodiments, the D-ribulose-5-phosphate 3-epimerase is RPE1 (NP_012414) of *Saccharomyces cerevisiae*. In some embodiments, the D-ribulose-5-phosphate 3-epimerase is rpe of bacteria. In certain embodiments, the D-ribulose-5-phosphate 3-epimerase is rpe (NP_417845) of *E. coli*.

In one embodiment, the expression of an NADP+-dependent isocitrate dehydrogenase is increased to increase intracellular levels of a coenzyme. In one embodiment, an NADP+ dependent isocitrate dehydrogenase oxidizes D-threo-isocitrate to 2-oxoglutarate with concomitant generation of NADPH. In another embodiment, an NADP+ dependent isocitrate dehydrogenase oxidizes D-threo-isocitrate to 2-oxalosuccinate with concomitant generation of NADPH. In some embodiments, the NADP+-dependent isocitrate dehydrogenase is IDP from yeast. In certain embodiments, the NADP+-dependent isocitrate dehydrogenase is IDP2 (YLR174W) from *Saccharomyces cerevisiae*. In some embodiments, the NADP+-dependent isocitrate dehydrogenase is icd from bacteria. In certain embodiments, the NADP+-dependent isocitrate dehydrogenase is icd (NP_415654) from *E. coli*.

In some embodiments, the expression of a malic enzyme that decarboxylates malate to pyruvate with concomitant generation of NADH or NADPH is increased to increase intracellular levels of a coenzyme. In one embodiment, the malic enzyme is NAD+ dependent. In another embodiment, the malic enzyme is NADP+ dependent. In one embodiment, the malic enzyme is an NAD+ dependent malate dehydrogenase from bacteria. In some embodiments, the NAD+ dependent malate dehydrogenase is maeA (NP_415996) from *E. coli*. In some embodiments, the NAD+ dependent malate dehydrogenase is maeE (CAQ68119) from *Lactobacillus casei*. In another embodiment, the malic enzyme is a mitochondrial NAD+ dependent malate dehydrogenase from yeast. In some embodiments, the NAD+ dependent malate dehydrogenase is MAE1 (YKL029C) from *S. cerevisiae*. In another embodiment, the malic enzyme is a mitochondrial NAD+ dependent malate dehydrogenase from a parasitic nematode. In some embodiments, the NAD+ dependent malate dehydrogenase is M81055 from *Ascaris suum*. In one embodiment, the malic enzyme is an NADP+ dependent malate dehydrogenase from bacteria. In some embodiments, the NADP+ dependent malate dehydrogenase is maeB (NP_416958) from *E. coli*. In one embodiment, the malic enzyme is an NADP+ dependent malate dehydrogenase from corn. In some embodiments, the NADP+ dependent malate dehydrogenase is me1 from *Zea mays*.

In some embodiments, the expression of an aldehyde dehydrogenase that oxidizes an aldehyde to a carboxylic acid with concomitant generation of NADH or NADPH is increased to increase intracellular levels of a coenzyme. In one embodiment, the aldehyde dehydrogenase is NAD+ dependent. In another embodiment, the aldehyde dehydrogenase is NADP+ dependent. In one embodiment, the aldehyde dehydrogenase is an NAD+ dependent aldehyde dehydrogenase from bacteria. In some embodiments, the NAD+ dependent aldehyde dehydrogenase is aldA (NP_415933) from *E. coli*. In another embodiment, the aldehyde dehydrogenase is a cytosolic NADP+ dependent aldehyde dehydrogenase from yeast. In some embodiments, the NADP+ dependent aldehyde dehydrogenase is ALD6 (YPL061W) from *S. cerevisiae*. In another embodiment, the aldehyde dehydrogenase is a cytosolic NADP+ dependent aldehyde dehydrogenase from bacteria. In some embodiments, the NADP+ dependent aldehyde dehydrogenase is aldB (NP_418045) from *E. coli*.

In one embodiment, overexpression of an enzyme to increase intracellular levels of a coenzyme comprises coupling supplementation of a co-substrate and overexpression of the enzyme. In one embodiment, the overexpression of an enzyme coupled with supplementation of a co-substrate of that enzyme increase flux through a biochemical pathway. In one embodiment, an NAD+ or NADP+ dependent alcohol dehydrogenase is expressed with a co-substrate. In certain embodiments, an alcohol dehydrogenase is expressed with an isopropanol co-substrate. In one embodiment, an NAD+ or NADP+ dependent glucose dehydrogenase is expressed with a co-substrate. In certain embodiments, a glucose dehydrogenase is expressed with a glucose co-substrate.

In one embodiment, the expression of a transhydrogenase is increased to interconvert NADH and NADPH. In some embodiments, the transhydrogenase is a pyridine nucleotide transhydrogenase. In some embodiments, the pyridine nucleotide transhydrogenase is from bacteria. In certain embodiments, the pyridine nucleotide transhydrogenase is pntAB (beta subunit: NP_416119; alpha subunit: NP_416120) from *E. coli*. In some embodiments, the pyridine nucleotide transhydrogenase is from human. In certain embodiments, the pyridine nucleotide transhydrogenase is NNT (NP_036475) from *Homo sapiens*. In certain embodiments, the pyridine nucleotide transhydrogenase is from *Solanum tuberosum*. In certain embodiments, the pyridine nucleotide transhydrogenase is from *Spinacea oleracea*.

In some embodiments, it may be useful to increase the expression of endogenous or exogenous proteins to induce endoplasmic reticulum (ER) membrane proliferation. In some embodiments, the induction of endoplasmic reticulum membrane proliferation can improve production of fatty alcohols, aldehydes, or acetates. In one embodiment, the expression of an inactivated HMG-CoA reductase (hydroxymethylglutaryl-CoA reductase) containing one or more ER facing loops is increased. In certain embodiments, the one or more loops is between transmembrane domains 6 and 7 of an inactivated HMG-CoA reductase. In some embodiments, the inactivated HMG-CoA reductase comprises an inactivated protein or chimera which codes for the first 500 amino acids or a subsequence of the first 500 amino acids of *Yarrowia lipolytica* YALI0E04807p. In other embodiments, the inactivated HMG-CoA reductase comprises an inactivated protein or chimera which codes for the first 522 amino acids or a subsequence of the first 522 amino acids of HMG1 from *Saccharomyces cerevisiae* (NP_013636.1). In other embodiments, the inactivated HMG-CoA reductase comprises an inactivated protein or chimera which codes for the first 522 amino acids or a subsequence of the first 522 amino acids of HMG2 from *Saccharomyces cerevisiae* (NP_013555.1). In some embodiments, the expression of one or more regulatory proteins is increased to improve production of fatty alcohols, aldehydes, or acetates. In certain embodiments, the regulatory protein comprises HAC1 transcription factor from *Saccharomyces cerevisiae* (NP_116622.1). In certain embodiments, the regulatory protein comprises HAC1 transcription factor from *Yarrowia lipolytica* (YALI0B12716p).

Increased synthesis or accumulation can be accomplished by, for example, overexpression of nucleic acids encoding one or more of the above-described a fatty alcohol pathway enzymes. Overexpression of a fatty alcohol pathway enzyme or enzymes can occur, for example, through increased expression of an endogenous gene or genes, or through the expression, or increased expression, of an exogenous gene or genes. Therefore, naturally occurring organisms can be readily modified to generate non-natural, fatty alcohol producing microorganisms through overexpression of one or more nucleic acid molecules encoding a fatty alcohol biosynthetic pathway enzyme. In addition, a non-naturally occurring organism can be generated by mutagenesis of an endogenous gene that results in an increase in activity of an enzyme in the fatty alcohol biosynthetic pathways.

Equipped with the present disclosure, the skilled artisan will be able to readily construct the recombinant microorganisms described herein, as the recombinant microorganisms of the disclosure can be constructed using methods well known in the art as exemplified above to exogenously express at least one nucleic acid encoding a fatty alcohol pathway enzyme in sufficient amounts to produce a fatty alcohol.

Methods for constructing and testing the expression levels of a non-naturally occurring fatty alcohol-producing host can be performed, for example, by recombinant and detection methods well known in the art. Such methods can be found described in, for example, Sambrook et al., *Molecular Cloning: A Laboratory Manual*, Third Ed., Cold Spring Harbor Laboratory, New York (2001); Ausubo et al., *Current Protocols in Molecular Biology*, John Wiley and Sons, Baltimore, Md. (1999).

A variety of mechanisms known in the art can be used to express, or overexpress, exogenous or endogenous genes. For example, an expression vector or vectors can be constructed to harbor one or more fatty alcohol biosynthetic pathway enzyme encoding nucleic acids as exemplified herein operably linked to expression control sequences functional in the host organism. Expression vectors applicable for use in the microbial host organisms of the invention include, for example, plasmids, phage vectors, viral vectors, episomes and artificial chromosomes, including vectors and selection sequences or markers operable for stable integration into a host chromosome. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more exogenous encoding nucleic acids are to be co-expressed, both nucleic acids can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The transformation of exogenous nucleic acid sequences involved in a metabolic or synthetic pathway can be confirmed using methods well known in the art.

Expression control sequences are known in the art and include, for example, promoters, enhancers, polyadenylation signals, transcription terminators, internal ribosome entry sites (IRES), and the like, that provide for the expression of the polynucleotide sequence in a host cell. Expression control sequences interact specifically with cellular proteins involved in transcription (Maniatis et al., *Science*. 236: 1237-1245 (1987)). Exemplary expression control sequences are described in, for example, Goeddel, *Gene Expression Technology: Methods in Enzymology*, Vol. 185, Academic Press, San Diego, Calif. (1990).

In various embodiments, an expression control sequence may be operably linked to a polynucleotide sequence. By "operably linked" is meant that a polynucleotide sequence and an expression control sequence(s) are connected in such a way as to permit gene expression when the appropriate molecules (e.g., transcriptional activator proteins) are bound to the expression control sequence(s). Operably linked promoters are located upstream of the selected polynucleotide sequence in terms of the direction of transcription and translation. Operably linked enhancers can be located upstream, within, or downstream of the selected polynucleotide.

In some embodiments, the recombinant microorganism is manipulated to delete, disrupt, mutate, and/or reduce the activity of one or more endogenous enzymes that catalyzes a reaction in a pathway that competes with the biosynthesis pathway for the production of a mono- or poly-unsaturated $C_6$-$C_{24}$ fatty alcohol, aldehyde, or acetate.

In some embodiments, the recombinant microorganism is manipulated to delete, disrupt, mutate, and/or reduce the activity of one or more endogenous enzymes that catalyzes the conversion of a fatty acid into a ω-hydroxyfatty acid. In some such embodiments, the enzymes that catalyze the conversion of a fatty acid into a ω-hydroxyfatty acid are selected from the group consisting of XP_504406, XP_504857, XP_504311, XP_500855, XP_500856, XP_500402, XP_500097, XP_501748, XP_500560, XP_501148, XP_501667, XP_500273, BAA02041, CAA39366, CAA39367, BAA02210, BAA02211, BAA02212, BAA02213, BAA02214, AAO73952, AAO73953, AAO73954, AAO73955, AAO73956, AAO73958, AAO73959, AAO73960, AAO73961, AAO73957, XP_002546278, BAM49649, AAB80867, AAB17462, ADL27534, AAU24352, AAA87602, CAA34612, ABM17701, AAA25760, CAB51047, AAC82967, WP_011027348, or homologs thereof.

In other embodiments, the recombinant microorganism is manipulated to delete, disrupt, mutate, and/or reduce the activity of one or more endogenous enzymes that catalyzes the conversion of a fatty acyl-CoA into α,β-enoyl-CoA. In some such embodiments, the enzymes that catalyze the conversion of a fatty acyl-CoA into α,β-enoyl-CoA are selected from the group consisting of CAA04659, CAA04660, CAA04661, CAA04662, CAA04663, CAG79214, AAA34322, AAA34361, AAA34363, CAA29901, BAA04761, AAA34891, AAB08643, CAB15271, BAN55749, CAC44516, ADK16968, AEI37634, WP_000973047, WP_025433422, WP_035184107, WP_026484842, CEL80920, WP_026818657, WP_005293707, WP_005883960, or homologs thereof.

In some embodiments, the recombinant microorganism is manipulated to delete, disrupt, mutate, and/or reduce the activity of one or more proteins involved in peroxisome biogenesis. In such embodiments, the one or more proteins involved in peroxisome biogenesis are selected from the group consisting of XP_505754, XP_501986, XP_501311, XP_504845, XP_503326, XP_504029, XP_002549868, XP_002547156, XP_002545227, XP_002547350, XP_002546990, EIW11539, EIW08094, EIW11472, EIW09743, EIW0828, or homologs thereof.

In some embodiments, the recombinant microorganism is manipulated to delete, disrupt, mutate, and/or reduce the activity of one or more endogenous enzymes that catalyzes a reaction in a pathway that competes with the biosynthesis pathway for one or more unsaturated fatty acyl-CoA intermediates. In one embodiment, the one or more endogenous enzymes comprise one or more diacylglycerol acyltransferases. In the context of a recombinant yeast microorganism, the recombinant yeast microorganism is engineered to delete, disrupt, mutate, and/or reduce the activity of one or more diacylglycerol acyltransferases selected from the group consisting of YALI0E32769g, YALI0D07986g and CTRG_06209, or homolog thereof. In another embodiment, the one or more endogenous enzymes comprise one or more glycerolphospholipid acyltransferases. In the context of a recombinant yeast microorganism, the recombinant yeast microorganism is engineered to delete, disrupt, mutate, and/or reduce the activity of one or more glycerolphospholipid acyltransferases selected from the group consisting of YALI0E16797g and CTG_04390, or homolog thereof. In another embodiment, the one or more endogenous enzymes comprise one or more acyl-CoA/sterol acyltransferases. In the context of a recombinant yeast microorganism, the recombinant yeast microorganism is engineered to delete, disrupt, mutate, and/or reduce the activity of one or more acyl-CoA/sterol acyltransferases selected from the group consisting of YALI0F06578g, CTRG_01764 and CTRG_01765, or homolog thereof.

In another embodiment, the recombinant microorganism is manipulated to delete, disrupt, mutate, and/or reduce the activity of one or more endogenous enzymes that catalyzes a reaction in a pathway that oxidizes fatty aldehyde intermediates. In one embodiment, the one or more endogenous enzymes comprise one or more fatty aldehyde dehydrogenases. In the context of a recombinant yeast microorganism, the recombinant yeast microorganism is engineered to delete, disrupt, mutate, and/or reduce the activity of one or more fatty aldehyde dehydrogenases selected from the group consisting of YALI0A17875g, YALI0E15400g, YALI0B01298g, YALI0F23793g, CTRG_05010 and CTRG_04471, or homolog thereof.

In another embodiment, the recombinant microorganism is manipulated to delete, disrupt, mutate, and/or reduce the activity of one or more endogenous enzymes that catalyzes a reaction in a pathway that consumes fatty acetate products. In one embodiment, the one or more endogenous enzymes comprise one or more sterol esterases. In the context of a recombinant yeast microorganism, the recombinant yeast microorganism is engineered to delete, disrupt, mutate, and/or reduce the activity of one or more sterol esterases selected from the group consisting of YALI0E32035g, YALI0E00528g, CTRG_01138, CTRG_01683 and CTRG_04630, or homolog thereof. In another embodiment, the one or more endogenous enzymes comprise one or more triacylglycerol lipases. In the context of a recombinant yeast microorganism, the recombinant yeast microorganism is engineered to delete, disrupt, mutate, and/or reduce the activity of one or more triacylglycerol lipases selected from the group consisting of YALI0D17534g, YALI0F10010g, CTRG_00057 and CTRG_06185, or homolog thereof. In another embodiment, the one or more endogenous enzymes comprise one or more monoacylglycerol lipases. In the context of a recombinant yeast microorganism, the recombinant yeast microorganism is engineered to delete, disrupt, mutate, and/or reduce the activity of one or more monoacylglycerol lipases selected from the group consisting of YALI0C14520g, CTRG_03360 and CTRG_05049, or homolog thereof. In another embodiment, the one or more endogenous enzymes comprise one or more extracellular lipases. In the context of a recombinant yeast microorganism, the recombinant yeast microorganism is engineered to delete, disrupt, mutate, and/or reduce the activity of one or more extracellular lipases selected from the group consisting of YALI0A20350g, YALI0D19184g, YALI0B09361g, CTRG_05930, CTRG_04188, CTRG_02799, CTRG_03052 and CTRG_03885, or homolog thereof.

In another embodiment, the recombinant microorganism is manipulated to delete, disrupt, mutate, and/or reduce the activity of one or more endogenous reductase or desaturase enzymes that interferes with the unsaturated $C_6$-$C_{24}$ fatty alcohol, aldehyde, or acetate, i.e., catalyzes the conversion of a pathway substrate or product into an unwanted by-product.

Chemical Conversion of Product from Microorganism Synthesis

The present disclosure describes chemical conversions that can be used to convert a product synthesized by recombinant microorganism into a down-stream product.

In some embodiments, an unsaturated fatty alcohol, aldehyde, acetate, or carboxylic acid produced by a microorganism can undergo subsequent chemical conversion to produce a pheromone, fragrance, flavor, polymer, or polymer intermediate. Non-limiting examples of chemical transformations include esterification, metathesis, and polymerization.

Unsaturated fatty carboxylic acids can be esterified by methods known in the art. For example, Fischer esterification can be used to covert a fatty carboxylic acid to a corresponding fatty ester. See, e.g., Komura, K. et al., *Synthesis* 2008. 3407-3410.

Elongation of the carbon chain can be performed by known methods to covert an unsaturated fatty alcohol into an elongated derivative thereof. Olefin metastasis catalysts can be performed to increase the number of carbons on the fatty carbon chain and impart Z or E stereochemistry on the corresponding unsaturated product.

In general, any metathesis catalyst stable under the reaction conditions and nonreactive with functional groups on the fatty substrate (e.g., alcohol, ester, carboxylic acid, aldehyde, or acetate) can be used with the present disclosure. Such catalysts are, for example, those described by Grubbs (Grubbs, R H., "Synthesis of large and small molecules using olefin metathesis catalysts." *PMSE Prepr.*, 2012), herein incorporated by reference in its entirety. Depending on the desired isomer of the olefin, as cis-selective metathesis catalyst may be used, for example one of those described by Shahane et al. (Shahane, S., et al. *ChemCatChem*, 2013. 5(12): p. 3436-3459), herein incorporated by reference in its entirety. Specific catalysts 1-5 exhibiting cis-selectivity are shown below (Scheme 1) and have been described previously (Khan, R. K., et al. *J. Am. Chem. Soc.*, 2013. 135(28): p. 10258-61; Hartung, J. et al. *J. Am. Chem. Soc.*, 2013. 135(28): p. 10183-5; Rosebrugh, L. E., et al. *J. Am. Chem. Soc.*, 2013. 135(4): p. 1276-9; Marx, V. M., et al. *J. Am. Chem. Soc.*, 2013. 135(1): p. 94-7; Herbert, M. B., et al. *Angew. Chem. Int. Ed. Engl.*, 2013. 52(1): p. 310-4; Keitz, B. K., et al. *J. Am. Chem. Soc.*, 2012. 134(4): p. 2040-3; Keitz, B. K., et al. *J. Am. Chem. Soc.*, 2012. 134(1): p. 693-9; Endo, K. et al. *J. Am. Chem. Soc.*, 2011. 133(22): p. 8525-7).

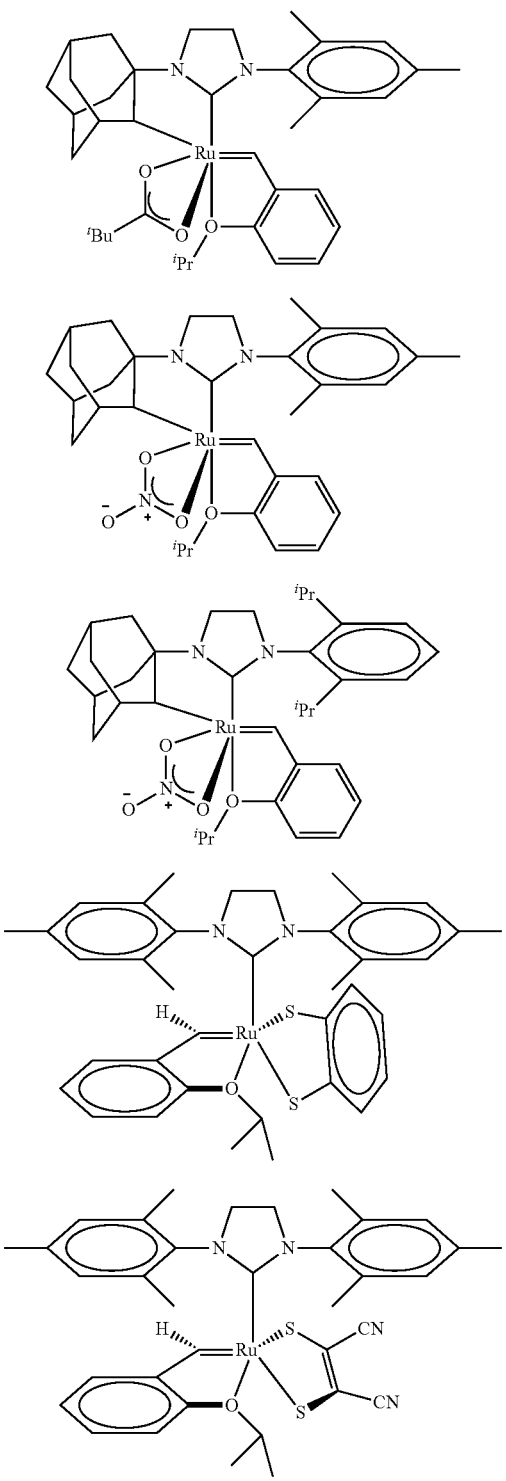

Additional Z-selective catalysts are described in (Cannon and Grubbs 2013; Bronner et al. 2014; Hartung et al. 2014; Pribisko et al. 2014; Quigley and Grubbs 2014) and are herein incorporated by reference in their entirety. Due to their excellent stability and functional group tolerance, in some embodiments metathesis catalysts include, but are not limited to, neutral ruthenium or osmium metal carbene complexes that possess metal centers that are formally in the +2 oxidation state, have an electron count of 16, are penta-coordinated, and are of the general formula LL'AA'M=CRbRc or LL'AA'M=(C=)nCRbRc (Pederson and Grubbs 2002); wherein M is ruthenium or osmium;

L and L' are each independently any neutral electron donor ligand and selected from phosphine, sulfonated phosphine, phosphite, phosphinite, phosphonite, arsine, stibnite, ether, amine, amide, imine, sulfoxide, carboxyl, nitrosyl, pyridine, thioether, or heterocyclic carbenes; and A and A' are anionic ligands independently selected from halogen, hydrogen, $C_1$-$C_{20}$ alkyl, aryl, $C_1$-$C_{20}$ alkoxide, aryloxide, $C_2$-$C_{20}$ alkoxycarbonyl, arylcarboxylate, $C_1$-$C_{20}$ carboxylate, arylsulfonyl, $C_1$-$C_{20}$ alkylsulfonyl, $C_1$-$C_{20}$ alkylsulfinyl; each ligand optionally being substituted with $C_1$-$C_5$ alkyl, halogen, $C_1$-$C_5$ alkoxy; or with a phenyl group that is optionally substituted with halogen, $C_1$-$C_5$ alkyl, or $C_1$-$C_5$ alkoxy; and A and A' together may optionally comprise a bidentate ligand; and $R_b$ and $R_c$ are independently selected from hydrogen, $C_1$-$C_{20}$ alkyl, aryl, $C_1$-$C_{20}$ carboxylate, $C_1$-$C_{20}$ alkoxy, aryloxy, $C_1$-$C_{20}$ alkoxycarbonyl, $C_1$-$C_{20}$ alkylthio, $C_1$-$C_{20}$ alkylsulfonyl and $C_1$-$C_{20}$ alkylsulfinyl, each of $R_b$ and $R_c$ optionally substituted with $C_1$-$C_5$ alkyl, halogen, $C_1$-$C_5$ alkoxy or with a phenyl group that is optionally substituted with halogen, $C_1$-$C_5$ alkyl, or $C_1$-$C_5$ alkoxy.

Other metathesis catalysts such as "well defined catalysts" can also be used. Such catalysts include, but are not limited to, Schrock's molybdenum metathesis catalyst, 2,6-diisopropylphenylimido neophylidenemolybdenum (VI) bis (hexafluoro-t-butoxide), described by Grubbs et al. (*Tetrahedron* 1998, 54: 4413-4450) and Basset's tungsten metathesis catalyst described by Couturier, J. L. et al. (*Angew. Chem. Int. Ed. Engl.* 1992, 31: 628).

Catalysts useful in the methods of the disclosure also include those described by Peryshkov, et al. *J. Am. Chem. Soc.* 2011, 133: 20754-20757; Wang, et al. *Angewandte Chemie*, 2013, 52: 1939-1943; Yu, et al. *J. Am. Chem. Soc.*, 2012, 134: 2788-2799; Halford. *Chem. Eng. News.* 2011, 89 (45): 11; Yu, et al. *Nature*, 2011, 479: 88-93; Lee. *Nature*, 2011, 471: 452-453; Meek, et al. *Nature*, 2011: 471, 461-466; Flook, et al. *J. Am. Chem. Soc.* 2011, 133: 1784-1786; Zhao, et al. *Org Lett.*, 2011, 13(4): 784-787; Ondi, et al. "High activity, stabilized formulations, efficient synthesis and industrial use of Mo- and W-based metathesis catalysts" *XiMo Technology Updates*. 2015: http://www.ximo-inc.com/files/ximo/uploads/download/Summary_3.11.15.pdf; Schrock, et al. *Macromolecules*, 2010: 43, 7515-7522; Peryshkov, et al. *Organometallics* 2013: 32, 5256-5259; Gerber, et al. *Organometallics* 2013: 32, 5573-5580; Marinescu, et al. *Organometallics* 2012: 31, 6336-6343; Wang, et al. *Angew. Chem. Int. Ed.* 2013: 52, 1939-1943; Wang, et al. *Chem. Eur. J.* 2013: 19, 2726-2740; and Townsend et al. *J. Am. Chem. Soc.* 2012: 134, 11334-11337.

Catalysts useful in the methods of the disclosure also include those described in International Pub. No. WO 2014/155185; International Pub. No. WO 2014/172534; U.S. Pat. Appl. Pub. No. 2014/0330018; International Pub. No. WO 2015/003815; and International Pub. No. WO 2015/003814.

Catalysts useful in the methods of the disclosure also include those described in U.S. Pat. Nos. 4,231,947; 4,245,131; 4,427,595; 4,681,956; 4,727,215; International Pub. No. WO 1991/009825; U.S. Pat. Nos. 5,087,710; 5,142,073; 5,146,033; International Pub. No. WO 1992/019631; U.S.

Pat. Nos. 6,121,473; 6,346,652; 8,987,531; U.S. Pat. Appl. Pub. No. 2008/0119678; International Pub. No. WO 2008/066754; International Pub. No. WO 2009/094201; U.S. Pat. Appl. Pub. No. 2011/0015430; U.S. Pat. Appl. Pub. No. 2011/0065915; U.S. Pat. Appl. Pub. No. 2011/0077421; International Pub. No. WO 2011/040963; International Pub. No. WO 2011/097642; U.S. Pat. Appl. Pub. No. 2011/0237815; U.S. Pat. Appl. Pub. No. 2012/0302710; International Pub. No. WO 2012/167171; U.S. Pat. Appl. Pub. No. 2012/0323000; U.S. Pat. Appl. Pub. No. 2013/0116434; International Pub. No. WO 2013/070725; U.S. Pat. Appl. Pub. No. 2013/0274482; U.S. Pat. Appl. Pub. No. 2013/0281706; International Pub. No. WO 2014/139679; International Pub. No. WO 2014/169014; U.S. Pat. Appl. Pub. No. 2014/0330018; and U.S. Pat. Appl. Pub. No. 2014/0378637.

Catalysts useful in the methods of the disclosure also include those described in International Pub. No. WO 2007/075427; U.S. Pat. Appl. Pub. No. 2007/0282148; International Pub. No. WO 2009/126831; International Pub. No. WO 2011/069134; U.S. Pat. Appl. Pub. No. 2012/0123133; U.S. Pat. Appl. Pub. No. 2013/0261312; U.S. Pat. Appl. Pub. No. 2013/0296511; International Pub. No. WO 2014/134333; and U.S. Pat. Appl. Pub. No. 2015/0018557.

Catalysts useful in the methods of the disclosure also include those set forth in the following table:

| Structure | Name |
|---|---|
| 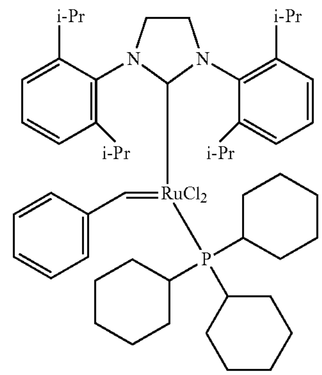 | dichloro[1,3-bis(2,6-isopropylphenyl)-2-imidazolidinylidene](benzylidene)(tricyclohexylphosphine)ruthenium(II) |
| 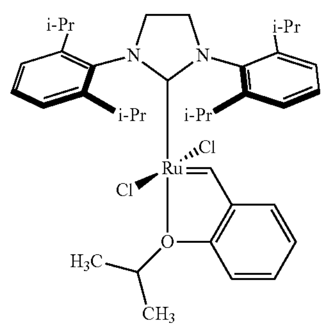 | dichloro[1,3-bis(2,6-isopropylphenyl)-2-imidazolidinylidene](2-isopropoxyphenylmethylene)ruthenium(II) |
| 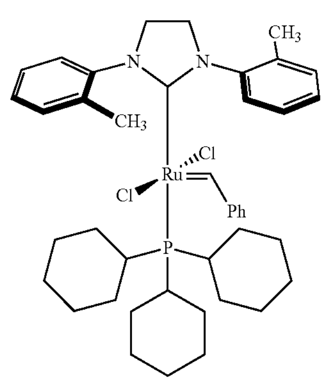 | dichloro[1,3-Bis(2-methylphenyl)-2-imidazolidinylidene](benzylidene)(tricyclohexylphosphine)ruthenium(II) |

| Structure | Name |
|---|---|
| 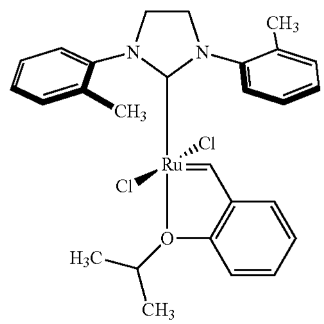 | dichloro[1,3-bis(2-methylphenyl)-2-imidazolidinylidene](2-isopropoxyphenylmethylene)ruthenium(II) |
| 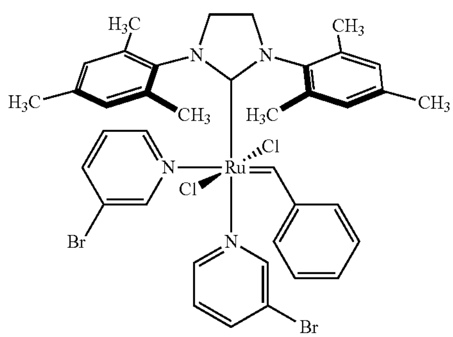 | dichloro[1,3-bis(2,4,6-trimethylphenyl)-2-imidazolidinylidene](benzylidene)bis(3-bromopyridine)ruthenium(II) |
| 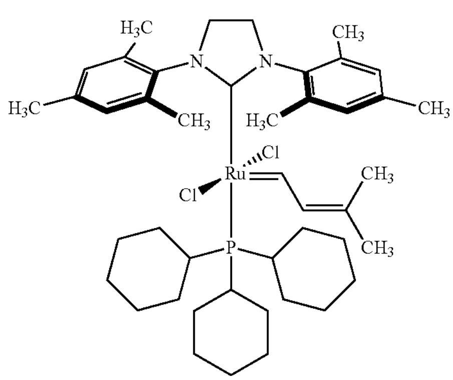 | dichloro[1,3-bis(2,4,6-trimethylphenyl)-2-imidazolidinylidene](3-methyl-2-butenylidene)(tricyclohexylphosphine)ruthenium(II) |
| 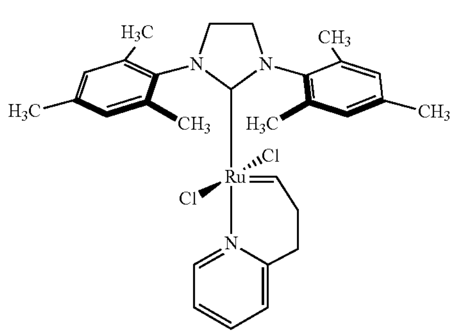 | dichloro[1,3-bis(2,4,6-trimethylphenyl)-2-imidazolidinylidene][3-(2-pyridinyl)propylidene]ruthenium(II) |

| Structure | Name |
|---|---|
| 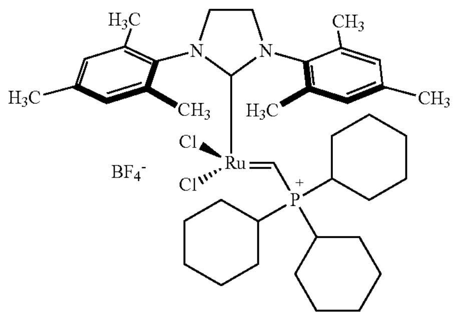 | dichloro[1,3-bis(2,4,6-trimethylphenyl)-2-imidazolidinylidene][(tricyclohexylphosphoranyl)methylidene]ruthenium(II) tetrafluoroborate |
| 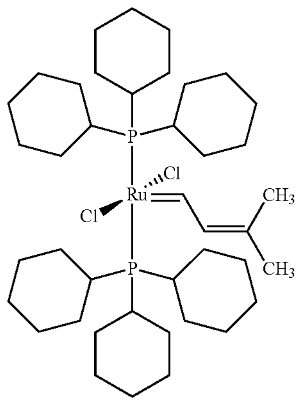 | dichloro(3-methyl-2-butenylidene)bis(tricyclohexylphosphine)ruthenium(II) |
| 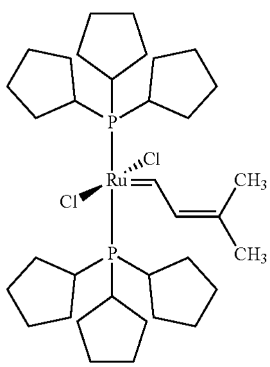 | dichloro(3-methyl-2-butenylidene)bis(tricyclopentylphosphine)ruthenium(II) |
| 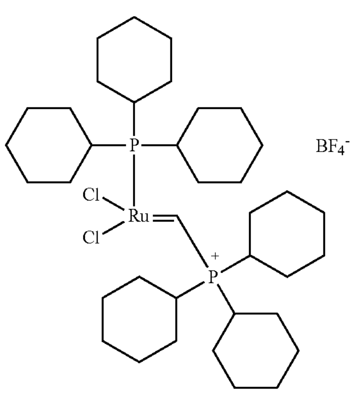 | dichloro(tricyclohexylphosphine)[(tricyclohexyl-phosphoranyl)methylidene]ruthenium(II) tetrafluoroborate |

-continued

| Structure | Name |
|---|---|
| 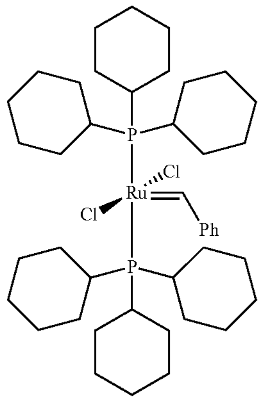 | bis(tricyclohexylphosphine) benzylidine ruthenium(IV) dichloride |
| 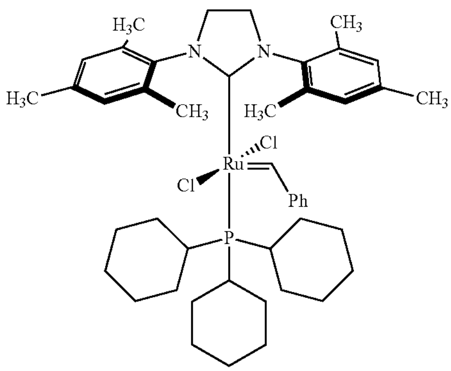 | [1,3-bis-(2,4,6-trimethylphenyl)-2-imidazolidinylidene]dichloro(phenylmethylene)(tricyclohexylphosphine)ruthenium |
| 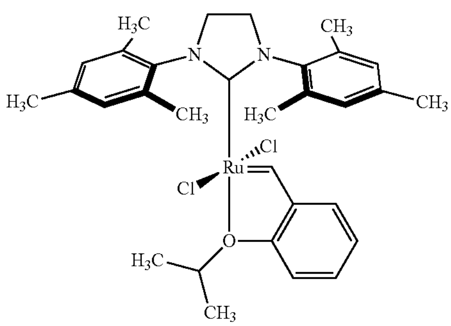 | (1,3-bis-(2,4,6-trimethylphenyl)-2-imidazolidinylidene)dichloro(o-isopropoxyphenylmethylene)ruthenium |
| 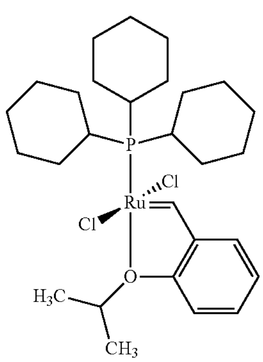 | dichloro(o-isopropoxyphenylmethylene)(tricyclohexyl-phosphine)ruthenium(II) |

| Structure | Name |
|---|---|
| (structure image) | [2-(1-methylethoxy-O)phenylmethyl-C](nitrato-O,O'){rel-(2R,5R,7R)-adamantane-2,1-diyl[3-(2,4,6-trimethylphenyl)-1-imidazolidinyl-2-ylidene]}ruthenium |

Catalysts useful in the methods of the disclosure also include those described in U.S. Pat. Appl. Pub. No. 2008/0009598; U.S. Pat. Appl. Pub. No. 2008/0207911; U.S. Pat. Appl. Pub. No. 2008/0275247; U.S. Pat. Appl. Pub. No. 2011/0040099; U.S. Pat. Appl. Pub. No. 2011/0282068; and U.S. Pat. Appl. Pub. No. 2015/0038723.

Catalysts useful in the methods of the disclosure include those described in International Pub. No. WO 2007/140954; U.S. Pat. Appl. Pub. No. 2008/0221345; International Pub. No. WO 2010/037550; U.S. Pat. Appl. Pub. No. 2010/0087644; U.S. Pat. Appl. Pub. No. 2010/0113795; U.S. Pat. Appl. Pub. No. 2010/0174068; International Pub. No. WO 2011/091980; International Pub. No. WO 2012/168183; U.S. Pat. Appl. Pub. No. 2013/0079515; U.S. Pat. Appl. Pub. No. 2013/0144060; U.S. Pat. Appl. Pub. No. 2013/0211096; International Pub. No. WO 2013/135776; International Pub. No. WO 2014/001291; International Pub. No. WO 2014/067767; U.S. Pat. Appl. Pub. No. 2014/0171607; and U.S. Pat. Appl. Pub. No. 2015/0045558.

The catalyst is typically provided in the reaction mixture in a sub-stoichiometric amount (e.g., catalytic amount). In certain embodiments, that amount is in the range of about 0.001 to about 50 mol % with respect to the limiting reagent of the chemical reaction, depending upon which reagent is in stoichiometric excess. In some embodiments, the catalyst is present in less than or equal to about 40 mol % relative to the limiting reagent. In some embodiments, the catalyst is present in less than or equal to about 30 mol % relative to the limiting reagent. In some embodiments, the catalyst is present in less than about 20 mol %, less than about 10 mol %, less than about 5 mol %, less than about 2.5 mol %, less than about 1 mol %, less than about 0.5 mol %, less than about 0.1 mol %, less than about 0.015 mol %, less than about 0.01 mol %, less than about 0.0015 mol %, or less, relative to the limiting reagent. In some embodiments, the catalyst is present in the range of about 2.5 mol % to about 5 mol %, relative to the limiting reagent. In some embodiments, the reaction mixture contains about 0.5 mol % catalyst. In the case where the molecular formula of the catalyst complex includes more than one metal, the amount of the catalyst complex used in the reaction may be adjusted accordingly.

In some cases, the methods described herein can be performed in the absence of solvent (e.g., neat). In some cases, the methods can include the use of one or more solvents. Examples of solvents that may be suitable for use in the disclosure include, but are not limited to, benzene, p-cresol, toluene, xylene, diethyl ether, glycol, diethyl ether, petroleum ether, hexane, cyclohexane, pentane, methylene chloride, chloroform, carbon tetrachloride, dioxane, tetrahydrofuran (THF), dimethyl sulfoxide, dimethylformamide, hexamethyl-phosphoric triamide, ethyl acetate, pyridine, triethylamine, picoline, and the like, as well as mixtures thereof. In some embodiments, the solvent is selected from benzene, toluene, pentane, methylene chloride, and THF. In certain embodiments, the solvent is benzene.

In some embodiments, the method is performed under reduced pressure. This may be advantageous in cases where a volatile byproduct, such as ethylene, may be produced during the course of the metathesis reaction. For example, removal of the ethylene byproduct from the reaction vessel may advantageously shift the equilibrium of the metathesis reaction towards formation of the desired product. In some embodiments, the method is performed at a pressure of about less than 760 torr. In some embodiments, the method is performed at a pressure of about less than 700 torr. In some embodiments, the method is performed at a pressure of about less than 650 torr. In some embodiments, the method is performed at a pressure of about less than 600 torr. In some embodiments, the method is performed at a pressure of about less than 550 torr. In some embodiments, the method is performed at a pressure of about less than 500 torr. In some embodiments, the method is performed at a pressure of about less than 450 torr. In some embodiments, the method is performed at a pressure of about less than 400 torr. In some embodiments, the method is performed at a pressure of about less than 350 torr. In some embodiments, the method is performed at a pressure of about less than 300 torr. In some embodiments, the method is performed at a pressure of about less than 250 torr. In some embodiments, the method is performed at a pressure of about less than 200 torr. In some embodiments, the method is performed at a pressure of about less than 150 torr. In some embodiments, the method is performed at a pressure of about less than 100 torr. In some embodiments, the method is performed at a pressure of about less than 90 torr. In some embodiments, the method is performed at a pressure of about less than 80 torr. In some embodiments, the method is performed at a pressure of about less than 70 torr. In some embodiments, the method is performed at a pressure of about less than 60 torr. In some embodiments, the method is performed at a pressure of about less than 50 torr. In some embodiments, the method is performed at a pressure of about less than 40 torr. In some embodiments, the method is performed at a pressure of about less than 30 torr. In some embodiments, the method is performed at a pressure of about less than 20 torr. In some embodiments, the method is performed at a pressure of about 20 torr.

In some embodiments, the method is performed at a pressure of about 19 torr. In some embodiments, the method is performed at a pressure of about 18 torr. In some embodiments, the method is performed at a pressure of about 17 torr. In some embodiments, the method is performed at a pressure of about 16 torr. In some embodiments, the method is performed at a pressure of about 15 torr. In some embodiments, the method is performed at a pressure of about 14 torr. In some embodiments, the method is performed at a pressure of about 13 torr. In some embodiments, the method is performed at a pressure of about 12 torr. In some embodiments, the method is performed at a pressure of about 11 torr. In some embodiments, the method is performed at a pressure of about 10 torr. In some embodiments, the method is performed at a pressure of about 10 torr. In some embodiments, the method is performed at a pressure of about 9 torr. In some embodiments, the method is performed at a pressure of about 8 torr. In some embodiments, the method is performed at a pressure of about 7 torr. In some embodiments, the method is performed at a pressure of about 6 torr. In some embodiments, the method is performed at a pressure of about 5 torr. In some embodiments, the method is performed at a pressure of about 4 torr. In some embodiments, the method is performed at a pressure of about 3 torr. In some embodiments, the method is performed at a pressure of about 2 torr. In some embodiments, the method is performed at a pressure of about 1 torr. In some embodiments, the method is performed at a pressure of less than about 1 torr.

In some embodiments, the two metathesis reactants are present in equimolar amounts. In some embodiments, the two metathesis reactants are not present in equimolar amounts. In certain embodiments, the two reactants are present in a molar ratio of about 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, or 1:20. In certain embodiments, the two reactants are present in a molar ratio of about 10:1. In certain embodiments, the two reactants are present in a molar ratio of about 7:1. In certain embodiments, the two reactants are present in a molar ratio of about 5:1. In certain embodiments, the two reactants are present in a molar ratio of about 2:1. In certain embodiments, the two reactants are present in a molar ratio of about 1:10. In certain embodiments, the two reactants are present in a molar ratio of about 1:7. In certain embodiments, the two reactants are present in a molar ratio of about 1:5. In certain embodiments, the two reactants are present in a molar ratio of about 1:2.

In general, the reactions with many of the metathesis catalysts disclosed herein provide yields better than 15%, better than 50%, better than 75%, or better than 90%. In addition, the reactants and products are chosen to provide at least a 5° C. difference, a greater than 20° C. difference, or a greater than 40° C. difference in boiling points. Additionally, the use of metathesis catalysts allows for much faster product formation than byproduct, it is desirable to run these reactions as quickly as practical. In particular, the reactions are performed in less than about 24 hours, less than 12 hours, less than 8 hours, or less than 4 hours.

One of skill in the art will appreciate that the time, temperature and solvent can depend on each other, and that changing one can require changing the others to prepare the pyrethroid products and intermediates in the methods of the disclosure. The metathesis steps can proceed at a variety of temperatures and times. In general, reactions in the methods of the disclosure are conducted using reaction times of several minutes to several days. For example, reaction times of from about 12 hours to about 7 days can be used. In some embodiments, reaction times of 1-5 days can be used. In some embodiments, reaction times of from about 10 minutes to about 10 hours can be used. In general, reactions in the methods of the disclosure are conducted at a temperature of from about 0° C. to about 200° C. For example, reactions can be conducted at 15-100° C. In some embodiments, reaction can be conducted at 20-80° C. In some embodiments, reactions can be conducted at 100-150° C.

Unsaturated fatty esters can be reduced using a suitable reducing agent which selectively reduces the ester to the corresponding aldehyde or alcohol but does not reduce the double bond. An unsaturated fatty ester can be reduced to the corresponding unsaturated fatty aldehyde using di-isobutyl aluminum halide (DIBAL) or Vitride®. The unsaturated fatty aldehyde can be reduced to the corresponding fatty alcohol with, e.g., DIBAL or Vitride®. In some embodiments, the unsaturated fatty ester can be reduced to the corresponding fatty alcohol using $AlH_3$ or 9-Borabicyclo (3.3.1)nonane (9-BBN). (See Galatis, P. *Encyclopedia of Reagents for Organic Synthesis.* 2001. New York: John Wiley & Sons; and Carey & Sunderburg. *Organic Chemistry. Part B: Reactions and Synthesis,* $5^{th}$ edition. 2007. New York. Springer Sciences)

Pheromone Compositions and Uses Thereof

As described above, products made via the methods described herein are pheromones. Pheromones prepared according to the methods of the invention can be formulated for use as insect control compositions. The pheromone compositions can include a carrier, and/or be contained in a dispenser. The carrier can be, but is not limited to, an inert liquid or solid.

Examples of solid carriers include but are not limited to fillers such as kaolin, bentonite, dolomite, calcium carbonate, talc, powdered magnesia, Fuller's earth, wax, gypsum, diatomaceous earth, rubber, plastic, China clay, mineral earths such as silicas, silica gels, silicates, attaclay, limestone, chalk, loess, clay, dolomite, calcium sulfate, magnesium sulfate, magnesium oxide, ground synthetic materials, fertilizers such as ammonium sulfate, ammonium phosphate, ammonium nitrate, thiourea and urea, products of vegetable origin such as cereal meals, tree bark meal, wood meal and nutshell meal, cellulose powders, attapulgites, montmorillonites, mica, vermiculites, synthetic silicas and synthetic calcium silicates, or compositions of these.

Examples of liquid carriers include, but are not limited to, water; alcohols, such as ethanol, butanol or glycol, as well as their ethers or esters, such as methylglycol acetate; ketones, such as acetone, cyclohexanone, methylethyl ketone, methylisobutylketone, or isophorone; alkanes such as hexane, pentane, or heptanes; aromatic hydrocarbons, such as xylenes or alkyl naphthalenes; mineral or vegetable oils; aliphatic chlorinated hydrocarbons, such as trichloroethane or methylene chloride; aromatic chlorinated hydrocarbons, such as chlorobenzenes; water-soluble or strongly polar solvents such as dimethylformamide, dimethyl sulfoxide, or N-methylpyrrolidone; liquefied gases; waxes, such as beeswax, lanolin, shellac wax, carnauba wax, fruit wax (such as bayberry or sugar cane wax) candelilla wax, other waxes such as microcrystalline, ozocerite, ceresin, or montan; salts such as monoethanolamine salt, sodium sulfate, potassium sulfate, sodium chloride, potassium chloride, sodium acetate, ammonium hydrogen sulfate, ammonium chloride, ammonium acetate, ammonium formate, ammonium oxalate, ammonium carbonate, ammonium hydrogen carbonate, ammonium thiosulfate, ammonium hydrogen diphosphate, ammonium dihydrogen monophosphate, ammonium sodium hydrogen phosphate, ammonium thiocyanate, ammonium sulfamate or ammonium carbamateand mixtures thereof. Baits or feeding stimulants can also be added to the carrier.

Synergist

In some embodiments, the pheromone composition is combined with an active chemical agent such that a synergistic effect results. The synergistic effect obtained by the taught methods can be quantified according to Colby's formula (i.e. $(E)=X+Y-(X*Y/100)$. See Colby, R. S., "Calculating Synergistic and Antagonistic Responses of Herbicide Combinations", 1967 Weeds, vol. 15, pp. 20-22, incorporated herein by reference in its entirety. Thus, by "synergistic" is intended a component which, by virtue of its presence, increases the desired effect by more than an additive amount. The pheromone compositions and adjuvants of the present methods can synergistically increase the effectiveness of agricultural active compounds and also agricultural auxiliary compounds.

Thus, in some embodiments, a pheromone composition can be formulated with a synergist. The term, "synergist," as used herein, refers to a substance that can be used with a pheromone for reducing the amount of the pheromone dose or enhancing the effectiveness of the pheromone for attracting at least one species of insect. The synergist may or may not be an independent attractant of an insect in the absence of a pheromone.

In some embodiments, the synergist is a volatile phytochemical that attracts at least one species of Lepidoptera. The term, "phytochemical," as used herein, means a compound occurring naturally in a plant species. In a particular embodiment, the synergist is selected from the group comprising β-caryophyllene, iso-caryophyllene, α-humulene, inalool, Z3-hexenollyl acetate, β-farnesene, benzaldehyde, phenylacetaldehyde, and combinations thereof.

The pheromone composition can contain the pheromone and the synergist in a mixed or otherwise combined form, or it may contain the pheromone and the synergist independently in a non-mixed form.

Insecticide

The pheromone composition can include one or more insecticides. In one embodiment, the insecticides are chemical insecticides known to one skilled in the art. Examples of the chemical insecticides include one or more of pyrethoroid or organophosphorus insecticides, including but are not limited to, cyfluthrin, permethrin, cypermethrin, bifinthrin, fenvalerate, flucythrinate, azinphosmethyl, methyl parathion, buprofezin, pyriproxyfen, flonicamid, acetamiprid, dinotefuran, clothianidin, acephate, malathion, quinolphos, chloropyriphos, profenophos, bendiocarb, bifenthrin, chlorpyrifos, cyfluthrin, diazinon, pyrethrum, fenpropathrin, kinoprene, insecticidal soap or oil, neonicotinoids, diamides, avermectin and derivatives, spinosad and derivatives, azadirachtin, pyridalyl, and mixtures thereof.

In another embodiment, the insecticides are one or more biological insecticides known to one skilled in the art. Examples of the biological insecticides include, but are not limited to, azadirachtin (neem oil), toxins from natural pyrethrins, *Bacillus thuringiencis* and *Beauveria bassiana*, viruses (e.g., CYD-X™, CYD-X HP™, Germstar™, Madex HP™ and Spod-X™), peptides (Spear-T™, Spear-P™, and Spear-C™)

In another embodiment, the insecticides are insecticides that target the nerve and muscle. Examples include acetylcholinesterase (AChE) inhibitors, such as carbamates (e.g., methomyl and thiodicarb) and organophosphates (e.g., chlorpyrifos) GABA-gated chloride channel antagonists, such as cyclodiene organochlorines (e.g., endosulfan) and phenylpyrazoles (e.g., fipronil), sodium channel modulators, such as pyrethrins and pyrethroids (e.g., cypermethrin and λ-cyhalothrin), nicotinic acetylcholine receptor (nAChR) agonists, such as neonicotinoids (e.g., acetamiprid, tiaclorprid, thiamethoxam), nicotinic acetylcholine receptor (nAChR) allosteric modulators, such as spinosyns (e.g., spinose and spinetoram), chloride channel activators, such as avermectins and milbemycins (e.g., abamectin, emamectin benzoate), Nicotinic acetylcholine receptor (nAChR) blockers, such as bensultap and cartap, voltage dependent sodium channel blockers, such as indoxacarb and metaflumizone, ryanodine receptor modulator, such as diamides (e.g. dhlorantraniliprole and flubendiamide). In another embodiment, the insecticides are insecticides that target respiration. Examples include chemicals that uncouple oxidative phosphorylation via disruption of the proton gradient, such as chlorfenapyr, and mitochondrial complex I electron transport inhibitors.

In another embodiment, the insecticides are insecticides that target midgut. Examples include microbial disruptors of insect midgut membranes, such as *Bacillus thuringiensis* and *Bacillus sphaericus*.

In another embodiment, the insecticides are insecticides that target growth and development. Examples include juvenile hormone mimics, such as juvenile hormone analogues (e.g. fenoxycarb), inhibitors of chitin biosynthesis, Type 0, such as benzoylureas (e.g., flufenoxuron, lufenuron, and novaluron), and ecdysone receptor agonists, such as diacylhydrazines (e.g., methoxyfenozide and tebufenozide)

Stabilizer

According to another embodiment of the disclosure, the pheromone composition may include one or more additives that enhance the stability of the composition. Examples of additives include, but are not limited to, fatty acids and vegetable oils, such as for example olive oil, soybean oil, corn oil, safflower oil, canola oil, and combinations thereof.

Filler

According to another embodiment of the disclosure, the pheromone composition may include one or more fillers. Examples of fillers include, but are not limited to, one or more mineral clays (e.g., attapulgite). In some embodiments, the attractant-composition may include one or more organic thickeners. Examples of such thickeners include, but are not limited to, methyl cellulose, ethyl cellulose, and any combinations thereof.

Solvent

According to another embodiment, the pheromone compositions of the present disclosure can include one or more solvents. Compositions containing solvents are desirable when a user is to employ liquid compositions which may be applied by brushing, dipping, rolling, spraying, or otherwise applying the liquid compositions to substrates on which the user wishes to provide a pheromone coating (e.g., a lure). In some embodiments, the solvent(s) to be used is/are selected so as to solubilize, or substantially solubilize, the one or more ingredients of the pheromone composition. Examples of solvents include, but are not limited to, water, aqueous solvent (e.g., mixture of water and ethanol), ethanol, methanol, chlorinated hydrocarbons, petroleum solvents, turpentine, xylene, and any combinations thereof.

In some embodiments, the pheromone compositions of the present disclosure comprise organic solvents. Organic solvents are used mainly in the formulation of emulsifiable concentrates, ULV formulations, and to a lesser extent granular formulations. Sometimes mixtures of solvents are used. In some embodiments, the present disclosure teaches the use of solvents including aliphatic paraffinic oils such as kerosene or refined paraffins. In other embodiments, the present disclosure teaches the use of aromatic solvents such as xylene and higher molecular weight fractions of C9 and C10 aromatic solvents. In some embodiments, chlorinated hydrocarbons are useful as co-solvents to prevent crystallization when the formulation is emulsified into water. Alcohols are sometimes used as co-solvents to increase solvent power.

Solubilizing Agent

In some embodiments, the pheromone compositions of the present disclosure comprise solubilizing agents. A solubilizing agent is a surfactant, which will form micelles in water at concentrations above the critical micelle concentration. The micelles are then able to dissolve or solubilize water-insoluble materials inside the hydrophobic part of the micelle. The types of surfactants usually used for solubilization are non-ionics: sorbitan monooleates; sorbitan monooleate ethoxylates; and methyl oleate esters.

Binder

According to another embodiment of the disclosure, the pheromone composition may include one or more binders. Binders can be used to promote association of the pheromone composition with the surface of the material on which said composition is coated. In some embodiments, the binder can be used to promote association of another additive (e.g., insecticide, insect growth regulators, and the like) to the pheromone composition and/or the surface of a material. For example, a binder can include a synthetic or natural resin typically used in paints and coatings. These may be modified to cause the coated surface to be friable enough to allow insects to bite off and ingest the components of the composition (e.g., insecticide, insect growth regulators, and the like), while still maintaining the structural integrity of the coating.

Non-limiting examples of binders include polyvinylpyrrolidone, polyvinyl alcohol, partially hydrolyzed polyvinyl acetate, carboxymethylcellulose, starch, vinylpyrrolidone/vinyl acetate copolymers and polyvinyl acetate, or compositions of these; lubricants such as magnesium stearate, sodium stearate, talc or polyethylene glycol, or compositions of these; antifoams such as silicone emulsions, long-chain alcohols, phosphoric esters, acetylene diols, fatty acids or organofluorine compounds, and complexing agents such as: salts of ethylenediaminetetraacetic acid (EDTA), salts of trinitrilotriacetic acid or salts of polyphosphoric acids, or compositions of these.

In some embodiments, the binder also acts a filler and/or a thickener. Examples of such binders include, but are not limited to, one or more of shellac, acrylics, epoxies, alkyds, polyurethanes, linseed oil, tung oil, and any combinations thereof.

Surface-Active Agents

In some embodiments, the pheromone compositions comprise surface-active agents. In some embodiments, the surface-active agents are added to liquid agricultural compositions. In other embodiments, the surface-active agents are added to solid formulations, especially those designed to be diluted with a carrier before application. Thus, in some embodiments, the pheromone compositions comprise surfactants. Surfactants are sometimes used, either alone or with other additives, such as mineral or vegetable oils as adjuvants to spray-tank mixes to improve the biological performance of the pheromone on the target. The surface-active agents can be anionic, cationic, or nonionic in character, and can be employed as emulsifying agents, wetting agents, suspending agents, or for other purposes. In some embodiments, the surfactants are non-ionics such as: alkyl ethoxylates, linear aliphatic alcohol ethoxylates, and aliphatic amine ethoxylates. Surfactants conventionally used in the art of formulation and which may also be used in the present formulations are described, in *McCutcheon's Detergents and Emulsifiers Annual*, MC Publishing Corp., Ridgewood, N.J., 1998, and in Encyclopedia of Surfactants, Vol. I-III, Chemical Publishing Co., New York, 1980-81. In some embodiments, the present disclosure teaches the use of surfactants including alkali metal, alkaline earth metal or ammonium salts of aromatic sulfonic acids, for example, ligno-, phenol-, naphthalene- and dibutylnaphthalenesulfonic acid, and of fatty acids of arylsulfonates, of alkyl ethers, of lauryl ethers, of fatty alcohol sulfates and of fatty alcohol glycol ether sulfates, condensates of sulfonated naphthalene and its derivatives with formaldehyde, condensates of naphthalene or of the naphthalenesulfonic acids with phenol and formaldehyde, condensates of phenol or phenolsulfonic acid with formaldehyde, condensates of phenol with formaldehyde and sodium sulfite, polyoxyethylene octylphenyl ether, ethoxylated isooctyl-, octyl- or nonylphenol, tributylphenyl polyglycol ether, alkylaryl polyether alcohols, isotridecyl alcohol, ethoxylated castor oil, ethoxylated triarylphenols, salts of phosphated triarylphenolethoxylates, lauryl alcohol polyglycol ether acetate, sorbitol esters, lignin-sulfite waste liquors or methylcellulose, or compositions of these.

In some embodiments, the present disclosure teaches other suitable surface-active agents, including salts of alkyl sulfates, such as diethanolammonium lauryl sulfate; alkylarylsulfonate salts, such as calcium dodecylbenzenesulfonate; alkylphenol-alkylene oxide addition products, such as nonylphenol-C18 ethoxylate; alcohol-alkylene oxide addition products, such as tridecyl alcohol-C16 ethoxylate; soaps, such as sodium stearate; alkylnaphthalene-sulfonate salts, such as sodium dibutyl-naphthalenesulfonate; dialkyl esters of sulfosuccinate salts, such as sodium di(2-ethylhexyl)sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono and dialkyl phosphate esters; vegetable oils such as soybean oil, rapeseed/canola oil, olive oil, castor oil, sunflower seed oil, coconut oil, corn oil, cottonseed oil, linseed oil, palm oil, peanut oil, safflower oil, sesame oil, tung oil and the like; and esters of the above vegetable oils, particularly methyl esters.

Wetting Agents

In some embodiments, the pheromone compositions comprise wetting agents. A wetting agent is a substance that when added to a liquid increases the spreading or penetration power of the liquid by reducing the interfacial tension between the liquid and the surface on which it is spreading. Wetting agents are used for two main functions in agrochemical formulations: during processing and manufacture to increase the rate of wetting of powders in water to make concentrates for soluble liquids or suspension concentrates; and during mixing of a product with water in a spray tank or other vessel to reduce the wetting time of wettable powders and to improve the penetration of water into water-dispersible granules. In some embodiments, examples of wetting agents used in the pheromone compositions of the present disclosure, including wettable powders, suspension concentrates, and water-dispersible granule formulations are: sodium lauryl sulphate; sodium dioctyl sulphosuccinate; alkyl phenol ethoxylates; and aliphatic alcohol ethoxylates.

Dispersing Agent

In some embodiments, the pheromone compositions of the present disclosure comprise dispersing agents. A dispersing agent is a substance which adsorbs onto the surface of particles and helps to preserve the state of dispersion of the particles and prevents them from reaggregating. In some embodiments, dispersing agents are added to pheromone compositions of the present disclosure to facilitate dispersion and suspension during manufacture, and to ensure the particles redisperse into water in a spray tank. In some embodiments, dispersing agents are used in wettable powders, suspension concentrates, and water-dispersible granules. Surfactants that are used as dispersing agents have the ability to adsorb strongly onto a particle surface and provide a charged or steric barrier to re-aggregation of particles. In some embodiments, the most commonly used surfactants are anionic, non-ionic, or mixtures of the two types.

In some embodiments, for wettable powder formulations, the most common dispersing agents are sodium lignosulphonates. In some embodiments, suspension concentrates provide very good adsorption and stabilization using polyelectrolytes, such as sodium naphthalene sulphonate formaldehyde condensates. In some embodiments, tristyrylphenol ethoxylated phosphate esters are also used. In some embodiments, such as alkylarylethylene oxide condensates and EO-PO block copolymers are sometimes combined with anionics as dispersing agents for suspension concentrates.

Polymeric Surfactant

In some embodiments, the pheromone compositions of the present disclosure comprise polymeric surfactants. In some embodiments, the polymeric surfactants have very long hydrophobic 'backbones' and a large number of ethylene oxide chains forming the 'teeth' of a 'comb' surfactant. In some embodiments, these high molecular weight polymers can give very good long-term stability to suspension concentrates, because the hydrophobic backbones have many anchoring points onto the particle surfaces. In some embodiments, examples of dispersing agents used in pheromone compositions of the present disclosure are: sodium lignosulphonates; sodium naphthalene sulphonate formaldehyde condensates; tristyrylphenol ethoxylate phosphate esters; aliphatic alcohol ethoxylates; alky ethoxylates; EO-PO block copolymers; and graft copolymers.

Emulsifying Agent

In some embodiments, the pheromone compositions of the present disclosure comprise emulsifying agents. An emulsifying agent is a substance, which stabilizes a suspension of droplets of one liquid phase in another liquid phase. Without the emulsifying agent the two liquids would separate into two immiscible liquid phases. In some embodiments, the most commonly used emulsifier blends include alkylphenol or aliphatic alcohol with 12 or more ethylene oxide units and the oil-soluble calcium salt of dodecylbenzene sulphonic acid. A range of hydrophile-lipophile balance ("HLB") values from 8 to 18 will normally provide good stable emulsions. In some embodiments, emulsion stability can sometimes be improved by the addition of a small amount of an EO-PO block copolymer surfactant.

Gelling Agent

In some embodiments, the pheromone compositions comprise gelling agents. Thickeners or gelling agents are used mainly in the formulation of suspension concentrates, emulsions, and suspoemulsions to modify the rheology or flow properties of the liquid and to prevent separation and settling of the dispersed particles or droplets. Thickening, gelling, and anti-settling agents generally fall into two categories, namely water-insoluble particulates and water-soluble polymers. It is possible to produce suspension concentrate formulations using clays and silicas. In some embodiments, the pheromone compositions comprise one or more thickeners including, but not limited to: montmorillonite, e.g. bentonite; magnesium aluminum silicate; and attapulgite. In some embodiments, the present disclosure teaches the use of polysaccharides as thickening agents. The types of polysaccharides most commonly used are natural extracts of seeds and seaweeds or synthetic derivatives of cellulose. Some embodiments utilize xanthan and some embodiments utilize cellulose. In some embodiments, the present disclosure teaches the use of thickening agents including, but are not limited to: guar gum; locust bean gum; carrageenam; alginates; methyl cellulose; sodium carboxymethyl cellulose (SCMC); hydroxyethyl cellulose (HEC). In some embodiments, the present disclosure teaches the use of other types of anti-settling agents such as modified starches, polyacrylates, polyvinyl alcohol, and polyethylene oxide. Another good anti-settling agent is xanthan gum.

Anti-Foam Agent

In some embodiments, the presence of surfactants, which lower interfacial tension, can cause water-based formulations to foam during mixing operations in production and in application through a spray tank. Thus, in some embodiments, in order to reduce the tendency to foam, anti-foam agents are often added either during the production stage or before filling into bottles/spray tanks. Generally, there are two types of anti-foam agents, namely silicones and non-silicones. Silicones are usually aqueous emulsions of dimethyl polysiloxane, while the nonsilicone anti-foam agents are water-insoluble oils, such as octanol and nonanol, or silica. In both cases, the function of the anti-foam agent is to displace the surfactant from the air-water interface.

Preservative

In some embodiments, the pheromone compositions comprise a preservative.

Additional Active Agent

According to another embodiment of the disclosure, the pheromone composition may include one or more insect feeding stimulants. Examples of insect feeding stimulants include, but are not limited to, crude cottonseed oil, fatty acid esters of phytol, fatty acid esters of geranyl geraniol, fatty acid esters of other plant alcohols, plant extracts, and combinations thereof.

According to another embodiment of the disclosure, the pheromone composition may include one or more insect growth regulators ("IGRs"). IGRs may be used to alter the growth of the insect and produce deformed insects. Examples of insect growth regulators include, for example, dimilin.

According to another embodiment of the disclosure, the attractant-composition may include one or more insect sterilants that sterilize the trapped insects or otherwise block their reproductive capacity, thereby reducing the population in the following generation. In some situations allowing the sterilized insects to survive and compete with non-trapped insects for mates is more effective than killing them outright.

Sprayable Compositions

In some embodiments, the pheromone compositions disclosed herein can be formulated as a sprayable composition (i.e., a sprayable pheromone composition). An aqueous solvent can be used in the sprayable composition, e.g., water or a mixture of water and an alcohol, glycol, ketone, or other water-miscible solvent. In some embodiments, the water content of such mixture is at least about 10%, at least about 20%, at least about 30%, at least about 40%, 50%, at least about 60%, at least about 70%, at least about 80%, or at least about 90%. In some embodiments, the sprayable composition is concentrate, i.e. a concentrated suspension of the pheromone, and other additives (e.g., a waxy substance, a stabilizer, and the like) in the aqueous solvent, and can be diluted to the final use concentration by addition of solvent (e.g., water).

In some embodiments, the a waxy substance can be used as a carrier for the pheromone and its positional isomer in the sprayable composition. The waxy substance can be, e.g., a biodegradable wax, such as bees wax, camauba wax and the like, candelilla wax (hydrocarbon wax), montan wax, shellac and similar waxes, saturated or unsaturated fatty acids, such as lauric, palmitic, oleic or stearic acid, fatty acid amides and esters, hydroxylic fatty acid esters, such as hydroxyethyl or hydroxypropyl fatty acid esters, fatty alcohols, and low molecular weight polyesters such as polyalkylene succinates.

In some embodiments, a stabilizer can be used with the sprayable pheromone compositions. The stabilizer can be used to regulate the particle size of concentrate and/or to allow the preparation of a stable suspension of the pheromone composition. In some embodiments, the stabilizer is selected from hydroxylic and/or ethoxylated polymers. Examples include ethylene oxide and propylene oxide copolymer, polyalcohols, including starch, maltodextrin and other soluble carbohydrates or their ethers or esters, cellulose ethers, gelatin, polyacrylic acid and salts and partial esters thereof and the like. In other embodiments, the stabilizer can include polyvinyl alcohols and copolymers thereof, such as partly hydrolyzed polyvinyl acetate. The stabilizer may be used at a level sufficient to regulate particle size and/or to prepare a stable suspension, e.g., between 0.1% and 15% of the aqueous solution.

In some embodiments, a binder can be used with the sprayable pheromone compositions. In some embodiments, the binder can act to further stabilize the dispersion and/or improve the adhesion of the sprayed dispersion to the target locus (e.g., trap, lure, plant, and the like). The binder can be polysaccharide, such as an alginate, cellulose derivative (acetate, alkyl, carboxymethyl, hydroxyalkyl), starch or starch derivative, dextrin, gum (arabic, guar, locust bean, tragacanth, carrageenan, and the like), sucrose, and the like. The binder can also be a non-carbohydrate, water-soluble polymer such as polyvinyl pyrrolidone, or an acidic polymer such as polyacrylic acid or polymethacrylic acid, in acid and/or salt form, or mixtures of such polymers.

Microencapsulated Pheromones

In some embodiments, the pheromone compositions disclosed herein can be formulated as a microencapsulated pheromone, such as disclosed in Ill'lchev, A L et al., *J. Econ. Entomol.* 2006; 99(6):2048-54; and Stelinki, L L et al., *J. Econ. Entomol.* 2007; 100(4):1360-9. Microencapsulated pheromones (MECs) are small droplets of pheromone enclosed within polymer capsules. The capsules control the release rate of the pheromone into the surrounding environment, and are small enough to be applied in the same method as used to spray insecticides. The effective field longevity of the microencapsulated pheromone formulations can range from a few days to slightly more than a week, depending on inter alia climatic conditions, capsule size and chemical properties.

Slow-Release Formulation

Pheromone compositions can be formulated so as to provide slow release into the atmosphere, and/or so as to be protected from degradation following release. For example, the pheromone compositions can be included in carriers such as microcapsules, biodegradable flakes and paraffin wax-based matrices. Alternatively, the pheromone composition can be formulated as a slow release sprayable.

In certain embodiments, the pheromone composition may include one or more polymeric agents known to one skilled in the art. The polymeric agents may control the rate of release of the composition to the environment. In some embodiments, the polymeric attractant-composition is impervious to environmental conditions. The polymeric agent may also be a sustained-release agent that enables the composition to be released to the environment in a sustained manner.

Examples of polymeric agents include, but are not limited to, celluloses, proteins such as casein, fluorocarbon-based polymers, hydrogenated rosins, lignins, melamine, polyurethanes, vinyl polymers such as polyvinyl acetate (PVAC), polycarbonates, polyvinylidene dinitrile, polyamides, polyvinyl alcohol (PVA), polyamide-aldehyde, polyvinyl aldehyde, polyesters, polyvinyl chloride (PVC), polyethylenes, polystyrenes, polyvinylidene, silicones, and combinations thereof. Examples of celluloses include, but are not limited to, methylcellulose, ethyl cellulose, cellulose acetate, cellulose acetate-butyrate, cellulose acetate-propionate, cellulose propionate, and combinations thereof.

Other agents which can be used in slow-release or sustained-release formulations include fatty acid esters (such as a sebacate, laurate, palmitate, stearate or arachidate ester) or a fatty alcohols (such as undecanol, dodecanol, tridecanol, tridecenol, tetradecanol, tetradecenol, tetradecadienol, pentadecanol, pentadecenol, hexadecanol, hexadecenol, hexadecadienol, octadecenol and octadecadienol).

Pheromones prepared according to the methods of the invention, as well as compositions containing the pheromones, can be used to control the behavior and/or growth of insects in various environments. The pheromones can be used, for example, to attract or repel male or female insects to or from a particular target area. The pheromones can be used to attract insects away from vulnerable crop areas. The pheromones can also be used example to attract insects as part of a strategy for insect monitoring, mass trapping, lure/attract-and-kill or mating disruption.

Lures

The pheromone compositions of the present disclosure may be coated on or sprayed on a lure, or the lure may be otherwise impregnated with a pheromone composition.

Traps

The pheromone compositions of the disclosure may be used in traps, such as those commonly used to attract any insect species, e.g., insects of the order Lepidoptera. Such traps are well known to one skilled in the art, and are commonly used in many states and countries in insect eradication programs. In one embodiment, the trap includes one or more septa, containers, or storage receptacles for holding the pheromone composition. Thus, in some embodiments, the present disclosure provides a trap loaded with at least one pheromone composition. Thus, the pheromone compositions of the present disclosure can be used in traps for example to attract insects as part of a strategy for insect monitoring, mass trapping, mating disruption, or lure/attract and kill for example by incorporating a toxic substance into the trap to kill insects caught.

Mass trapping involves placing a high density of traps in a crop to be protected so that a high proportion of the insects are removed before the crop is damaged. Lure/attract-and-kill techniques are similar except once the insect is attracted to a lure, it is subjected to a killing agent. Where the killing agent is an insecticide, a dispenser can also contain a bait or feeding stimulant that will entice the insects to ingest an effective amount of an insecticide. The insecticide may be an insecticide known to one skilled in the art. The insecticide may be mixed with the attractant-composition or may be separately present in a trap. Mixtures may perform the dual function of attracting and killing the insect.

Such traps may take any suitable form, and killing traps need not necessarily incorporate toxic substances, the insects being optionally killed by other means, such as drowning or electrocution. Alternatively, the traps can contaminate the insect with a fungus or virus that kills the insect later. Even where the insects are not killed, the trap can serve to remove the male insects from the locale of the female insects, to prevent breeding.

It will be appreciated by a person skilled in the art that a variety of different traps are possible. Suitable examples of such traps include water traps, sticky traps, and one-way traps. Sticky traps come in many varieties. One example of a sticky trap is of cardboard construction, triangular or wedge-shaped in cross-section, where the interior surfaces are coated with a non-drying sticky substance. The insects contact the sticky surface and are caught. Water traps include pans of water and detergent that are used to trap insects. The detergent destroys the surface tension of the water, causing insects that are attracted to the pan, to drown in the water. One-way traps allow an insect to enter the trap but prevent it from exiting. The traps of the disclosure can be colored brightly, to provide additional attraction for the insects.

In some embodiments, the pheromone traps containing the composition may be combined with other kinds of trapping mechanisms. For example, in addition to the pheromone composition, the trap may include one or more florescent lights, one or more sticky substrates and/or one or more colored surfaces for attracting moths. In other embodiments, the pheromone trap containing the composition may not have other kinds of trapping mechanisms.

The trap may be set at any time of the year in a field. Those of skill in the art can readily determine an appropriate amount of the compositions to use in a particular trap, and can also determine an appropriate density of traps/acre of crop field to be protected.

The trap can be positioned in an area infested (or potentially infested) with insects. Generally, the trap is placed on or close to a tree or plant. The aroma of the pheromone attracts the insects to the trap. The insects can then be caught, immobilized and/or killed within the trap, for example, by the killing agent present in the trap.

Traps may also be placed within an orchard to overwhelm the pheromones emitted by the females, so that the males simply cannot locate the females. In this respect, a trap need be nothing more than a simple apparatus, for example, a protected wickable to dispense pheromone.

The traps of the present disclosure may be provided in made-up form, where the compound of the disclosure has already been applied. In such an instance, depending on the half-life of the compound, the compound may be exposed, or may be sealed in conventional manner, such as is standard with other aromatic dispensers, the seal only being removed once the trap is in place.

Alternatively, the traps may be sold separately, and the compound of the disclosure provided in dispensable format so that an amount may be applied to trap, once the trap is in place. Thus, the present disclosure may provide the compound in a sachet or other dispenser.

Dispenser

Pheromone compositions can be used in conjunction with a dispenser for release of the composition in a particular environment. Any suitable dispenser known in the art can be used. Examples of such dispensers include but are not limited to, aerosol emitters, hand-applied dispensers, bubble caps comprising a reservoir with a permeable barrier through which pheromones are slowly released, pads, beads, tubes rods, spirals or balls composed of rubber, plastic, leather, cotton, cotton wool, wood or wood products that are impregnated with the pheromone composition. For example, polyvinyl chloride laminates, pellets, granules, ropes or spirals from which the pheromone composition evaporates, or rubber septa. One of skill in the art will be able to select suitable carriers and/or dispensers for the desired mode of application, storage, transport or handling.

In another embodiment, a device may be used that contaminates the male insects with a powder containing the pheromone substance itself. The contaminated males then fly off and provide a source of mating disruption by permeating the atmosphere with the pheromone substance, or by attracting other males to the contaminated males, rather than to real females.

Behavior Modification

Pheromone compositions prepared according to the methods disclosed herein can be used to control or modulate the behavior of insects. In some embodiments, the behavior of the target insect can be modulated in a tunable manner inter alia by varying the ratio of the pheromone to the positional isomer in the composition such that the insect is attracted to a particular locus but does not contact said locus or such the insect in fact contacts said locus. Thus, in some embodiments, the pheromones can be used to attract insects away from vulnerable crop areas. Accordingly, the disclosure also provides a method for attracting insects to a locus. The method includes administering to a locus an effective amount of the pheromone composition.

The method of mating disruption may include periodically monitoring the total number or quantity of the trapped insects. The monitoring may be performed by counting the number of insects trapped for a predetermined period of time such as, for example, daily, Weekly, bi-Weekly, monthly, once-in-three months, or any other time periods selected by the monitor. Such monitoring of the trapped insects may help estimate the population of insects for that particular period, and thereby help determine a particular type and/or dosage of pest control in an integrated pest management system. For example, a discovery of a high insect population can necessitate the use of methods for removal of the insect. Early warning of an infestation in a new habitat can allow action to be taken before the population becomes unmanageable. Conversely, a discovery of a low insect population can lead to a decision that it is sufficient to continue monitoring the population. Insect populations can be monitored regularly so that the insects are only controlled when they reach a certain threshold. This provides cost-effective control of the insects and reduces the environmental impact of the use of insecticides.

Mating Disruption

Pheromones prepared according to the methods of the disclosure can also be used to disrupt mating. Mating disruption is a pest management technique designed to control insect pests by introducing artificial stimuli (e.g., a pheromone composition as disclosed herein) that confuses the insects and disrupts mating localization and/or courtship, thereby preventing mating and blocking the reproductive cycle.

In many insect species of interest to agriculture, such as those in the order Lepidoptera, females emit an airborne trail of a specific chemical blend constituting that species' sex pheromone. This aerial trail is referred to as a pheromone plume. Males of that species use the information contained in the pheromone plume to locate the emitting female (known as a "calling" female). Mating disruption exploits the male insects' natural response to follow the plume by introducing a synthetic pheromone into the insects' habitat, which is designed to mimic the sex pheromone produced by the female insect. Thus, in some embodiments, the synthetic pheromone utilized in mating disruption is a synthetically derived pheromone composition comprising a pheromone having a chemical structure of a sex pheromone and a positional isomer thereof which is not produced by the target insect.

The general effect of mating disruption is to confuse the male insects by masking the natural pheromone plumes, causing the males to follow "false pheromone trails" at the expense of finding mates, and affecting the males' ability to respond to "calling" females. Consequently, the male population experiences a reduced probability of successfully locating and mating with females, which leads to the eventual cessation of breeding and collapse of the insect infestation Strategies of mating disruption include confusion, trail-masking and false-trail following. Constant exposure of insects to a high concentration of a pheromone can prevent male insects from responding to normal levels of the pheromone released by female insects. Trail-masking uses a pheromone to destroy the trail of pheromones released by females. False-trail following is carried out by laying numerous spots of a pheromone in high concentration to present the male with many false trails to follow. When released in sufficiently high quantities, the male insects are unable to find the natural source of the sex pheromones (the female insects) so that mating cannot occur.

In some embodiments, a wick or trap may be adapted to emit a pheromone for a period at least equivalent to the breeding season(s) of the midge, thus causing mating disruption. If the midge has an extended breeding season, or repeated breeding season, the present disclosure provides a wick or trap capable of emitting pheromone for a period of time, especially about two weeks, and generally between about 1 and 4 weeks and up to 6 weeks, which may be rotated or replaced by subsequent similar traps. A plurality of traps containing the pheromone composition may be placed in a locus, e.g., adjacent to a crop field. The locations of the traps, and the height of the traps from ground may be selected in accordance with methods known to one skilled in the art.

Alternatively, the pheromone composition may be dispensed from formulations such as microcapsules or twist-ties, such as are commonly used for disruption of the mating of insect pests.

Attract and Kill

The attract and kill method utilizes an attractant, such as a sex pheromone, to lure insects of the target species to an insecticidal chemical, surface, device, etc., for mass-killing and ultimate population suppression, and can have the same effect as mass-trapping. For instance, when a synthetic female sex pheromone is used to lure male pests, e.g., moths, in an attract-and-kill strategy, a large number of male moths must be killed over extended periods of time to reduce matings and reproduction, and ultimately suppress the pest population. The attract-and-kill approach may be a favorable alternative to mass-trapping because no trap-servicing or other frequent maintenance is required. In various embodiments described herein, a recombinant microorganism can co-express (i) a pathway for production of an insect pheromone and (ii) a protein, peptide, oligonucleotide, or small molecule which is toxic to the insect. In this way, the recombinant microorganism can co-produce substances suitable for use in an attract-and-kill approach.

As will be apparent to one of skill in the art, the amount of a pheromone or pheromone composition used for a particular application can vary depending on several factors such as the type and level of infestation; the type of composition used; the concentration of the active components; how the composition is provided, for example, the type of dispenser used; the type of location to be treated; the length of time the method is to be used for; and environmental factors such as temperature, wind speed and direction, rainfall and humidity. Those of skill in the art will be able to determine an effective amount of a pheromone or pheromone composition for use in a given application.

As used herein, an "effective amount" means that amount of the disclosed pheromone composition that is sufficient to affect desired results. An effective amount can be administered in one or more administrations. For example, an effective amount of the composition may refer to an amount of the pheromone composition that is sufficient to attract a given insect to a given locus. Further, an effective amount of the composition may refer to an amount of the pheromone composition that is sufficient to disrupt mating of a particular insect population of interest in a given locality.

EXAMPLES

Prophetic Example 1. Production of Pheromones Products from Enzymatically-Derived Gondoic Acid Through Metathesis and Chemical Conversion This prophetic example illustrates that different fatty acids can be used as a starting material for the biosynthetic production of a pheromone or pheromone precursor. The product obtained from the biosynthetic process disclosed herein can be subject to further chemical conversions to generate different products.

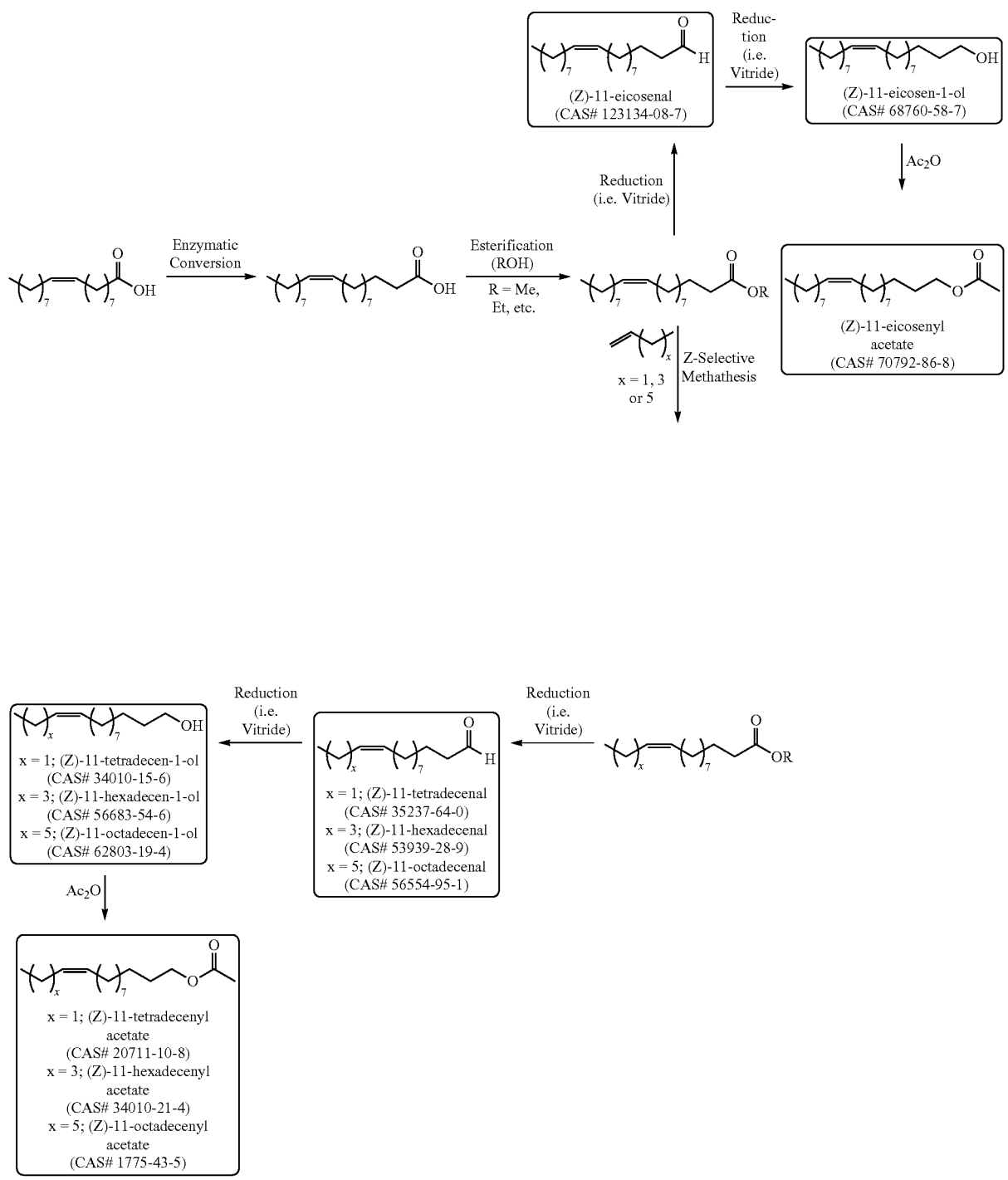

Enzymatic two carbon elongation of oleic acid yields gondoic acid. After esterification, gondoic fatty acid methyl ester (FAME) can then converted via Z-selective olefin metathesis into C16 and C18 FAME products containing a C11 unsaturation. Upon reduction of the ester, aldehyde and fatty alcohol pheromone materials can be produced. Acetylation of the fatty alcohol product can generate the corresponding fatty acetate pheromones. Additionally, gondoic acid can be directly converted into C20 fatty aldehyde, alcohol and acetate pheromones through application of the same chemical transformation of enzymatically modified oleic acid.

Prophetic Example 2: Tailored Synthetic Blends

This prophetic example illustrates that the recombinant microorganisms disclosed herein can be used to create synthetic blends of insect pheromones.

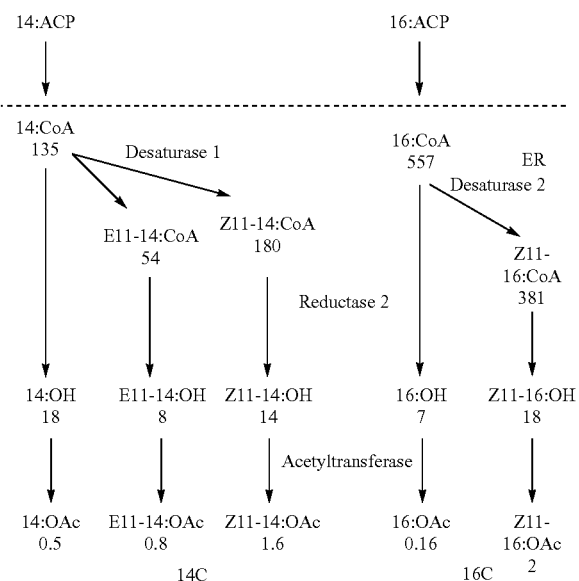

As shown in the above scheme, using tetradecyl-ACP (14:ACP), a blend of E- and Z-tetradecenyl acetate (E11-14:OAc and Z11-14:OAC) pheromones can be produced with the recombinant microorganism. This blend is produced by a variety of insects, e.g., *Choristoneura roseceana* (a moth of the Tortricidae family).

Similarly, using hexadecyl-ACP (16:ACP), a blend of Z- and E hexadecenyl acetate pheromones (E11-16:OAc and Z11-16:OAc) can be produced with the recombinant microorganism.

The microorganism can be engineered with different desaturases, or other enzymes such as reductases, etc. to produce the desired blend of pheromones. One blend of particular relevance capable of being produced using the recombinant microorganisms and methods of the instant invention is a 97:3 ratio of (Z)-11-hexadecenal (Z11-16:Ald) and (Z)-9-hexadecenal (Z9-16:Ald).

Example 3: Expression of Transmembrane Alcohol-Forming Reductases in *S. cerevisiae*

Background and Rationale

Engineering microbial production of insect fatty alcohols from fatty acids entails the functional expression of a synthetic pathway. One such pathway comprises a transmembrane desaturase, and an alcohol-forming reductase to mediate the conversion of fatty acyl-CoA into regio- and stereospecific unsaturated fatty acyl-CoA, and subsequently into fatty alcohols. A number of genes encoding these enzymes are found in some insects (as well as some microalgae in the case of fatty alcohol reductase) and can be used to construct the synthetic pathway in yeasts, which are preferred production hosts. A number of transmembrane desaturases and alcohol-forming reductase variants will be screened to identify ensembles which allow high level synthesis of a single insect fatty alcohol or a blend of fatty alcohols. Additionally, these enzymes will be screened across multiple hosts (*Saccharomyces cerevisiae*, *Candida tropicalis*, and *Yarrowia lipolytica*) to optimize the search toward finding a suitable host for optimum expression of these transmembrane proteins.

Summary of Approach

Three alcohol-forming reductases of insect origin were selected.

Nucleic acids encoding the reductases were synthesized (synthons) with codon optimization for expression in *S. cerevisiae*.

Each nucleic acid encoding a given reductase was subcloned into an episomal expression cassette under the GalI promoter.

*S. cerevisiae* wild-type and beta-oxidation deletion mutant were transformed with expression constructs.

Heterologous protein was induced by galactose, and functional expression of the reductases was assessed in vivo via bioconversion of Z11-hexadecenoic acid into Z11-hexedecenol.

GC-MS analysis was used to identify and quantify metabolites.

Results

Figure 5:
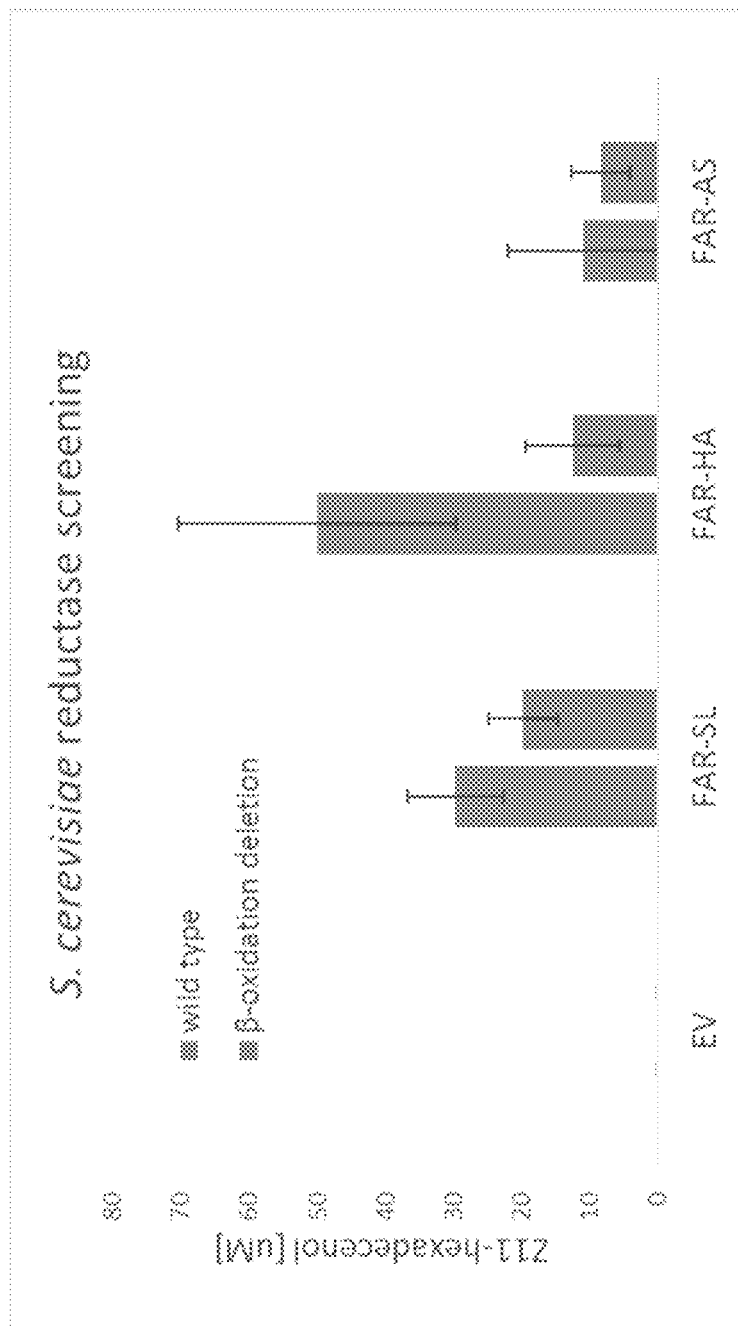
FIG. 5 shows Z11-hexadecenol production from W303A and BY4742 ΔPOX1. Strain expressing empty vector (EV), *S. littoralis* reductase (FAR-SL), *H. armigera* reductase (FAR-HA), *A. segetum* reductase (FAR-AS). Error bars represent standard deviation derived from N=2 biologically-independent samples.
Figure 7A:
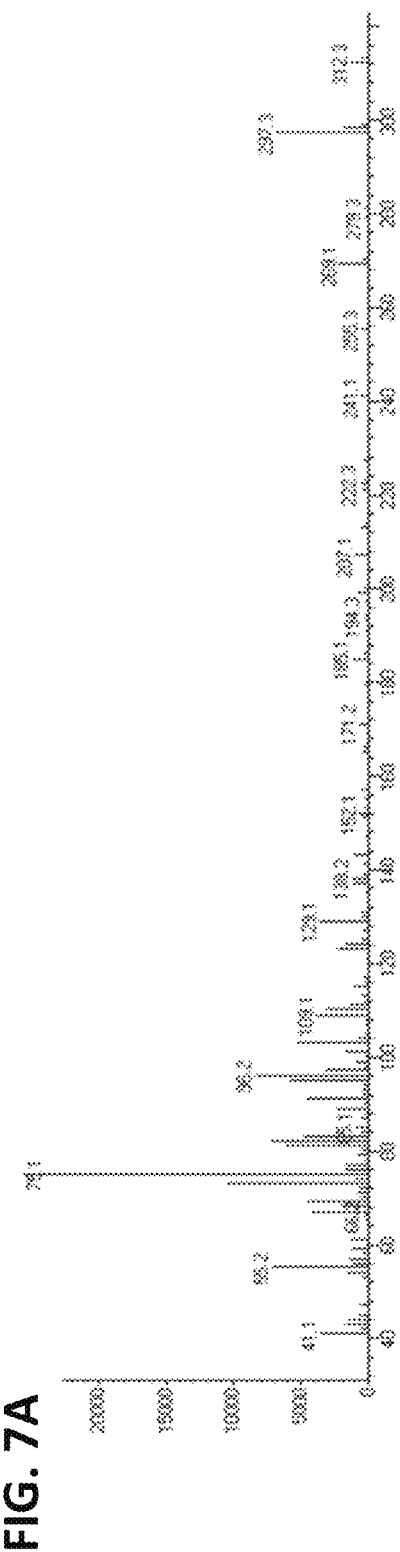
FIG. 7A-FIG. 7B shows a comparison of GC-MS fragmentation pattern of Z11-hexadecenol authentic compound (FIG. 7A), and Z11-hexadecenol biologically derived (FIG. 7B).
Figure 7B:
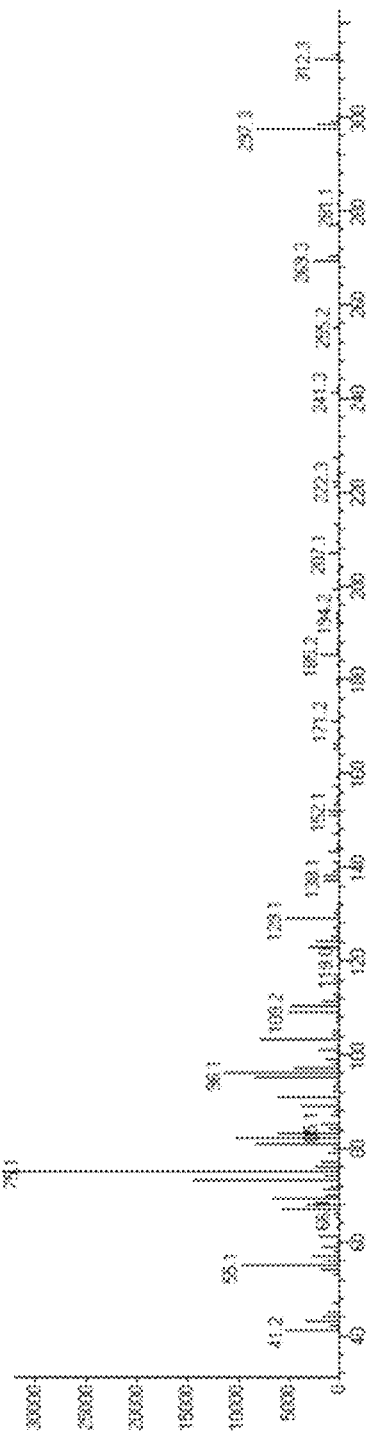
Figure 8:
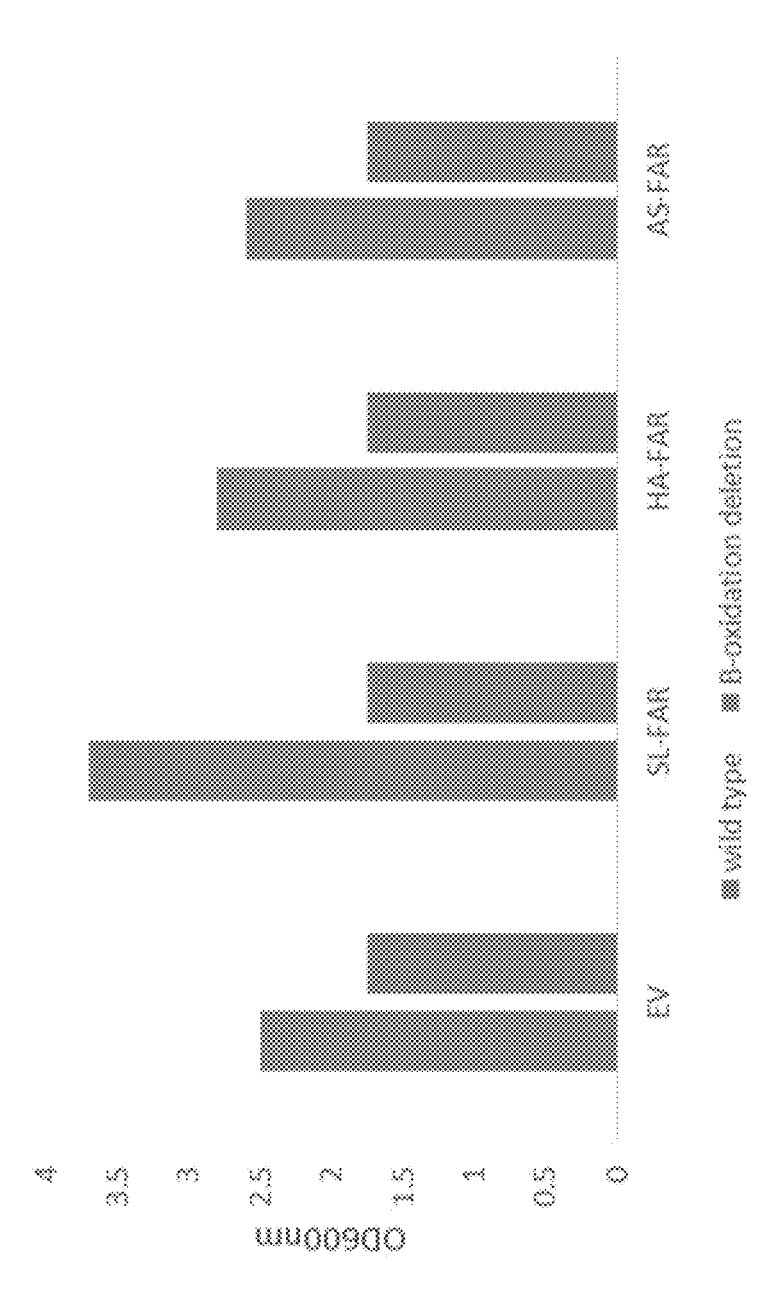
FIG. 8 shows biomass at the time of harvesting for product analysis of W303A (wild type) and BY4742 ΔPOX1 (beta-oxidation deletion mutant). Strain expressing empty vector (EV), *S. littoralis* reductase (FAR-SL), *H. armigera* reductase (FAR-HA), *A. segetum* reductase (FAR-AS). Error bars represent standard deviation derived from N=2 biologically-independent samples.

Alcohol-forming reductase variants were screened for activity in *S. cerevisiae* W303 (wild type) and BY4742 ΔPOX1 (beta-oxidation deletion mutant). Z11-hexadecenoic acid was chosen as a substrate in assessing enzyme activity. The in vivo bioconversion assay showed that the expression of enzyme variants derived from *Spodoptera littoralis*, *Helicoverpa armigera*, and *Agrotis segetum* (Ding, B-J., Löfstedt, C. Analysis of the *Agrotis segetum* pheromone gland transcriptome in the light of sex pheromone biosynthesis. BMC Genomics 16:711 (2015)) in W303A conferred Z11-hexadecenol production, and reached up-to ~37 μM (8 mg/L), ~70 μM (~16 mg/L), and 11 μM (~3 mg/L), respectively, within 48 h of protein induction (FIG. 5 and FIG. 6). Biologically-produced Z11-hexadecenol matched authentic Z11-hexadecenol standard (Bedoukian) as determined via GC-MS (FIG. 7). BY4742 ΔPOX1 was also explored as an expression host since deletion in the key beta-oxidation pathway enzyme could limit the degradation of Z11-hexadecenoic acid. Expressing the reductase variants in the beta-oxidation deletion mutant, however, reduced the product titer when compared to expression in the wild-type host (FIG. 5). One contributing factor of titer reduction when using BY4742 ΔPOX1 as a host was the reduction of biomass when compared to W303 (FIG. 8).

Therefore, functional expression of at least two alcohol-forming reductases in *S. cerevisiae* conferred bioconversion of Z11-hexadecenoic acid into Z11-hexedecenol.

Conclusions

Functional expression of insect transmembrane alcohol-forming reductase in *S. cerevisiae* was demonstrated. Among the reductases tested, the variant derived from *Helicoverpa armigera* is most active toward Z11-hexadecenoic acid.

The bioconversion of other fatty acid substrates can be explored to assess enzyme plasticity.

Materials & Methods

Strain Construction and Functional Expression Assay

*S. cerevisiae* W303 (MATA ura3-1 trp1-1 leu2-3_112 his3-1_15 ade2-1 can1-100) and BY4742 (MATa POX1::kanMX his3Δ1 leu2Δ0 lys2Δ0 ura3Δ0) were used as expression hosts. DNA sequences which encode fatty alcohol reductase variants were redesigned to optimize expression in *S. cerevisiae* (SEQ ID NOs: 1-3). Generated synthons (Genscript) were cloned into pESC-URA vector using BamHI-XhoI sites to facilitate protein expression utilizing the GalI promoter. The resulting plasmid constructs were used to transform W303, and positive transformants were selected on CM agar medium (with 2% glucose, and lacking uracil) (Teknova). To assess functional expression, two positive transformation clones that have been patched on CM agar medium (with 2% glucose, and lacking uracil) were used to seed CM liquid medium using a 24 deep-well plate format. To induce protein expression, the overnight cultures that had been grown at 28° C. were then supplemented with galactose, raffinose, and YNB to a final concentration of 2%, 1%, and 6.7 g/L, respectively. Post 24 h of protein induction, the bioconversion substrate Z11-hexadecenoic acid (in ethanol) or heptadecanoic acid (in ethanol) was added to a final concentration of 300 mg/L. Bioconversion assay proceeded for 48 h at 28° C. prior to GC-MS analysis.

Metabolite Extraction and GC-MS Detection

Figure 9:
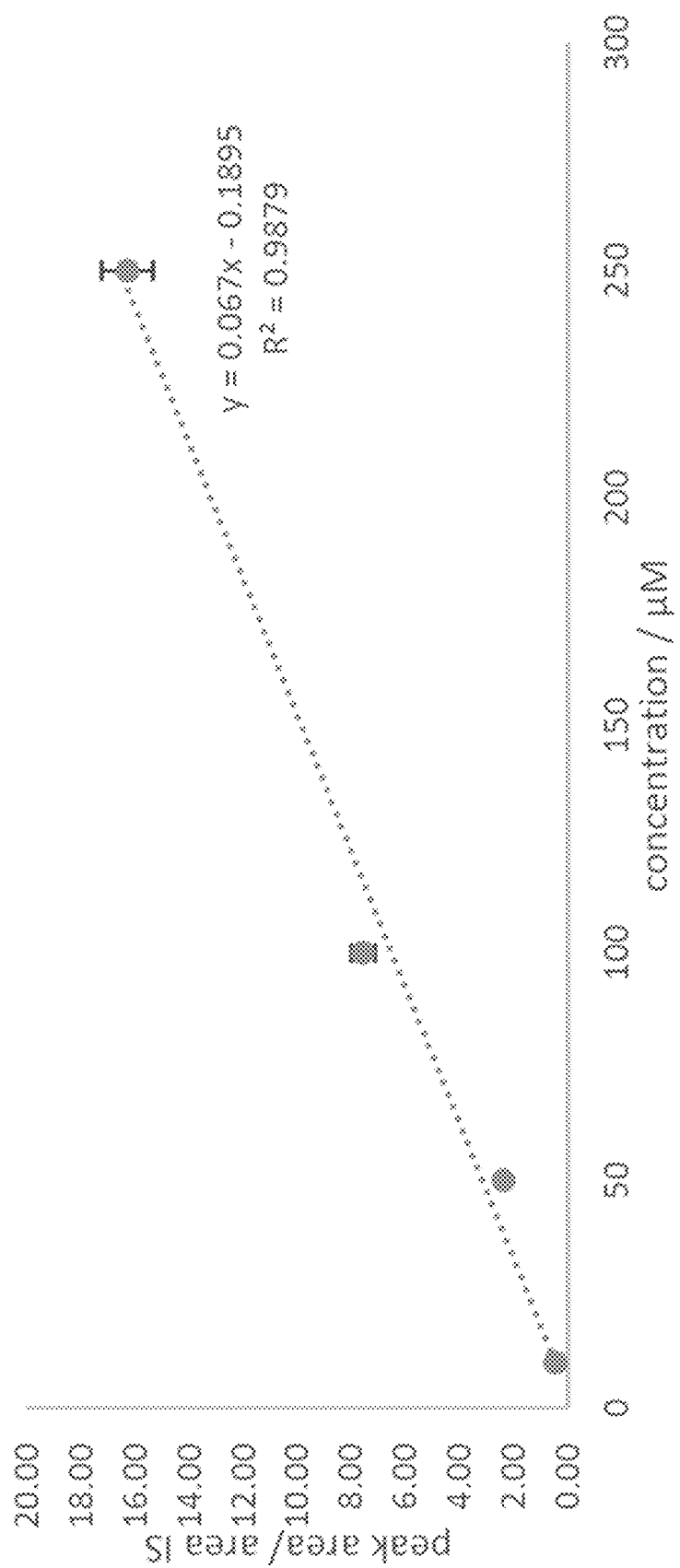
FIG. 9 shows a Z11-hexedecenol calibration curve constructed using an authentic standard. The samples were generated with the extraction and analysis method described in Materials and Methods of Example 3. Error bars represent standard deviation derived from N=3 samples.

The lipids were extracted according to a modified procedure of Hagström et al. (2012) (Hagström, A. K., Lidnard, M. A., Groot, A. T., Hedenström, E. & Löfstedt, C. Semi-Selective Fatty Acyl Reductases from Four Heliothine Moths Influence the Specific Pheromone Composition. PLoS One 7: e37230 (2012)). 1.5 mL-cell culture was transferred to a 15 mL falcon tube. The cell suspension was acidified with 1 mL 5 N HCl. 5 µL tetradecanedioic acid (10 mM in ethanol) was added as internal standard. The mixture was extracted by adding 1.5 mL hexane, then shaken for 1 h at 37° C., 250 rpm. To facilitate phase separation, the sample was centrifuged for 10 min at 2000 g. 1 mL of the organic hexane phase was then transferred to a 1.5 mL plastic tube. The solvent was removed by heating the sample 30 min at 90° C. After the sample was evaporated to dryness, 50 µL of BSTFA (N,O-bis(trimethylsilyl) trifluoroacetamide containing 1% of trimethylchlorosilane) was added. The 1.5 mL plastic tubes were shaken vigorously two times for 10 s. Prior to the transfer into a screw cap GC glass vial containing a glass insert, the sample was centrifuged for 1 min (13000 rpm). The vials were capped and heated for 30 min at 90° C. The trimethylsilyl-esters, which were generated by this method were subsequently analyzed by GC-MS analysis. GC-MS parameters are specified in Table 6. The use of SIM mode (characteristic product and IS ions) increases detection sensitivity by reducing background noise, allowing detection of the product as low as 2.4 µM (0.6 mg/L). A further reduction in the split ratio offers the possibility to further increase the sensitivity for future applications. A Z11-hexadecenol calibration curve shown in FIG. 9 was used to quantify the Z11-hexadecenol produced from yeasts. The bioconversion of heptadecanoic acid was also tested since the easily distinguished heptadecanol product could be used to benchmark successful GC-MS runs. However, none of the reductase tested showed any activity toward heptadecanoic acid.

TABLE 6

GC-MS parameters

| | |
|---|---|
| System | Agilent 6890 N GC, ChemStation G1701EA E.02.01.1177 |
| Column | Rtx-5 30 m × 320 µm × 25 µm<br>Pressure = 11.74 psi; Flow = 7.1 mL/min |
| Inlet | Heater = 250° C.; Pressure = 11.74 psi;<br>Total Flow {He} = 19.5 mL/min |
| Carrier | He @ 147 cm/sec, 11.74 psi |
| Signal | Data rate = 2 Hz/0.1 min |
| Oven | 150° C. for 1 min<br>Ramp 12° C./min to 220° C., hold 3 min<br>Ramp 35° C./min to 300° C., hold 4 min |
| Injection | Split, 250° C.<br>Split ratio - 20:1 |
| Detector | HP 5973 MSD in SIM mode (m/z: 297.3 and 387.3),<br>100 msec Dwell, EMV mode: Gain factor 1,<br>3 min solvent delay, 8.33 cycles/sec| |
| Sample | Injection volume = 1 uL |

Example 4: Expression of Transmembrane Desaturases in S. cerevisiae

Background and Rationale

Engineering microbial production of insect fatty alcohols from fatty acids requires the functional expression of a synthetic pathway. One such pathway comprises a transmembrane desaturase, and an alcohol-forming reductase to mediate the conversion of fatty acyl-CoA into regio- and stereospecific unsaturated fatty acyl-CoA, and subsequently into fatty alcohols. A number of genes encoding these enzymes are found in some insects as well as some microalgae. A number of transmembrane desaturases and alcohol-forming reductase variants will be screened to identify ensembles which allow high level synthesis of a single insect fatty alcohol or a blend of fatty alcohols. Additionally, these enzymes will be screened across multiple hosts (Saccharomyces cerevisiae, Candida tropicalis, and Yarrowia lipolytica) to optimize the search toward finding a suitable host for optimum expression of these transmembrane proteins.

Summary of Approach

A small set of desaturases (insect origin: Agrotis segetum, Trichoplusia ni, Amyelois transitella, Helicoverpa zea, and marine diatom: Thalassiosira pseudonana) were selected as a test case to explore and establish functional expression assays, metabolite extraction methods, and analytical chemistry.

A synthetic cassette for expression of the desaturases in S. cerevisiae was constructed. The cassette consists of the OLE1 promoter region, OLE1 N-terminal leader sequence, and VSP13 terminator.

The expression cassette was tested for functionality via expression of a GFP variant. Validation of the cassette allowed its utilization for exploring expression of insect desaturase.

S. cerevisiae ΔOLE1 was transformed with expression constructs containing heterologous desaturases. Functionality of the desaturases was assessed via the ability to rescue growth of ΔOLE1 without exogenous supplementation of unsaturated fatty acid (UFA). S. cerevisiae desaturase (OLE1) was used as a positive control of successful complementation.

Functionality of the desaturase was validated via an in vivo bioconversion of hexadecanoic acid (palmitic acid) into (Z)-11-hexadecenoic acid (palmitvaccenic acid).

GC-MS analysis was used to identify and quantify metabolites.

Results

Figure 10:
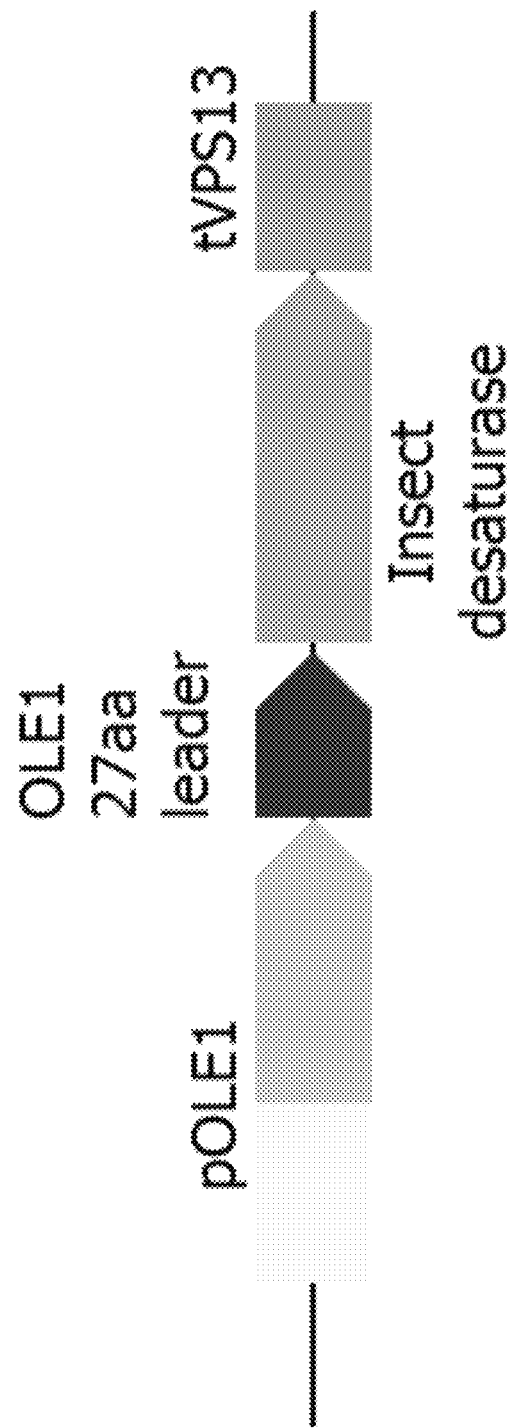
FIG. 10 shows a pOLE1 cassette comprising an extended OLE1 promoter sequence (light yellow), OLE1 promoter (orange), OLE1 leader sequence (dark grey), a synthon such as an insect desaturase sequence (light grey), and the VSP13 terminator sequence (blue).
Figure 11E:
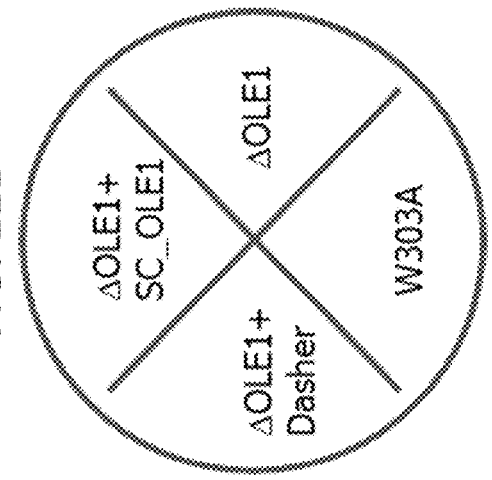
FIG. 11A-FIG. 11E shows validation of the pOLE1 cassette, and complementation assay.
Figure 11A:
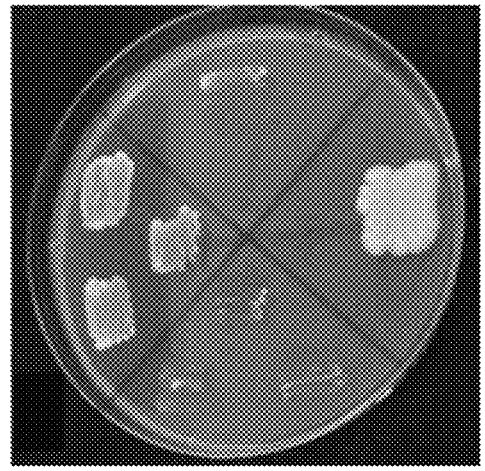
Figure 11B:
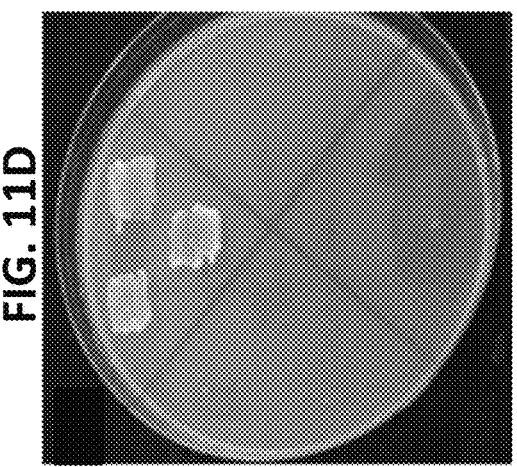
Figure 11C:
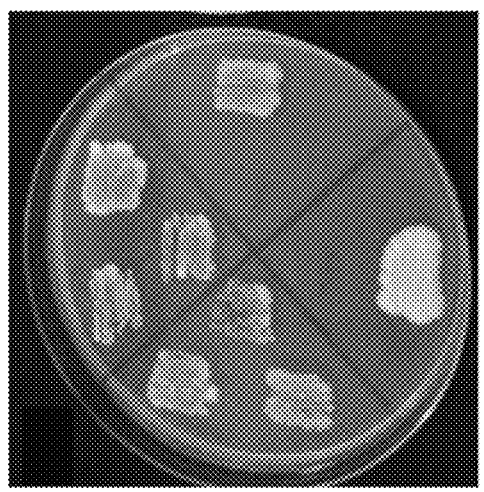
Figure 11D:
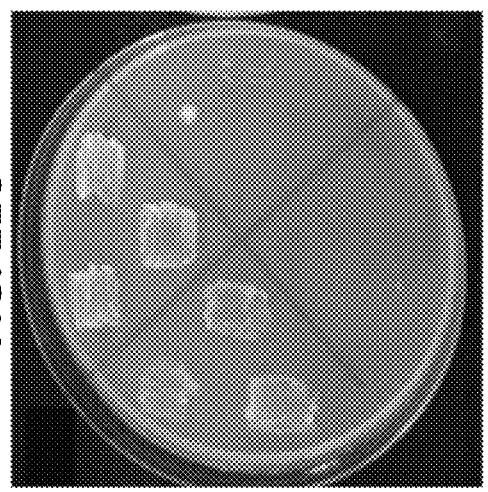

Transmembrane desaturase variants were screened in S. cerevisiae. Three variants were initially tested to explore and establish functional expression assays, metabolite extraction methods, and analytical chemistry. To allow functional expression of these desaturases in S. cerevisiae, an episomal synthetic expression cassette termed pOLE1 cassette (FIG. 10) was constructed, which consisted of an OLE1 promoter region, an N-terminal leader sequence encoding for the first 27 amino acids of S. cerevisiae OLE1, and a terminator region of VPS13 (a protein involved in the protospore membrane formation, the terminator of which has been previously characterized to increase heterologous protein expression potentially by extending mRNA half-life). The functionality of the pOLE1 cassette was validated via its ability to express a GFP (FIG. 11A-FIG. 11E). Subsequently, insect desaturase synthons, and yeast OLE1 synthon were cloned into the pOLE1 cassette, and expressed in S. cerevisiae ΔOLE1 strain. This strain was chosen since deletion of the OLE1 allele (which encodes for palmitoyl:CoA/stearoyl: CoA (z)-9-desaturase) allows its utilization as a tool to screen for functional insect desaturase. Specifically, an active desaturase would allow complementation of growth without requiring exogenous supplementation of UFAs. Expression of OLE1 using pOLE1 cassette complemented growth of ΔOLE1 growth without UFA (FIG. 11A-FIG. 11E); therefore, it serves as a positive control in the complementation assays. When insect desaturases were expressed, we observed that they rescued ΔOLE1 growth without UFA at varying degree. On rich medium (YPD) agar plate, expression of S. cerevisiae OLE1 conferred the highest level of growth, followed by T. ni desaturase (FIG. 12A). The latter indicated that production of unsaturated fatty acyl: CoA by T. ni desaturase could act as a surrogate to the missing (Z)-9-hexadecenoyl:CoA biosynthesis in ΔOLE1. Expression of T. pesudonana and A. segetum desaturases did not appear to rescue growth on YPD very well (FIG. 12A). When patched on minimal medium (CM-Ura glucose) agar plate, only expression of S. cerevisiae OLE1 and T. ni desaturase rescued ΔOLE1 growth without exogenous UFA (FIG. 12B). Expression of T. pseudonana and A. segetum desaturases did not confer growth of ΔOLE1 on minimal medium agar, suggesting their limited activity in producing UFA (results not shown). Screening a desaturase library in Candida tropicalis identified functional expression of A. transitella and H. zea desaturases. When these desaturases were expressed in ΔOLE1, they conferred growth without UFA on both YPD and CM-Ura glucose media similar to expression of T. ni desaturase (FIG. 12B).

Figure 13A:
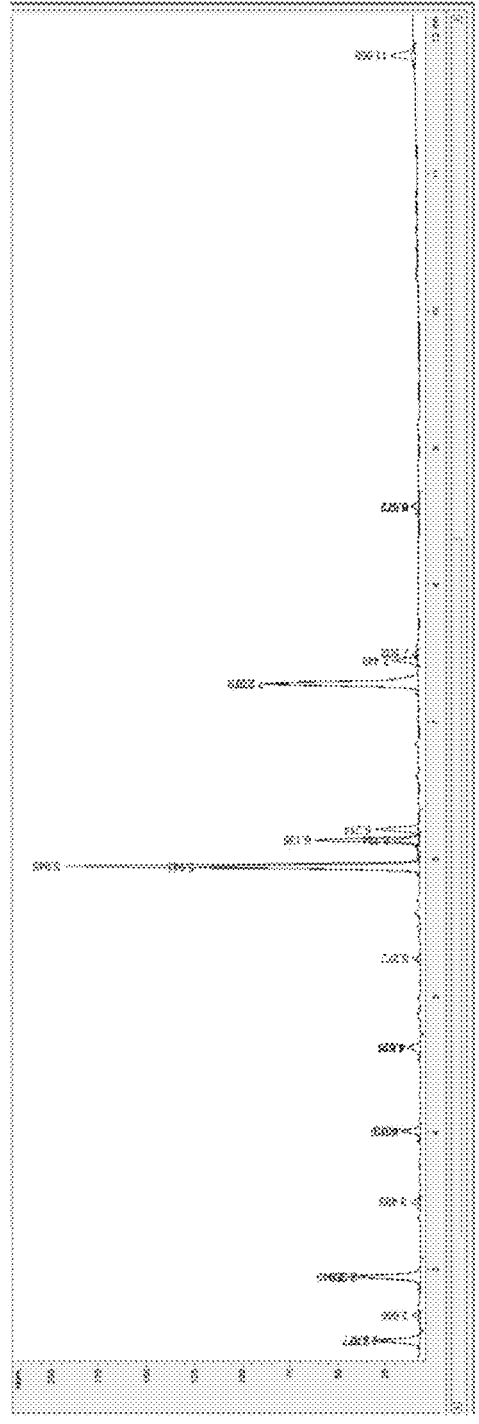
FIG. 13A shows the full fatty acid spectrum of a ΔOLE1 strain expressing: *S. cerevisiae* OLE1 desaturase (blue), chimeric *T. ni* desaturase (red).
Figure 13B:
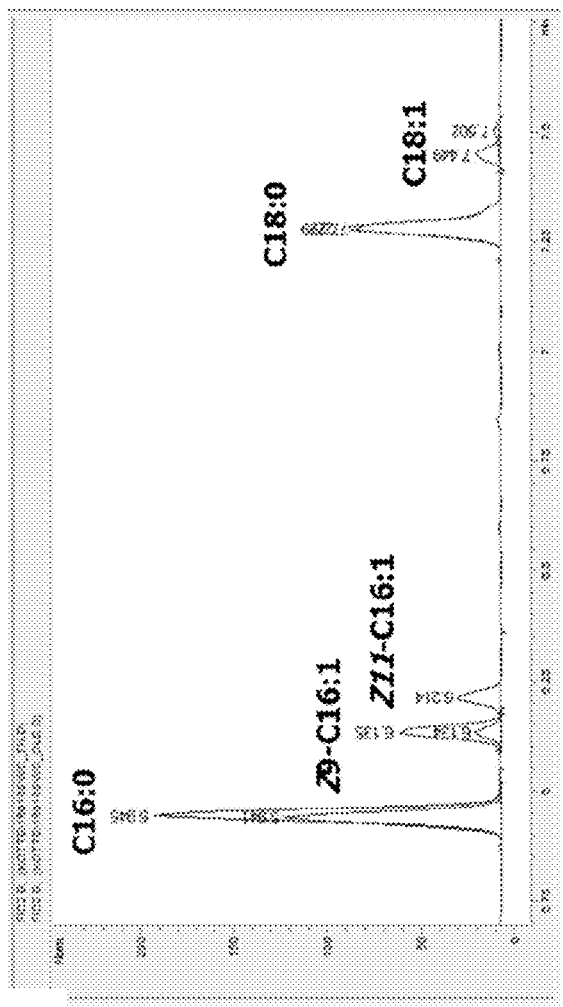
FIG. 13B shows a focused fatty acid spectrum within 5.5-min-8-min retention time of *S. cerevisiae* ΔOLE1 strain expressing *S. cerevisiae* OLE1 desaturase (red) and chimeric *T. ni* desaturase (blue).

Functional expression of the heterologous desaturases was further characterized via in vivo bioconversion of palmitic acid into insect-specific UFA. Post ~96 h-cultivation in minimal medium containing palmitic acid, total fatty acid analysis of S. cerevisiae ΔOLE1 expressing T. ni desaturase revealed production of a new fatty acid species (Z)-1-hexadecenoic acid that is not present in the control strain which expresses native yeast OLE1 desaturase (FIG. 13A-FIG. 13B). (Z)-11-hexadecenoic acid is not detected in strains expressing A. segetum, or T. pseudonana desaturase (results not shown). In addition to (Z)-11-hexadecenoic acid, (Z)-9-hexadecenoic acid was also detected in ΔOLE1 strain expressing T. ni desaturase (FIG. 13A-FIG. 13B). Under the cultivation condition, C16-fatty acid in the ΔOLE1 expressing T. ni desaturase is composed of approximately 84.7% hexadecanoic acid, 5.6% (Z)-9-hexadecenoic acid and 9.8% (Z)-11-hexadeceneoic acid. In comparison, the C16 fatty acid fraction of ΔOLE1 expressing OLE desaturase is composed of approximately 68.6% hexadecanoic acid and 31.4% (Z)-9-hexadecenoic acid. (Z)-11-hexadecenoic acid biosynthesis in ΔOLE1 expressing T. ni desaturase account for ~1.5 mg/L. The amount of total fatty acids and each fatty acid within this mixture can be quantified. The biologically produced (Z)-11-hexadecenoic acid also match the retention time and fragmentation pattern of authentic standard (Z)-11-hexadecenoic acid (Larodan) as determined by GC-MS (FIG. 14A-FIG. 14B). Therefore, the regio- and stereoisomer of the biologically produced (Z)-11-hexadecenoic acid was confirmed. In vivo characterization of A. transitella and H. zea desaturase can also be done.

In summary, at least three insect desaturases capable of rescuing growth of S. cerevisiae ΔOLE1 without exogenous supplementation of UFA, i.e. (Z)-9-hexadecenoic acid (palmitoleic acid), were identified.

The extent of growth on rich medium (YPD) of S. cerevisiae ΔOLE1 bearing the expression construct was in the following order of desaturase content: OLE1, T. ni. T. pseudonana, and A. segetum.

The extent of growth on minimal medium (CM Glucose w/out uracil) of S. cerevisiae ΔOLE1 bearing the expression construct was in the following order of desaturase content: OLE1, T. ni.

Complementation assays using A. transitella and H. zea desaturases were also done, demonstrating functional expression in Candida tropicalis shown via in vivo bioconversion assay. These desaturases also complemented S. cerevisiae ΔOLE1 growth on rich and minimal media at least as well as T. ni desaturase.

Expression of T. pseudonana and A. segetum desaturases did not confer growth of S. cerevisiae ΔOLE1 on minimal medium without UFAs even after an extended incubation period up to 14 days. No (Z)-11-hexadecenoic acid was observed in strains harboring T. pseudonana or A. segetum desaturase.

Conclusions

Functional expression of transmembrane desaturases of insect origin in S. cerevisiae has been achieved.

The activity of a given heterologous desaturase can be assessed from its ability to complement growth of S. cerevisiae ΔOLE1 without exogenous palmitoleic supplementation, and its ability to convert palmitic acid into insect pheromone precursors (Z)-11-hexadecenoic acid.

Functional expression and/or activity of insect desaturase in S. cerevisiae varies widely depending on sequence origin. Variants derived from T. ni exhibited the best activity compared to A. segetum and T. pseudonana, as measured by the above criteria.

Desaturases derived from A. transitella and H. zea complemented ΔOLE1 as well as T. ni desaturase. Bioconversion assays using these desaturases can be done.

The bioconversion of other fatty acid substrates can be explored to assess enzyme plasticity.

Materials & Methods

Strain Construction and Functional Expression Assay

S. cerevisiae ΔOLE1 (MATA OLE1::LEU2 ura3-52 his4) was used as an expression host. A synthetic expression cassette termed pOLE1 (FIG. 10, SEQ ID NO: 4) which comprises the OLE1 promoter region (SEQ ID NOs: 5 and 6), nucleotides encoding for 27 N-terminal amino acids of the OLE1 leader sequence (SEQ ID NO: 7), and a VPS13 terminator sequence (SEQ ID NO: 8) was created, and cloned into pESC-URA vector in between SacI and EcoRI sites. To test the functionality of the pOLE1 cassette, Dasher GFP synthon was inserted in between SpeI and NotI sites to create pOLE1-GFP plasmid. Competent ΔOLE1 was transformed with pOLE1-GFP, and plated on CM-Ura glucose agar plate (Teknova) containing UFA (20 mm CM-URA glucose agar plate was coated with 100 μL CM-Ura glucose medium containing 1% tergitol, and 3 μL palmitoleic acid). After incubation at 30° C. for 5 days, Dasher GFP expression was apparent as displayed by green coloration of ΔOLE1 transformants. This result showed that the pOLE1 cassette was capable of driving heterologous protein expression. Validation of ΔOLE1 complementation was performed by restoring OLE1 activity. Specifically, native S. cerevisiae OLE1 synthon was inserted into pOLE1 cassette devoid of the leader sequence to create pOLE1-OLE1 plasmid. After transformation of ΔOLE1, and selection on CM-Ura glucose agar containing UFA, single colonies were patched onto YPD and CM-Ura glucose without UFA. After incubation at 30° C. for 5 days, growth was observed (FIG. 11A-FIG.

11E). As expected, Dasher GFP expression could not complement ΔOLE1 growth without UFA (FIG. 11A-FIG. 11E). DNA sequences which encode for desaturase variants were synthesized (to include nucleotide changes which remove restriction sites used for cloning purposes), and cloned into pOLE1 using SpeI-NotI sites (Genscript, SEQ ID NOs: 9-13). Complementation assay of ΔOLE1 with insect desaturases were performed in the same way as with OLE1 desaturase.

To assess functional expression, two positive transformation clones that had been patched on CM-Ura glucose agar medium containing UFA were inoculated in 1.5 mL CM-Ura glucose liquid medium containing palmitic acid (in ethanol) at a final concentration of 300 mg/L, and with 6.7 g/L of YNB. For (z)-11-hexadecenoic isomer confirmation, a 20 mL culture was generated. Bioconversion assay proceeded for 96 h at 28° C. prior to GC-MS analysis.

Metabolite Extraction and GC-MS Detection

Total lipid composition as well as the (Z)-11-hexadecenoic acid quantification was based on modified procedures by Moss et al. (1982) (Moss, C. W., Shinoda, T. & Samuels, J. W. Determination of cellular fatty acid compositions of various yeasts by gas-liquid chromatography. *J. Clin. Microbiol.* 16: 1073-1079 (1982)) and Yousuf et al (2010) (Yousuf, A., Sannino, F., Addorisio, V. & Pirozzi, D. Microbial Conversion of Olive Oil Mill Wastewaters into Lipids Suitable for Biodiesel Production. *J. Agric. Food Chem.* 58: 8630-8635 (2010)). The pelleted cells (in 1.5 mL plastic tubes), usually about 10 mg to 80 mg, were resuspended in methanol containing 5% (w/w) of sodium hydroxide. The alkaline cell suspension was transferred into a 1.8 mL screw-cap GC-vial. The mixture was heated for 1 h in the heat block at 90° C. Prior to acidification with 400 2.5 N HCl the vial was allowed to cool to room temperature. 500 μL chloroform containing 1 mM heptadecanoic were added and the mixture was shaken vigorously, then both aqueous and organic phase were transferred into a 1.5 mL plastic tube. The mixture was centrifuged at 13,000 rpm, afterwards 450 μL of the organic phase were transferred into a new 1.5 mL plastic tube. The aqueous phase was extracted a second time with 500 μL chloroform, this time without heptadecanoic acid. The combined organic phases were evaporated at 90° C. After cooling to room temperature, residual fatty acid methyl esters and free fatty acids were dissolved and derivatized in methanol containing 0.2 M TMSH (trimethylsulfonium hydroxide).

The regioselectivity of biologically produced (Z)-11-hexadecenoic acid was determined by comparing the fragmentation patterns of the dimethyl disulfide (DMDS) derivative with the DMDS derivative of an authentic standard. A yeast culture was split into 12 aliquots (to not change any parameters in the developed procedure). The cells were pelleted, which yielded 63 mg cells (ccw) on average (755 mg from 18 mL culture). The pellets were subjected to base methanolysis as described above. However, after acidification the samples were combined in a 50 mL Falcon tube. The combined sample was extracted two times with 10 mL chloroform. The mixture was centrifuged 10 min at 3000 rpm to achieve a better phase separation. The combined organic phases, which were combined in a new 50 mL Falcon and were washed consecutively with 10 mL brine and 10 mL water. The organic phase was dried with anhydrous sodium sulfate and concentrated in vacuo. The concentrated oil was dissolved in 1.5 mL chloroform and transferred to a 1.5 mL plastic tube. The chloroform was evaporated at 90° C. The remaining sample was the dissolved in 50 μL methyl tert-butyl ether (MTBE). The 50 μL were split into 1, 5, 10 and 20 μL and transferred into GC-vials without insert. To each vial 200 μL DMDS (dimethyl disulfide) and 50 μL MTBE (containing 60 mg/mL iodine) were added. After the mixture was heated 48 h at 50° C., excess iodine was removed by the addition of 100 μL saturated sodium thiosulfate solution. The samples were transferred to plastic vials and extracted to times with 500 μL dichloromethane. The combined organic phases were transferred to a new 1.5 mL plastic vial and evaporated at 90° C. The samples were taken up in 50 μL DCM and transferred to a GC-vial. The sample was analyzed by GC-MS (Table 7) using the method of Hagström et al. (2013) (Hagström, A. K. et al. A moth pheromone brewery: production of (Z)-11-hexadecenol by heterologous co-expression of two biosynthetic genes from a noctuid moth in a yeast cell factory. *Microb. Cell Fact.* 12: 125 (2013)).

TABLE 7

Analytical parameters used for GC-MS analysis of DMDS-derivatives

| | |
|---|---|
| System | Agilent 6890 N GC, ChemStation G1701EA E.02.01.1177 |
| Column | Rtx-5 30 m × 320 μm × 25 μm |
| | Pressure = 11.74 psi; Flow = 7.1 mL/min |
| Inlet | Heater = 250° C.; Pressure = 11.74 psi; |
| | Total Flow {He} = 19.5 mL/min |
| Carrier | He @ 147 cm/sec, 11.74 psi |
| Signal | Data rate = 2 Hz/0.1 min |
| Oven | 80° C. for 2 min |
| | Ramp 10° C./min to 180° C. |
| | Ramp 3° C./min to 260° C. |
| | Ramp 20° C./min to 280° C., hold 10 min |
| Injection | Split, 250° C. |
| | Split ratio - 1:1 |
| Detector | HP 5973 MSD in SCAN mode (mass range: 41 to 550 amu) |
| | 100 msec Dwell, EMV mode: Gain factor 1, |
| | 3 min solvent delay, 8.33 cycles/sec |
| Sample | Injection volume = 1 uL |

Example 5: *S. cerevisiae* as a Production Platform for Insect Fatty Alcohol Synthesis Background and Rationale Engineering microbial production of insect fatty alcohols from fatty acids requires the functional expression of a synthetic pathway. One such pathway comprises a transmembrane desaturase, and an alcohol-forming reductase to mediate the conversion of fatty acyl-CoA into regio- and stereospecific unsaturated fatty acyl-CoA, and subsequently into fatty alcohols. A number of genes encoding these enzymes are found in some insects as well as some microalgae. A number of gene variants were screened to identify enzyme activities that allow the creation of pathways capable of high level synthesis of a single or a blend of insect fatty alcohols. Additionally, these enzymes were screened across multiple hosts (*Saccharomyces cerevisiae*, *Candida tropicalis*, and *Yarrowia lipolytica*) in order to find a suitable host for optimum expression of these transmembrane proteins.

Summary of Approach

*S. cerevisiae* was engineered previously to express select functional transmembrane desaturase variants to allow synthesis of (Z)-11-hexadecenoic acid from palmitic acid. This allowed the identification and rank-ordering of the variants based on their bioconversion performance (see Example 4).

*S. cerevisiae* was engineered previously to express select functional transmembrane reductase variants to allow synthesis of (Z)-11-hexadecenol (Z11-16OH) from (Z)-11-hexadecenoic acid. This allowed the identification and rank-ordering of the variants based on their bioconversion performance (see Example 3).

Several fatty alcohol pathways comprised of the most active variant desaturases and reductases identified in the previous screens were assembled.

S. cerevisiae W303A and ΔOLE1 were transformed with the pathway constructs. Functionality of the pathway was assessed via the ability of the recombinant yeasts to synthesize Z11-16OH from palmitic acid.

GC-MS analysis was used to identify and quantify metabolites.

Results

The goal was to engineer one or more insect fatty alcohol biosynthetic pathways in S. cerevisiae. Previously, the functional expression of several transmembrane desaturases of insect origin in S. cerevisiae was demonstrated (see Example 4). Briefly, heterologous desaturase expression was enabled by designing an expression cassette which consists of an OLE1 promoter region, an N-terminal leader sequence encoding the first 27 amino acids of S. cerevisiae OLE, and a terminator region of VPS13. Screening for active desaturases was done by using two approaches. First, active desaturases were screened for their ability to rescue ΔOLE1 growth without exogenous addition of unsaturated fatty acid (UFA), and second, active desaturases were screened via an in vivo screen for bioconversion of palmitic acid into (Z)-11-hexadecenoic acid. These screening strategies allowed the identification of several active variants, and the rank ordering of their relative activity. Based on these screening results, desaturases from Trichoplusia ni (TN_desat) and S. cerevisiae (SC_desat) were selected for combinatorial expression in fatty alcohol pathways. S. cerevisiae desaturase is known to form palmitoleic acid and oleic acid.

The functional expression of several transmembrane alcohol forming reductases of insect origin in S. cerevisiae had also been previously demonstrated (see Example 3). An expression cassette comprising the GAL 1 promoter and CYC terminator was used to enable the functional expression of the reductases in S. cerevisiae. Screening several reductases via in vivo bioconversion of (Z)-11-hexadecenoic acid into Z11-16OH allowed the identification of active variants and rank ordering of their relative activity. Based on this screen, reductases from Helicoverpa armigera (HA_reduc), and Spodoptera littoralis (SL_reduc) were chosen for assembly of the fatty alcohol pathways.

Figure 15:
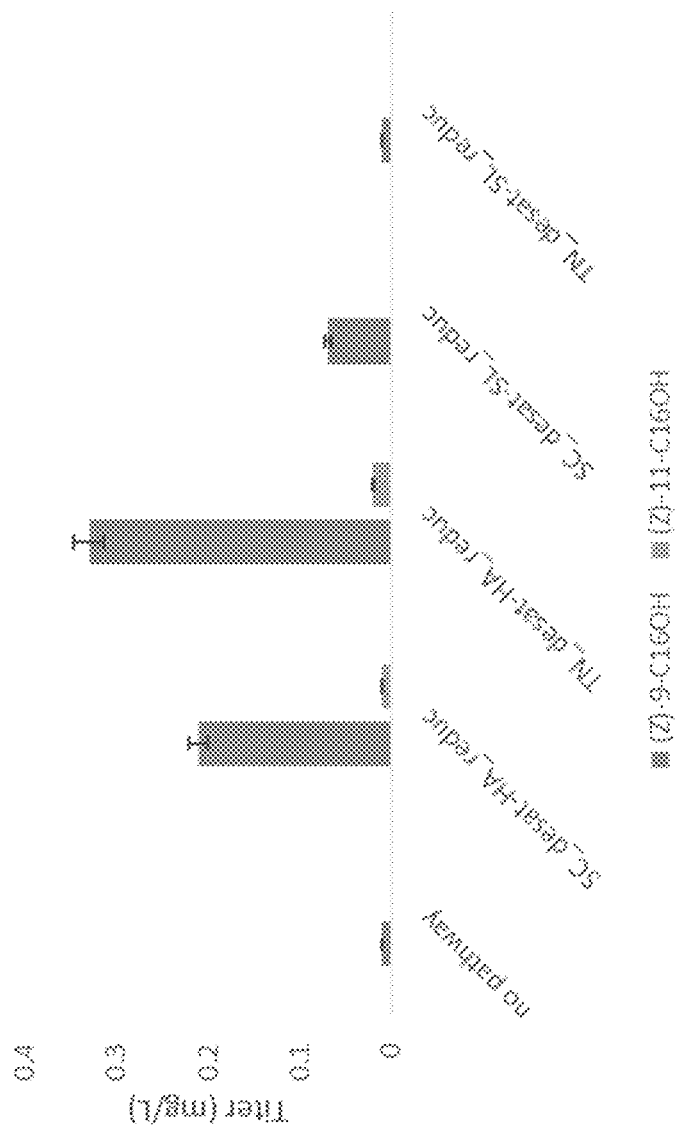
FIG. 15 shows C16 fatty alcohol production from ΔOLE1 expressing various fatty alcohol pathway variants in culture supplemented with palmitic and palmitoleic acid. Error bars represent 5% uncertainty of metabolite quantification accuracy.
Figure 16:
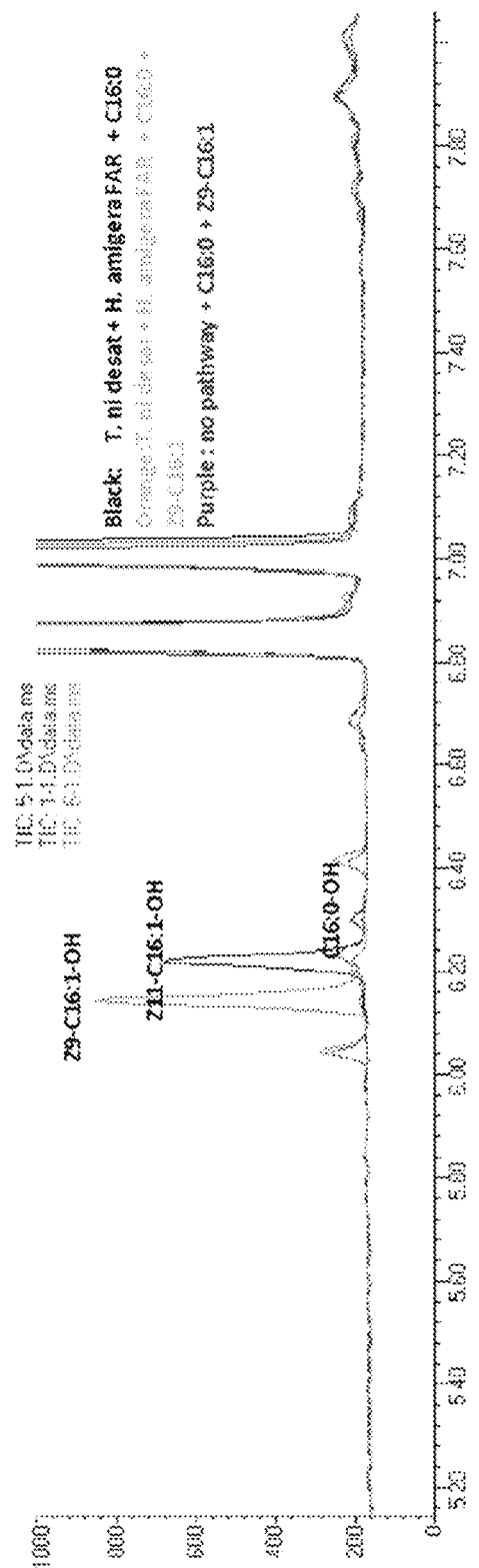
FIG. 16 shows representative chromatograms of biotransformation product C16 fatty acids using *S. cerevisiae* expressing fatty alcohol pathways TN_desat-HA_reduc when fed with palmitic acid (black) and when fed with palmitic and palmitoleic acids (orange). Profile of a negative control strain (harboring an empty vector) fed with palmitic acid (purple).
Figure 17:
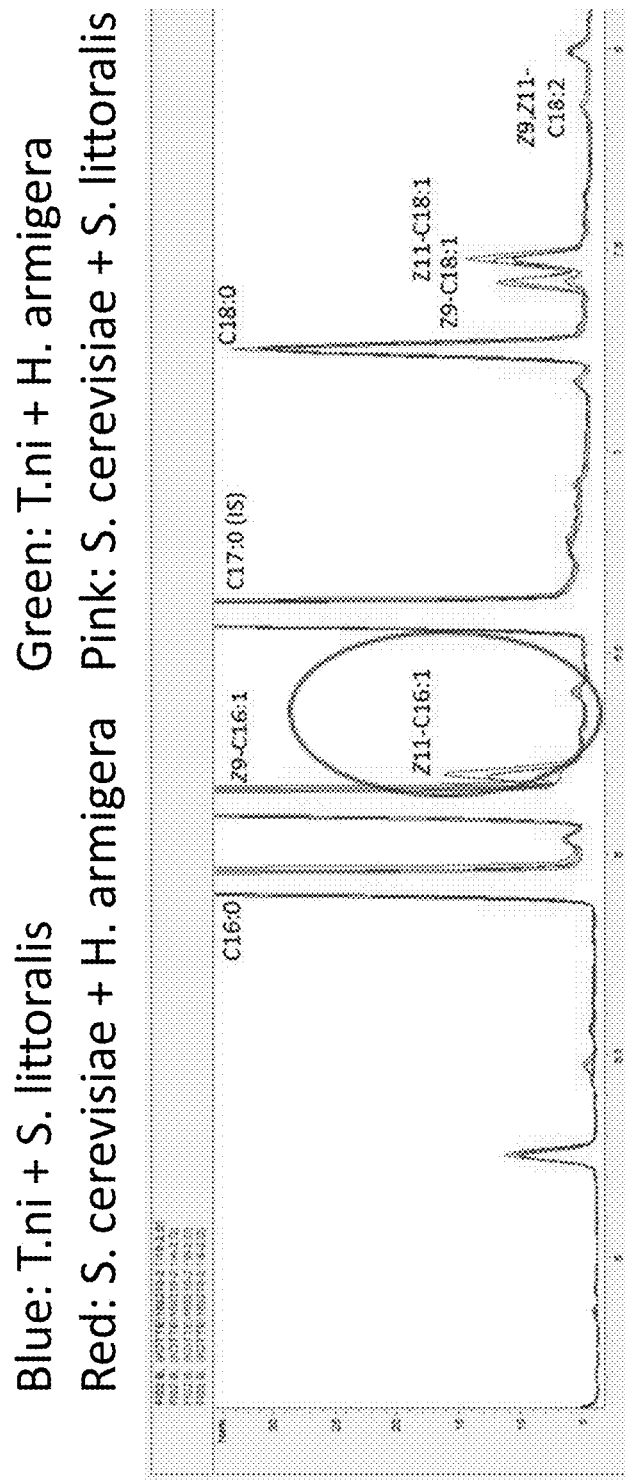
FIG. 17 shows that (Z)-11-hexadecenoic acid was detected in the cell pellets of *S. cerevisiae* expressing fatty alcohol pathways TN_desat-SL_reduc (blue), SC_desat-HA_reduc (red), TN_desat-HA_reduc (green), SC_desat-SL_reduc (pink).

Combinatorial assembly created four fatty alcohol pathways, i.e. TN_desat-HA_reduc, TN_desat-SL_reduc, SC_desat-HA_reduc, and SC_desat-SL_reduc. Pathways with SC_desat served as negative control for insect Z11-16OH synthesis. S. cerevisiae ΔOLE1 and W303A were transformed with constructs harboring these pathways, and transformants that grew on CM-Ura with 2% glucose and coated with palmitoleic acid were isolated. To test for fatty alcohol production, individual clones were inoculated into CM-Ura medium containing 2% glucose, 1% raffinose, 2% galactose. 300 mg/L palmitic acid, and 360 mg/L palmitoleic acid were added as bioconversion substrates. Bioconversion using palmitic acid without palmitoleic was also tested. Post ~96 h-cultivation in the presence of palmitic and palmitoleic acid, culture broth analysis revealed synthesis of Z11-9OH as a major C16 alcohol product at ~0.2 mg/L, and ~0.3 mg/L in cultivation of ΔOLE1 strains harboring SC_desat-HA_reduc, and TN_desat-HA_reduc, respectively (FIG. 15, FIG. 16). A minute amount of Z11-16OH was also detected in pathways with T. ni or S. cerevisiae desaturase, and H. armigera reductase. In general, it was expected that in the presence of palmitic acid and palmitoleic acid, Z9-16OH synthesis was more favorable than Z11-16OH synthesis because (Z)-11-hexadecenoic acid must be biosynthesized from T. ni desaturase, whereas exogenous addition of palmitoleic acid resulted in a more readily available substrate for synthesis of Z9-16OH. Fatty acid analysis was also performed. The results showed higher accumulation of (Z)-11-hexadecenoic acid (FIG. 17) in pathways containing insect desaturase than in pathways expressing S. cerevisiae desaturase. Albeit at minute quantities, detection of Z11-16OH, and (Z)-11-hexadecenoic acid from pathways harboring S. cerevisiae desaturase (which was unexpected) opens the possibility of a minor Δ11 desaturation activity by S. cerevisiae desaturase. Low level synthesis of Z11-16COOH fatty acid moieties can also be derived from elongation of Z9-14COOH fatty acyl intermediate. The data shown in FIG. 15 also showed that in comparison to pathways with H. armigera reductase, the inclusion of S. littoralis reductase resulted in the reduction of (up-to ~30 fold) in Z9-16OH titer. No Z11-16OH could be detected in pathways employing S. littoralis reductase. These results are consistent with the reductase screening assay, which showed superior bioconversion of (Z)-11-hexadecenoic acid using H. armigera reductase in comparison to S. littoralis reductase.

Figure 18:
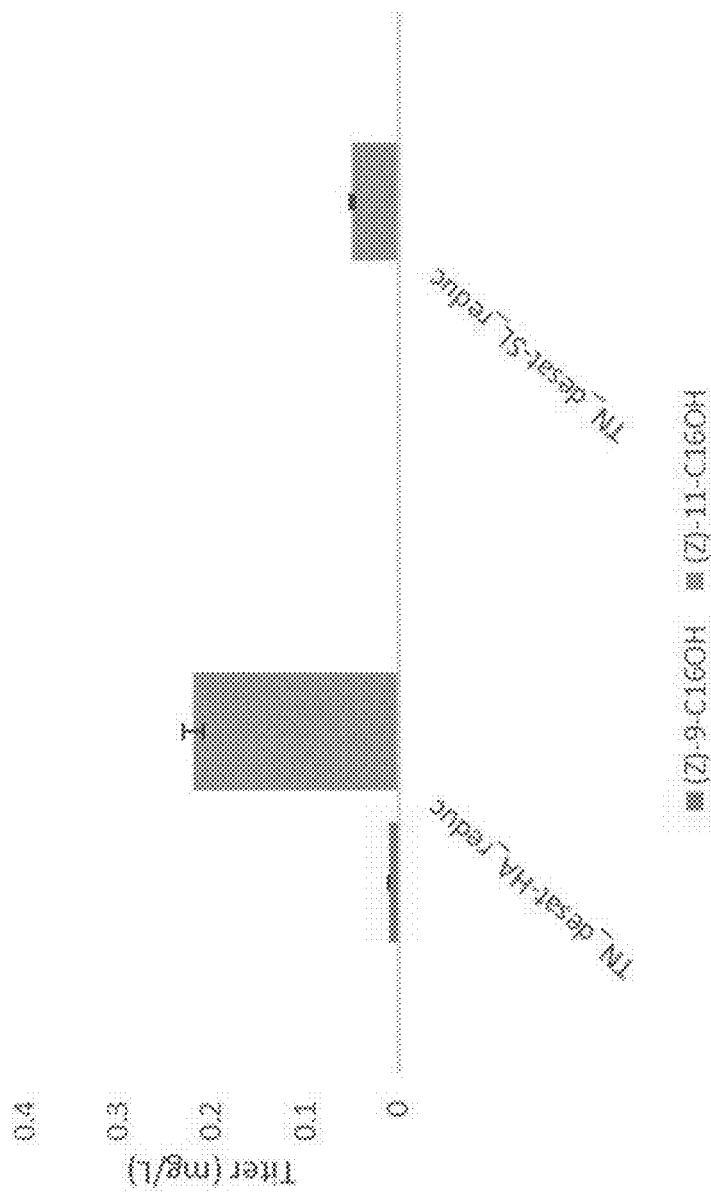
FIG. 18 shows C16 fatty alcohol production from ΔOLE1 expressing various fatty alcohol pathway variants in culture supplemented with palmitic acid only. Error bars represent 5% uncertainty of metabolite quantification accuracy.
Figure 19:
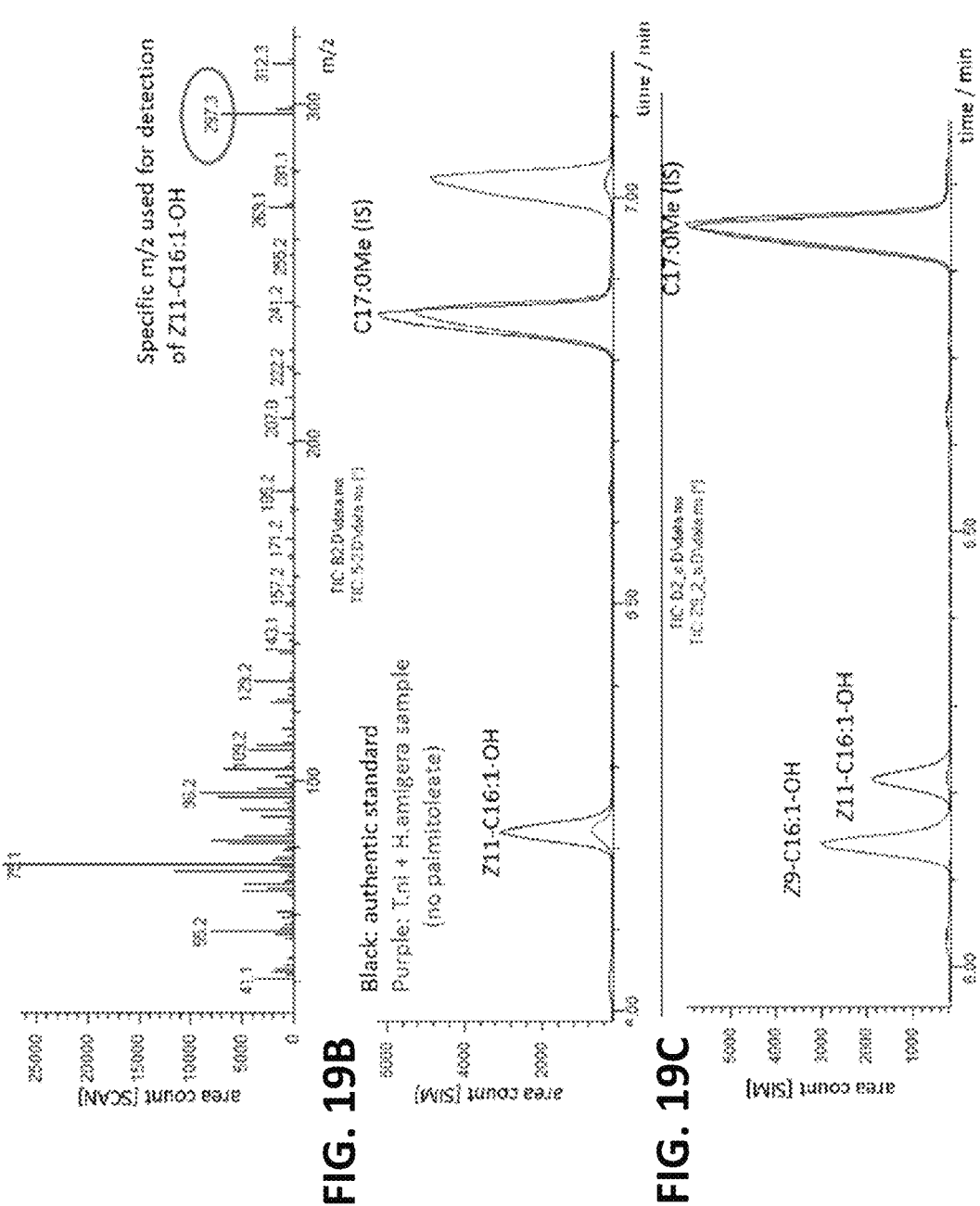
FIG. 19A-FIG. 19C shows detection of (Z)-11-hexadecenol.

The bioconversion of palmitic acid was also tested alone (without exogenous addition of palmitoleic acid) by ΔOLE1 strains expressing TN_desat-HA_reduc and TN_desat-SL_reduc (FIG. 18). Culture broth analysis determined the synthesis of Z11-16OH as the dominant unsaturated C16 fatty acid product (FIG. 16). In this assay, up to 0.22 mg/L, and 0.05 mg/L Z11-16OH was synthesized by a pathway harboring H. armigera reductase and S. littoralis reductase, respectively. The biologically produced Z11-16OH also matched the retention time and exhibited the characteristic 297.3 m/z peak like the authentic standard Z11-16OH as determined by GC-MS (SIM). Therefore, the regio- and stereoisomer of the biologically produced Z11-16OH was confirmed (FIG. 19). Furthermore, Z9-16OH (0.01 mg/L) was also observed in the cultivation of strain co-expressing T. ni desaturase and H. armigera reductase. This suggested that T. ni desaturase may also possess Δ9 desaturation activity.

OLE1 deletion impairs growth. Therefore, pathway expression was also explored in W303A, a host with intact OLE1 allele. However, despite growth improvement, pathway expression in this host resulted in more than two-fold reduction of Z11-16OH titers. This result was likely due to the repression of OLE1 promoter (which drove heterologous desaturase expression) by endogenous unsaturated fatty acyl:CoAs, the products of OLE1. The S. cerevisiae OLE1 promoter has been previously characterized with structural regions found to be positively and negatively regulated by saturated and unsaturated fatty acid, respectively (Choi, J-Y. et al. Regulatory Elements That Control Transcription Activation and Unsaturated Fatty Acid-mediated Repression of the Saccharomyces cerevisiae OLE1 Gene. J. Biol. Chem. 271: 3581-3589 (1996)). In addition to cis-transcriptional regulation, unsaturated fatty acids also interact with OLE1 promoter elements to regulate mRNA stability (Gonzales, C. I. et al. Fatty acid-responsive control of mRNA stability. Unsaturated fatty acid-induced degradation of the Saccharomyces OLE1 transcript. J. Biol. Chem. 271: 25801-25809 (1996)). Due to this inherent complexity of the OLE1 promoter, the utilization of unregulated orthogonal promoters, such as the OLE1 promoter from S. kluyveri (Kajiwara, S. Molecular cloning and characterization of the v9 fatty acid desaturase gene and its promoter region from Saccharomyces kluyveri. FEMS Yeast. Res. 2: 333-339 (2002)) to drive insect desaturase expression can be explored to enhance fatty alcohol production.

In summary, functional expression of synthetic pheromone pathway variants in S. cerevisiae ΔOLE1 resulted in the synthesis of Z11-16OH and Z9-16OH from palm oil fatty acids (palmitic acid and palmitoleic acid) up to approximately 0.2 mg/L and 0.3 mg/L, respectively.

The engineered pathway that resulted in the highest fatty alcohols is comprised of T. ni desaturase and H. armigera reductase.

Accumulation of (Z)-11-hexadecenoic acid, an intermediate of the pathway, was also observed in strains that produced Z11-16OH.

No Z11-16OH was produced and only trace Z9-16OH was detected in the negative control strain (harboring vector only).

The regio- and stereochemistry of the biologically produced Z11-16OH were confirmed by comparing the retention time and fragmentation pattern to the authentic standard compound via GC-MS.

Conclusions

The engineering of Baker's yeast for synthesis of Z11-16OH and Z9-16OH, fatty alcohol precursors of insect pheromones, was demonstrated.

Fatty alcohol production varies depending on the selection of the desaturase and reductase variants.

Accumulation of (Z)-11-hexadecenoic acid suggested the possibility of further fatty alcohol improvement by increasing the performance of alcohol forming reductase. However, it is also possible that detection of (Z)-11-hexadecenoic acid was due to its incorporation as phospholipid into any membrane other than the endoplasmic reticulum membrane (such as mitochondrial membranes, peroxisome, nuclear envelope, etc), therefore inaccessible to alcohol forming reductase (presumably translocated into the endoplasmic reticulum) which must utilize (Z)-11-hexadecenoic acid in its CoA thioester moiety as its substrate.

Culture conditions can be explored to increase fatty alcohol titers. The T. ni desaturase can be replaced in the pathway by A. transitella desaturase, another variant that also showed high activity and rescued ΔOLE1 growth faster than T. ni desaturase. The synthetic pathway can be imported into Candida tropicalis and Yarrowia lipolytica, which are yeasts with high adhesion property to hydrophobic substrates such as palmitic and palmitoleic acid. By increasing substrate accessibility to the microbial production platform, it is foreseeable that product titer and yield can be improved.

Materials & Methods

Strain Construction and Functional Expression Assay

S. cerevisiae ΔOLE1 (MATA OLE1::LEU2 ura3-52 his4), and W303A (MATA ura3-1 trp1-1 leu2-3_112 his3-11_15 ade2-1 can1-100) were used as expression hosts. Modular design allows combinatorial pathway assembly utilizing BamHI and XhoI to excise reductase synthons (see Example 3) and subcloning into plasmids containing pOLE1-desaturase constructs (see Example 4). Competent yeasts were transformed with pathway constructs and plated on CM-Ura glucose agar plate (Teknova). In the case of ΔOLE1 transformation, colony plating utilized 20 mM CM-Ura glucose agar plates that were coated with 100 μL CM-Ura glucose medium containing 1% tergitol and 3 μL palmitoleic acid.

To assess functional expression, transformants were inoculated in ~20 mL CM-Ura liquid medium containing 6.7 g/L of YNB, 2% glucose, 1% raffinose, and 2% galactose. Fatty acid substrates, i.e. palmitic acid (in ethanol), was added at a final concentration of 300 mg/L. Palmitoleic acid was added at a final concentration of 360 mg/L. Bioconversion assay proceeded for 96 h at 28° C. prior to GC-MS analysis.

Metabolite Extraction and GC-MS Detection

Fatty acid analysis was as described in Example 4, except that instead of extracting the sample two times, the sample was only extracted once with chloroform containing 1 mM methyl heptadecanoate (C17:0Me). Fatty alcohol analysis was as described in Example 3, except that instead of hexane (containing tetradecanedioic acid), chloroform (containing 1 mM methyl heptadecanoate) was used. The extraction time was reduced from 1 h to 20 s. Afterwards the samples were collected in a 1.8 mL GC vial and not in a 1.5 mL plastic tube. The mass spectrometer was used in SIM mode (m/z 208, 297.3 and 387.3).

Example 6: Expression of Transmembrane Desaturases in Candida tropicalis

Background and Rationale

Engineering microbial production of insect fatty alcohols from fatty acids requires the functional expression of a synthetic pathway. One such pathway comprises a transmembrane desaturase, and an alcohol-forming reductase to mediate the conversion of fatty acyl-CoA into regio- and stereospecific unsaturated fatty acyl-CoA, and subsequently into fatty alcohols. A number of genes encoding these enzymes are found in some insects as well as some microalgae. A number of gene variants were screened to identify enzyme activities that allow the creation of pathways capable of high level synthesis of a single or a blend of insect fatty alcohols. Additionally, these enzymes can be screened across multiple hosts (Saccharomyces cerevisiae, Candida tropicalis, and Yarrowia lipolytica) to optimize the search toward finding a suitable host for optimum expression of these transmembrane proteins.

Summary of Approach

A small set of desaturases (insect origin: Agrotis segetum, Amyelois transitella, Helicoverpa zea, Trichoplusia ni, Ostrinia furnacalis, and Lampronia capitella and marine diatom: Thalassiosira pseudonana) were selected as a test case to explore and establish functional expression assays, metabolite extraction methods, and analytical chemistry.

Successful integration and functional expression of mCherry control from pXICL expression cassette in SPV053 were confirmed.

Figure 20:
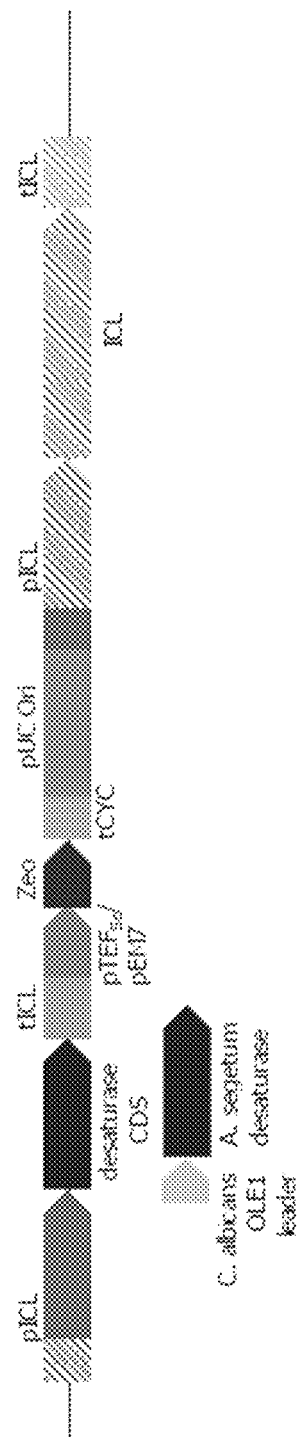
FIG. 20 shows pXICL expression cassette architecture. The *C. albicans* OLE1 leader-*A. segetum* desaturase fusion is also shown.

A recombinant desaturase library using the same pXICL vector in SPV053 background was integrated (FIG. 20). One variant, the Z11 desaturase of Agrotis segetum, was also cloned to produce a protein product with the first 27 amino acids of Candida albicans Ole1p fused to the N-terminus of the insect desaturase (SEQ ID NO: 15).

Functionality of the desaturase was validated via an in vivo bioconversion of hexadecanoic acid (palmitic acid) into (Z)-11-hexadecenoic acid (palmitvaccenic acid).

GC-FID and GC-MS analyses were used to identify and quantify metabolites.

Results

Library Construction

This study focused on the screening for transmembrane desaturase variants in C. tropicalis (SPV053). Five insect desaturases with reported Z11 desaturase activity on palmitoyl-CoA (C16:0) (SEQ ID NOs: 16-19, 23) and three insect desaturases with reported Z9 desaturase activity (SEQ ID NOs: 20-22) were included in the screen. One variant, the Z11 desaturase from A. segetum (SEQ ID NO: 16), was also cloned with 27 amino acids of the Candida albicans OLE1

N-terminus fused upstream of the insect sequence (FIG. 20, SEQ ID NO: 15). At the time of construction, the *A. segetum* Z11 desaturase was believed to be a positive control and the *C. albicans* OLE1 fusion was constructed to test if inclusion of a *Candida* leader sequence would improve functional expression. The construct was designed to mimic those used in *Saccharomyces cerevisiae* desaturase screening (See Example 4). Finally, a control construct expressing mCherry red fluorescent protein (SEQ ID NO: 14) was included to act as a positive control for integration and expression and a negative control for recombinant desaturase activity (FIG. 21A-FIG. 21D).

Figure 22:
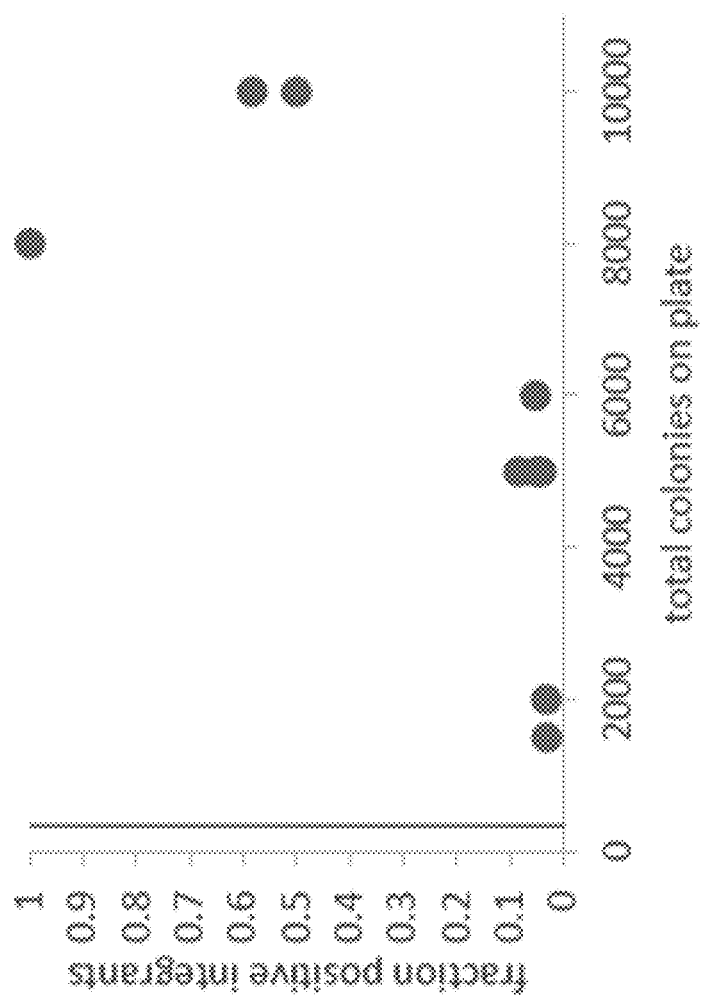
FIG. 22 shows integration efficiency as a function of total observed colonies. A control plate with no DNA added to the transformation was observed to have 350 colonies (indicated by orange line). The fraction of clones confirmed to be positive integrants is positively correlated with total colony count. A sharp increase is observed above 6,000 total colonies. The data suggests that the presence of positive integrants increases the observed background growth. For some transformations the efficiency was high enough that the background population was small relative to the positive integrant population.

Transformation efficiencies of linearized plasmids into SPV053 varied greatly across constructs. Despite low efficiencies, at least 3 clonal isolates were identified for each variant (Tables 8 and 9). It had been hypothesized that larger colonies on transformation plates were more likely to be positive integrants because the presence of the Zeocin resistance marker should increase growth rate under Zeocin selection. Analysis of the screening results suggested that the number of large colonies is not correlated to transformation efficiency. Instead total colony (small and large) count correlated best with observed efficiency (FIG. 22). In addition, in some cases positive clones were found among the small colonies. It is possible that at lower plating density growth rate may be correlated with integration events (i.e. positive integrants grow faster). A secondary screen of repatching colonies on YPD+Zeocin proved effective in enriching for positive integrants. Fast growing patches were more likely to be positive integrants than the general population of colonies on transformation plates.

TABLE 8

Desaturase transformations in SPV053. Efficiency of transformation varied across constructs with a relatively high degree of background under Zeocin selection.

| specificity | source species | pXICL plasmid | DNA ug | large colonies (control plate) | total colonies (control plate) |
|---|---|---|---|---|---|
| control | mCherry_Ct | pPV0137 | 1.1 | 60 (30) | 2,000 (600) |
| Z11 | Argotis segetum-OLE1_Ca | pPV0138 | 1.2 | 120 (78) | >10,000 (320) |
|  | Agrotis segetum | pPV0139 | 1.3 | 115 (78) | 8,000 (320) |
|  | Amyelois transitella | pPV0140 | 1.1 | 220 (78) | 5,000 (320) |
|  | Trichoplusia ni | pPV0141 | 1.1 | 100 (78) | >10,000 (320) |
|  | Helicoverpa zea | pPV0142 | 1.0 | 350 (78) | 5,000 (320) |
|  | Thalassiosira pseudonana | pPV0146 | 1.1 | 140 (78) | 1,500 (320) |
| Z9 | Ostrina Furnacalis | pPV0143 | 0.9 | 220 (78) | 6,000 (320) |
|  | Lampronia capitella | pPV0144 | 1.2 | 230 (78) | 5,000 (320) |
|  | Helicoverpa zea | pPV0145 | 1.2 | 72 (78) | 2,000 (320) |

TABLE 9

Desaturase SPV053 library construction. Five insect desaturases with putative Z11 desaturation activity and 3 insect desaturases with putative Z9 desaturation activity were integrated into the SPV053 background using the pXICL vector. In addition, a control strain expressing mCherry was constructed with the same vector.

| specificity | source species | pXICL plasmid | Total positives | Total screened | Fraction positive |
|---|---|---|---|---|---|
| control | mCherry_Ct | pPV0137 | 16 | 16 | 1.00 |
| Z11 | Argotis segetum-OLE1_Ca | pPV0138 | 7 | 12 | 0.58 |
|  | Agrotis segetum | pPV0139 | 12 | 12 | 1.00 |
|  | Amyelois transitella | pPV0140 | 5 | 60 | 0.08 |
|  | Trichoplusia ni | pPV0141 | 6 | 12 | 0.50 |
|  | Helicoverpa zea | pPV0142 | 5 | 120 | 0.04 |
|  | Thalassiosira pseudonana | pPV0146 | 3 | 96 | 0.03 |
| Z9 | Ostrina Furnacalis | pPV0143 | 3 | 57 | 0.05 |
|  | Lampronia capitella | pPV0144 | 3 | 58 | 0.05 |
|  | Helicoverpa zea | pPV0145 | 3 | 94 | 0.03 |

Functional Expression Assay

Functional expression of the heterologous desaturases was characterized by a series of in vivo bioconversion experiments. *C. tropicalis* SPV053 derived stains expressing insect desaturases were cultured in rich (YPD) or defined (CM glucose) media supplemented with ethanol (for induction) and saturated acid substrates (palmitic acid, methyl palmitate, methyl myristate). Small scale (2 ml) cultures were cultivated for a total of 72 hours in 24 deep well plates with substrate added after the initial 24 hours.

Figure 23:
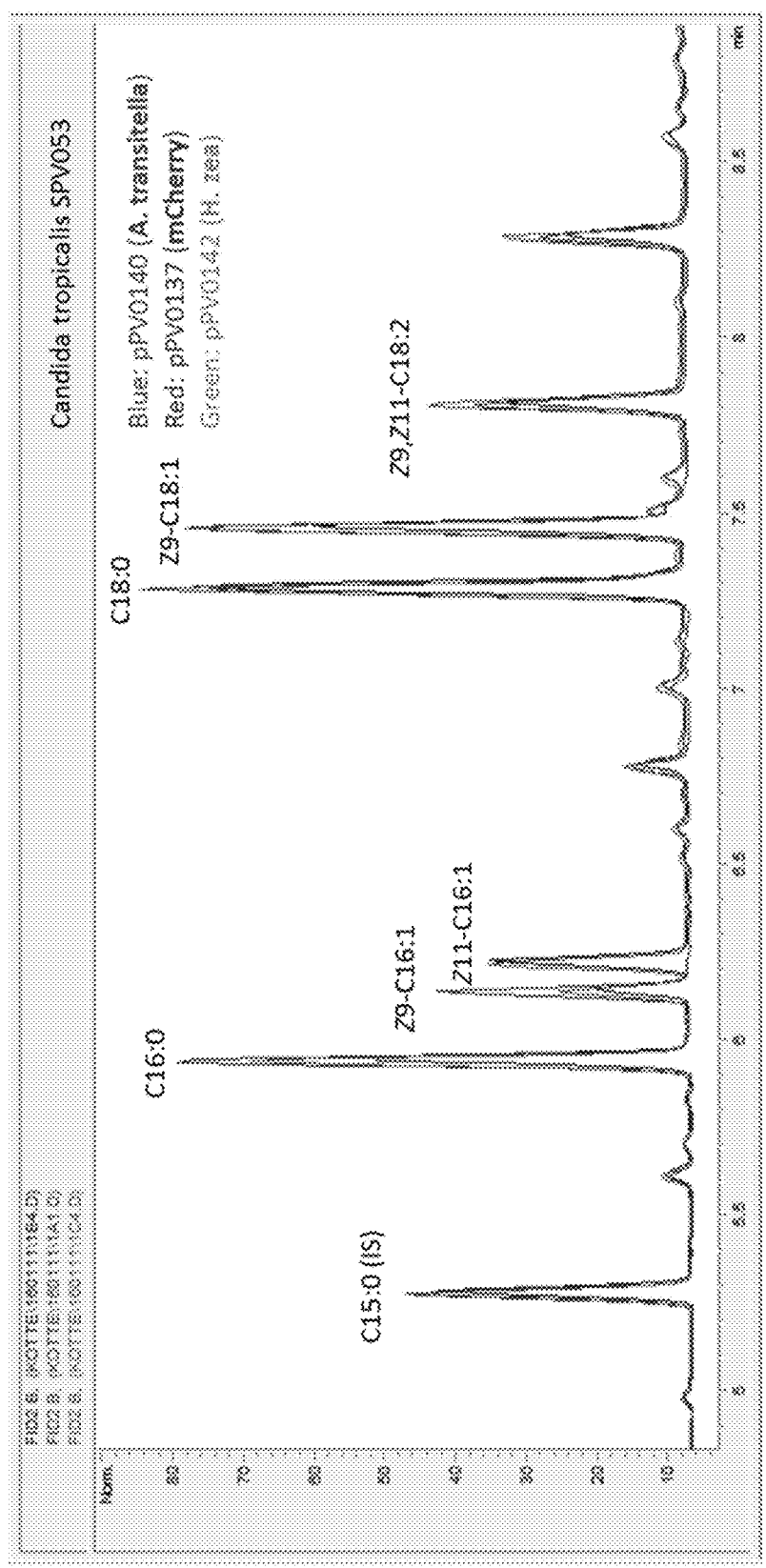
FIG. 23 shows a chromatogram overlay of *Candida tropicalis* SPV053 strains. Compared to the mCherry (red) control experiment a clear peak at 6.22 min is observable for the *A. transitella* (blue) and *H. zea* (green) desaturase. Therefore, the formation of Z-11-hexadecenoic acid is only observable in strains expressing an active Z11-desaturase.

The first screen examined multiple bioconversion media with supplementation of a palmitic acid substrate. Two functional palmitoyl-CoA (Z)-11 desaturases were identified by fatty acid methyl ester (FAME) analysis of the cellular lipid content. Strains expressing *A. transitella* or *H. zea* Z11 desaturases (SPV0305-SPV0310) produced a fatty acid species not observed in the mCherry control strains (SPV0302-SPV0304) which eluted with the (Z)-1-hexadecenoic acid standard (FIG. 23). No other tested strains produced non-native fatty acid species (data not shown). Approximate fatty acid composition of the C16-fraction is listed in Table 10. The native palmitoyl-CoA (Z)-9 desaturase is still present in the SPV053 background which means the (Z)-9/(Z)-11 specificity of the desaturases cannot be rigorously determined. Supplementation of palmitic acid in the media increased the (Z)-11/(Z)-9 hexadecenoic acid ratio from 0.6 to 1.4 for *H. zea* desaturase expressing strains. (Z)-11-hexadecenoic acid titers were observed to be approximately 5.62 mg/L for strains expressing *A. transitella* desaturase and 5.96 mg/L for strains expressing *H. zea* desaturase. Similar performance was observed with methyl palmitate supplementation (data not shown).

TABLE 10

Composition of the C16-fatty acid fraction in different *C. tropicalis* SPV053 expressing different desaturases.

|  | C16:0 [%] | Z9-C16:1 [%] | Z11-C16:1 [%] | Z11/Z9 ratio |
|---|---|---|---|---|
| mCherry | 72.9 | 27.1 | 0.0 | 0.0 |
| Hzea-YPD_NS | 50.0 | 30.9 | 19.1 | 0.6 |

TABLE 10-continued

Composition of the C16-fatty acid fraction in different *C. tropicalis* SPV053 expressing different desaturases.

| | C16:0 [%] | Z9-C16:1 [%] | Z11-C16:1 [%] | Z11/Z9 ratio |
|---|---|---|---|---|
| *Hzea*-YPD | 58.1 | 17.5 | 24.4 | 1.4 |
| AT-YPD | 55.5 | 14.5 | 30.0 | 2.1 |

*NS = no substrate (hexadecanoic acid) was added.

The bioconversion assay was scaled-up to 20 ml in shake flasks in order to generate enough biomass for additional characterization of the putative (Z)-11-hexadecenoic acid species. While the observed species eluted with the (Z)-11-hexadecenoic acid standard and independently of the (Z)-9-hexadecenoic acid standard, it was possible that a different fatty acid isomer (e.g. (E)-9-hexadecenoic acid) could have a similar retention time to (Z)-11-hexadecenoic acid. As different stereoisomers elute differently on the DB-23 the occurrence of (E)-11-hexadecenoic could be excluded. Final confirmation of (Z)-11-hexadecenoic acid production was completed by using mass spectroscopy detection of DMDS derivatized fatty acids to confirm the 11-regioselectivity. Using this derivatization technique (Z)-11 and (E)-11 isomers could in principle also be resolved. The fragmentation pattern of experimental samples could be matched to the (Z)-11-hexadecenoic acid standard (FIG. 24A-24E). Using this technique, production of the specific (Z)-11-hexadecenoic acid regio- and stereoisomer was confirmed for both *A. transitella* and *H. zea* desaturase expressing strains.

Finally, methyl myristate (C14:0) was tested as substrate for the entire desaturase library. A non-native fatty acid species which elutes between myristate (C14:0) and (Z)-9-tetradecenoic acid (Z9-C14:1) was observed in strains expressing either *A. transitella* or *H. zea* Z11 desaturases (FIG. 25A). It is hypothesized that this non-native species is (Z)-11-tetradecenoic acid, and this can be confirmed with an authentic standard. In addition, *A. segetum* Z11 desaturase, *O. furnacalis* Z9 desaturase, and *H. zea* Z9 desaturase all produced a shoulder peak which eluted just after the myristate (C14:0) peak (FIG. 25B). Other C14 derived species (e.g. tetradecanedioic acid) were observed in all strains. These results suggest that *A. transitella* and *H. zea* desaturases have some activity on myristoyl-CoA. Confirmation of unknown species and quantification is required to draw further conclusions about desaturase substrate specificity in vivo.

In summary, two desaturases from *Helicoverpa zea* (AAF81787) and from *Amyelois transitella* (JX964774), were expressed in SPV053 and conferred synthesis of (Z)-11-hexadecenoic acid from either endogenously produced or supplemented palmitic acid.

Functional expression of *H. zea* and *A. transitella* desaturases in *C. tropicalis* SPV053 was confirmed using an in vivo bioconversion assay in both rich (YPD) and defined (CM glucose) media. The active desaturases generated intracellular (Z)-11-hexadecenoic acid which was not observed in mCherry expressing control strains. C16-fatty acid composition of SPV053 expressing *H. zea* desaturase is approximately 50.0% hexadecanoic acid, 30.91% (Z)-9-hexadecenoic acid and 19.1% (Z)-11-hexadeceneoic acid. With palmitic acid supplementation the composition is 58.1% hexadecanoic acid, 17.5% (Z)-9-hexadecenoic acid and 24.4% (Z)-11-hexadeceneoic acid. The C16-fatty acid composition of SPV053 expressing *A. transitella* desaturase is 55.5% hexadecanoic acid, 14.5% (Z)-9-hexadecenoic acid and 30.0% (Z)-11-hexadeceneoic acid. In comparison, SPV053 expressing mCherry produced a C16-fatty acid composition of approximately 72.9% hexadecanoic acid, 27.1% (Z)-9-hexadecenoic acid and no (Z)-11-hexadeceneoic acid. (Z)-11-hexadecenoic acid was produced at approximately 5.5 mg/L in both strains expressing functional Z11 desaturases.

No (Z)-11-hexadecenoic acid was observed in strains harboring *T. ni*, *T. pseudonana*, or *A. segetum* desaturase.

No difference in fatty acid composition was observed for strains expressing Z9 insect desaturases from *H. zea*, *O. furnacalis*, or *L. capitella*.

The regio- and stereoisomer of the biologically produced (Z)-11-hexadecenoic acid were confirmed by comparing the retention time and fragmentation pattern of the authentic standard compound via GC-MS after DMDS derivatization.

Bioconversions of SPV053 expressing *A. transitella* and *H. zea* desaturases with supplementation of methyl myristate produced an unidentified metabolite not observed in the mCherry expressing negative control strain. The GC retention time of this metabolite is found between myristate (C14:0) and (Z)-9-tetradecenoic acid.

Conclusions

Functional expression of transmembrane desaturase of insect origin in *C. tropicalis* SPV053 has been achieved.

The active desaturases identified via screening in *C. tropicalis* also complemented OLE1 function when expressed in *S. cerevisiae* ΔOLE1 (See Example 4).

An in vivo assay can be used to assay desaturase activity in *C. tropicalis* for non-native fatty acid isomers (e.g. (Z)-11-hexadecenoic acid). Enhanced ratios of non-native fatty acids can be produced with supplementation of saturated acid substrates such as palmitic acid or methyl myristate.

Functional expression and/or activity of insect desaturases varies widely in *C. tropicalis* SPV053 depending on sequence origin. Similar to results observed in the *S. cerevisiae* screen (See Example 4), *A. segetum* and *T. pseudonana* variants did not produce detectable (Z)-11-hexadecenoic acid. Interestingly, *T. ni* desaturase also failed to produce detectable (Z)-11-hexadecenoic acid under assay conditions. Unlike in the *S. cerevisiae* assay, the *T. ni* expression construct did not include a chimeric OLE leader sequence.

The inclusion of the *C. albicans* OLE1 leader sequence on the functional *H. zea* variant and non-functional *T. ni* variant can be tested.

The functional expression of additional desaturase variants to identify C14-specific desaturases can be explored.

Expression of functional desaturase with reductase variants can be done and subsequent screen for unsaturated fatty alcohol production can be performed.

Materials & Methods

Strain Construction

A conservative approach was used for recoding of genes. Native sequences were unaltered except for replacement of CTG leucine codons with ITA. All genes were cloned into pPV0053 using NcoI and NotI restriction sites by Genscript. After transformation into *E. coli* NEB10β, plasmids were miniprepped using the Zyppy Plasmid Miniprep Kit (Zymo Research, Irvine, Calif.). Plasmids were linearized by digestion with BsiWI (New England Biolabs, Ipswich, Mass.) before transformation into SPV053. After digestion, DNA was isolated using Clean and Concentrator Kit (Zymo Research, Irvine, Calif.). Approximately 1 pg of DNA was transformed by electroporation. Instead of incubation with TE+100 mM lithium acetate+DTF, cells were incubated in only TE+100 mM lithium acetate for 2 hours. Positive integrants were found to be site-specific and genotyping was conducted by check PCR. A two-stage approach was adopted for further screening of low efficiency transformations. Approximately 60 colonies were re-patched on YPD+ 300 µg/ml Zeocin and grown overnight. The subset of patches which grew quickly (dense growth within 24 hours) were screened by colony PCR. The vast majority of rapid growing patches were identified as positive integrants.

Functional Expression Assay

Palmitic acid supplementation in YPD and CM glucose

Positive isolates were re-patched onto YPD+300 µg/ml Zeocin and grown overnight and then stored at 4° C. Strains were inoculated from patch plates into 2 ml of YPD in 24 deep well plates (square well, pyramid bottom). Three positive clones were inoculated for each desaturase variant and the mCherry expressing control strain. Deep well plates were incubated at 30° C., 1000 rpm, and 80% humidity in the Infors HT Multitron Pro plate shaker for 24 hrs. After 24 hrs of incubation, cultures were split into equal 1 ml volumes to make two sets of identical plates. Both sets of plates were pelleted by centrifugation at 500×g. One set of plates was resuspended in 2 ml of YPD+0.3% (v/v) ethanol and the second set was resuspended in 2 ml of CM glucose+ 0.3% ethanol. Ethanol was added at this stage to induce recombinant enzyme expression from the ICL promoter. Cultures were incubated for another 24 hours under the same conditions before 300 mg/L palmitic acid was added to cultures from a 90 g/L stock solution in ethanol. The result was the addition of a fresh 0.3% ethanol in conjunction with the palmitic acid. A subset of strains was also cultured without palmitic acid addition. These cultures had 0.3% ethanol added instead. All cultures were incubated for an additional 24 hrs before a final addition of 0.3% ethanol. After another 24 hr period of incubation, 1.5 ml of each culture was harvested in 1.7 ml microcentrifuge tubes and pelleted. Supernatant was saved in fresh tubes and pellets were processed as described below. A subset of supernatant samples was also extracted to look for free acid in the extracellular medium.

Repeated Screening with Alternate Substrates

The mCherry control and confirmed positive variants were rescreened using both palmitic acid and methyl palmitate as substrates. The culturing was conducted as described above with equimolar (1.17 mM) amounts of substrate added from ethanol stock solutions (methyl palmitate 94 g/L stock, 313 mg/L final concentration). The same protocol was also repeated with the full panel of strains using an 84 g/L stock of methyl myristate (C14:0). The final concentration of substrate was again 1.17 mM.

Confirmation of (Z)-11-Hexadecenoic Acid Isomer

The in vivo bioconversion assay was scaled up for confirmation of (Z)-11-hexadecenoic acid synthesis. 2 ml YPD seed cultures of strains SPV0302, SPV0303, and SPV0304 (mCherry), SPV0304, SPV0305, and SPV0306 (*A. transitella* Z11 desaturase), and SPV0307, SPV0308, and SPV0309 (*H. zea* Z11 desaturase) were grown overnight at 30° C., 1000 rpm, 80% humidity in the Infors HT Multitron plate shaker. 200 µl of overnight culture from each of the three clonal isolates was pooled and inoculated into a single 125 ml baffled flask containing 20 ml YPD. The resulting three flasks were grown for 24 hrs at 30° C. and 250 rpm (Infors Flask shaker). Cultures were pelleted by centrifugation at 500×g and resuspended in 20 ml of YPD+0.3% (v/v) ethanol and returned to 125 ml baffled shake flasks. Cultures were incubated for an additional 24 hours before addition of 300 mg/L palmitic acid in a 90 g/L stock in ethanol (221 µl per flask). After 24 hours of incubation another 0.3% (v/v) ethanol (221 µl) was added to each flask for sustained induction. Flasks were incubated for an additional 24 hours before cells were harvested for FAME analysis and DMDS derivatization.

Metabolite Extraction and GC-MS Detection

Total lipid composition as well as the (Z)-11-hexadecenoic acid quantification was based on modified procedures by Moss et al. (1982) and Yousuf et al (2010). The pelleted cells (in 1.5 mL plastic tubes), usually about 10 mg to 80 mg, were resuspended in methanol containing 5% (w/w) of sodium hydroxide. The alkaline cell suspension was transferred into a 1.8 mL screw-cap GC-vial. The mixture was heated for 1 h in the heat block at 90° C. Prior to acidification with 400 2.5 N HCl the vial was allowed to cool to room temperature. 500 µL chloroform containing 1 mM heptadecanoic were added and the mixture was shaken vigorously, then both aqueous and organic phase were transferred into a 1.5 mL plastic tube. The mixture was centrifuged at 13,000 rpm, afterwards 450 µL of the organic phase were transferred into a new 1.5 mL plastic tube. The aqueous phase was extracted a second time with 500 µL chloroform, this time without heptadecanoic acid. The combined organic phases were evaporated at 90° C. After cooling to room temperature, residual fatty acid methyl esters and free fatty acids were dissolved and derivatized in methanol containing 0.2 M TMSH (trimethylsulfonium hydroxide).

The regioselectivity of biologically produced (Z)-11-hexadecenoic acid was determined by comparing the fragmentation patterns of the dimethyl disulfide (DMDS) derivative with the DMDS derivative of an authentic standard. A yeast culture was split into 12 aliquots (to not change any parameters in the developed procedure). The cells were pelleted, which yielded 63 mg cells (ccw) on average (755 mg from 18 mL culture). The pellets were subjected to base methanolysis as described above. However, after acidification the samples were combined in a 50 mL falcon tube. The combined sample was extracted two times with 10 mL chloroform. The mixture was centrifuged 10 min at 3000 rpm to achieve a better phase separation. The combined organic phases were combined in a new 50 mL falcon and were washed consecutively with 10 mL brine and 10 mL water. The organic phase was dried with anhydrous sodium sulfate and concentrated in vacuo. The concentrated oil was dissolved in 1.5 mL chloroform and transferred to a 1.5 mL plastic tube. The chloroform was evaporated at 90° C. The remaining sample was the dissolved in 50 µL methyl tert-butyl ether (MTBE). The 50 µL were split into 1, 5, 10 and 20 µL and transferred into GC-vials without insert. To each vial 200 µL DMDS (dimethyl disulfide) and 50 µL MTBE (containing 60 mg/mL iodine) were added. After the mixture was heated 48 h at 50° C., excess iodine was removed by the addition of 100 µL saturated sodium thiosulfate solution; however, due to excessive formation of detergents from the *Candida* strain, the layer did not mix properly. The samples were therefore diluted in a 15 mL falcon tube to a final sample composition of 200 µL, 3.55 mL MTBE (containing iodine and analyte), 500 µL dichloromethane, 1.5 mL water and 1 mL ethanol. The organic phase was evaporated stepwise at 85° C. in a 1.8 mL glass vial. The samples were taken up in 500 µL dichloromethane and the sample was analyzed by GC-MS using the method of Hagström et al. (2013) as in Example 4.

Example 7: Expression of Transmembrane Desaturases in Yarrowia lipolytica

Background and Rationale

Engineering microbial production of insect fatty alcohols from fatty acids requires the functional expression of a synthetic pathway. One such pathway comprises a transmembrane desaturase, and an alcohol-forming reductase to mediate the conversion of fatty acyl-CoA into regio- and stereospecific unsaturated fatty acyl-CoA, and subsequently into fatty alcohols. A number of genes encoding these enzymes are found in some insects as well as some microalgae. Alternatively, regio- and stereospecific desaturases can be used to produce a microbial oil rich in fatty acid precursors. The microbial oil can then be derivatized and reduced to active ingredients. A number of gene variants were screened to identify enzyme activities that allow the creation of pathways capable of high level synthesis of a single or a blend of insect fatty acids and alcohols. Additionally, these enzymes were screened across multiple hosts (*Saccharomyces cerevisiae, Candida viswanathii* (*tropicalis*), and *Yarrowia lipolytica*) to optimize the search toward finding a suitable host for optimum expression of these transmembrane proteins.

Initial screening of desaturases in *S. cerevisiae* and *C. viswanathii* (*tropicalis*) identified three active Z11-C16:1 desaturase variants from *Amyelois transitella, Helicoverpa zea*, and *Trichoplusia ni*. The *S. cerevisiae* screening used coding sequences with an N-terminal leader sequence of the *S. cerevisiae* Ole1p Z9 desaturase fused to the full length insect Z11 desaturase sequence. This strategy has been used previously in the scientific literature to express eukaryotic desaturases in *S. cerevisiae*. All three of the above desaturases displayed Z11 desaturase activity with the Ole1p leader fusion when expressed in a OLE1 deletion background. An analogous design with a *C. albicans* Ole1p leader sequence was used with the Z11 desaturase from *H. zea*. While active, this Ole1p-*H. zea* desaturase fusion did not significantly increase Z11-hexadecenoic acid titer. Additionally, a conservatively optimized *A. transitella* Z11 desaturase was active in both *S. cerevisiae* and *C. viswanathii*. The following study focused on testing the functional expression of the *H. zea, T. ni*, and *A. transitella* Z11 desaturases in two different *Y. lipolytica* strains, SPV140 and SPV300. Both native and *Homo sapiens* codon optimized sequences were used for the *H. zea* and *T. ni* desaturases while only the native sequence was used for *A. transitella*. Finally, the N-terminus of the *Y. lipolytica* Ole1p Z9 stearoly-CoA desaturase aligns more closely with insect desaturases than the N-terminus of Ole1p from either *S. cerevisiae* or *C. albicans*. Based on this alignment two additional desaturase versions were created. A putative leader sequence was swapped from the *Y. lipolytica* Ole1p onto the *T. ni* and *H. zea* desaturases.

Summary of Approach

A focused library of Z11 desaturases (insect origin: *Amyelois transitella. Helicoverpa zea. Trichoplusia ni*), which had observed activity in either *S. cerevisiae* or *C. viswanathii* were cloned into a double crossover cassette targeting the XPR2 locus with a URA3 selection marker. Protein coding sequences use either the native insect sequence (SEQ ID NOs: 24, 25), *Homo sapiens* optimized coding sequence (SEQ ID NOs: 26, 27), or the *Homo sapiens* optimized sequence with the N-terminal 84 bases (*H. zea*, SEQ ID NO: 29) or 81 bases (*T. ni*, SEQ ID NO: 28) swapped for the N-terminal 96 bases of the *Y. lipolytica* OLE1 (YALI0C05951) gene. Unlike in the *S. cerevisiae* and *C. viswanathii* screens, the leader sequence chimeras test a direct swap of leader sequences instead of concatenating a host leader sequence to the N-terminus of the full length desaturase coding sequence. Only the native coding sequence was used for the *A. transitella* desaturase (SEQ ID NO: 30).

Each of the 7 desaturase constructs was transformed into SPV140 (PO1f) and SPV300 (H222 ΔP ΔA ΔF ΔURA3) and site-specific integrants were confirmed.

Desaturase activity was tested via an in vivo bioconversion of hexadecanoic acid (palmitic acid) into (Z)-11-hexadecenoic acid (palmitvaccenic acid) in YPD medium.

GC-FID analyses were used to identify and quantify metabolites.

Results

Strain Construction

Desaturase variants were cloned into the pPV101 vector which contains a *Y. lipolytica* expression cassette targeting integration into the XPR2 locus.

The *T. ni* and *H. zea* desaturases were each synthesized with the native insect sequence (SEQ ID NOs: 24, 25), full length insect sequence codon optimized for *Homo sapiens* (SEQ ID NOs: 26, 27), or with the putative leader sequence replaced by the leader sequence from *Y. lipolytica* OLE1 desaturase (SEQ ID NOs: 28, 29). The *A. transitella* desaturase was also synthesized using the native insect coding sequence (SEQ ID NO: 30). All seven desaturase variants were transformed into SPV140. Based on previous activity results, only the *H. zea* and *A. transitella* desaturase variants were transformed into SPV300.

Functional Expression Assay

Functional activity was assessed by a modification of the protocol used for transmembrane desaturase expression in *C. viswanathii* SPV053 (See Example 6). Briefly, *Y. lipolytica* SPV140 and SPV300 derived stains expressing insect desaturases were cultured in rich (YPD) to generate biomass. Using the YPD generated biomass, small scale (2 ml) cultures were cultivated with palmitic acid for a total of 48 hours in 24 deep well plates (See Materials & Methods for detail).

Figure 26:
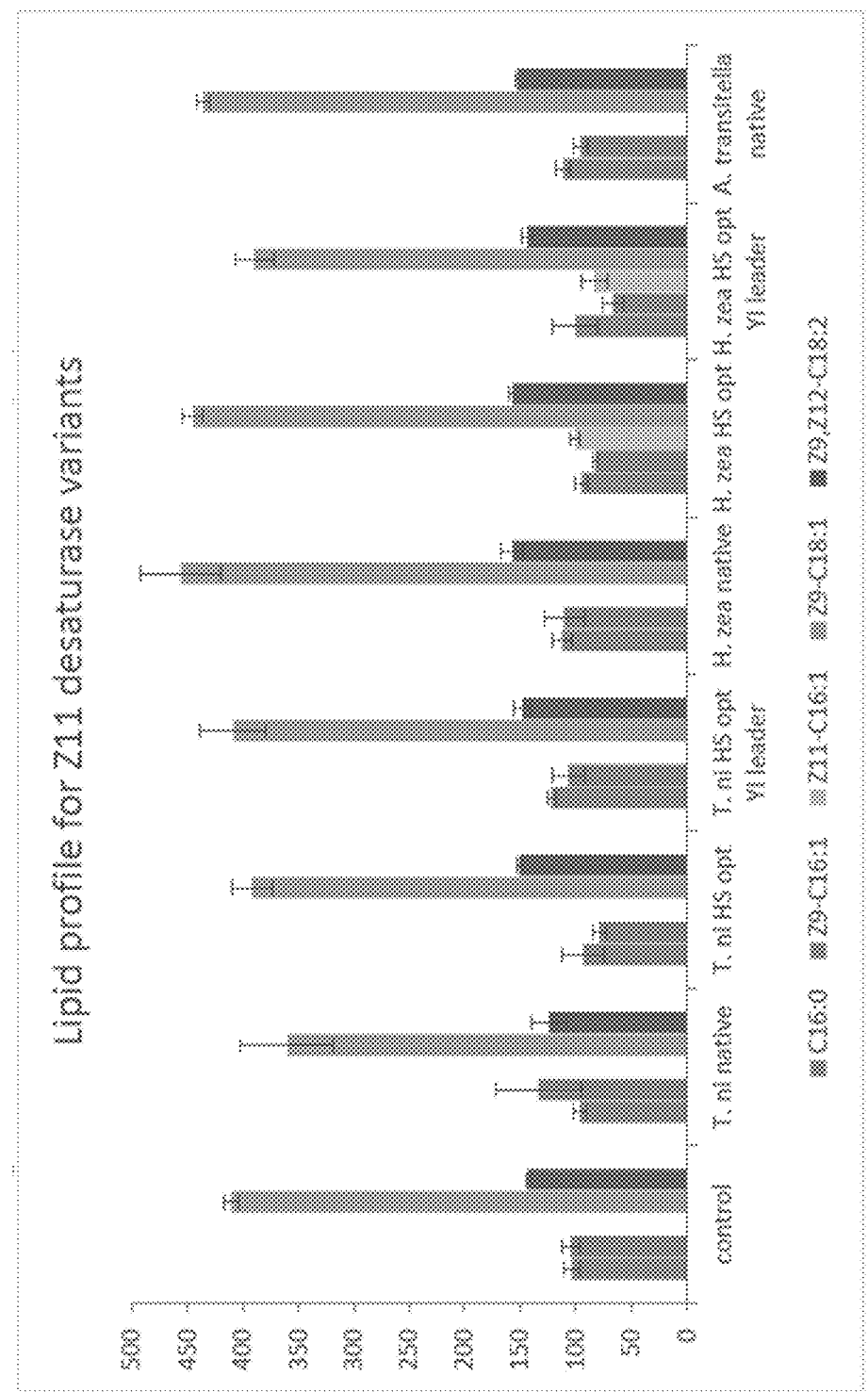
FIG. 26 shows only codon optimized *H. zea* desaturase variants produce detectable Z11-hexadecenoic acid in SPV140 screen. control=pPV101 integrants of SPV140, *T. ni* native=*T. ni* Z11 desaturase with native codon usage (pPV195), *T. ni* HS opt=*T. ni* Z11 desaturase with *Homo sapiens* codon optimization (pPV196), *T. ni* HS opt Y1 leader=*T. ni* Z11 desaturase with *Homo sapiens* codon optimization and swapped *Y. lipolytica* OLE1 leader sequence (pPV197), *H. zea* native=*H. zea* Z11 desaturase with native codon usage (pPV198), *H. zea* HS opt=*H. zea* Z11 desaturase with *Homo sapiens* codon optimization (pPV199), *H. zea* HS opt Y1 leader=*H. zea* Z11 desaturase with *Homo sapiens* codon optimization and swapped *Y. lipolytica* OLE1 leader sequence (pPV200), *A. transitella* native=*A. transitella* Z11 desaturase with native codon usage (pPV201). All data average of 3 biological replicates. Error bars represent standard deviation.

In the initial screen of *T. ni, H. zea*, and *A. transitella* variants, only *H. zea* desaturase variants that were codon optimized for *Homo sapiens* produced detectable Z11-hexadecenoic acid (FIG. 26). Expression of native *H. zea* desaturase conferred production of 100±5 mg/L Z11-hexadecenoic acid and the version with a *Y. lipolytica* OLE1 leader sequence produced 83±11 mg/L. As seen in FIG. 26, the distribution of the other major fatty acid species was relatively unaffected by functional desaturase expression. In the active strains, Z11-hexadecenoic acid made up ~10% (g/g) of the fatty acid species (including palmitic acid substrate which may be adsorbed to the outer cell surface).

Figure 27:
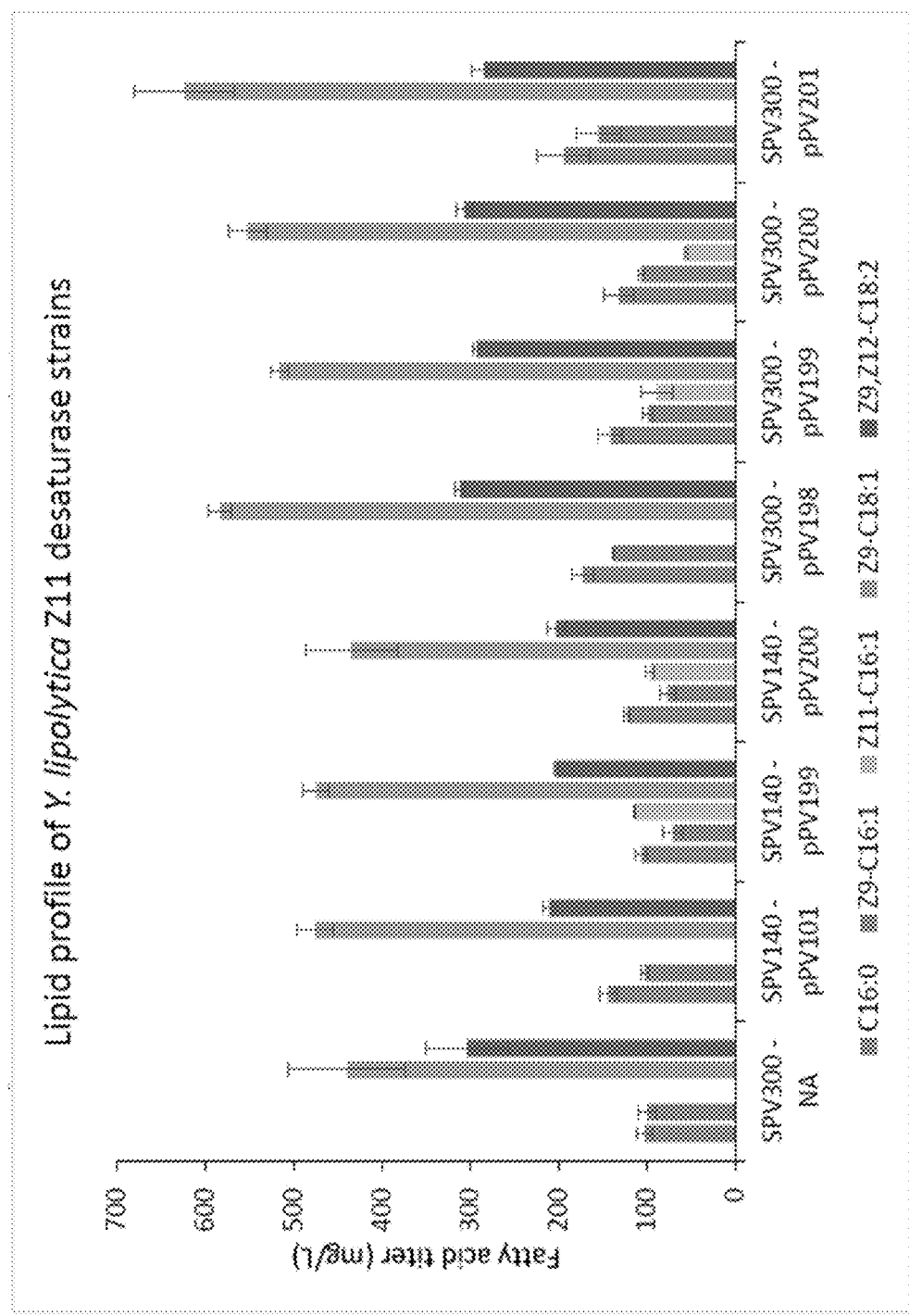
FIG. 27 shows only codon optimized *H. zea* desaturase variants produce detectable Z11-hexadecenoic acid in SPV300 screen. Labels indicate parent strain and plasmid of desaturase expression cassette. pPV101=hrGFP control, pPV198=*H. zea* Z11 desaturase with native codon usage, pPV199=*H. zea* Z11 desaturase with *Homo sapiens* codon optimization, pPV200=*H. zea* Z11 desaturase with *Homo sapiens* codon optimization and swapped *Y. lipolytica* OLE1 leader sequence, pPV201=*A. transitella* Z11 desaturase with native codon usage.
Figure 28:
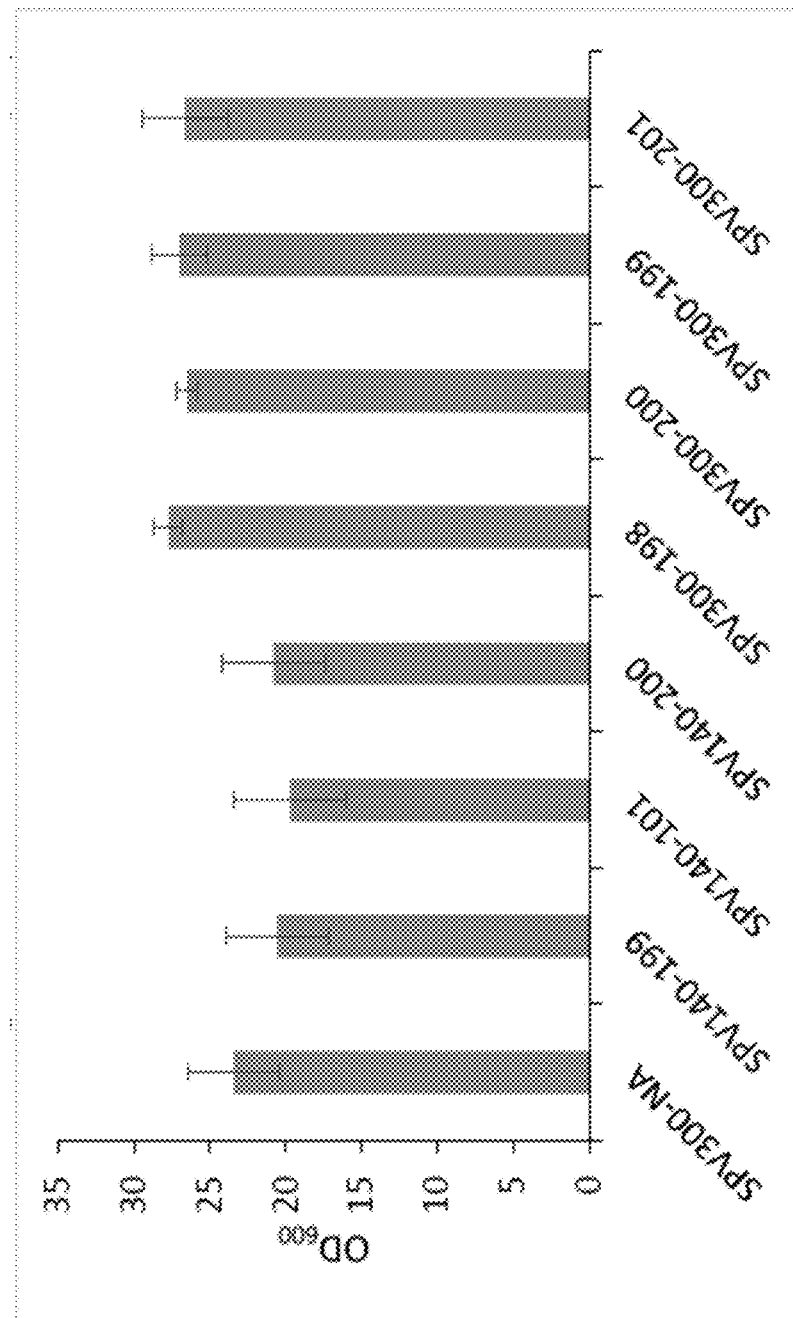
FIG. 28 shows final cell densities for desaturase screen in SPV140 and SPV300 backgrounds. SPV300 strains with integrated desaturase cassettes grew to higher cell densities.
Figure 29:
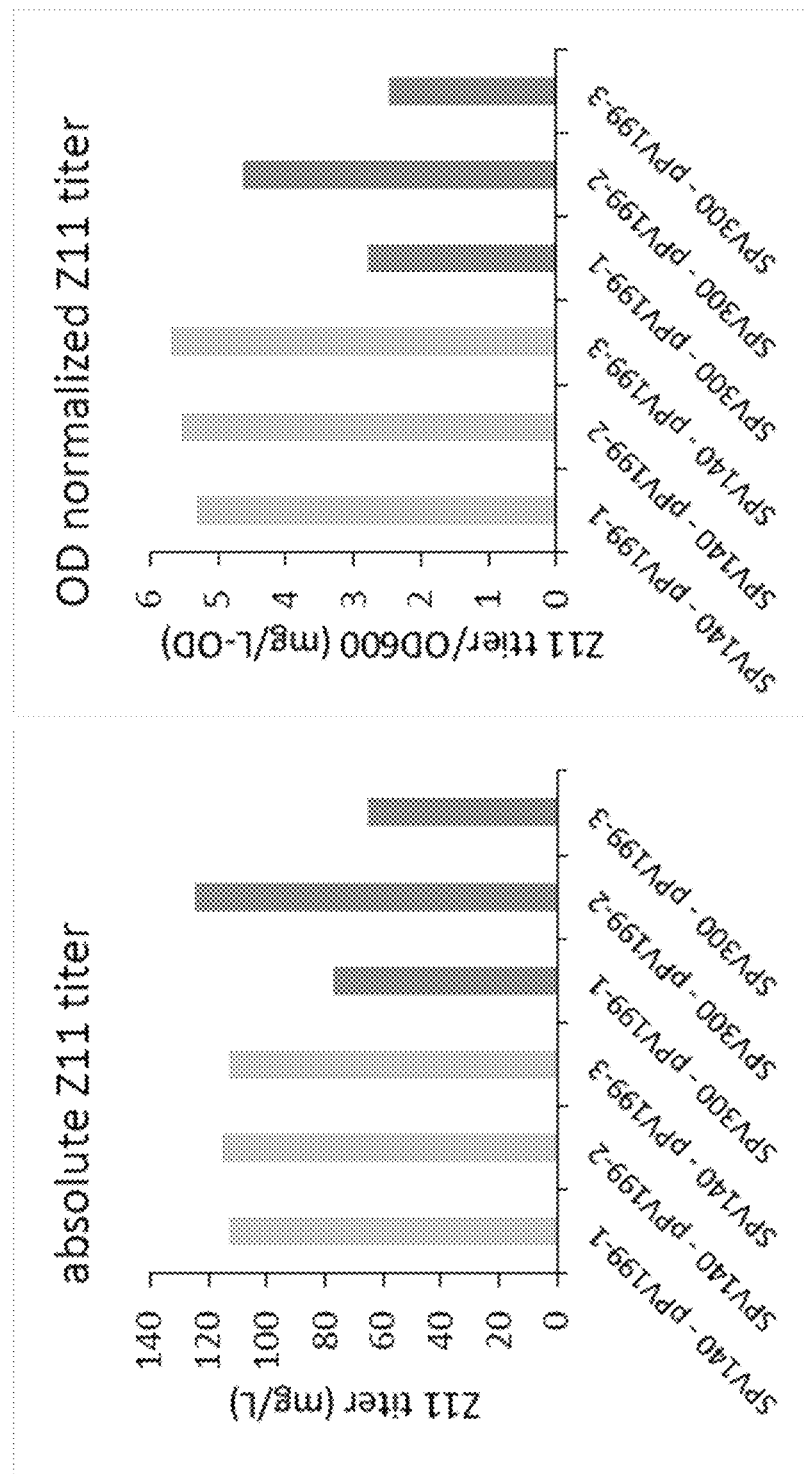
FIG. 29 shows individual isolate Z11-hexadecenoic acid titers for SPV140 and SPV300 strains expressing *H. zea* Z11 desaturase with *H. sapiens* codon optimization.

A follow up experiment was conducted comparing active variants in the SPV140 background to SPV300 derived desaturase strains. The parent SPV300 and SPV140 expressing hrGFP were used as negative controls. The same bioconversion assay protocol was used. As in SPV140, only *H. sapiens* optimized variants produced detectable activity (FIG. 27). SPV300 strains grew to higher final cell densities (SPV300 OD600=26-28, SPV140 OD600=19-22) (FIG. 28). The highest titers were observed for strains expressing the native *H. zea* Z11-desaturase with *H. sapiens* codon optimization (pPV199). The retested SPV140 strains produced 113±1 mg/L (5.5±0.2 mg/L/OD) Z11-hexadecenoic acid which is 13% higher than titers observed in the first experiment (FIG. 29). SPV300 strains expressing the same desaturase generated a wider range of productivity. On average they produced 89±18 mg/L (3.3±1.2 mg/L/OD) Z11-hexadecenoic acid, but one clone produced 124 mg/L (4.6 mg/L/OD) Z11-hexadecenoic acid.

In summary, only the *H. zea* Z11 desaturase variants with *Homo sapiens* codon optimization produced detectable Z11-hexadecenoic acid. Under the current assay condition, marginally higher titers were observed in the SPV140 background over SPV300. Table 11 summarizes the Z11-hexadecenoic acid titers.

TABLE 11

Z11-hexadecenoic acid titers obtained from expression of exemplary desaturases in *Yarrowia lipolytica*

| Desaturase | Codon optimization | Parent Strain | Z11-hexadecenoic acid titer (mg/L) |
|---|---|---|---|
| Z11 *T. ni* | Native | SPV140 | ND (no detection) |
| Z11 *T. ni* | *Homo sapiens* | SPV140 | ND |
| *Yl* OLE1-Z11 *T. ni* | *Homo sapiens* | SPV140 | ND |
| Z 11 *H. zea* | Native | SPV140 | ND |
|  |  | SPV300 | ND |
| Z11 *H. zea* | *Homo sapiens* | SPV140 | 100 ± 5 |
|  |  | SPV300 | 87 ± 18 |
| *Yl* OLE1-Z11 *H. zea* | *Homo sapiens* | SPV140 | 83 ± 11 |
|  |  | SPV300 | 55 ± 1 |
| Z11 *A. transitella* | Native | SPV140 | ND |
|  |  | SPV300 | ND |

In SPV300, one non-site-specific integrant of pPV200 (*Y. lipolytica* OLE1-*H. zea* Z11 desaturase with *Homo sapiens* codon optimization) was tested. This integrant did not produce detectable Z11-hexadecenoic acid, while the two site-specific integrants produced 55+1 mg/L.

No major hydroxy or diacid peaks were observed from pellets of SPV140 or SPV300 derived strains, and deletion of β-oxidation/ω-oxidation genes in SPV300 did not increase Z11-hexadecenoic acid accumulation under the current assay condition (relatively low substrate concentration, rich medium).

Conclusions

The *H. zea* Z11 desaturase is active and confers production of ~100 mg/L Z11-hexadecenoic acid, from ~500 mg/L palmitic acid substrate. The functional expression was demonstrated across three positive integrants and replicate experiments in a 24 well plate assay.

*H. zea* desaturase required codon optimization (*Homo sapiens* or potentially *Y. lipolytica*) for activity in *Y. lipolytica*.

The *T. ni* Z11 desaturase, while active in *S. cerevisiae*, does not produce detectable Z11-hexadecenoic acid in *Y. lipolytica*.

The reproducibility of the assay for *Y. lipolytica* strains can be confirmed starting from glycerol stock.

*A. transitella* desaturase can be codon optimized for expression in *Y. lipolytica*.

Since *Y. lipolytica* is a candidate production host, additional copies of active desaturases can be integrated in *Y. lipolytica*, culture conditions to improve bioconversion can be identified, and substrate conversion can be quantified.

Materials & Methods

Strain Construction

All desaturase genes were synthesized (Genscript). Either native sequences or *Homo sapiens* codon optimization was used. Synthesized genes were subcloned into pPV101. Plasmids were transformed and prepped from *E. coli* EPI400 using the Zyppy Plasmid Miniprep Kit (Zymo Research, Irvine, Calif.). Approximately ~1-2 μg of linearized DNA was transformed using Frozen-EZ Yeast Transformation II Kit (Zymo Research, Irvine, Calif.). The entire transformation mixture was plated on CM glucose-ura agar plates. Positive integrants were found to be site-specific and genotyping was conducted by check PCR.

Functional Expression Assay

Palmitic Acid Supplementation in YPD

Positive isolates were re-patched onto YPD, grown overnight, and then stored at 4° C. Strains were inoculated from patch plates into 2 ml of YPD in 24 deep well plates (square well, pyramid bottom). Three positive clones were inoculated for each desaturase variant. Three isolates of pPV101 in SPV140 and the parent SPV300 were used as negative controls. Deep well plates were incubated at 28° C. and 250 rpm in the Infors Multitron refrigerated flask shaker for 24 hrs. After 24 hrs of incubation, a 1 ml volume of each culture was pelleted by centrifugation at 500×g. Each pellet was resuspended in 2 ml of YPD. 500 mg/L palmitic acid was added to cultures from a 90 g/L stock solution in ethanol. The result was the addition of 0.5% ethanol with the palmitic acid substrate. All cultures were incubated for 48 hours before endpoint sampling. Final cell densities were measured with the Tecan Infinite 200pro plate reader. 0.75 or 0.8 ml of each culture was harvested in 1.7 ml microcentrifuge tubes and pelleted. Supernatant was removed and pellets were processed as described below.

Metabolite Extraction and GC-FID Analysis

Total lipid composition as well as the (Z)-11-hexadecenoic acid quantification was based on modified procedures by Moss et al. (1982) and Yousuf et al (2010). The pelleted cells (in 1.5 mL plastic tubes), usually about 10 mg to 80 mg, were resuspended in methanol containing 5% (w/w) of sodium hydroxide. The alkaline cell suspension was transferred into a 1.8 mL crimp vial. The mixture was heated for 1 h in the heat block at 90° C. Prior to acidification with 400 2.5 N HCl the vial was allowed to cool to room temperature. 500 μL chloroform containing 1 mM methyl heptadecanoate were added and the mixture was shaken vigorously, then both aqueous and organic phase were transferred into a 1.5 mL plastic tube. The mixture was centrifuged at 13,000 rpm, afterwards 450 μL of the organic phase were transferred into a GC vial. For the analysis of lipids and the quantification of fatty acids 50 μL of 0.2 M TMSH (trimethylsulfonium hydroxide in methanol) was added and the sample analyzed by GC-FID.

Example 8: *Candida viswanathii* (*tropicalis*) as a Production Platform for Insect Fatty Alcohol Synthesis Background and Rationale Variants of insect transmembrane desaturases and reductases were previously screened and rank-ordered based on their functional expression in either *Candida* viswanathii or *Saccharomyces cerevisiae* (see Examples 3, 4 and 6). *Helicoverpa zea* desaturase and *Helicoverpa armigera* reductase were selected to assemble a synthetic insect fatty alcohol pathway in *C. viswanathii*. Simultaneous expression of codon optimized *H. zea* desaturase under *Candida* isocitrate lyase (ICL) promoter, and codon optimized *H. armigera* reductase under *Candida* transcription elongation factor (TEF) promoter was achieved via genomic integration of the full fatty alcohol pathway. Accumulation of Z11-16OH was achieved in cultures of the recombinant strain (SPV0490) using simple carbon sources and palmitic acid.

Summary of Approach

Integration plasmids were designed containing a functional *Helicoverpa zea* desaturase (See Example 6) paired with a *Helicoverpa armigera* reductase driven by a putatively constitutive *C. tropicalis* promoter (pTEF).

Functionality of the full pathway was assessed via an in vivo bioconversion of hexadecanoic acid (palmitic acid) into Z11-16OH.

GC-FID and GC-MS analyses were used to identify and quantify metabolites.

Results

Figure 30:
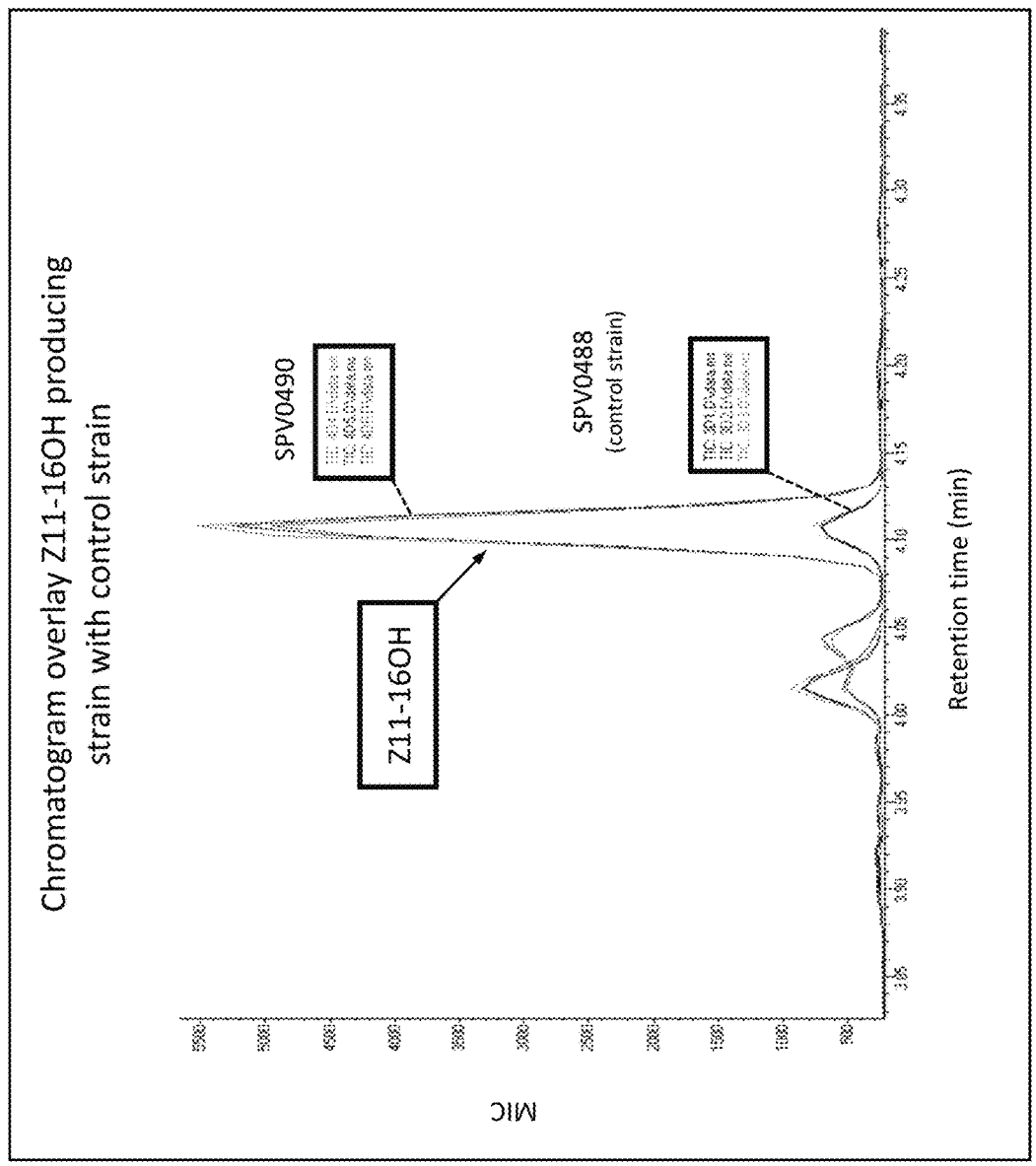
FIG. 30 shows a chromatogram overlay of extracted metabolites for Z11-16OH producing strain (SPV0490) versus control strain (SPV0488) of *Candida viswanathii* (*tropicalis*).
Figure 31:
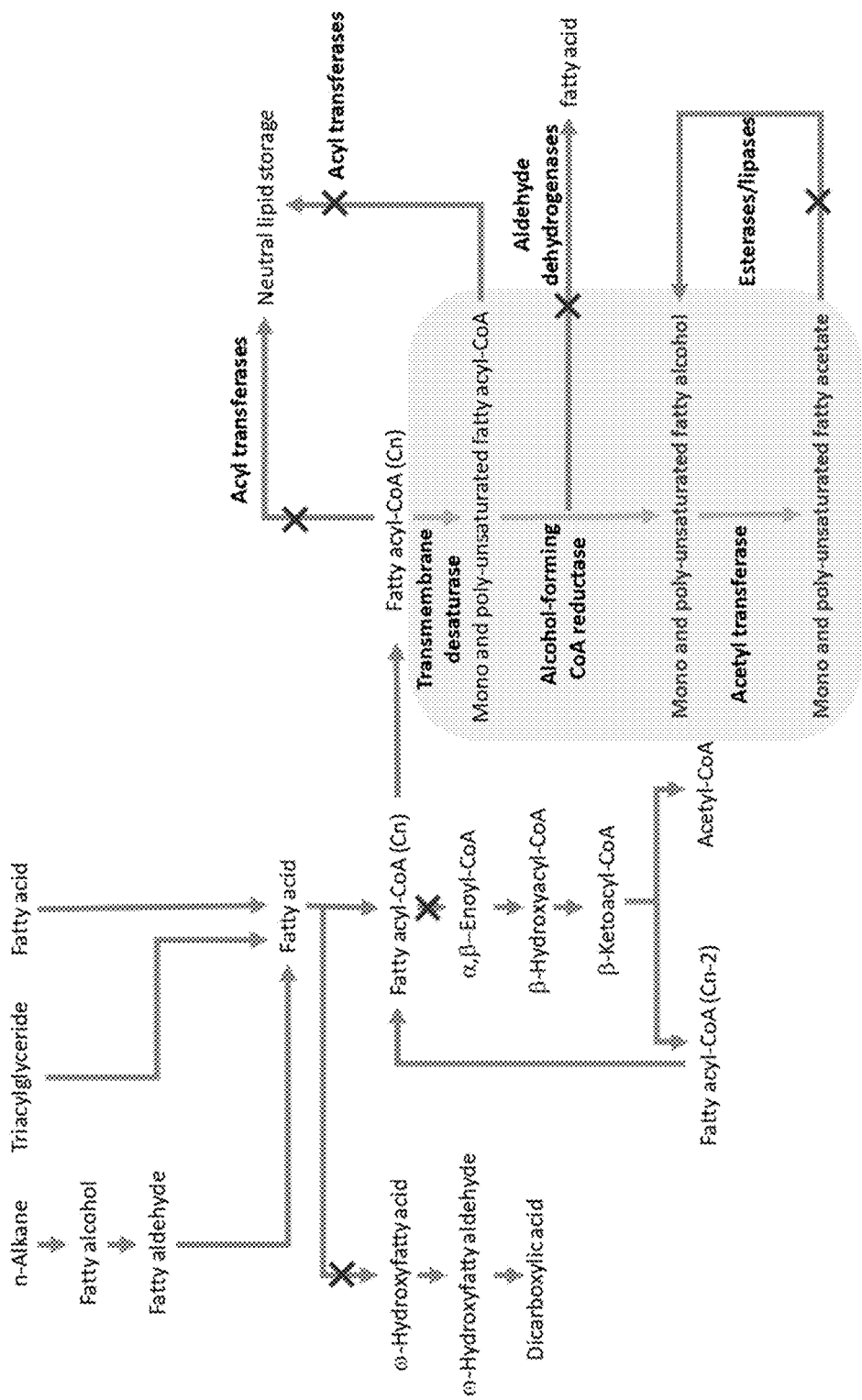
FIG. 31 illustrates pathways that can be deleted or disrupted to reduce or eliminate competition with the biosynthesis pathway for the production of a mono- or poly-unsaturated $C_6$-$C_{24}$ fatty alcohol, aldehyde, or acetate.

Accumulation of Z11-16OH was detected in cultures of *Candida* engineered to express *H. zea* desaturase under an ICL promoter and *H. armigera* reductase under a TEF promoter (Table 12 and FIG. 30).

TABLE 12

Tabulated Z11-16OH titers from *Candida viswanathii* bioconversion assay. SPV088 is *C. viswanathii* which was engineered to express mCherry (negative control). SPV0490 is *C. viswanathii* which was engineered to express the insect fatty alcohol pathway.

Z11-16OH titers (mg/L)

|  | SPV0488 (negative control) | SPV0490 |
|---|---|---|
| Sample 1 | 0.08 | 1.03 |
| Sample 2 | 0.07 | 0.93 |
| Sample 3 | 0.06 | 0.88 |
| Average | 0.07 | 0.95 |
| StDev | 0.01 | 0.06 |

Materials & Methods
Strain Construction

The integration plasmid (ppV0228) was designed to contain two expression cassettes. The first cassette contains *H. zea* codon-optimized desaturase (SEQ ID NO: 31) that was driven by the *C. viswanathii* ICL promoter (SEQ ID NO: 33). The second cassette contains codon-optimized *H. armigera* reductase (SEQ ID NO: 32) driven by the *C. tropicalis* TEF promoter (SEQ ID NO: 34). Gene expression in the ICL promoter cassette is terminated by the ICL terminator sequence (SEQ ID NO: 35). Gene expression in the TEF promoter cassette is terminated by the TEF terminator sequence (SEQ ID NO: 36). A conservative approach was used for recoding of genes. Native gene sequences were unaltered except for replacement of CTG leucine codons with TTA. After transformation into *E. coli* NEB10β, plasmids were miniprepped using the Zyppy Plasmid Miniprep Kit (Zymo Research, Irvine, Calif.). Plasmids were linearized by digestion with BsiWI (New England Biolabs, Ipswich, Mass.) before transformation into SPV053. After digestion, DNA was isolated using Clean and Concentrator Kit (Zymo Research, Irvine, Calif.). Approximately 3-5 μg of DNA was transformed by electroporation. Positive integrants were found to be site-specific and genotyping was conducted by check PCR. A two-stage approach was adopted for further screening of low efficiency transformations. Approximately 100 colonies were re-patched on YPD+250 pg/ml Zeocin and grown overnight. The subset of patches which grew quickly (dense growth within 24 hours) were screened by colony PCR.

Functional Expression Assay
  Palmitic Acid Supplementation in YPD

Positive isolates were re-patched onto YPD+300 μg/ml Zeocin, grown overnight and then stored at 4° C. Strains were inoculated from patch plates into 2 ml of YPD in 24 deep well plates (square well, pyramid bottom). Four positive clones were inoculated for each desaturase and reductase variant and three positive clones were inoculated for each desaturase and mCherry expressing control strain. Deep well plates were incubated at 30° C., 1000 rpm, and 80% humidity in the Infors HT Multitron Pro plate shaker for 24 hrs. After 24 hrs of incubation, a 1 ml volume of each culture was pelleted by centrifugation at 500×g. Each pellet was resuspended in 2 ml of YPD+0.3% (v/v) ethanol. Ethanol was added at this stage to induce recombinant enzyme expression from the ICL promoter. Cultures were incubated for another 24 hours under the same conditions before 300 mg/L palmitic acid was added to cultures from a 90 g/L stock solution in ethanol. The result was the addition of a fresh 0.3% ethanol in conjunction with the palmitic acid. All cultures were incubated for an additional 24 hrs before a final addition of 0.3% ethanol. After another 24 hr period of incubation, 1.5 ml of each culture was harvested in 1.7 ml microcentrifuge tubes and pelleted. Supernatant was removed and pellets were processed as described below.

Metabolite Extraction and GC-MS Detection

The pelleted cells (in 1.5 mL plastic tubes), usually about 10 mg to 80 mg, were resuspended in methanol containing 5% (w/w) of sodium hydroxide. The alkaline cell suspension was transferred into a 1.8 mL crimp vial. The mixture was heated for 1 h in a heat block at 90° C. Prior to acidification with 400 μL 2.5 N HCl the vial was allowed to cool to room temperature. 500 μL chloroform containing 1 mM methyl heptadecanoate were added and the mixture was shaken vigorously, then both aqueous and organic phase were transferred into a 1.5 mL plastic tube. The mixture was centrifuged at 13,000 rpm, afterwards 450 μL of the organic phase were transferred into a GC vial. The organic phase was evaporated in a heat block at 90° C. for 30 min. The residue was dissolved in 50 μL N,O-Bis(trimethylsilyl) trifluoroacetamide containing 1% trimethylchlorosilane. Prior to transfer into glass inserts the mixture was heated 5 min at 90° C. The samples were analyzed by GC-MS (Table 13).

TABLE 13

Analytical parameters used for GC-MS analysis of metabolites

| System | Agilent 6890 N GC, ChemStation G1701EA E.02.01.1177 |
|---|---|
| Column | DB23 30 m × 25 μm × 25 μm Pressure = 11.60 psi; Flow = 0.6 mL/min |
| Inlet | Heater = 250° C., Pressure = 11.74 psi; Total Flow {He} = 111 mL/min |
| Carrier | He @ 29 cm/sec, 11.60 psi |
| Signal | Data rate = 2 Hz/0.1 min |
| Oven | 150° C. for 1 min Ramp 12° C./min to 220° C., hold 3 min Ramp 35° C./min to 300° C., hold 4 min |
| Injection | Splitless, 250° C. |
| Detector | HP 5973 MSD in SIM mode (m/z: 208.0, 297.3 and 387.3), 100 msec Dwell, EMV mode: Gain factor 1, 2.4 min solvent delay, 3.09 cycles/sec |
| Sample | Injection volume = 1 μL |

Example 9: Insect Fatty Alcohol Production from *Yarrowia lipolytica*

Background and Rationale

*Yarrowia lipolytica* was engineered as a production platform for insect fatty alcohol (Z11-16OH and Z9-16OH) synthesis from palmitic acid.

After individually confirming functional expression of a Z11 desaturase (Example 7) and fatty acyl-CoA reductase (FAR), the full Z11-16OH and Z9-16OH pathways (Bdr)

were engineered in *Y. lipolytica*. For the purpose of improving fatty alcohol titers, cultivations designed for promoting growth vs. for eliciting lipid storage were also explored. A growth condition favors high biomass production, but limits fatty acyl-CoA pool size used by the engineered pathway and directs fatty acyl-CoA intermediates to membrane synthesis. Conversely, a lipid storage condition creates a strong sink for production of fatty acyl-CoAs which is desirable. However, fatty acyl-CoA transport towards lipid bodies creates a strong competition for FAR activity. Under this second scenario, even though Z11-16Acid or Z9-16Acid accumulates in the cell, most of it is inaccessible to the FAR. On the other hand, there may be a continual flux of lipid remobilization under lipid storage conditions which leads to a sustained pool of Z11-16CoA or Z9-16CoA which is available to the FAR.

Summary of Approach

Two biodesaturation-reduction (Bdr) pathway variants were tested in the H222 ΔPΔAΔF (SPV300) background. The first combined recombinant expression of *Helicoverpa zea* Z11 desaturase paired with a *Helicoverpa armigera* fatty acyl-CoA reductase (FAR) creating a Z11-16OH synthesis pathway. The second combined native *Y. lipolytica* Z9 desaturase activity with *H. armigera* fatty acyl-CoA reductase (FAR) expression creating a Z9-16OH pathway.

Two integration plasmids were constructed to express the *H. zea* desaturase and the *H. armigera* FAR. The TEF promoter was used for desaturase expression and the EXP1 (export protein) or the TAL1 (transaldolase) promoter was used for reductase expression.

Successful integration of the Z11-16OH pathway cassette into the H222 ΔPΔAΔF (SPV300) background was confirmed by colony PCR.

Functionality of the full Z11-16OH pathway was assessed via an in vivo bioconversion of 16Acid (palmitic acid) into Z11-16OH (Z-11-hexadecenol).

Functionality of a full Z9-16OH pathway was assessed via an in vivo bioconversion of 16Acid (palmitic acid) using previously constructed SPV471 (H222 ΔPΔAΔF derived) which expresses the *H. armigera* FAR driven by the TEF promoter.

GC-MS analysis was used to identify and quantify Z9-16OH and Z11-16OH. GC-FID analysis was used to identify and quantify fatty acids.

Summary

Ten isolates expressing the *H. zea* desaturase (pTEF) and *H. armigera* reductase (pEXP1) were screened. The in vivo bioconversion assay confirmed Z11-16OH production from all isolates.

Relatively low, detectable Z11-16OH titers (0.26±0.09 mg/L) were observed in a YPD medium supplemented with 10 g/L methyl palmitate. The Z11-16Acid precursor was measured at 220±11 mg/L (across clones 2, 4, 9, 17, 23).

Higher Z11-16OH titers were observed in a semi-defined medium with C:N ratio of ~80. Across all 10 isolates Z11-16OH was produced at 2.65±0.36 mg/L. The Z11-16Acid precursor titer was 900±30 mg/L. One isolate (SPV578) produced 3.68±0.31 mg/L Z11-16OH (Z11-16Acid 840±14 mg/L).

Nine isolates expressing the *H. zea* desaturase (pTEF) and *H. armigera* reductase (pTAL1) were screened. The in vivo bioconversion assay confirmed Z11-16OH production from all isolates.

One isolate (SPV603) produced 6.82±1.11 mg/L Z11-16OH in a semi-defined medium (Z11-16Acid 1.36 g/L).

The previously tested reductase strain, SPV471 (H222 ΔPΔAΔF expressing *H. armigera* FAR), produced 4.30±2.33 mg/L Z9-16OH and 450±80 mg/L Z9-16Acid using a semi-defined medium (C:N ratio of ~80).

TABLE 14

Summary table of Z11/Z9-16OH titers from $B_{dr}$ pathway strains in in vivo bioconversion assay.

| Strain | Medium | Z11-16OH (mg/L) | Z9-16OH (mg/L) |
|---|---|---|---|
| pTEF-*H. zea* Z11 desaturase pEXP-*H. armigera* FAR Clone 17 (SPV578) | Semi-Defined C:N = 80 | 3.99 ± 0.37 (n = 4) | 0.22 ± 0.03 (n = 4) |
| pTEF-*H. zea* Z11 desaturase pTAL-*H. armigera* FAR Clone 9 (SPV603) | Semi-Defined C:N = 80 | 6.82 ± 1.11 (n = 2) | 0.22 ± 0.01 (n = 2) |
| pOLE1-*Y. lipolytica* OLE1 (native) pTEF-*H. armigera* FAR (SPV471) | Semi-Defined C:N = 80 | 0.22 ± 0.03 (n = 2) | 4.30 ± 2.23 (n = 2) |

Results

Strain Construction

Evidence in the literature suggests both insect desaturases and FARs are localized in the membrane of the endoplasmic reticulum with active sites oriented towards the cytoplasm. Of the functional variants, the Z11 desaturase from *H. zea* and the FAR from *H. armigera* were selected, one hypothesis being that using enzymes from the same genus (*Helicoverpa*) could better conserve protein-protein interactions that may occur in the ER membrane.

Two new constructs were ordered from Genscript and cloned into the previously assembled *H. zea* desaturase plasmid, pPV0199. Two FAR synthons with either the EXP1 or TAL1 promoter from *Y. lipolytica* were cloned into this expression cassette.

One dual expression plasmid (with EXP1 promoter) was transformed into the parent strain SPV300 (H222 Δpox1 Δpox2 Δpox3 Δpox4 Δpox5 Δpox6 Δadh1 Δadh2 Δadh3 Δadh4 Δadh5 Δadh6 Δadh7 Δfao1 Δura3). Two different competent cell preparations of the same parent strain were transformed to study variability in strain performance resulting from competent cell preparation. Approximately 25% of URA+ clones were confirmed to be targeted integrants at the XPR2 locus (20% for preparation 1, 33% for preparation 2). Two clones from Comp. Cell Preparation 1 and all eight targeted clones from Comp. Cell Preparation 2 were selected for screening in the functional expression assay.

The second dual expression plasmid (with TAL1 promoter) was integrated into the same parent strain (SPV300). Twenty-three colonies were screened by check PCR and 11 were found to be targeted integrants (48%). Nine integrants were selected for screening in the functional expression assay.

The construct of SPV471 (H222 ΔPΔAΔF expressing *H. armigera* FAR) was described previously.

Z11-16OH Functional Expression Assay

An in vivo, 24-well plate assay was used to evaluate production of Z11-16OH. The assay was based on designs used for screening desaturase and reductase variants as well as conditions used to increase fatty acid accumulation. A rich medium (YPD) and a semi-defined medium were used with 10 g/L methyl palmitate supplemented as bioconversion substrate. The semi-defined medium had a C:N ratio of ~80 and included 5 g/L glycerol and 60 g/L glucose (See Materials & Methods for further details).

The initial screen of strains harboring the *H. zea* desaturase driven by the TEF promoter and the *H. armigera* FAR driven by the EXP1 promoter confirmed that the presence of FAR was required to produce Z11-16OH. No hexadecenol was observed from both the parent and desaturase-only control strains under any condition. Under both media conditions Z11-16OH and to a lesser extent Z9-16OH were detected from clones expressing the full desaturase-reductase pathway. When the conversion was completed in rich medium, 0.26±0.09 mg/L Z11-16OH and 0.06±0.01 mg/L Z9-16OH were produced (FIG. 32A). A 10-fold increase in Z11-16OH titer and 3-fold increase in Z9-16OH titer was observed when the Semi-Defined medium was used (FIG. 32B). Across all pathway clones 2.65±0.29 mg/L Z11-16OH and 0.18±0.02 mg/L Z9-16OH were produced. The enrichment of Z11-16OH over Z9-16OH supports the potential for engineering a regiospecific Bdr pathway. Consistency between technical replicates varied across clones under the Semi-Defined medium condition. Titers for Clones 2, 4, 6, 9, and 17 were consistent with CVs <20. Clones 1, 7, and 23 have CVs >40%. The highest consistent Z11-16OH titer was observed for Clone 17, 3.68+31 mg/L (Table 15).

TABLE 15

Summary table of Z11/Z9-16OH titers for pEXP1 clones. A population of ten isolates expressing the *H. zea* desaturase driven by pTEF and *H. armigera* reductase driven by pEXP1, from two independent competent cell preparations, were assayed for Z11-16OH and Z9-16OH production under two different media conditions. Alcohol production across isolates and from select clones are presented.

| pTEF-Hz_desat pEXP-Ha_FAR Clone(s) | Medium | Z11-16OH (mg/L) | Z9-16OH (mg/L) | Z11-16OH fold increase (relative to YPD) | Z9-16OH fold increase (relative to YPD) |
|---|---|---|---|---|---|
| All clones | YPD | 0.26 ± 0.09 | 0.06 ± 0.01 | — | — |
| All clones | Semi-Defined | 2.65 ± 0.29 | 0.18 ± 0.02 | 10 | 3 |
| Clone 2 (SPV574) | YPD | 0.18 ± 0.09 | 0.05 ± 0.03 | — | — |
| Clone 2 (SPV574) | Semi-Defined | 2.08 ± 0.26 | 0.14 ± 0.04 | 12 | 3 |
| Clone 4 (SPV575) | YPD | 0.28 ± 0.01 | 0.11 ± 0.01 | — | — |
| Clone 4 (SPV575) | Semi-Defined | 3.24 ± 0.28 | 0.21 ± 0.03 | 12 | 2 |
| Clone 9 (SPV576) | YPD | 1.03 ± 0.84 | 0.05 ± 0.01 | — | — |
| Clone 9 (SPV576) | Semi-Defined | 1.56 ± 0.28 | 0.11 ± 0.02 | 1.5 | 2 |
| Clone 23 (SPV577) | YPD | 0.16 ± 0.14 | 0.05 ± 0.05 | — | — |
| Clone 23 (SPV577) | Semi-Defined | 3.35 ± 1.85 | 0.26 ± 0.15 | 21 | 5 |
| Clone 17 (SPV578) | YPD | 0.19 ± 0.01 | 0.06 ± 0.01 | — | — |
| Clone 17 (SPV578) | Semi-Defined | 3.68 ± 0.31 | 0.26 ± 0.02 | 14 | 4 |

Figure 33A:
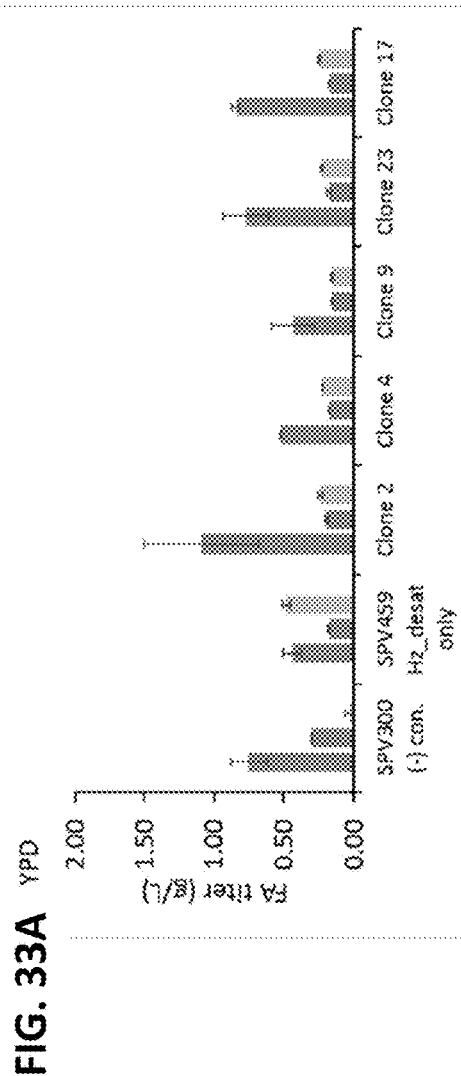
FIG. 33A-FIG. 33B shows profiles of 16-carbon fatty acid species in YPD (FIG. 33A) and Semi-Defined C:N=80 (FIG. 33B) media for pEXP1 clones. The 16-carbon lipid profiles of 5 select clones expressing the *H. zea* desaturase under the TEF promter and *H. armigera* reductase under the EXP promoter are compared to a parental negative control (SPV300) and a desaturase only negative control (SPV459 Hz_desat only). Error bars represent the SEM (standard error of the mean) measured from technical replicates for each strain and condition (N=2).
Figure 33B:
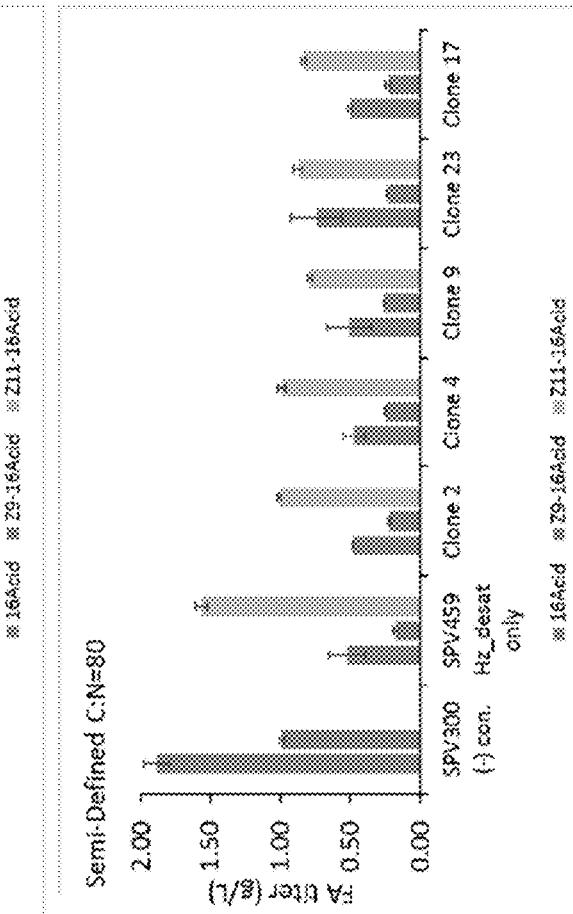

The lipid profiles of the full pathway clones were also quantified. For simplicity the 16 carbon fatty acid species are plotted for select clones in FIG. 33A-33B. In general, the full Bdr pathway clones accumulated less Z11-16Acid than the desaturase only control (0.25<0.5 g/L in YPD, 0.8-1.0<1.5 g/L in Semi-Defined). Lower Z11-16Acid titers in full Bdr pathway clones may result from reduced desaturase expression in the dual expression cassette or potentially from Z11-16Acid consumption by FAR and subsequent byproduct pathways. No trend in 16Acid titer was observed in YPD, while 16Acid titers were similar for desaturase only and full pathway strains in the Semi-Defined medium.

Figure 34:
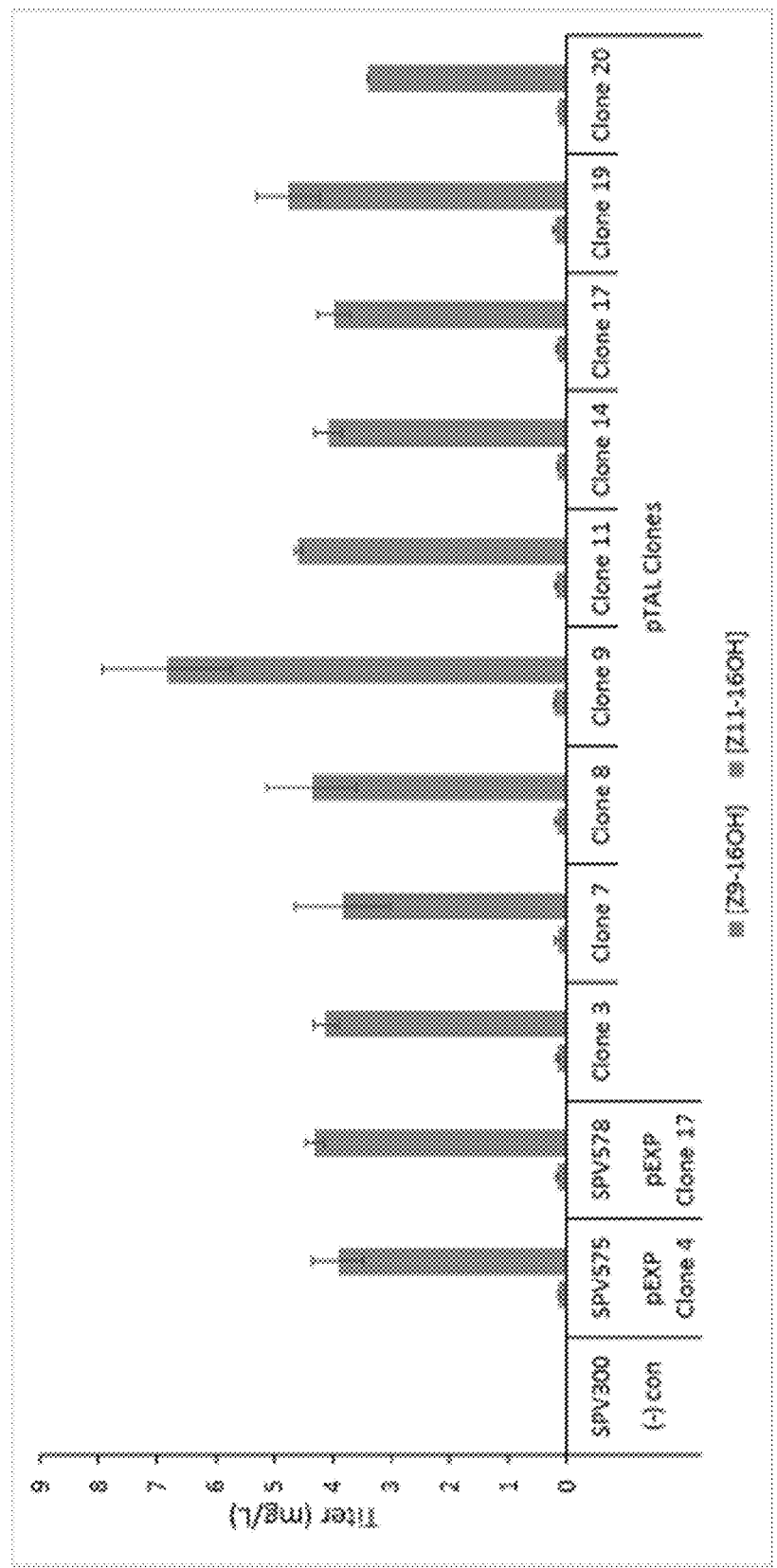
FIG. 34 shows Z9-16OH and Z11-16OH titers in Semi-Defined C:N=80 media for pTAL1 clones. Nine isolates expressing the *H. zea* desaturase under the TEF promoter and *H. armigera* reductase under the TAL promoter were compared to a parental negative control (SPV300) and positive Bdr pathway controls using the EXP promoter to drive *H. armigera* FAR expression (SPV575, SPV578). Error bars represent the SEM (standard error of the mean) measured from technical replicates for each strain and condition (N=2).

Strains using the second dual expression cassette (pTAL-Ha_FAR) were assayed under the same Semi-Defined medium condition used to evaluate the pEXP clones. Nine pTAL clones were assayed against SPV300 (parent), SPV575 (pEXP-Ha_FAR Clone 4), and SPV578 (pEXP-Ha_FAR Clone 17) controls. As expected, no alcohol products were observed from the negative control. Alcohol titers from pEXP positive control strains replicated results observed in the initial assay of pEXP clones (FIG. 34, Table 16). Excluding one outlier clone, Clone 9, Z11-16OH titer was equivalent from pTAL clones (4.19±0.16 mg/L) and pEXP clones (4.10±0.22 mg/L). Clone 9 produced Z11-16OH at 6.82±1.11 mg/L. As in the first assay with pEXP clones, low, but detectable titers of Z9-16OH were observed (FIG. 34, Table 16).

TABLE 16

Summary table of Z11/Z9-16OH titers for pTAL1 clones. A population of nine isolates expressing the *H. zea* desaturase under the TEF promoter and *H. armigera* reductase under the TAL promoter were assayed for Z11-16OH and Z9-16OH production under a Semi-Defined medium condition. Clones were compared to positive controls expressing the *H. zea* desaturase under the TEF promoter and *H. armigera* reductase under the EXP promoter. Alcohol production across isolates and from select clones are presented.

| pTEF-Hz_desat pEXP-Ha_FAR Clone(s) | Medium | Z11-16OH (mg/L) | Z9-16OH (mg/L) |
|---|---|---|---|
| EXP Clone 4 (SPV575) | Semi-Defined | 3.91 ± 0.44 | 0.15 ± 0.01 |
| EXP Clone 17 (SPV578) | Semi-Defined | 4.30 ± 0.16 | 0.17 ± 0.02 |
| pTAL clones excluding | Semi-Defined | 4.19 ± 0.16 | 0.18 ± 0.01 |

TABLE 16-continued

Summary table of Z11/Z9-16OH titers for pTAL1 clones. A population of nine isolates expressing the *H. zea* desaturase under the TEF promoter and *H. armigera* reductase under the TAL promoter were assayed for Z11-16OH and Z9-16OH production under a Semi-Defined medium condition. Clones were compared to positive controls expressing the *H. zea* desaturase under the TEF promoter and *H. armigera* reductase under the EXP promoter. Alcohol production across isolates and from select clones are presented.

| pTEF-Hz_desat pEXP-Ha_FAR Clone(s) | Medium | Z11-16OH (mg/L) | Z9-16OH (mg/L) |
|---|---|---|---|
| Clone 9 | | | |
| pTAL Clone 9 (SPV603) | Semi-Defined | 6.82 ± 1.11 | 0.22 ± 0.01 |

Figure 35:
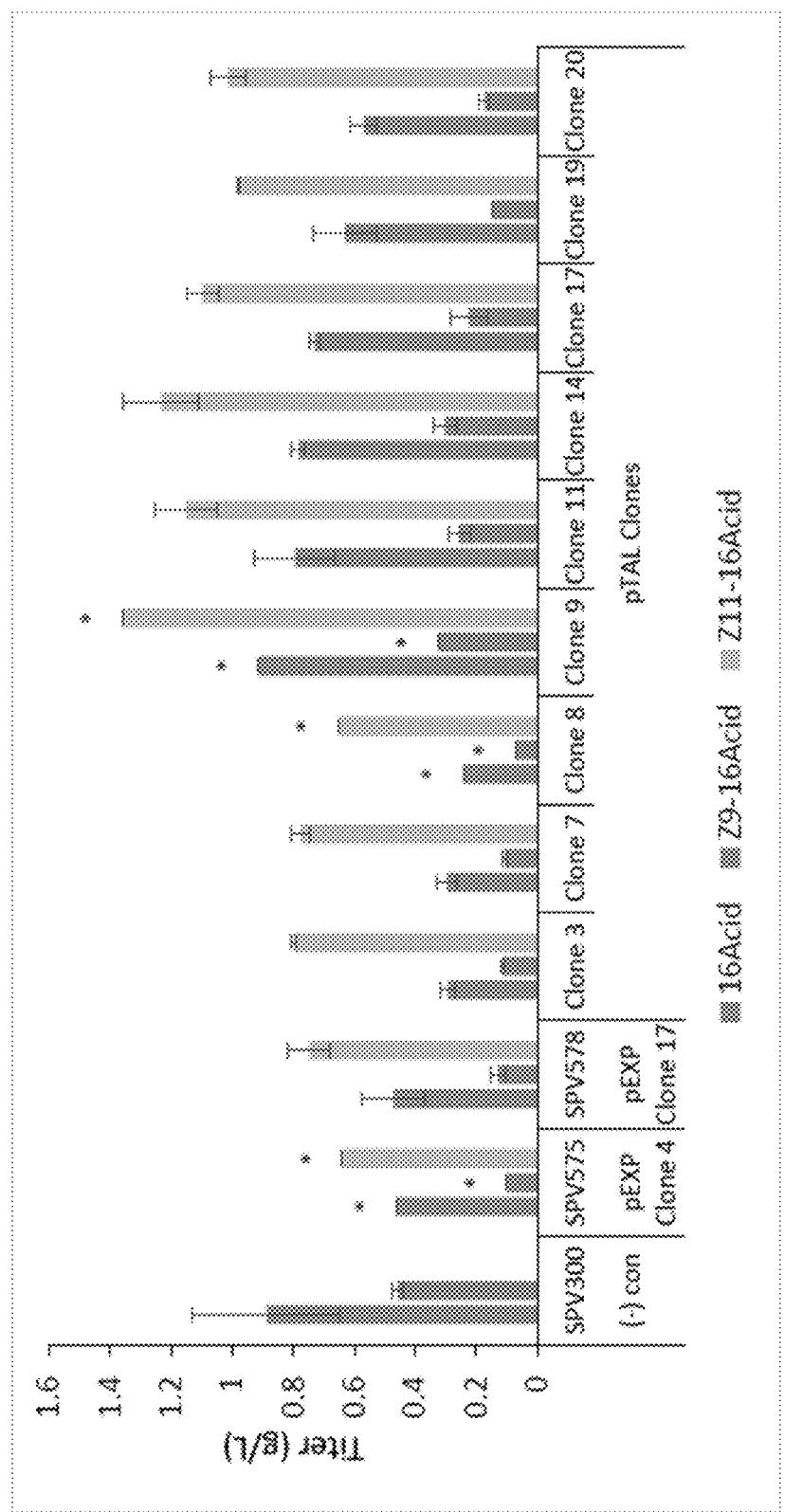
FIG. 35 shows profiles of 16-carbon fatty acid species in Semi-Defined C:N=80 medium for pTAL1 clones. The 16-carbon lipid profiles of 5 select clones expressing the *H. zea* desaturase under the TEF promoter and *H. armigera* reductase under the EXP promoter are compared to a parental negative control (SPV300) and positive Bdr pathway controls using the EXP promoter to drive *H. armigera* FAR expression (SPV575, SPV578). Error bars represent the SEM (standard error of the mean) measured from technical replicates for each strain and condition (N=2).* indicates clones for which one of the replicates was lost during sample processing, N=1.
Figure 36:
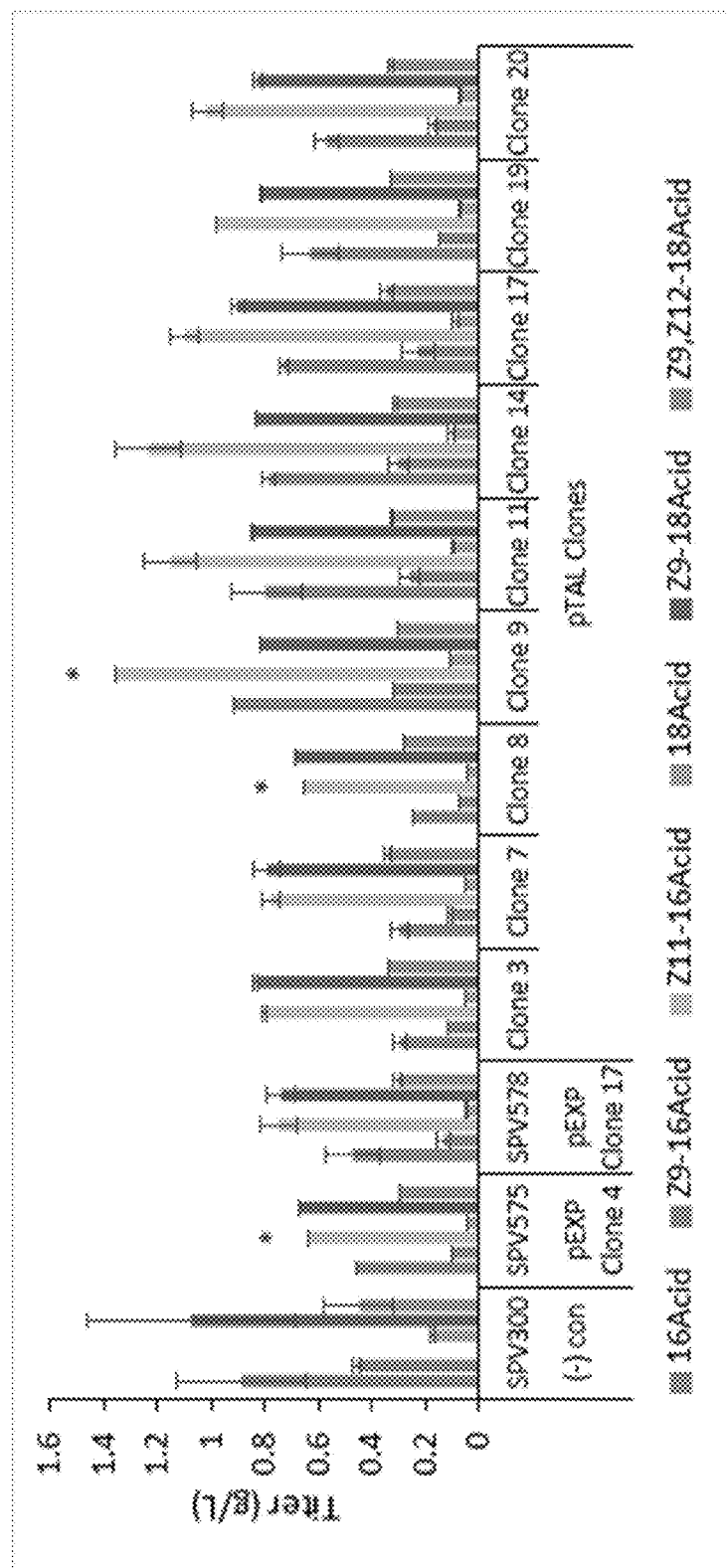
FIG. 36 shows full Bdr pathway pTAL1 screen (strains expressing *H. zea* Z11 desaturase (pTEF) and *H. armigera* FAR) full lipid profiles in Semi-Defined C:N=80 medium after 48 hours of bioconversion. Error bars represent the SEM (standard error of the mean) measured from technical replicates for each strain and condition (N=2).* indicates clones for which one of the replicates was lost during sample processing, N=1.

The lipid profiles of all strains in the second (pTAL) full pathway screen were also quantified. For simplicity the 16 carbon fatty acid species are plotted in FIG. 35. As expected, Z11-16Acid is present only for strains expressing the desaturase. Complete lipid profiles were similar to those observed previously (FIG. 36). Z9-18Acid (oleic acid) was the second most abundant fatty acid species after Z11-16Acid.

Z9-16OH Functional Expression Assay

Figure 37B:
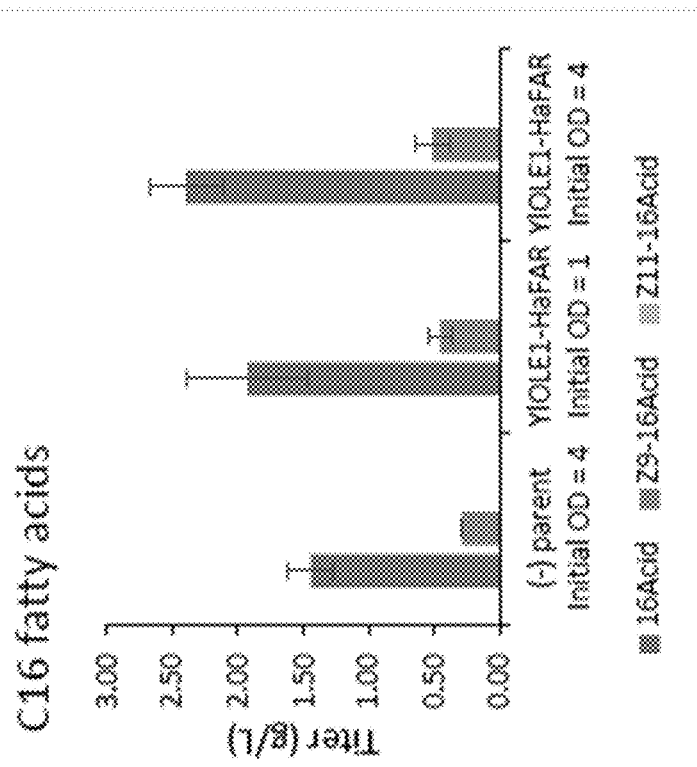
FIG. 37A-FIG. 37B shows SPV471 (H222 ΔPΔAΔF expressing native *Y. lipolytica* OLE1 and *H. armigera* FAR) Z9-16OH (FIG. 37A) and fatty acid (FIG. 37B) titers in Semi-Defined C:N=80 medium after 24 hours of bioconversion. Error bars represent the SEM (standard error of the mean) measured from technical replicates for each strain and condition (N=2).
Figure 37A:
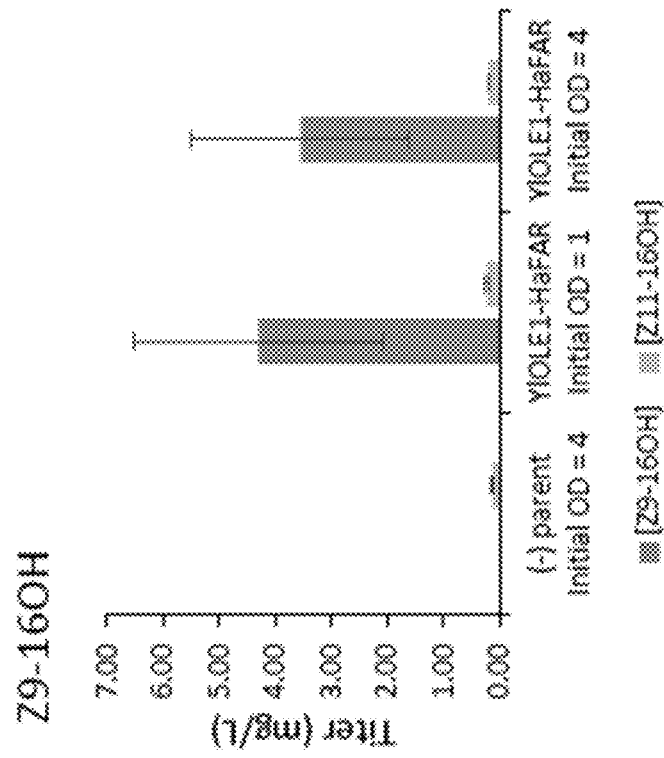
Figure 38:
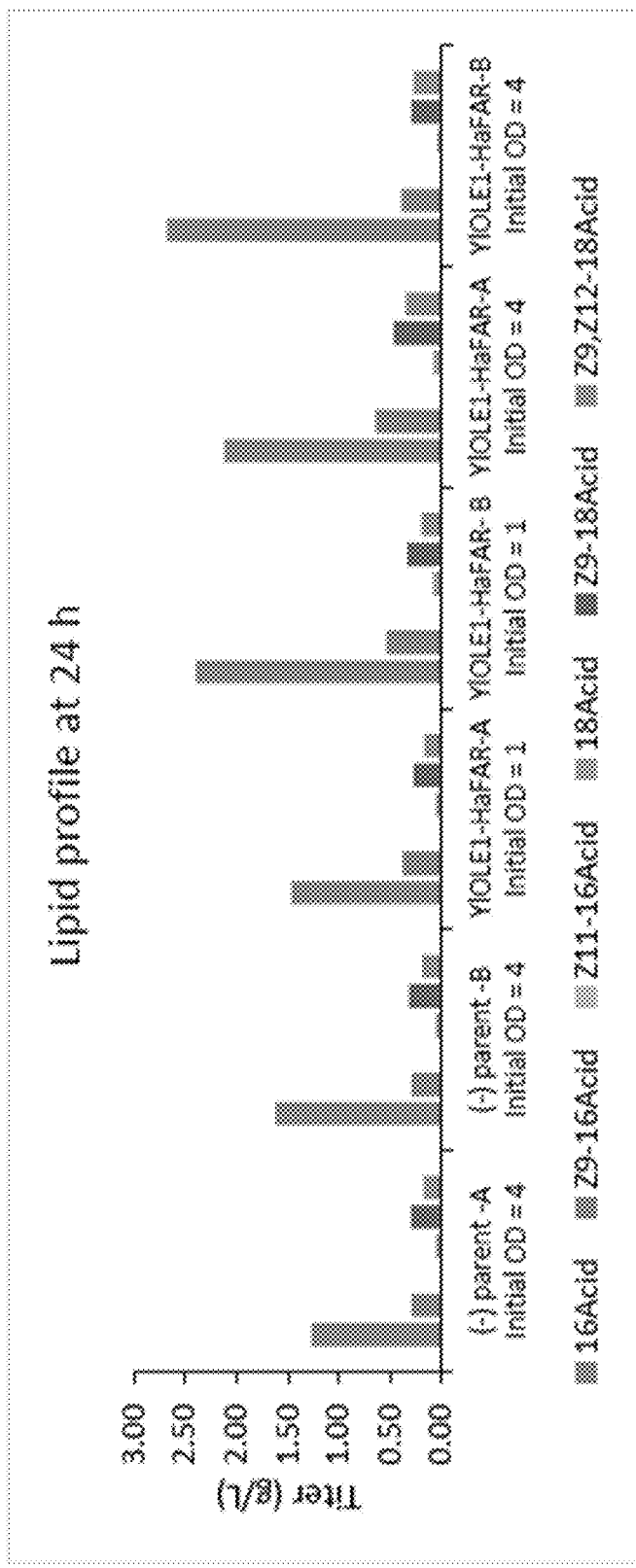
FIG. 38 shows SPV471 (H222 ΔPΔAΔF expressing native *Y. lipolytica* OLE1 and *H. armigera* FAR) full lipid profiles in Semi-Defined C:N=80 medium after 24 hours of bioconversion.
Figure 39B:
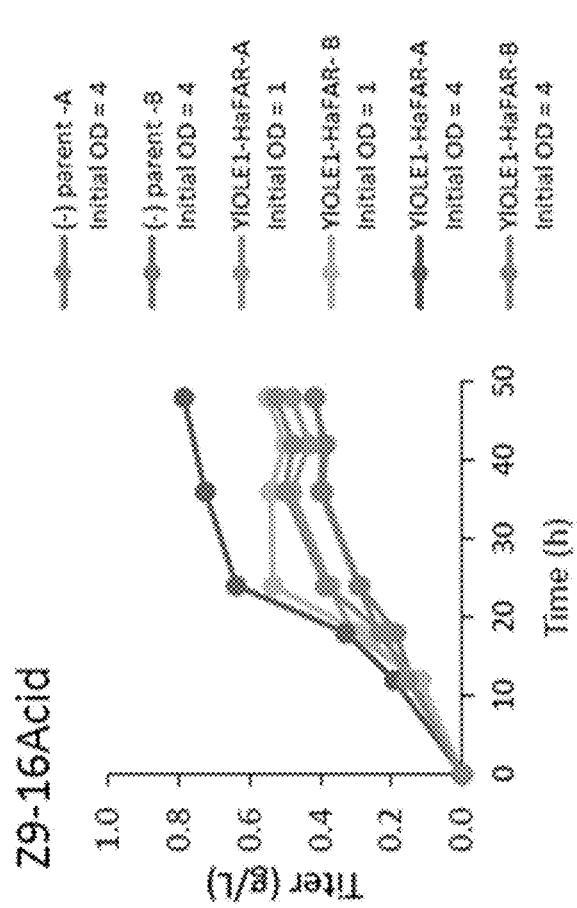
FIG. 39A-FIG. 39B shows SPV471 (H222 ΔPΔAΔF expressing native *Y. lipolytica* OLE1 and *H. armigera* FAR) Z9-16OH (FIG. 39A) and Z9-16Acid (FIG. 39B) titer time courses. Bioconversion of 16Acid was conducted in Semi-Defined C:N=80 medium using a methyl palmitate (16Acid) substrate.
Figure 39A:
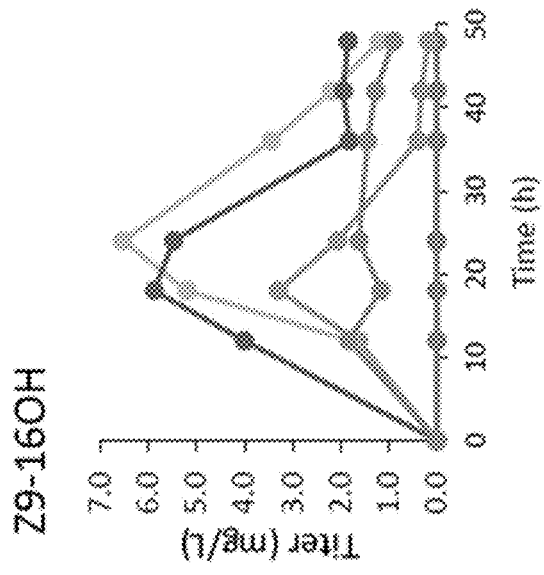

An in vivo, flask scale assay was used to test for Z9-16OH production. The parent control strain, H222 ΔPΔAΔF (SPV300), was compared to a strain expressing *H. armigera* FAR which relied on native Z9 desaturase activity to synthesize the Z9-16CoA precursor (SPV471). Biomass was generated through a YPD seed culture, mimicking the plate assay. Bioconversion flasks were inoculated at an initial OD600=1 or OD600=4 into the same Semi-Defined C:N=80 medium used in the Z11-16OH plate assay (See Materials & Methods for details). As expected, control flasks did not produce detectable Z9-16OH while SPV471 flasks produced up to 4.30±2.23 mg/L after 24 hours of incubation (FIG. 37A-FIG. 37B). While there was large variability between replicates, all SPV471 (*H. armigera* FAR) replicates exceeded 1 mg/L titer. Increased seeding density did not increase Z9-16Acid or Z9-16OH titer. The precursor Z9-16Acid titer at 24 hours was significantly less (<0.5 g/L) than the Z11-16Acid precursor observed for dual expression cassette strains used to produce Z11-16OH. The relative abundance of other fatty acid species was similar to previously observed profiles, with Z9-18Acid as the next most abundant species (FIG. 38). Both lipid and alcohol samples were taken over the course of 48 hours to produce a time course of Z9-16OH and lipid titers. Z9-16OH titer peaked at 24 hours before decreasing over the second day (FIG. 39A). Z9-16Acid increased rapidly over the first 24 hours before stabilizing or increasing slowly over the second 24 hours (FIG. 39B). Since the employed analytical method utilizes only the cell pellet, the decrease in Z9-16OH titer supports the hypothesis of downstream consumption or secretion of the alcohol products. They may be oxidized ($\omega$-oxidation), secreted as free alcohol, or derivatized and secreted as an ester. Analysis of supernatant samples using FID and MS SCAN detection revealed no detectable Z9-16OH or Z9-16OH derivatives supporting the hypothesis of consumption via oxidation pathways.

Conclusions

Combining expression of *Helicoverpa* Z11 desaturase and fatty acyl-CoA reductase led to production of Z11-16OH in *Y. lipolytica* H222 $\Delta$P$\Delta$A$\Delta$F (SPV300) at titers >1 mg/L.

High C:N ratio conditions improved Z11-16OH titer relative to a rich medium condition.

Under lipid accumulating conditions the combination of native Z9 desaturase and *H. armigera* FAR activities are sufficient for synthesis of >1 mg/L Z9-16OH.

Titers are increased, for example, by deleting pathways consuming fatty alcohol products and/or fatty acid precursors; identifying FAR variants which exhibit higher turn-over rate than *H. armigera* FAR; and/or increasing pathway copy number.

Key undesired byproducts are identified.

The possibility that some of the fatty alcohol product is converted into fatty acetate by the activity of one or more endogenous acetyltransferases is explored.

Improved host strains are engineered to eliminate the co-oxidation pathway and components of the lipid storage pathway.

Additional copies of desaturase and FAR are integrated into *Y. lipolytica*.

Materials & Methods

Strain Construction

All desaturase and reductase genes were ordered from Genscript. *Homo sapiens* codon optimization was used (Genscript algorithm). The newly synthesized expression cassette was subcloned into pPV199 by Genscript using the SapI restriction site. Plasmids were transformed and prepped from *E. coli* EPI400 using the Zyppy Plamnsid Miniprep Kit (Zymo Research, Irvine, Calif.). Plasmids were digested with PmeI (New England Biolabs, Ipswich, Mass.) and purified by gel extraction using Zymoclean Gel DNA recovery Kit (Zymo Research, Irvine, Calif.). DNA was further concentrated using Clean and Concentrator Kit (Zymo Research, Irvine, Calif.). Approximately ~1-2 pg of DNA was transformed using Frozen-EZ Yeast Transformation II Kit (Zymo Research, Irvine, Calif.). The manufacturer's protocol was modified as follows: A 2 ml YPD seed culture was inoculated at 9 am the day before competent cell preparation. The seed was grown 8 hours (until 5 pm) before 40 ml of YPD in a 250 ml baffled shake flask (or 20 ml in a 125 ml baffled flask) was inoculated to an initial OD600 of 0.0005. The culture was incubated at 28° C. and 250 rpm ~24 hours. Cells were harvested at an OD600=0.5-1. Instead of resuspending 10 ml of culture in 1 ml of Solution 2 as in the manufacturer's instructions (OD600-10), 10 ml of SPV140 culture was resuspended in 0.5 ml (OD600-20-30). All Solution 2 aliquots were slowly frozen to −80° C. by placing the tubes in a closed Styrofoam box before putting in the −80° C. freezer. 50 µl aliquots of competent cells in 1.7 ml Eppendorf tubes were thawed on ice, DNA eluted in water was added directly to the cells, and 500 µl of Solution 3 was used to suspend the cells with gentle pipetting. Tubes were incubated at 28° C. for 3 hours with gentle vortexing every 30 minutes. The entire transformation mixture was plated on CM glucose-ura agar plates. Positive integrants were found to be site-specific and genotyping was conducted by check PCR.

Z11-16OH Functional Expression Assay

Positive isolates were repatched onto YPD, grown overnight, and then stored at 4° C. Strains were inoculated from patch plates into 2 ml of YPD in 24 deepwell plates (square well, pyramid bottom). Replicate inoculations were made from each patch. Negative control strains were struck out on YPD from glycerol stocks and individual colonies were used to inoculate. Deepwell plates were incubated at 28° C. and 250 rpm in the Infors Multitron refrigerated flask shaker for 24 hrs. After 24 hrs of incubation, a 0.85 ml volume of each culture was pelleted by centrifugation at 800×g. Each pellet was resuspended in either 2 ml of YPD or Semi-defined medium (described in Table 17 below). 10 g/L methyl palmitate (pre-warmed to ~50° C.) was added to cultures. All cultures were incubated for 48 hours before endpoint sampling. Final cell densities were measured with the Tecan Infinite 200pro plate reader. 1.5 ml (alcohol analysis) or 500 µl (lipid analysis) was transferred to 1.7 ml microcentrifuge tubes and pelleted. Supernatant was transferred to clean tubes and samples were processed as described below.

TABLE 17

Semi-defined (C:N = 80) medium composition.
Components of the semi-defined base medium used to induce lipid storage are described.

| Media Components | Conc. | Units |
|---|---|---|
| Yeast Extract | 2 | g/L |
| Peptone | 1 | g/L |
| Potassium phosphate buffer pH7 | 0.1 | M |
| YNB w/o aa, NH4 | 1.7 | g/L |
| Glucose | 60 | g/L |
| Glycerol | 5 | g/l |

Z9-16OH Functional Expression Assay

SPV300 (negative control) and SPV471 were struck out onto YPD agar plates, grown overnight, and then stored at 4° C. Strains were inoculated from colonies into 2 ml of YPD and incubated at 28° C. and 250 rpm in 14 ml round bottom culture tubes for ~8 hours. After incubation, 2 ml of culture was used to inoculate 20 ml of YPD in a 125 ml baffled shake flask. Shake flasks were incubated 24 hrs at 28° C. and 250 rpm. After incubation, cell density in shake flasks was measured using a Tecan Infinite 200pro plate reader. An appropriate volume of culture was pelleted in order to resuspend cells in 25 ml of Semi-defined C:N=80 medium (see Table 17 above) at an initial OD600=1 (~1 gDCW/L) or 4 (~4 gDCW/L). The resuspended culture was added to 250 ml baffled shake flasks. Neat methyl palmitate was added at 10 g/L final concentration after pre-heating to 50° C. After substrate addition, flasks were incubated at 28° C. and 250 rpm for two days. At 12, 18, 24, 36, 42, and 48 hours 500 μl (lipid analysis) and 1.5 ml (alcohol analysis) samples were taken in 1.7 ml microcentrifuge tubes. Samples were pelleted and the supernatant was transferred to a clean microcentrifuge tube.

Metabolite Extraction and GC-MS Detection

Alcohol Analysis

The pelleted cells (in 1.5 mL plastic tubes), usually about 10 mg to 80 mg, were resuspended in methanol containing 5% (w/w) of sodium hydroxide. The alkaline cell suspension was transferred into a 1.8 mL crimp vial. The mixture was heated for 1 h in the heat block at 90° C. Prior to acidification with 400 μL 2.5 N HCl the vial was allowed to cool to room temperature. 500 μL chloroform containing 1 mM methyl heptadecanoate were added and the mixture was shaken vigorously, then both aqueous and organic phase were transferred into a 1.5 mL plastic tube. The mixture was centrifuged at 13,000 rpm, afterwards 450 μL of the organic phase were transferred into a GC vial. The organic phase was evaporated in a heat block at 90° C. for 30 min. The residue was dissolved in 50 JAL N,O-Bis(trimethylsilyl) trifluoroacetamide containing 1% trimethylchlorosilane. Prior to transfer into glass inserts the mixture was heated 5 min at 90° C. The samples were analyzed by GC-MS (Table 18).

TABLE 18

| GC-MS parameters | |
|---|---|
| System | Agilent 6890 N GC, ChemStation G1701EA E.02.01.1177 |
| Column | DB23 30 m × 25 μm × 25 μm |
| | Pressure = 11.60 psi; Flow = 0.6 mL/min |
| Inlet | Heater = 250° C.; Pressure = 11.74 psi; |
| | Total Flow {He} = 111 mL/min |
| Carrier | He @ 29 cm/sec, 11.60 psi |
| Signal | Data rate = 2 Hz/0.1 min |
| Oven | 150° C. for 1 min |
| | Ramp 12° C./min to 220° C., hold 3 min |
| | Ramp 35° C./min to 300° C., hold 4 min |

TABLE 18-continued

| GC-MS parameters | |
|---|---|
| Injection | Splitless, 250° C. |
| Detector | Initial strain screening and first technical triplicate; HP 5973 MSD in SIM mode (m/z: 208.0, 297.3 and 387.3), SPV488/SPV490 alcohol quantification: HP 5973 MSD in SIM mode (m/z: 284.0 and 297.3), 100 msec Dwell, EMV mode: Gain factor 1, 2.4 min solvent delay, 3.09 cycles/sec |
| Sample | Injection volume = 1 uL |

Lipid Analysis

Total lipid composition was based on modified procedures by Moss et al. (1982) and Yousuf et al (2010). The pelleted cells (in 1.5 mL plastic tubes), usually about 10 mg to 80 mg, were resuspended in methanol containing 5% (w/w) of sodium hydroxide. The alkaline cell suspension was transferred into a 1.8 mL glass crimp GC-vial. The mixture was heated for 1 h in the heat block at 90° C. Prior to acidification with 400 μL 2.5 N HCl, the vial was allowed to cool to room temperature. 500 μL chloroform containing 1 mM methyl heptadecanoate were added and the mixture was shaken vigorously, then both aqueous and organic phase were transferred into a 1.5 mL plastic tube. The mixture was centrifuged at 13,000 rpm, afterwards 450 μL of the organic phase was transferred into a new 1.8 mL glass screw-cap GC-vial. After cooling to room temperature residual fatty acid methyl esters and free fatty acids were dissolved and derivatized in methanol containing 0.2 M TMSH (trimethylsulfonium hydroxide) (Table 19).

TABLE 19

| GC-MS parameters | |
|---|---|
| System | Agilent 6890 GC, ChemStation Rev. 8.03.02 (341) |
| Column | J&W DB-23 30 m × 25 mm × 25 μm |
| | Pressure = 16 psi; Flow = 0.9 mL/min; Run Time = 14.4 min |
| Inlet | Heater = 240° C.; Pressure = 16 psi; |
| | Total Flow {He} = 31.4 mL/min |
| Carrier | H$_2$ @ 1 mL/min, 9 psi, 35 cm/sec |
| Signal | Data rate = 2 Hz/0.1 min |
| Oven | 150° C. for 1 min |
| | Ramp 12° C./min to 220° C., hold 3 min |
| | Ramp 35° C./min to 240° C., hold 6 min |
| | Equilibration Time: 2 min |
| Injection | Split, 240° C. |
| | Split ratio - 30:1; 29.1 mL/min |
| Detector | FID, 240° C. |
| | H$_2$ @ 35.0 mL/min, Air @ 350 mL/min;; Electrometer {Lit Offset} @ 2.0 pA |
| Sample | Injection volume = 1 uL |

SEQUENCE LISTING

SEQ ID NO: 1  Agrotis segetum FAR_S. cerevisiae codon. opt
ATGCCAGTTTTGACTTCTAGAGAAGATGAAAAGT
TGTCAGTTCCAGAATTTTACGCTGGTAAATCTATCTTCGTTACAG
GTGGTACTGGTTTCTTGGGTAAAGTTTTTATTGAAAAGTTGTTGT
ACTGTTGTCCAGATATTGATAAAATCTATATGTTAATTAGAGAAA
AGAAAAATTTGTCTATTGATGAAAGAATGTCAAAGTTCTTGGATG
ATCCATTATTTTCTAGATTGAAGGAAGAAAGACCTGGTGACTTGG
AAAAGATTGTTTTGATTCCAGGTGACATTACAGCTCCAAATTTGG
GTTTATCAGCAGAAAACGAAAGAATTTTGTTAGAAAAAGTTTCTG
TTATTATTAATTCAGCTGCAACTGTTAAGTTTAATGAACCATTGC
CAATCGCTTGGAAGATTAATGTTGAAGGTACAAGAATGTTGTTGG
CATTGTCTAGAAGAATGAAGAGAATCGAAGTTTTTATTCATATTT
CTACTGCTTACTCAAATGCATCTTCAGATAGAATCGTTGTTGATG
AAATCTTGTATCCAGCTCCAGCAGATATGGATCAAGTTTACCAAT
TGGTTAAAGATGGTGTTACAGAAGAAGAAACTGAAAGATTGTTGA
ACGGTTTGCCAAACACTTACACTTTTACTAAGGCTTTGACAGAAC

| SEQUENCE LISTING | |
|---|---|
| | ATTTGGTTGCAGAACATCAAACATACGTTCCAACTATCATCATCA<br>GACCATCTGTTGTTGCTTCAATTAAAGATGAACCAATCAGAGGTT<br>GGTTATGTAATTGGTTTGGTGCTACAGGTATCTCTGTTTTTACTG<br>CAAAGGGTTTGAACAGAGTTTTGTTGGGTAAAGCTTCAAACATCG<br>TTGATGTTATCCCAGTTGATTACGTTGCAAATTTGGTTATTGTTG<br>CTGGTGCAAAATCTGGTGGTCAAAAATCAGATGAATTAAAGATCT<br>ATAACTGTTGTTCTTCAGATTGTAACCCAGTTACTTTGAAGAAAA<br>TTATTAAAGAGTTTACTGAAGATACTATTAAAAATAAGTCTCATA<br>TTATGCCATTGCCAGGTTGGTTCGTTTTTACTAAGTACAAGTGGT<br>TGTTGACATTGTTAACTATTATTTTTCAAATGTTACCAATGTATT<br>TGGCTGATGTTTACAGAGTTTTGACAGGTAAAATCCCAAGATACA<br>TGAAGTTGCATCATTTGGTTATTCAAACAAGATTGGGTATCGATT<br>TCTTTACTTCTCATTCATGGGTTATGAAGACAGATAGAGTTAGAG<br>AATTATTCGGTTCTTTGTCATTGGCAGAAAAGCATATGTTTCCAT<br>GTGATCCATCTTCAATCGATTGGACAGATTATTTGCAATCATACT<br>GTTACGGTGTTAGAAGATTTTTGGAAAAGAAGAAATAA |
| SEQ ID NO: 2 | Spodoptera littoralis FAR1_S. cerevisiae codon opt<br>ATGGTTGTTTTGACTTCAAAGGAAAAATCAAACA<br>TGTCTGTTGCTGATTTCTACGCTGGTAAATCTGTTTTTATTACAG<br>GTGGTACTGGTTTCTTGGGTAAAGTTTTTATTGAAAAGTTGTTGT<br>ACTCATGTCCAGATATTGATAAATCTATATGTTGATCAGAGAAA<br>AGAAAGGTCAATCTATCAGAGAAAGATTAACTAAAATTGTTGATG<br>ATCCATTGTTTAATAGATTGAAGGATAAGAGACCAGATGATTTGG<br>GTAAAATCGTTTTGATCCCAGGTGACATCACAGTTCCAGGTTTGG<br>GTATTTCTGAAGAAAACGAAACAATCTTGACTGAACCAGTTTCAG<br>TTGTTATTCATTCTGCTGCAACTGTTAAGTTTAATGAACCATTGG<br>CTACTGCATGGAACGTTAACGTTGAAGGTACAAGAATGATCATGG<br>CATTATCAAGAAGAATGAAGAGAATCGAAGTTTTTATTCATATTT<br>CTACTGCTTACACTAACACAAACAGAGCAGTTATTGATGAAGTTT<br>TGTATCCACCACCAGCTGATATCAACGATGTTCATCAACATGTTA<br>AAAATGGTGTTACAGAAGAAGAAACTGAAAAGATTTTGAACGGTA<br>GACCAAACACTTACACTTTTACTAAGGCTTTGACTGAACATTTGG<br>TTGCAGAAAACCAATCATACATGCCAACAATCATTGTTAGACCAT<br>CTATTGTTGGTGCTATTAAAGATGATCCAATTAGAGGTTGGTTGG<br>CTAATTGGTATGGTGCAACAGGTTTGTCAGTTTTTACTGCAAAGG<br>GTTTGAACAGAGTTATATATGGTCATTCTAACCATGTTGTTGATT<br>TGATTCCAGTTGATTACGTTGCTAATTTGGTTATTGTTGCTGGTG<br>CAAAGACATACCATTCAAACGAAGTTACTATCTATAACTCTTGTT<br>CTTCATCTTGTAACCCAATCACTATGAAGAGATTGGTTGGTTTGT<br>TTATTGATTACACAGTTAAGCATAAGTCATACGTTATGCCATTGC<br>CAGGTTGGTATGTTTACTCTAACTACAAGTGGTTGGTTTCTTGG<br>TTACTGTTATTTTCCAAGTTATTCCAGCTTACTTAGGTGACATTG<br>GTAGAAGATTGTTAGGTAAAAATCCAAGATACTACAAGTTGCAAA<br>ATTTGGTTGCTCAAACACAAGAAGCAGTTCATTTCTTTACATCAC<br>ATACTTGGGAAATTAAATCAAAGAGAACTTCTGAATTGTTTTCAT<br>CTTTGTCTTTGACAGATCAAAGAATGTTTCCATGTGATGCTAACA<br>GAATCGATTGGACAGATTACATCACTGATTACTGTTCTGGTGTTA<br>GACAATTTTTGGAAAAGATTAAATAA |
| SEQ ID NO: 3 | Helicoverpa armigera FAR3_S. cerevisiae codon opt<br>ATGGTTGTTTTGACTTCAAAGGAAACAAAGCCAT<br>CTGTTGCTGAATTTTACGCTGGTAAATCAGTTTTTATTACAGGTG<br>GTACTGGTTTCTTGGGTAAAGTTTTTATTGAAAAGTTGTTGTACT<br>CTTGTCCAGATATTGAAAATCTCTATATGTTGATCAGAGAAAGA<br>AAAGGTTTGTCAGTTTCTGAAAGAATTAAACAATTTTTAGATGATC<br>CATTGTTTACAAGATTGAAGGATAAGAGACCAGCTGATTTGGAAA<br>AGATTGTTTTGATCCCAGGTGACATCACTGCACCAGATTGGGTA<br>TTAATTCTGAAAACGAAAAGATGTTGATTGAAAAAGTTTCAGTTA<br>TTATTCATTCTGCTGCAACTGTTAAGTTTAATGAACCATTACCAA<br>CAGCTTGGAAGATTAATGTTGAAGGTACTAGAATGATGTTGGCAT<br>TGTCAAGAAGAATGAAGAGAATCGAAGTTTTTATTCATATTTCTA<br>CAGCTTACACTAACACAAACAGAGAAGTTGTTGATGAAATCTTGT<br>ATCCAGCTCCAGCAGATATCGATCAAGTTCATCAATACGTTAAGG<br>ATGGTATCTCAGAAGAAGATACTGAAAAGATTTTGAACGGTAGAC<br>CAAACACTTACACTTTTACTAAGGCTTTGACAGAACATTTGGTTG<br>CTGAAAATCAAGCATACGTTCCAACTATTATTGTTAGACCATCTG<br>TTGTTGCTGCAATTAAAGATGAACCATTGAAAGGTTGGTTGGGTA<br>ATTGGTTTGGTGCTACAGGTTTGACTGTTTTTACAGCAAAGGGTT<br>TGAACAGAGTTATATATGGTCATTCTTCATACATCGTTGATTTGA<br>TCCCAGTTGATTACGTTGCTAATTTGGTTATTGCTGCAGGTGCAA<br>AATCTTCAAAGTCAACAGAATTGAAGGTTTACAACTGTTGTTCTT<br>CATCTTGTAACCCAGTTACTATCGGTACATTGATGTCAATGTTCG<br>CTGATGATGCAATTAAACAAAAATCTTACGCTATGCCATTGCCAG<br>GTTGGTACATTTTACAAAGTACAAGTGGTTGGTTTTGTTGTTGA<br>CATTTTTGTTCCAAGTTATTCCAGCATACGTTACTGATTTGTCAA<br>GACATTTGATCGGTAAATCTCCAAGATACATCAAGTTGCAATCAT |

SEQUENCE LISTING

|  |  |
|---|---|
|  | TGGTTAACCAAACTAGATCATCTATCGATTTCTTTACAAACCATT<br>CTTGGGTTATGAAAGCTGATAGAGTTAGAGAATTGTACGCTTCAT<br>TGTCTCCAGCTGATAAGTACTTATTCCCATGTGATCCAACTGATA<br>TCAACTGGACACATTACATCCAAGATTACTGTTGGGGTGTTAGAC<br>ATTTCTTGGAAAAGAAATCTTACGAATAA |
| SEQ ID NO: 4 | pOLE1 cassette<br>CTTGCTGAAAAGATGATGTTCTGAGGTATTCGTATCGCTAGCTTGATACGCTTTT<br>AACAAAAGTAAGCTTTTCGTTTGCAGGTTTGGTTACTTTTCTGTACGAGATGATA<br>TCGCTAAGTTTATAGTCATCTGTGAAATTTCTCAAAAACCTCATGGTTTCTCCAT<br>CACCCATTTTTCATTTCATTTGCCGGGCGGAAAAAAAAAGGAAAAAAAAAAAA<br>AAAAAAATAAATGACACATGGAAATAAGTCAAGGATTAGCGGATATGTAGTTCCA<br>GTCCGGGTTATACCATCACGTGATAATAAATCCAAATGAGAATGAGGGTGTCATA<br>TCTAATCATTATGCACGTCAAGATTCTCCGTGACTATGGCTCTTTTCTGAAGCAT<br>TTTTCGGGCGCCCGGTGGCAAAAAACTAACTCCGAGCCCGGGCATGTCCCGGGGT<br>TAGCGGGCCAACAAAGGCGCTTATCTGGTGGGCTTCCGTAGAAGAAAAAAAGCT<br>GTTGAGCGAGCTATTTCGGGTATCCCAGCCTTCTCTGCAGACCGCCCCAGTTGGC<br>TTGGCTCTGGTGCTGTTCGTTAGCATCACATCGCCTGTGACAGGCAGAGGTAATA<br>ACGGCTTAAGGTTCTCTTCGCATAGTCGGCAGCTTTCTTTCGGACGTTGAACACT<br>CAACAAACCTTATCTAGTGCCCAACCAGGTGTGCTTCTACGAGTCTTGCTCACTC<br>AGACACACCTATCCCTATTGTTACGGCTATGGGGATGGCACACAAAGGTGGAAAT<br>AATAGTAGTTAACAATATATGCAGCAAATCATCGGCTCCTGGCTCATCGAGTCTT<br>GCAAATCAGCATATACATATATATATGGGGGCAGATCTTGATTCATTTATTGTTC<br>TATTTCCATCTTTCCTACTTCTGTTTCCGTTTATATTTTGTATTACGTAGAATAG<br>AACATCATAGTAATAGATAGTTGTGGTGATCATATTATAAACAGCACTAAAACAT<br>TACAACAAAGAATGCCAACTTCTGGAACTACTATTGAATTGATTGACGACCAATT<br>TCCAAAGGATGACTCTGCCAGCAGTGGCATTGTCGACACTAGTGCGGCCGCTCAC<br>ATATGAAAGTATATACCCGCTTTTGTACACTATGTAGCTATAATTCAATCGTATT<br>ATTGTAGCTCCGCACGACCATGCCTTAGAAATATCCGCAGCGCG |
| SEQ ID NO: 5 | Extended OLE1 promoter region<br>CTTGCTGAAAAGATGATGTTCTGAGGTATTCGTATCGCTAGCTTGATACGCTTTT<br>AACAAAAGTAAGCTTTTCGTTTGCAGGTTTGGTTACTTTTCTGTACGAGATGATA<br>TCGCTAAGTTTATAGTCATCTGTGAAATTTCTCAAAAACCTCATGGTTTCTCCAT<br>CACCCATTTTTCATTTCATTTGCCGGGCGGAAAAAAAAAGGAAAAAAAAAAAA<br>AAAAAAATAAATGACACATGGAAATAAGTCAAGGATTAGCGGATATGTAGTTCCA<br>GTCCGGGTTATACCATCACGTGATAATAAATCCAAATGAGAATGAGGGTGTCATA<br>TCTAATCATTATGCACGTCAAGATTCTCCGTGACTATGGCTCTTTTCTGAAGCAT<br>TTTTCGGGCGCCCGGTGGCAAAAAACTAACTCCGAGCCCGGGCATGTCCCGGGGT<br>TAGCGGGCCCAACAAAGGCGCTTATCTGGTGGGCTTCCGTAGAAGAAAAAAAGCT<br>GTTGAGCGAGCTATTTCGGGTATCCCAGCCTTCTCTGCAGACCGCCCCAGTTGGC<br>TTGGCTCTGGTGCTGTTCGTTAGCATCACATCGCCTGTGACAGGCAGAGGTAATA<br>ACGGCTTAAGGTTCTCTTCGCATAGTCGGCAGCTTTCTTTCGGACGTTGA |
| SEQ ID NO: 6 | OLE1 promoter region<br>ACACTCAACAAACCTTATCTAGTGCCCAACCAGGTGTGCTTCTACGAGTCTTGCT<br>CACTCAGACACACCTATCCCTATTGTTACGGCTATGGGGATGGCACACAAAGGTG<br>GAAATAATAGTAGTTAACAATATATGCAGCAAATCATCGGCTCCTGGCTCATCGA<br>GTCTTGCAAATCAGCATATACATATATATATGGGGGCAGATCTTGATTCATTTAT<br>TGTTCTATTTCCATCTTTCCTACTTCTGTTTCCGTTTATATTTTGTATTACGTAG<br>AATAGAACATCATAGTAATAGATAGTTGTGGTGATCATATTATAAACAGCACTAA<br>AACATTACAACAAAGA |
| SEQ ID NO: 7 | OLE1 27aa leader<br>ATGCCAACTTCTGGAACTACTATTGAATTGATTGACGACCAATTTCCAAAGGATG<br>ACTCTGCCAGCAGTGGCATTGTCGAC |
| SEQ ID NO: 8 | Vsp13 terminator region<br>TCACATATGAAAGTATATACCCGCTTTTGTACACTATGTAGCTATAATTCAATCG<br>TATTATTGTAGCTCCGCACGACCATGCCTTAGAAATATCCGCAGCGCG |
| SEQ ID NO: 9 | T. ni desaturase<br>ATGGCTGTGATGGCTCAAACAGTACAAGAAACGGCTACAGTGTTGGAAGAGGAAG<br>CTCGCACAGTGACTCTTGTGGCTCCAAAGACAACGCCAAGGAAATATAAATATAT<br>ATACACCAACTTTCTTACATTTTCATATGCGCATTTAGCTGCATTATACGGACTT<br>TATTTGTGCTTCACCTCTGCGAAATGGGAAACATTGCTATTCTCTTTCGTACTCT<br>TCCACATGTCAAATATAGGCATCACCGCAGGGGCTCACCGACTCTGGACTCACAA<br>GACTTTCAAAGCCAAATTGCCTTTGGAAATTGTCCTCATGATATTCAACTCTTTA<br>GCCTTTCAAAACACGGCTATTACATGGGCTAGAGAACATCGGCTACATCACAAAT<br>ACAGCGATACTGATGCTGATCCCCACAATGCGTCAAGAGGGTTCTTCTACTCGCA<br>TGTTGGCTGGCTATTAGTAAAAAAACATCCCGATGTCCTGAAATATGGAAAACT<br>ATAGACATGTCGGATGTATACAATAATCCTGTGTTAAAATTTCAGAAAAAGTACG<br>CAGTACCCTTAATTGGAACAGTTTGTTTTGCTCTGCCAACTTTGATTCCAGTCTA<br>CTGTTGGGCGAATCGTGGAACAACGCTTGGCACATAGCCTTATTTCGATACATA<br>TTCAATCTTAACGTGACTTTCCTAGTCAACAGTGCTGCGCATATCTGGGGGAATA<br>AGCCTTATGATAAAAGCATCTTGCCCGCTCAAAACCTGCTGGTTTCCTTCCTAGC<br>AAGTGGAGAAGGCTTCCATAATTACCATCACGTCTTTCCATGGGATTACCGCACA |

| SEQUENCE LISTING |
| --- |
| GCAGAATTAGGGAATAACTTCCTGAATTTGACGACGCTGTTCATTGATTTTTGTG
CCTGGTTTGGATGGGCTTATGACTTGAAGTCTGTATCAGAGGATATTATAAAACA
GAGAGCTAAACGAACAGGTGACGGTTCTTCAGGGGTCATTTGGGGATGGGACGAC
AAAGACATGGACCGCGATATAAAATCTAAAGCTAACATTTTTTATGCTAAAAAGG
AATGA |

SEQ ID NO: 10  A. segetum desaturase
ATGGCTCAAGGTGTCCAAACAACTACGATATTGAGGGAGGAGGAGCCGTCATTGA
CTTTCGTGGTACCTCAAGAACCGAGAAAGTATCAAATCGTGTACCCAAACCTTAT
CACATTTGGGTACTGGCATATAGCTGGTTTATACGGGCTATATTTGTGCTTTACT
TCGGCAAAATGGCAAACAATTTTTATTCAGTTTCATGCTCGTTGTGTTAGCAGAGT
TGGGAATAACAGCCGGCGCTCACAGGTTATGGGCCCACAAAACATATAAAGCGAA
GCTTCCCTTACAAATTATCCTGATGATACTGAACTCCATTGCCTTCCAAATTCC
GCCATTGATTGGGTGAGGG
ACCACCGTCTCCATCATAAGTACAGTGACACTGATGCAGACCCTCACAATGCTAC
TCGTGGTTTCTTCTATTCTCATGTTGGATGGTTGCTCGTAAGAAAACATCCAGAA
GTCAAGAGACGTGGAAAGGAACTTGACATGTCTGATATTTACAACAATCCAGTGC
TGAGATTTCAAAAGAAGTATGCTATACCCTTCATCGGGGCAATGTGCTTCGGATT
ACCAACTTTTATCCCTGTTTACTTCTGGGGAGAAACCTGGAGTAATGCTTGGCAT
ATCACCATGCTTCGGTACATCCTCAACCTAAACATTACTTTCCTGGTCAACAGTG
CTGCTCATATCTGGGGATACAAACCTTATGACATCAAAATATTGCCTGCCCAAAA
TATAGCAGTTTCCATAGTAACCGGCGGCGAAGTTTCCATAACTACCACCACGTTT
TTTCCTTGGGATTATCGTGCAGCAGAATTGGGGAACAATTATCTTAATTTGACGA
CTAAGTTCATAGATTTCTTCGCTTGGATCGGATGGGCTTACGATCTTAAGACGGT
GTCCAGTGATGTTATAAAAAGTAAGGCGGAAAGAACTGGTGATGGGACGAATCTT
TGGGGTTTAGAAGACAAAGGTGAAG
AAGATTTTTTGAAAATCTGGAAAGACAATTAA SEQ ID NO: 11  T. pseudonana desaturase
ACTAGTATGGACTTTCTCTCCGGCGATCCTTTCCGGACAC
TCGTCCTTGCAGCACTTGTTGTCATCGGATTTGCTGCGGCGTGGC
AATGCTTCTACCCGCCGAGCATCGTCGGCAAGCCTCGTACATTAA
GCAATGGTAAACTCAATACCAGAATCCATGGCAAATTGTACGACC
TCTCATCGTTTCAGCATCCAGGAGGCCCCGTGGCTCTTTCTCTTG
TTCAAGGTCGCGACGGAACAGCTCTATTTGAGTCACACCATCCCT
TCATACCTCGAAAGAATCTACTTCAGATCCTCTCCAAGTACGAGG
TTCCGTCGACTGAAGACTCTGTTTCCTTCATCGCCACCCTAGACG
AACTCAATGGTGAATCTCCGTACGATTGGAAGGACATTGAAAATG
ATGATTTCGTATCTGACCTACGAGCTCTCGTAATTGAGCACTTTT
CTCCTCTCGCCAAGGAAAGGGGAGTTTCACTCGTTGAGTCGTCGA
AGGCAACACCTCAGCGGTGGATGGTGGTTCTACTGCTCCTTGCGT
CGTTCTTCCTCAGCATCCCATTATATTTGAGTGGTTCGTGGACTT
TCGTTGTCGTCACTCCCATCCTCGCTTGGCTGGCGGTTGTCAATT
ACTGGCACGATGCTACTCACTTTGCATTGAGCAGCAACTGGATTT
TGAATGCTGCGCTCCCATATCTCCTCCCTCTCCTATCGAGTCCGT
CAATGTGGTATCATCATCACGTCATTGGACATCACGCATACACCA
ACATTTCCAAAAGAGATCCAGATCTTGCTCACGCTCCACAACTCA
TGAGAGAACACAAGAGTATCAAATGGAGACCATCTCACTTAAATC
AAACACAGCTTCCGCGGATTCTCTTCATCGGTCGATTGCAGTCG
GTATTGGGTTGAACTTACTGAACGACGTGAGAGCACTAACCAAGC
TTTCATACAACAACGTTGTTCGGGTGGAGAAGATGTCATCGTCGC
GAACATTACTCCATTTCCTTGGACGTATGTTGCACATCTTTGTGA
CTACACTTTGGCCCTTTTTGGCGTTTCCGGTGTGGAAGGCCATCG
TTTGGGCGACTGTACCGAATGCCATACTGAGTTTGTGCTTCATGC
TGAATACGCAAATCAATCACCTCATCAACACGTGTGCACATGCTT
CCGATAACAACTTTTACAAGCATCAAGTTGTAACTGCTCAGAACT
TTGGCCGATCAAGTGCCTTTTGCTTCATCTTCTCGGGAGGTCTCA
ACTACCAAATTGAACATCATTTGTTGCCGACGGTGAACCATTGCC
ATTTGCCAGCTTTGGCCCCGGGTGTAGAGCGTTTGTGTAAGAAAC
ACGGGGTGACATACAACTCTGTTGAAGGATACAGAGAGGCCATCA
TTGCACACTTTGCACATACCAAAGATATGTCGACGAAGCCTACTG
ATTGA SEQ ID NO: 12  A. transitella desaturase
ATGGTCCCTAACAAGGGTTCCAGTGACGTTTTGTCTGAACATTCTGAGCCCCAGT
TCACTAAACTCATAGCTCCACAAGCAGGGCCGAGGAAATACAAGATAGTGTATCG
AAATTTGCTCACATTCGGCTATTGGCACTTATCAGCTGTTTATGGGCTCTACTTG
TGCTTTACTTGTGCGAAATGGGCTACCATCTTATTTGCATTTTTCTTATACGTGA
TCGCGGAAATCGGTATAACAGGTGGCGCTCATAGGCTATGGGCACATCGGACTTA
TAAAGCCAAGTTGCCTTTAGAGATTTTGTTACTCATAATG
AACTCTATTGCCTTCCAAGACACTGCTTTCACCTGGGCTCGTGATCACCGCCTTC
ATCACAAATATTCGGATACTGACGCTGATCCCCACAATGCTACCAGAGGGTTTTT
CTATTCACATGTAGGCTGGCTTTTGGTGAAGAAACACCCTGAAGTCAAAGCAAGA
GGAAAATACTTGTCGTTAGATGATCTTAAGAATAATCCATTGCTTAAATTCCAAA
AGAAATACGCTATTCTAGTTATAGGCACGTTATGCTTCCTTATGCCAACATTTGT
GCCCGTATACTTCTGGGGCGAGGGCATCAGCACGGCCTGGAACATCAATCTATTG
CGATACGTCATGAATCTTAACATGACTTTCTTAGTTAACAGTGCAGCGCATATCT

| SEQUENCE LISTING |
|---|

```
              TTGGCAACAAACCATACGATAAGAGCATAGCCTCAGTCCAAAATATTTCAGTTAG
              CTTAGCTACTTTTGGCGAAGGATTCCATAATTACCATCACACTTACCCCTGGGAT
              TATCGTGCGGCAGAATTAGGAAATAATAGGCTAAATATGACTACTGCTTTCATAG
              ATTTCTTCGCTTGGATCGGCTGGGCTTATGACTTGAAGTCTGTGCCACAAGAGGC
              CATTGCAAAAGGTGTGCGAAAACTGGCGATGGAACGGATATGTGGGGTCGAAAA
              AGATAA

SEQ ID NO: 13  H. zea desaturase
              ATGGCCCAAAGCTATCAATCAACTACGGTTTTGAGTGAGGAGAAAGAACTAACAC
              TGCAACATTTGGTGCCCCAAGCATCGCCCAGGAAGTATCAAATAGTGTATCCGAA
              CCTCATTACGTTTGGTTACTGGCACATAGCCGGACTTTATGGCCTTTACTTGTGC
              TTCACTTCTGCTAAATGGGCTACGATTTTATTCAGCTACATCCTCTTCGTGTTAG
              CAGAAATAGGAATCACGGCTGGCGCTCACAGACTCTGGGCCCACAAAACTTACAA
              AGCGAAACTACCATTAGAAATACTCTTAATGGTATTCAACTCCATCGCTTTTCAA
              AACTCAGCCATTGACTGGGTGAGGGACCACCGACTCCACCATAAGTATAGCGATA
              CAGATGCTGATCCCCACAATGCCAGCCGAGGGTTCTTTTATTCCCATGTAGGATG
              GCTACTTGTGAGAAACATCCTGAAGTCAAAAAGCGAGGGAAAGAACTCAATATG
              TCCGATATTTACAACAATCCTGTCCTGCGGTTTCAGAAAAAATACGCCATACCCT
              TCATTGGGGCTGTTTGTTTCGCCTTACCTACAATGATACCTGTTTACTTCTGGGG
              AGAAACCTGGTCCAATGCTTGGCATATCACCATGCTTCGCTACATCATGAACCTC
              AATGTCACCTTTTTGGTAAACAGCGCTGCTCATATATGGGGAAACAAGCCTTATG
              ACGCAAAATATTACCTGCACAAAATGTAGCTGTGTCGGTCGCCACTGGTGGAGA
              AGGTTTCCATAATTACCACCATGTCTTCCCCTGGGATTATCGAGCAGCGGAACTC
              GGTAACAATAGCCTCAATCTGACGACTAAATTCATAGATTTATTCGCAGCAATCG
              GATGGGCATATGATCTGAAGACGGTTTCGGAGGATATGATAAAACAAAGGATTAA
              ACGCACTGGAGATGGAACGGATCTTTGGGGACACGAACAAAACTGTGATGAAGTG
              TGGGATGTAAAAGATAAATCAAGTTAA SEQ ID NO: 14  mCherry C. tropicalis optimized
              ATGGTTTCTAAGGGTGAAGAAGACAACATGGCAATCATCAAGGAATTTATGCGTT
              TTAAGGTCCATATGGAAGGCTCCGTTAACGGCCACGAGTTCGAGATCGAGGGAGA
              AGGTGAGGGTAGACCATACGAAGGTACTCAAACCGCCAAGTTGAAAGTTACAAAG
              GGTGGTCCATTGCCATTTGCTTGGGATATCTTGTCCCCACAATTTATGTACGGAT
              CAAAGGCATATGTCAAGCATCCTGCCGACATCCCAGATTACTTGAAGTTATCCTT
              TCCAGAAGGTTTTAAGTGGGAGAGAGTTATGAACTTTGAAGATGGCGGAGTTGTT
              ACTGTTACTCAGGACTCTTCCTTGCAAGATGGTGAATTTATCTATAAAGTGAAAT
              TGAGAGGTACTAACTTTCCATCCGACGGTCCAGTCATGCAAAAGAAGACAATGGG
              TTGGGAGGCTTCTTCCGAAAGAATGTACCCAGAAGACGGTGCATTGAAGGTGAA
              ATCAAGCAACGTTTAAAGTTGAAGGACGGTGGTCACTACGATGCCGAGGTCAAGA
              CCACTTATAAGGCTAAGAAGCCAGTCCAATTGCCAGGTGCTTATAACGTTAACAT
              CAAGTTAGATATTACTTCACACAACGAAGACTACACAATCGTTGAACAATATGAA
              AGAGCCGAAGGTAGACATTCTACCGGCGGCATGGACGAGTTATATAAGTAG SEQ ID NO: 15  CaOLE1-A. segetum Z11 desaturase
              ATGACTACAGTTGAACAACTTGAAACTGTTGATATCACTAAATTGAATGCCATTG
              CTGCTGGTACTAATAAGAAGGTGCCAATGGCTCAAGGTGTCCAAACAACTACGAT
              ATTGAGGGAGGAAGAGCCGTCATTGACTTTCGTGGTACCTCAAGAACCGAGAAAG
              TATCAAATCGTGTACCCAAACCTTATCACATTTGGGTACTGGCATATAGCTGGTT
              TATACGGGCTATATTTGTGCTTTACTTCGGCAAAATGGCAACAATTTTATTCAG
              TTTCATGCTCGTTGTGTTAGCAGAGTTGGGAATAACAGCCGGCGCTCACAGGTTA
              TGGGCCCACAAAACATATAAAGCGAAGCTTCCCTTACAAATTATCTTAATGATAT
              TAAACTCCATTGCCTTCCAAAATTCCGCCATTGATTGGGTGAGGGACCACCGTCT
              CCATCATAAGTACAGTGACACTGATGCAGACCCTCACAATGCTACTCGTGGTTTC
              TTCTATTCTCATGTTGGATGGTTGCTCGTAAGAAAACATCCAGAAGTCAAGAGAC
              GTGGAAAGGAACTTGACATGTCTGATATTTACAACAATCCAGTGTTAAGATTTCA
              AAAGAAGTATGCTATACCCTTCATCGGGGCAATGTGCTTCGGATTACCAACTTTT
              ATCCCTGTTTACTTCTGGGGAGAAACCTGGAGTAATGCTTGGCATATCACCATGC
              TTCGGTACATCCTCAACCTAAACATTACTTTCTTAGTCAACAGTGCTGCTCATAT
              CTGGGGATACAAACCTTATGACATCAAAATATTGCCTGCCCAAAATATAGCAGTT
              TCCATAGTAACCGGCGGCGAAGTTTCCATAACTACCACCACGTTTTTCCTTGGG
              ATTATCGTGCAGCAGAATTGGGGAACAATTATCTTAATTTGACGACTAAGTTCAT
              AGATTTCTTCGCTTGGATCGGATGGGCTTACGATCTTAAGACGGTGTCCAGTGAT
              GTTATAAAAAGTAAGGCGGAAAGAACTGGTGATGGGACGAATCTTTGGGGTTTAG
              AAGACAAAGGTGAAGAAGATTTTTTGAAAATCTGGAAAGACAATTAA SEQ ID NO: 16  A. segetum Z11 desaturase
              ATGGCTCAAGGTGTCCAAACAACTACGATATTGAGGGAGGAAGAGCCGTCATTGA
              CTTTCGTGGTACCTCAAGAACCGAGAAAGTATCAAATCGTGTACCCAAACCTTAT
              CACATTTGGGTACTGGCATATAGCTGGTTTATACGGGCTATATTTGTGCTTTACT
              TCGGCAAAATGGCAAACAATTTTATTCAGTTTCATGCTCGTTGTGTTAGCAGAGT
              TGGGAATAACAGCCGGCGCTCACAGGTTATGGGCCCACAAAACATATAAAGCGAA
              GCTTCCCTTACAAATTATCTTAATGATATTAAACTCCATTGCCTTCCAAAATTCC
              GCCATTGATTGGGTGAGGGACCACCGTCTCCATCATAAGTACAGTGACACT
              GATGCAGACCCTCACAATGCTACTCGTGGTTTCTTCTATTCTCATGTTGGATGGT
              TGCTCGTAAGAAAACATCCAGAAGTCAAGAGACGTGGAAAGGAACTTGACATGTC
              TGATATTTACAACAATCCAGTGTTAAGATTTCAAAAGAAGTATGCTATACCCTTC
              ATCGGGGCAATGTGCTTCGGATTACCAACTTTTATCCCTGTTTACTTCTGGGGAG
```

| SEQUENCE LISTING |
|---|
| AAACCTGGAGTAATGCTTGGCATATCACCATGCTTCGGTACATCCTCAACCTAAA
CATTACTTTCTTAGTCAACAGTGCTGCTCATATCTGGGGATACAAACCTTATGAC
ATCAAAATATTGCCTGCCCAAAATATAGCAGTTTCCATAGTAACCGGCGGCGAAG
TTTCCATAACTACCACCACGTTTTTTCCTTGGGATTATCGTGCAGCAGAATTGGG
GAACAATTATCTTAATTTGACGACTAAGTTCATAGATTTCTTCGCTTGGATCGGA
TGGGCTTACGATCTTAAGACGGTGTCCAGTGATGTTATAAAAAGTAAGGCGGAAA
GAACTGGTGATGGGACGAATCTTTGGGGTTTAGAAGACAAAGGTGAAGAAGATTT
TTTGAAAATCTGGAAAGACAATTAA |

SEQ ID NO: 17  *A. transitella* Z11 desaturase
ATGGTCCCTAACAAGGGTTCCAGTGACGTTTTGTCTGAACATTCTGAGCCCCAGT
TCACTAAACTCATAGCTCCACAAGCAGGGCCGAGGAAATACAAGATAGTGTATCG
AAATTTGCTCACATTCGGCTATTGGCACTTATCAGCTGTTTATGGGCTCTACTTG
TGCTTTACTTGTGCGAAATGGGCTACCATCTTATTTGCATTTTTCTTATACGTGA
TCGCGGAAATCGGTATAACAGGTGGCGCTCATAGGCTATGGGCACATCGGACTTA
TAAAGCCAAGTTGCCTTTAGAGATTTTGTTACTCATAATGAATTCTATTGCCTTC
CAAGACACTGCTTTCACCTGGGCTCGAGATCACCGCCTTCATCACAAATATTCGG
ATACTGACGCTGATCCCCACAATGCTACCAGAGGGTTTTTCTATTCACATGTAGG
CTGGCTTTTGGTGAAGAAACACCCTGAAGTCAAAGCAAGAGGAAAATACTTGTCG
TTAGATGATCTTAAGAATAATCCATTGCTTAAATTCCAAAAGAAATACGCTATTC
TAGTTATAGGCACGTTATGCTTCCTTATGCCAACATTTGTGCCCGTATACTTCTG
GGGCGAGGGCATCAGCACGGCCTGGAACATCAATCTATTGCGATACGTCATGAAT
CTTAACATGACTTTCTTAGTTAACAGTGCAGCGCATATCTTTGGCAACAAACCAT
ACGATAAGAGCATAGCCTCAGTCCAAAATATTTCAGTTAGCTTAGCTACTTTTGG
CGAAGGATTCCATAATTACCATCACACTTACCCCTGGGATTATCGTGCGGCAGAA
TTAGGAAATAATAGGCTAAATATGACTACTGCTTTCATAGATTTCTTCGCTTGGA
TCGGCTGGGCTTATGACTTGAAGTCTGTGCCACAAGAGGCCATTGCAAAAGGTG
TGCGAAAACTGGCGATGGAACGGATATGTGGGGTCGAAAAAGATAA SEQ ID NO: 18  *T. ni* Z11 desaturase
ATGGCTGTGATGGCTCAAACAGTACAAGAAACGGCTACAGTGTTGGAAGAGGAAG
CTCGCACAGTGACTCTTGTGGCTCCAAAGACAACGCCAAGGAAATATAAATATAT
ATACACCAACTTTCTTACATTTTCATATGCGCATTTAGCTGCATTATACGGACTT
TATTTGTGCTTCACCTCTGCGAAATGGGAAACATTGCTATTCTCTTTCGTACTCT
TCCACATGTCAAATATAGGCATCACCGCAGGGGCTCACCGACTCTGGACTCACAA
GACTTTCAAAGCCAAATTGCCTTTGGAAATTGTCCTCATGATATTCAACTCTTTA
GCCTTTCAAAACACGGCTATTACATGGGCTAGAGAACATCGGCTACATCACAAAT
ACAGCGATACTGATGCTGATCCCCACAATGCGTCAAGAGGGTTCTTCTACTCGCA
TGTTGGCTGGCTATTAGTAAAAAAACATCCCGATGTCTTAAAATATGGAAAAACT
ATAGACATGTCGGATGTATACAATAATCCTGTGTTAAAATTTCAGAAAAAGTACG
CAGTACCCCTTAATTGGAACAGTTTGTTTTGCTCTTCCAACTTTGATTCCAGTCTA
CTGTTGGGGCGAATCGTGGAACAACGCTTGGCACATAGCCTTATTTCGATACATA
TTCAATCTTAACGTGACTTTCCTAGTCAACAGTGCTGCGCATATCTGGGGGAATA
AGCCTTATGATAAAAGCATCTTGCCCGCTCAAAACTTATTAGTTTCCTTCCTAGC
AAGTGGAGAAGGCTTCCATAATTACCATCACGTCTTTCCATGGGATTACCGCACA
GCAGAATTAGGGAATAACTTCTTAAATTTGACGACGTTATTCATTGATTTTTGTG
CCTGGTTTGGATGGCTTATGACTTGAAGTCTGTATCAGAGGATATTATAAAACA
GAGAGCTAAACGAACAGGTGACGGTTCTTCAGGGGTCATTTGGGGATGGGACGAC
AAAGACATGGACCGCGATATAAAATCTAAAGCTAACATTTTTTATGCTAAAAAGG
AATGA SEQ ID NO: 19  *H. zea* Z11 desaturase
ATGGCCCAAAGCTATCAATCAACTACGGTTTTGAGTGAGGAGAAAGAACTAACAT
TACAACATTTGGTGCCCCAAGCATCGCCCAGGAAGTATCAAATAGTGTATCCGAA
CCTCATTACGTTTGGTTACTGGCACATAGCCGGACTTTATGGCCTTTACTTGTGC
TTCACTTCTGCTAAATGGGCTACGATTTTATTCAGCTACATCCTCTTCGTGTTAG
CAGAAATAGGAATCACGGCTGGCGCTCACAGACTCTGGGCCCACAAAACTTACAA
AGCGAAACTACCATTAGAAATACTCTTAATGGTATTCAACTCCATCGCTTTTCAA
AACTCAGCCATTGACTGGGTGAGGGACCACCGACTCCACCATAAGTATAGCGATA
CAGATGCTGATCCCCACAATGCCAGCCGAGGGTTCTTTTATTCCCATGTAGGATG
GCTACTTGTGAGAAAACATCCTGAAGTCAAAAGCGAGGGAAAGAACTCAATATG
TCCGATATTTACAACAATCCTGTCTTACGGTTTCAGAAAAAATACGCCATACCCT
TCATTGGGCTGTTTGTTTCGCCTTACCTACAATGATACCTGTTTACTTCTGGGG
AGAAACCTGGTCCAATGCTTGGCATATCACCATGCTTCGCTACATCATGAACCTC
AATGTCACCTTTTTGGTAAACAGCGCTGCTCATATATGGGGAAACAAGCCTTATG
ACGCAAAAATATTACCTGCACAAAATGTAGCTGTGTCGGTCGCCACTGGTGGAGA
AGGTTTCCATAATTACCACCATGTCTTCCCCTGGGATTATCGAGCAGCGGAACTC
GGTAACAATAGCCTCAATTTAACGACTAAATTCATAGATTTATTCGCAGCAATCG
GATGGGCATATGATTTAAAGACGGTTTCGGAGGATATGATAAAACAAGGATTAA
ACGCACTGGAGATGAACGGATCTTTGGGGACACGAACAAAACTGTGATGAAGTG
TGGGATGTAAAAGATAAATCAAGTTAA SEQ ID NO: 20  *O. furnacalis* Z9 desaturase
ATGGCTCCTAATATTAAGGACGGAGCTGATTTGAACGGAGTTTTATTTGAAGATG
ACGCTAGCACCCCCGATTATGCCCTTGCCACGGCCCCAGTCCAGAAAGCAGACAA
CTATCCCAGAAAACTAGTGTGGAGAAACATCATACTCTTTGCATACCTTCACCTT
GCCGCTGTGTATGGAGCATACCTATTCTTATTTTCAGCGAAATGGCAGACAGATA

| SEQUENCE LISTING |
|---|
| TTTTTGCCTACATTCTTTACGTGATCTCAGGACTCGGCATCACAGCGGGAGCCCA<br>CCGCCTTTGGGCGCACAAGTCATACAAGGCTAAGTGGCCACTTAGACTCATTCTT<br>ATTATCTTCAACACTGTATCATTCCAGGACTCTGCTCTCGACTGGTCACGTGACC<br>ACCGCATGCACCACAAATACTCGGAGACCGACGCCGACCCGCACAACGCGACTCG<br>AGGGTTCTTCTTCTCTCATATCGGCTGGTTATTAGTCCGCAAGCACCCGGAATTA<br>AAGAGAAAGGGCAAGGGATTAGACTTAAGCGACTTGTATGCTGATCCCATCCTCC<br>GTTTCCAGAAGAAGTACTATTTACTATTAATGCCTCTTGGCTGCTTCATCATGCC<br>GACGGTGGTCCCGGTGTACTTCTGGGGTGAGACTTGGACTAACGCTTTCTTCGTC<br>GCCGCGCTCTTCCGATACACCTTCATCCTCAATGTCACCTGGTTGGTCAACTCCG<br>CCGCGCACAAGTGGGGCCACAAGCCCTATGACAGCAGCATCAAGCCTTCCGAGAA<br>CCTCTCAGTCTCCTTATTCGCGTTGGGCGAAGGATTCCACAACTACCACCACACA<br>TTCCCCTGGGACTACAAAACTGCCGAGCTCGGCAACAACAGACTCAATTTCACAA<br>CAAACTTCATCAACTTCTTCGCTAAAATCGGATGGGCTTACGACTTGAAAACGGT<br>CTCCGACGAGATTATTCAGAATAGAGTCAAGCGCACAGGAGATGGCTCCCACCAC<br>TTATGGGGTTGGGGCGACAAGGATCAACCTAAAGAGGAGGTAAACGCAGCCATTA<br>GAATTAATCCTAAAGACGAGTAA |

SEQ ID NO: 21  L. capitella Z9 desaturase
ATGCCGCCGAACGTGACAGAGGCGAACGGAGTGTTATTTGAGAATGACGTGCAGA
CTCCTGACATGGGCGTAGAAGTGGCCCCTGTGCAGAAGGCTGACGAGCGTAAGAT
CCAGCTCGTTTGGAGGAACATCATCGCTTTTGCATGTCTTCATTTAGCAGCTGTG
TATGGAGCTTATTTATTCTTCACCTCGGCTATATGGCAGACAGACATATTTGCAT
ACATCCTTTACGTTATGTCTGGATTAGGAATCACGGCGGGAGCGCACAGATTATG
GGCTCATAAGTCATACAAGGCGAAGTGGCCGTTAAGATTAATCCTCGTCGCATTC
AACACTTTGGCATTCCAGGATTCGGCAATCGACTGGGCGCGCGACCACCGCATGC
ACCACAAGTACTCGGAGACGGATGCGGACCCACATAACGCCACTCGCGGCTTCTT
CTTTTCGCACATTGGTTGGTTACTCTGCCGAAAACACCCGGAGCTAAAGCGCAAG
GGCCAGGGCCTCGACTTAAGTGACCTCTACGCAGATCCTATTATTCGCTTCCAAA
AGAAGTACTACTTATTGTTAATGCCGTTAGCCTGCTTTGTTCTTCCCACCATAAT
TCCGGTCTACCTCTGGGGCGAGTCCTGGAAAAACGCGTTCTTCGTAGCTGCAATG
TTCCGTTACACGTTCATCCTCAACGTAACATGGCTCGTCAACTCCGCCGCCCACA
AATGGGGAGGCAAGCCCTATGATAAGAACATCCAGCCCGCTCAGAACATCTCTGT
AGCTATCTTCGCATTAGGCGAGGGCTTCCACAACTACCACCACACGTTCCCCTGG
GACTACAAGACCGCTGAATTAGGAAACAACAGGTTAAATTTCACAACTTCGTTTA
TCAATTTCTTCGCAAGCTTCGGATGGGCCTACGACTTAAAGACCGTGTCGGACGA
GATTATACAACAGCGCGTTAAGAGGACGGGAGATGGGAGCCATCACTTACGGGGC
TGGGGCGACCAGGACATACCGGCCGAAGAAGCTCAAGCTGCTTTACGCATTAACC
GTAAAGATGATTAG SEQ ID NO: 22  H. zea Z9 desaturase
ATGGCTCCAAATATATCGGAGGATGTGAACGGGGTGCTCTTCGAGAGTGATGCAG
CGACGCCGGACTTAGCGTTATCCACGCCGCCTGTGCAGAAGGCTGACAACAGGCC
CAAGCAATTAGTGTGGAGGAACATACTATTATTCGCGTATCTTCACTTAGCGGCT
CTTTACGGAGGTTATTTATTCCTCTTCTCAGCTAAATGGCAGACAGACATATTTG
CCTACATCTTATATGTGATCTCCGGGCTTGGTATCACGGCTGGAGCACATCGCTT
ATGGGCCCACAAGTCCTACAAAGCTAAATGGCCTCTCCGAGTTATCTTAGTCATC
TTTAACACAGTGGCATTCCAGGATGCCGCTATGGACTGGGCGCGCGACCACCGCA
TGCATCACAAGTACTCGGAAACCGATGCTGATCCTCATAATGCGACCCGAGGATT
CTTCTTCTCTCACATTGGCTGGTTACTTGTCAGGAAACATCCCGACCTTAAGGAG
AAGGGCAAGGGACTCGACATGAGCGACTTACTTGCTGACCCCATTCTCAGGTTCC
AGAAAAAATACTACTTAATCTTAATGCCCTTGGCTTGCTTCGTGATGCCTACCGT
GATTCCTGTGTACTTCTGGGGTGAAACCTGGACCAACGCATTCTTTGTGGCGGCC
ATGTTCCGCTACGCGTTCATCCTAAATGTGACGTGGCTCGTCAACTCTGCCGCTC
ACAAGTGGGGAGACAAGCCCTACGACAAAAGCATTAAGCCTTCCGAAAACTTGTC
GGTCGCCATGTTCGCTCTCGGAGAAGGATTCCACAACTACCACCACACTTTCCCT
TGGGACTACAAAACTGCTGAGTTAGGCAACAACAAACTCAACTTCACTACCACCT
TTATTAACTTCTTCGCTAAAATTGGCTGGGCTTACGACTTAAAGACAGTGTCTGA
TGATATCGTCAAGAACAGGGTGAAGCGCACTGGTGACGGCTCCCACCACTTATGG
GGCTGGGGAGACGAAAATCAATCCAAAGAAGAAATTGATGCCGCTATCAGAATCA
ATCCTAAGGACGATTAA SEQ ID NO: 23  T. pseudonana Z11 desaturase
ATGGACTTTCTCTCCGGCGATCCTTTCCGGACACTCGTCCTTGCAGCACTTGTTG
TCATCGGATTTGCTGCGGCGTGGCAATGCTTCTACCCGCCGAGCATCGTCGGCAA
GCCTCGTACATTAAGCAATGGTAAACTCAATACCAGAATCCATGGCAAATTGTAC
GACCTCTCATCGTTTCAGCATCCAGGAGGCCCCGTGGCTCTTTCTTCTTGTTCAAG
GTCGCGACGGAACAGCTCTATTTGAGTCACACCATCCCTTCATACCTCGAAAGAA
TCTACTTCAGATCCTCTCCAAGTACGAGGTTCCGTCGACTGAAGACTCTGTTTCC
TTCATCGCCACCCTAGACGAACTCAATGGTGAATCTCCGTACGATTGGAAGGACA
TTGAAAATGATGATTTCGTATCTGACCTACGAGCTCTCGTAATTGAGCACTTTTC
TCCTCTCGCCAAGGAAAGGGGAGTTTCACTCGTTGAGTCGTCGAAGGCAACACCT
CAGCGGTGGATGGTGGTTCTATTACTCCTTGCGTCGTTCTTCCTCAGCATCCCAT
TATATTTGAGTGGTTCGTGGACTTTCGTTGTCGTCACTCCCATCCTCGCTTGGTT
AGCGGTTGTCAATTACTGGCACGATGCTACTCACTTTGCATTGAGCAGCAACTGG
ATTTTGAATGCTGCGCTCCCATATCTCCTCCCTCTCCTATCGAGTCCGTCAATGT
GGTATCATCATCACGTCATTGGACATCACGCATACACCAACATTTCCAAAAGAGA
TCCAGATCTTGCTCACGCTCCACAACTCATGAGAGAACACAAGAGTATCAAATGG

SEQUENCE LISTING

```
                AGACCATCTCACTTAAATCAAACACAGCTTCCGCGGATTCTCTTCATCTGGTCGA
                TTGCAGTCGGTATTGGGTTGAACTTATTAAACGACGTGAGAGCACTAACCAAGCT
                TTCATACAACAACGTTGTTCGGGTGGAGAAGATGTCATCGTCGCGAACATTACTC
                CATTTCCTTGGACGTATGTTGCACATCTTTGTGACTACACTTTGGCCCTTTTTGG
                CGTTTCCGGTGTGGAAGGCCATCGTTTGGGCGACTGTACCGAATGCCATATTAAG
                TTTGTGCTTCATGTTAAATACGCAAATCAATCACCTCATCAACACGTGTGCACAT
                GCTTCCGATAACAACTTTTACAAGCATCAAGTTGTAACTGCTCAGAACTTTGGCC
                GATCAAGTGCCTTTTGCTTCATCTTCTCGGGAGGTCTCAACTACCAAATTGAACA
                TCATTTGTTGCCGACGGTGAACCATTGCCATTTGCCAGCTTTGGCCCCGGGTGTA
                GAGCGTTTGTGTAAGAAACACGGGGTGACATACAACTCTGTTGAAGGATACAGAG
                AGGCCATCATTGCACACTTTGCACATACCAAAGATATGTCGACGAAGCCTACTGA
                TTGA

SEQ ID NO: 24  Native T. ni Z11 desaturase
                ATGGCTGTGATGGCTCAAACAGTACAAGAAACGGCTACAGTGTTGGAAGAGGAAG
                CTCGCACAGTGACTCTTGTGGCTCCAAAGACAACGCCAAGGAAATATAAATATAT
                ATACACCAACTTTCTTACATTTTCATATGCGCATTTAGCTGCATTATACGGACTT
                TATTTGTGCTTCACCTCTGCGAAATGGGAAACATTGCTATTCTCTTTCGTACTCT
                TCCACATGTCAAATATAGGCATCACCGCAGGGGCTCACCGACTCTGGACTCACAA
                GACTTTCAAAGCCAAATTGCCTTTGGAAATTGTCCTCATGATATTCAACTCTTTA
                GCCTTTCAAAACACGGCTATTACATGGGCTAGAGAACATCGGCTACATCACAAAT
                ACAGCGATACTGATGCTGATCCCCACAATGCGTCAAGAGGGTTCTTCTACTCGCA
                TGTTGGCTGGCTATTAGTAAAAAAACATCCCGATGTCCTGAAATATGGAAAAACT
                ATAGACATGTCGGATGTATACAATAATCCTGTGTTAAAATTTCAGAAAAAGTACG
                CAGTACCCTTAATTGGAACAGTTTGTTTTGCTCTGCCAACTTTGATTCCAGTCTA
                CTGTTGGGGCGAATCGTGGAACAACGCTTGGCACATAGCCTTATTCGATACATA
                TTCAATCTTAACGTGACTTTCCTAGTCAACAGTGCTGCGCATATCTGGGGGAATA
                AGCCTTATGATAAAAGCATCTTGCCCGCTCAAAACCTGCTGGTTTCCTTCCTAGC
                AAGTGGAGAAGGCTTCCATAATTACCATCACGTCTTTCCATGGGATTACCGCACA
                GCAGAATTAGGGAATAACTTCCTGAATTTGACGACGCTGTTCATTGATTTTTGTG
                CCTGGTTTGGATGGGCTTATGACTTGAAGTCTGTATCAGAGGATATTATAAAACA
                GAGAGCTAAACGAACAGGTGACGGTTCTTCAGGGGTCATTTGGGGATGGGACGAC
                AAAGACATGGACCGCGATATAAAATCTAAAGCTAACATTTTTTATGCTAAAAAGG
                AATGA SEQ ID NO: 25  H. zea Z11 desaturase
                ATGGCCCAAAGCTATCAATCAACTACGGTTTTGAGTGAGGAGAAAGAACTAACAC
                TGCAACATTTGGTGCCCCAAGCATCGCCCAGGAAGTATCAAATAGTGTATCCGAA
                CCTCATTACGTTTGGTTACTGGCACATAGCCGGACTTTATGGCCTTTACTTGTGC
                TTCACTTCTGCTAAATGGGCTACGATTTTATTCAGCTACATCCTCTTCGTGTTAG
                CAGAAATAGGAATCACGGCTGGCGCTCACAGACTCTGGGCCCACAAAACTTACAA
                AGCGAAACTACCATTAGAAATACTCTTAATGGTATTCAACTCCATCGCTTTTCAA
                AACTCAGCCATTGACTGGGTGAGGGACCACCGACTCCACCATAAGTATAGCGATA
                CAGATGCTGATCCCCACAATGCCAGCCGAGGGTTCTTTTATTCCCATGTAGGATG
                GCTACTTGTGAGAAAACATCCTGAAGTCAAAAAGCGAGGGAAAGAACTCAATATG
                TCCGATATTTACAACAATCCTGTCCTGCGGTTTCAGAAAAAATACGCCATACCCT
                TCATTGGGGCTGTTTGTTTCGCCTTACCTACAATGATACCTGTTTACTTCTGGGG
                AGAAACCTGGTCCAATGCTTGGCATATCACCATGCTTCGCTACATCATGAACCTC
                AATGTCACCTTTTTGGTAAACAGCGCTGCTCATATATGGGGAAACAAGCCTTATG
                ACGCAAAAATATTACCTGCACAAAATGTAGCTGTGTCGGTCGCCACTGGTGGAGA
                AGGTTTCCATAATTACCACCATGTCTTCCCCTGGGATTATCGAGCAGCGGAACTC
                GGTAACAATAGCCTCAATCTGACGACTAAATTCATAGATTTATTCGCAGCAATCG
                GATGGGCATATGATCTGAAGACGGTTTCGGAGGATATGATAAAACAAAGGATTAA
                ACGCACTGGAGATGGAACGGATCTTTGGGGACACGAACAAAACTGTGATGAAGTG
                TGGGATGTAAAAGATAAATCAAGTTAA SEQ ID NO: 26  T. ni Z11 desaturase Homo sapiens optimized
                ATGGCCGTGATGGCCCAGACCGTGCAGGAGACCGCAACAGTGCTGGAGGAGGAGG
                CAAGGACCGTGACACTGGTGGCACCCAAGACCACACCTAGAAAGTACAAGTATAT
                CTACACCAACTTCCTGACCTTCAGCTACGCACACCTGGCCGCCCTGTATGGACTG
                TACCTGTGCTTTACCTCCGCCAAGTGGGAGACACTGCTGTTCTCTTTTGTGCTGT
                TCCACATGAGCAATATCGGAATCACCGCAGGAGCACACAGGCTGTGGACCCACAA
                GACATTCAAGGCCAAGCTGCCTCTGGAGATCGTGCTGATGATCTTCAACTCTCTG
                GCCTTTCAGAATACCGCCATCACATGGGCCCGGGAGCACAGACTGCACCACAAGT
                ATAGCGACACCGATGCAGACCCACACAACGCAAGCAGGGGCTTCTTTTACTCCCA
                CGTGGGCTGGCTGCTGGTGAAGAAGCACCCCGACGTGCTGAAGTATGGCAAGACA
                ATCGACATGTCCGACGTGTACAACAATCCCGTGCTGAAGTTTCAGAAGAAGTATG
                CCGTGCCTCTGATCGGCACCGTGTGCTTCGCCCTGCCAACACTGATCCCCGTGTA
                TTGTTGGGGCGAGTCTTGGAACATGCCTGGCACATCGCCCGTTCCGGTACATC
                TTTAACCTGAATGTGACCTTTCTGGTGAACTCCGCCGCCCACATCTGGGCAATA
                AGCCTTACGACAAGTCTATCCTGCCAGCCCAGAACCTGCTGGTGTCCTTCCTGGC
                CTCTGGCGAGGGCTTTCACAATTATCACCACGTGTTCCCATGGGACTACAGGACC
                GCAGAGCTGGGCAACAATTTTCTGAACCTGACCACACTGTTCATCGATTTTTGTG
                CCTGGTTCGGCTGGGCCTATGACCTGAAGTCTGTGAGCGAGGATATCATCAAGCA
                GAGGGCAAAGAGGACAGGCGATGGCAGCTCCGGCGTGATCTGGGGATGGGACGAT
                AAGGATATGGACAGAGATATCAAGAGCAAGGCCAATATCTTCTACGCCAAGAAGG
                AGTGA
```

-continued

SEQUENCE LISTING

SEQ ID NO: 27  H. zea Z11 desaturase *Homo sapiens* optimized
ATGGCACAGTCATATCAGAGCACTACCGTCCTGAGCGAAGAGAAGGAACTGACAC
TGCAGCACCTGGTCCCACAGGCATCACCTAGAAAGTACCAGATCGTGTATCCAAA
CCTGATCACCTTCGGCTACTGGCACATCGCCGGCCTGTACGGCCTGTATCTGTGC
TTTACCTCCGCCAAGTGGGCCACAATCCTGTTCTCTTACATCCTGTTTGTGCTGG
CAGAGATCGGAATCACCGCAGGAGCACACAGACTGTGGGCACACAAGACATATAA
GGCCAAGCTGCCCCTGGAGATCCTGCTGATGGTGTTCAACAGCATCGCCTTTCAG
AATTCCGCCATCGATTGGGTGCGGGACCACAGACTGCACCACAAGTACTCCGACA
CCGATGCCGACCCCCACAACGCCTCTAGGGGCTTCTTTTATAGCCACGTGGGATG
GCTGCTGGTGCGGAAGCACCCTGAGGTGAAGAAGAGAGGCAAGGAGCTGAATATG
TCTGATATCTACAACAATCCTGTGCTGCGCTTCCAGAAGAAGTATGCCATCCCAT
TCATCGGCGCCGTGTGCTTTGCCCTGCCCACCATGATCCCCGTGTACTTTTGGGG
CGAGACATGGAGCAACGCCTGGCACATCACAATGCTGCGGTATATCATGAACCTG
AATGTGACATTCCTGGTGAACTCCGCCGCCCACATCTGGGGCAATAAGCCATACG
ACGCCAAGATCCTGCCCGCCCAGAACGTGGCCGTGAGCGTGGCAACCGGAGGAGA
GGGCTTCCACAATTACCACCACGTGTTTCCTTGGGATTATCGGGCCGCCGAGCTG
GGCAACAATTCTCTGAATCTGACCACAAAGTTCATCGACCTGTTTGCCGCCATCG
GCTGGGCCTATGATCTGAAGACAGTGAGCGAGGACATGATCAAGCAGAGGATCAA
GCGCACCGGCGATGGCACAGACCTGTGGGGGCACGAGCAGAACTGTGATGAAGTG
TGGGATGTGAAAGACAAGTCCTCCTAA SEQ ID NO: 28  Y. lipolytica OLE1 leader-T. ni Z11 desaturase *Homo sapiens* optimized
ATGGTGAAGAACGTGGACCAGGTGGATCTGTCTCAGGTGGACACCATCGCAAGCG
GAAGGGATGTGAATTATAAGGTGAAGTACACATCTGGCGTGAAGACCACACCAAG
AAAGTACAAGTATATCTACACCAACTTCCTGACATTTTCTTACGCCCACCTGGCC
GCCCTGTATGGCCTGTACCTGTGCTTTACCAGCGCCAAGTGGGAGACACTGCTGT
TCTCCTTTGTGCTGTTCCACATGTCTAATATCGGAATCACCGCAGGAGCACACAG
GCTGTGGACCCACAAGACATTCAAGGCCAAGCTGCCCCTGGAGATCGTGCTGATG
ATCTTCAACTCCCTGGCCTTTCAGAATACCGCCATCACATGGGCCCGGGAGCACA
GACTGCACCACAAGTATTCTGACACCGATGCAGACCCACACAACGCAAGCAGGGG
CTTCTTTTACTCCCACGTGGGCTGGCTGCTGGTGAAGAAGCACCCTGACGTGCTG
AAGTATGGCAAGACAATCGACATGAGCGACGTGTACAACAATCCTGTGCTGAAGT
TTCAGAAGAAGTATGCCGTGCCACTGATCGGCACCGTGTGCTTCGCCCTGCCCAC
ACTGATCCCCGTGTACTGTTGGGGCGAGTCCTGGAACAATGCCTGGCACATCGCC
CTGTTCCGGTACATCTTTAACCTGAATGTGACCTTTCTGGTGAACAGCGCCGCCC
ACATCTGGGGCAATAAGCCATACGACAAGTCCATCCTGCCCGCCCAGAACCTGCT
GGTGTCCTTCCTGGCCTCTGGCGAGGGCTTTCACAATTATCACCACGTGTTCCCT
TGGGACTACAGGACCGCAGAGCTGGGCAACAATTTTCTGAACCTGACCACACTGT
TCATCGATTTTTGTGCCTGGTTCGGCTGGGCCTATGACCTGAAGTCTGTGAGCGA
GGATATCATCAAGCAGAGGGCAAAGAGGACAGGCGATGGCAGCTCCGGCGTGATC
TGGGGATGGGACGATAAGGATATGGACAGAGATATCAAGTCCAAGGCCAATATCT
TCTACGCCAAGAAGGAGTGA SEQ ID NO: 29  Y. lipolytica OLE1 leader-H. zea Z11 desaturase *Homo sapiens* optimized
ATGGTGAAAAACGTGGACCAAGTGGATCTCTCGCAGGTCGACACCATTGCCTCCG
GCCGAGATGTCAACTACAAGGTCAAGTACACCTCCGGCGTTCGCAAGTATCAGAT
CGTGTATCCTAACCTGATCACCTTCGGCTACTGGCATATCGCTGGACTGTACGGA
CTGTATCTGTGCTTCACTTCCGCCAAGTGGGCCACCATCCTGTTCTCTTACATCC
TGTTTGTGCTGGCAGAGATCGGAATCACCGCAGGAGCACACAGACTGTGGGCACA
CAAGACATATAAGGCCAAGCTGCCACTGGAGATCCTGCTGATGGTGTTCAACAGC
ATCGCCTTTCAGAATTCCGCCATCGATTGGGTGCGGGACCACAGACTGCACCACA
AGTACTCCGACACAGATGCCGACCCCCACAACGCCTCTAGGGGCTTCTTTTATAG
CCACGTGGGATGGCTGCTGGTGCGGAAGCACCCTGAGGTGAAGAAGAGAGGCAAG
GAGCTGAATATGTCTGATATCTACAACAATCCTGTGCTGCGCTTCCAGAAGAAGT
ATGCCATCCCATTCATCGGCGCCGTGTGCTTTGCCCTGCCCACCATGATCCCCGT
GTACTTTTGGGGCGAGACATGGAGCAACGCCTGGCACATCACAATGCTGCGGTAT
ATCATGAACCTGAATGTGACATTCCTGGTGAACTCCGCCGCCCACATCTGGGGCA
ATAAGCCATACGACGCCAAGATCCTGCCCGCCCAGAACGTGGCCGTGAGCGTGGC
AACCGGAGGAGAGGGCTTCCACAATTACCACCACGTGTTTCCATGGGATTATAGG
GCAGCAGAGCTGGGAAACAATTCTCTGAATCTGACCACAAAGTTCATCGACCTGT
TTGCCGCCATCGGCTGGGCCTATGATCTGAAGACAGTGAGCGAGGACATGATCAA
GCAGAGGATCAAGCGCACCGGCGATGGCACAGACCTGTGGGGGCACGAGCAGAAT
TGTGATGAAGTGTGGGATGTGAAGGATAAAAGCAGTTGA SEQ ID NO: 30  Native A. transitella Z11 desaturase
ATGGTCCCTAACAAGGGTTCCAGTGACGTTTTGTCTGAACATTCTGAGCCCCAGT
TCACTAAACTCATAGCTCCACAAGCAGGGCCGAGGAAATACAAGATAGTGTATCG
AAATTTGCTCACATTCGGCTATTGGCACTTATCAGCTGTTTATGGGCTCTACTTG
TGCTTTACTTGTGCGAAATGGGCTACCATCTTATTTGCATTTTTCTTATACGTGA
TCGCGGAAATCGGTATAACAGGTGGCGCTCATAGGCTATGGGCACATCGGACTTA
TAAAGCCAAGTTGCCTTTAGAGATTTTGTTACTCATAATGAATTCTATTGCCTTC
CAAGACACTGCTTTCACCTGGGCTCGAGATCACCGCCTTCATCACAAATATTCGG
ATACTGACGCTGATCCCCACAATGCTACCAGAGGGTTTTTCTATTCACATGTAGG
CTGGCTTTTGGTGAAGAAACACCCTGAAGTCAAAGCAAGAGGAAAATACTTGTCG

| SEQUENCE LISTING | |
|---|---|
| | TTAGATGATCTTAAGAATAATCCATTGCTTAAATTCCAAAAGAAATACGCTATTC<br>TAGTTATAGGCACGTTATGCTTCCTTATGCCAACATTTGTGCCCGTATACTTCTG<br>GGGCGAGGGCATCAGCACGGCCTGGAACATCAATCTATTGCGATACGTCATGAAT<br>CTTAACATGACTTTCTTAGTTAACAGTGCAGCGCATATCTTTGGCAACAAACCAT<br>ACGATAAGAGCATAGCCTCAGTCCAAAATATTTCAGTTAGCTTAGCTACTTTTGG<br>CGAAGGATTCCATAATTACCATCACACTTACCCCTGGGATTATCGTGCGGCAGAA<br>TTAGGAAATAATAGGCTAAATATGACTACTGCTTTCATAGATTTCTTCGCTTGGA<br>TCGGCTGGGCTTATGACTTGAAGTCTGTGCCACAAGAGGCCATTGCAAAAAGGTG<br>TGCGAAAACTGGCGATGGAACGGATATGTGGGGTCGAAAAAGATAA |
| SEQ ID NO: 31 | pPV0228_-_Z11_Helicoverpa zea_desaturase<br>ATGGCCCAAAGCTATCAATCAACTACGGTTTTGAGTGAGGAGAAAGAACTAACAT<br>TACAACATTTGGTGCCCCAAGCATCGCCCAGGAAGTATCAAATAGTGTATCCGAA<br>CCTCATTACGTTTGGTTACTGGCACATAGCCGGACTTTATGGCCTTTACTTGTGC<br>TTCACTTCTGCTAAATGGGCTACGATTTTATTCAGCTACATCCTCTTCGTGTTAG<br>CAGAAATAGGAATCACGGCTGGCGCTCACAGACTCTGGGCCCACAAAACTTACAA<br>AGCGAAACTACCATTAGAAATACTCTTAATGGTATTCAACTCCATCGCTTTTCAA<br>AACTCAGCCATTGACTGGGTGAGGGACCACCGACTCCACCATAAGTATAGCGATA<br>CAGATGCTGATCCCCACAATGCCAGCCGAGGGTTCTTTTATTCCCATGTAGGATG<br>GCTACTTGTGAGAAAACATCCTGAAGTCAAAAAGCGAGGGAAAGAACTCAATATG<br>TCCGATATTTACAACAATCCTGTCTTACGGTTTCAGAAAAAATACGCCATACCCT<br>TCATTGGGGCTGTTTGTTTCGCCTTACCTACAATGATACCTGTTTACTTCTGGGG<br>AGAAACCTGGTCCAATGCTTGGCATATCACCATGCTTCGCTACATCATGAACCTC<br>AATGTCACCTTTTTGGTAAACAGCGCTGCTCATATATGGGGAACAAGCCTTATG<br>ACGCAAAAATATTACCTGCACAAAATGTAGCTGTGTCGGTCGCCACTGGTGGAGA<br>AGGTTTCCATAATTACCACCATGTCTTCCCCTGGGATTATCGAGCAGCGGAACTC<br>GGTAACAATAGCCTCAATTTAACGACTAAATTCATAGATTTATTCGCAGCAATCG<br>GATGGGCATATGATTTAAAGACGGTTTCGGAGGATATGATAAACAAAGGATTAA<br>ACGCACTGGAGATGGAACGGATCTTTGGGGACACGAACAAAACTGTGATGAAGTG<br>TGGGATGTAAAAGATAAATCAAGTTAA |
| SEQ ID NO: 32 | pPV0228_-_Helicoverpa armigera reductase codon<br>optimized<br>ATGGTCGTTTTAACTTCTAAAGAGACAAAACCTTCAGTAGCTGAGTTTTATGCGG<br>GAAAATCTGTTTTTATTACGGGTGGCACTGGATTCCTTGGAAAGGTATTCATAGA<br>GAAACTTTTATATAGCTGTCCAGATATCGAGAATATCTACATGCTCATACGAGAG<br>AAGAAAGGTCTTTCTGTTAGCGAAAGAATAAAACAGTTCCTTGATGACCCGCTCT<br>TTACCAGACTAAAAGACAAAAGACCAGCTGACTTAGAGAAGATTGTATTAATACC<br>AGGAGATATTACTGCTCCTGACTTAGGCATTAATTCTGAAAACGAGAAGATGCTT<br>ATAGAGAAGGTATCGGTGATTATTCATTCGGCTGCTACGGTGAAGTTTAATGAGC<br>CTCTCCCTACGGCTTGGAAGATCAACGTGGAAGGAACCAGAATGATGTTAGCTTT<br>GAGTCGAAGAATGAAGCGGATTGAGGTTTTCATTCACATATCGACAGCATACACG<br>AACACAAACAGGGAAGTGGTTGACGAGATCTTATACCCAGCTCCTGCTGATATCG<br>ACCAAGTTCATCAGTATGTCAAAGATGGAATCTCTGAGGAAGACACTGAGAAAAT<br>ATTAAATGGTCGTCCAAATACGTACACGTTTACGAAAGCGTTAACTGAGCATTTA<br>GTTGCTGAGAACCAAGCCTACGTACCCACTATTATCGTCAGGCCGTCAGTCGTGG<br>CAGCAATAAAAGATGAGCCATTAAAAGGTTGGTTAGGCAACTGGTTTGGAGCGAC<br>TGGTCTCACCGTGTTCACCGCTAAGGGTCTCAACCGAGTCATCTACGGTCATTCT<br>AGCTACATCGTAGACTTAATTCCTGTGGATTATGTCGCTAATTTAGTGATTGCTG<br>CTGGGGCTAAGAGTAGCAAGTCAACTGAGTTGAAGGTATACAACTGCTGCAGCAG<br>CTCCTGCAATCCCGTCACTATTGGCACGTTAATGAGCATGTTTGCTGACGATGCC<br>ATCAAACAGAAGTCGTATGCTATGCCGCTACCGGGGTGGTACATATTCACGAAAT<br>ATAAGTGGTTAGTTCTTCTTTTAACATTTCTCTTCCAAGTTATACCGGCGTATGT<br>CACAGATCTCTCCAGGCACTTGATTGGGAAGAGTCCACGGTACATAAAACTCCAA<br>TCACTAGTAAATCAAACGCGCTCTTCAATCGACTTCTTCACGAATCACTCCTGGG<br>TGATGAAGGCAGACAGAGTGAGAGAGTTATATGCGTCTCTTTCCCCCGCAGACAA<br>GTACTTATTTCCCTGTGATCCTACGGACATTAACTGGACACATTACATACAAGAC<br>TACTGTTGGGGAGTCCGACATTTTTTGGAGAAAAAAAGCTACGAATAA |
| SEQ ID NO: 33 | pPV0228_-_ICL_ promoter<br>TATTAGGCGAAGAGGCATCTAGTAGTAGTGGCAGTGGTGAGAACGTGGGCGCTGC<br>TATAGTGAACAATCTCCAGTCGATGGTTAAGAAGAAGAGTGACAAACCAGCAGTG<br>AATGACTTGTCTGGGTCCGTGAGGAAAAGAAAGAAGCCCGACACAAAGGACAGTA<br>ACGTCAAGAAACCCAAGAAATAGGGGGACCTGTTTAGATGTATAGGAATAAAAA<br>CTCCGAGATGATCTCAATGTGTAATGGAGTTGTAATATTGCAAAGGGGGAAAATC<br>AAGACTCAAACGTGTGTATGAGTGAGCGTACGTATATCTCCGAGAGTAGTATGAC<br>ATAATGATGACTGTGAATCATCGTAATCTCACACAAAAACCCCATTGTCGGCCAT<br>ATACCACACCAAGCAACACCACATATCCCCCGGAAAAAAAACGTGAAAAAAGA<br>AACAATCAAAACTACAACCTACTCCTTGATCACACAGTCATTGATCAAGTTACAG<br>TTCCTGCTAGGGAATGACCAAGGTACAAATCAGCACCTTAATGGTTAGCACGCTC<br>TCTTACTCTCTCTCACAGTCTTCCGGCCCCTATTCAAAATTCTGCACTTCCATTT<br>GACCCCAGGGTTGGGAAACAGGGCCACAAAAGAAAAACCCGACGTGAATGAAAAA<br>ACTAAGAAAAGAAAAAAATTATCACACCAGAAATTTACCTAATTGGGTAATTCC<br>CATCGGTGTTTTTCCTGGATTGTCGCACGCACGCATGCTGAAAAAGTGTTCGAG<br>TTTTGCTTTTGCCTCGGAGTTTCACGCAAGTTTTTCGATCTCGGAACGGAGGGC<br>GGTCGCCTTGTTGTTTGTGATGTCGTGCTTTGGGTGTTCTAATGTGCTGTTATTG<br>TGCTCTTTTTTTTTCTTCTTTTTTGGTGATCATATGATATTGCTCGGTAGATTA |

| | |
|---|---|
| | CTTTCGTGTGTAGGTATTCTTTTAGACGTTTGGTTATTGGGTAGATATGAGAGAG<br>AGAGAGTGGGTGGGGGAGGAGTTGGTTGTAGGAGGGACCCCTGGGAGGAAGTGTA<br>GTTGAGTTTTCCCTGACGAATGAAAATACGTTTTTGAGAAGATAATACAGGAAAG<br>GTGTGTCGGTGAATTTCCATCTATCCGAGGATATGAGTGGAGGAGAGTCGTGTGC<br>GTGTGGTTAATTTAGGATCAGTGGAACACACAAAGTAACTAAGACAGAGAGACAG<br>AGAGAAAATCTGGGGAAGAGACAAAGAGTCAGAGTGTGTGAGTTATTCTGTATT<br>GTGAAATTTTTTGCCCAACTACATAATATTGCTGAAACTAATTTTACTTAAAAA<br>GAAAAGCCAACAACGTCCCCAGTAAAACTTTTCTATAAATATCAGCAGTTTTCCC<br>TTTCCTCCATTCCTCTTCTTGTCTTTTTTCTTACTTTCCCTTTTTTATACCTTTT<br>CATTATCATCCTTTATAATTGTCTAACCAACAACTATATATCTATCAA |
| SEQ ID NO: 34 | pPV0228_-_TEF Candida tropicalis_promoter_region<br>AGGAAGACAACCAAAAGAAAGATCAAATTGACTAAATGTTGAACAGACCAAAAAA<br>AAAGAACAACAAATAGATAAATTACAACATATTAATCTTTTGATATGTTGTTGAA<br>TATTCTAGTAAATCTAATGATCTCAATAGTGGTTATCATTCACTCTCTTCGTCCT<br>CCTCTCTCCCCTCCTCCTCTTGCAGTATATTAAAAGCAATAAAAAAAAAAAAAAA<br>AAGAAAATCTGCCAACACACACAAAAAAAACTTACATAGTCGTGTACCAGTGTCA<br>ATATTTCACCAGCGCAGAGAAAGAAGATGAACAGAAAAATTTTCTCTTTGGTTT<br>TGTCTTTGGTTTTGTATTAATCTCATTGAAAAATTTTTTCTCTCTCTCTCTCT<br>CTCTCTCACTCACACACTCACTCGCATTTCGTTTGGGTTACAGCAGAAGTCAGAC<br>AGAAAAAAAAAATCGTATATAACTCTCATCAAATGCCCTAGAGAAAAATTTTTCT<br>TCTATCCTTTTTTTTTCTTCTTCTTCTTTTCCTTTTTTCTTTTAGAAGATC<br>TTTTTGAATTCATCAAAGATATATATTTAATCAATC |
| SEQ ID NO: 35 | pPV0228_-_TEF_terminator<br>AAGAAAAAAGAAAAGGTAAAGAACTTCATTTGAGATGAACTTTTGTATATGACTT<br>TTAGTTTCTACTTTTTTTTTATTTATTGCTTAATTTTCTTTATTTCAATCCCCC<br>ATAGTTTGTGTAGAATATATTTATTCATTCTGGTAACTCAAACACGTAGCAAGCT<br>CGTTGCATCTCGCCTCGTCACGGGTACAGCTCTGGAACCAAAGACAAAAAAAAAA<br>GTTGATCCGAACCCTCTCGCTATTCCTTGCTATGCTATCCACGAGATGGGGTTTA<br>TCAGCCCAGGCAAGTCACTAAA |
| SEQ ID NO: 36 | pPV0228_-_TEF_terminator<br>GCTGATTAATGAATAATTAATAAGTATTGTTTTTTTTGTTTTTAATATATATATATCT<br>TGAAATTAGTATAAAAAAAATCTTTTTTTTTCTTTTTTATTTATTTTATCAATAGTT<br>TATATATATATATATATAAACTTGTAAGAGATTAGGTATATCTAACAGTGATACTACT<br>AATAGTGCTTAATATCTTTGTTAAACAAGAAAATAAAATAAAC |
| SEQ ID NO: 37 | SapI-tLIP2-pEXP1-HA_FAR-SapI (insert into pPV199<br>creating pPV247)<br>GCCTGAAGAGCGCTATTTATCACTCTTTACAACTTCTACCTCAACTATCTACT<br>TTAATAAATGAATATCGTTTATTCTCTATGATTACTGTATATGCGTTCCTCCA<br>TGGGAGTTTGGCGCCCGTTTTTTCGAGCCCCACACGTTTCGGTGAGTATGAGC<br>GGCGGCAGATTCGAGCGTTTCCGGTTTCCGCGGCTGGACGAGAGCCCATGATG<br>GGGGCTCCCACCACCAGCAATCAGGGCCCTGATTACACACCCACCTGTAATGT<br>CATGCTGTTCATCGTGGTTAATGCTGCTGTGTGCTGTGTGTGTGTTGTTTG<br>GCGCTCATTGTTGCGTTATGCAGCGTACACCACAATATTGGAAGCTTATTAGC<br>CTTTCTATTTTTCGTTTGCAAGGCTTAACAACATTGCTGTGGAGAGGGATGG<br>GGATATGGAGGCCGCTGGAGGGAGTCGGAGAGGCGTTTTGGAGCGGCTTGGCC<br>TGGCGCCCAGCTCGCGAAACGCACCTAGGACCCTTTGGCACGCCGAAATGTGC<br>CACTTTTCAGTCTAGTAACGCCTTACCTACGTCATTCCATGCATGCATGTTTG<br>CGCCTTTTTTCCCTTGCCCTTGATCGCCACACAGTACAGTGCACTGTACAGTG<br>GAGGTTTTGGGGGGGTCTTAGATGGGAGCTAAAAGCGGCCTAGCGGTACACTA<br>GTGGGATTGTATGGAGTGGCATGGAGCCTAGGTGGAGCCTGACAGGACGCACG<br>ACCGGCTAGCCCGTGACAGACGATGGGTGGCTCCTGTTGTCACCGCGTACAA<br>ATGTTTGGGCCAAAGTCTTGTCAGCCTTGCTTGCGAACCTAATTCCCAATTTT<br>GTCACTTCGCACCCCCATTGATCGAGCCCTAACCCCTGCCCATCAGGCAATCC<br>AATTAAGCTCGCATTGTCTGCCTTGTTTAGTTTGGCTCCTGCCCGTTTCGGCG<br>TCCACTTGCACAAACACAAACAAGCATTATATATAAGGCTCGTCTCTCCCTCC<br>CAACCACACTCACTTTTTTGCCCGTCTTCCCTTGCTAACACAAAAGTCAAGAA<br>CACAAACAACCACCCCAACCCCCTTACACACAAGACATATCTACAGCAATGGT<br>GGTGCTGACCAGCAAGGAGACAAAGCCTTCCGTGGCCGAGTTCTACGCCGGCA<br>AGTCCGTGTTTATCACAGGCGGCACCGGCTTCCTGGGCAAGGTGTTTATCGAG<br>AAGCTGCTGTACTCTTGCCCAGACATCGAGAACATCTATATGCTGATCCGGGA<br>GAAGAAGGGCCTGAGCGTGTCCGAGAGAATCAAGCAGTTCCTGGACGATCCCC<br>TGTTTACACGGCTGAAGGACAAGAGACCTGCCGATCTGGAGAGATCGTGCTG<br>ATCCCAGGCGACATCACCGCACCAGATCTGGGCATCAACTCCGAGAATGAGAA<br>GATGCTGATCGAGAAGGTGTCCGTGATCATCCACTCTGCCGCCACCGTGAAGT<br>TCAACGAGCCCCTGCCTACAGCCTGGAAGATCAATGTGGAGGGCACCAGGATG<br>ATGCTGGCCCTGAGCCGGAGAATGAAGCGCATCGAGGTGTTTATCCACATCTC<br>CACAGCCTACACCAACACAAATCGGGAGGTGGTGGACGAGATCCTGTACCCAG<br>CCCCCGCCGACATCGATCAGGTGCACCAGTATGTGAAGGACGCATCAGCGAG<br>GAGGATACCGAGAAGATCCTGAACGGCCGGCAAATACCTACACATTCACCAA<br>GGCCCTGACAGAGCACCTGGTGGCCGAGAACCAGGCCTATGCCTACCATCA<br>TCGTGAGACCATCCGTGGTGGCCGCCATCAAGGATGAGCCCCTGAAGGGATGG<br>CTGGGAAACTGGTTCGGAGCAACAGGACTGACCGTGTTTACAGCCAAGGGCCT<br>GAATAGAGTGATCTACGGCCACAGCTCCTATATCGTGGACCTGATCCCCGTGG |

```
                ATTACGTGGCAAACCTGGTCATCGCAGCAGGAGCCAAGTCTAGCAAGTCTACC
                GAGCTGAAGGTGTATAACTGCTGTTCCTCTAGCTGTAATCCTGTGACCATCGG
                CACACTGATGTCCATGTTCGCCGACGATGCCATCAAGCAGAAGTCTTACGCCA
                TGCCTCTGCCAGGCTGGTACATCTTTACAAAGTATAAGTGGCTGGTGCTGCTG
                CTGACCTTCCTGTTTCAGGTCATCCCAGCCTACGTGACCGATCTGTCTAGGCA
                CCTGATCGGCAAGAGCCCCCGCTATATCAAGCTGCAGTCTCTGGTGAACCAGA
                CCAGGTCCTCTATCGACTTCTTTACAAATCACAGCTGGGTCATGAAGGCCGAT
                AGGGTGCGCGAGCTGTACGCCTCTCTGAGCCCTGCCGACAAGTATCTGTTCCC
                CTGCGACCCTACCGATATCAATTGGACACACTACATCCAGGATTATTGTTGGG
                GCGTGCGCCACTTCCTGGAGAAGAAGTCCTATGAGTGAGCCTGAAGAGC

SEQ ID NO: 38  NcoI-pTAL-AleI (insert into pPV247 creating pPV248)
                CCATGGGTAAGCAGGTGGCTCCGTTTGTGTCTTTGTGTTTTTCCCCTCCTTTT
                TGGACCATTTGTCAGCATGTTGCGTAGGTCTGGGTGTTTGACTGTTCAGGTGG
                TGGATGACGGATGCATCATCTGACGGCAGAGTGGGTACCTGGCAGTGGCAGGC
                TCGCAGACGAGGTAGAGAGATTCTGAAAGGAGCCATTGACAGATGGAGAATTG
                GATACTCCTGGTATGTCCTCCGTTTCCACTTTTGACGTTGGTGACGTGCTCTG
                GAACGACTTTTTTCTTTTTCTTTAAAACAAAAAAAAGAAAGAAAAAAAAAACA
                TTTACTACTACCAGTAGTACACCTCAACATTGGGTCCAGAACGTCCCAACTGC
                ATGAGTCACTGGAGTCATGCCGAGGTCGCTAAGGTGCTGTAAAATACAACGTC
                AATTGAGAGAGACACAGGCGCAGCGCGCCGAGGGAGAAACGAGGCATTTATCT
                TCTGACCCTCCTTTTTACTCGTAATCTGTATCCCGGAACCGCGTCGCATCCAT
                GTTAATTAAATCAACACTTACACTTGCTTGCTTCGTATGATGAAGATTTCTGA
                CTGGCAACCCAGTCAGCAGCAGATTGGGGCAGATGTAGTAATGAAAAACACTG
                CAAGGTGTGACGTTTGAGACACTCCAATTGGTTAGAAAGCGACAAAGAAGACG
                TCGGAAAAATACCGGAAAAATCGAGTCTTTTTCTTTCTGCGTATTGGGCCCTT
                CTGCCTCCTTTGCCGCCCTTTCCACGCTCTTTCCACACCCTCACACTCCCTGA
                GCACTATGATCTCATTGCGCAATAAGATATACATGCACGTGCATTTGGTGAGC
                ACGCAGAACCTTGTTGGGGGAAGATGCCCTAACCCTAAGGGCGTTCCATACGG
                TTCGACAGAGTAACCTTGCTGTCGATTATAACGCATATATAGCCCCCCCCTTC
                GGACCCTCCTTCTGATTTCTGTTTCTGTATCAACATTACACACAAACACACAA
                TGGTG
```

The foregoing detailed description has been given for clearness of understanding only and no unnecessary limitations should be understood there from as modifications will be obvious to those skilled in the art.

While the disclosure has been described in connection with specific embodiments thereof, it will be understood that it is capable of further modifications and this application is intended to cover any variations, uses, or adaptations of the disclosure following, in general, the principles of the disclosure and including such departures from the present disclosure as come within known or customary practice within the art to which the disclosure pertains and as may be applied to the essential features hereinbefore set forth and as follows in the scope of the appended claims.

The disclosures, including the claims, figures and/or drawings, of each and every patent, patent application, and publication cited herein are hereby incorporated herein by reference in their entireties.

What is claimed is:

1. A recombinant *Yarrowia lipolytica* microorganism capable of producing a mono- or poly-unsaturated $C_6$-$C_{24}$ fatty alcohol from an endogenous or exogenous source of saturated $C_6$-$C_{24}$ fatty acid, comprising:
    a heterologous nucleic acid molecule encoding and expressing a *Helicoverpa zea* fatty acyl desaturase that catalyzes the conversion of a saturated $C_6$-$C_{24}$ fatty acyl-CoA to a corresponding mono- or poly-unsaturated $C_6$-$C_{24}$ fatty acyl-CoA, wherein the mono- or poly-unsaturated $C_6$-$C_{24}$ fatty acyl-CoA is converted to the corresponding mono- or poly-unsaturated $C_6$-$C_{24}$ fatty alcohol.

2. The recombinant *Yarrowia lipolytica* microorganism of claim 1, wherein the *Helicoverpa zea* fatty acyl desaturase is a Z11 desaturase.

3. The recombinant *Yarrowia lipolytica* microorganism of claim 1, wherein the heterologous nucleic acid molecule encoding a *Helicoverpa zea* fatty acyl desaturase comprises an amino acid sequence encoded by SEQ ID NO: 27 or a functionally active and expressed variant thereof.

4. The recombinant *Yarrowia lipolytica* microorganism of claim 1, wherein the recombinant *Yarrowia lipolytica* microorganism comprises a deletion of the fao1 gene.

5. The recombinant *Yarrowia lipolytica* microorganism of claim 1, wherein the recombinant *Yarrowia lipolytica* microorganism comprises a deletion of pox1, pox2, pox3, pox4, pox5, and pox6 genes.

6. The recombinant *Yarrowia lipolytica* microorganism of claim 1, wherein the recombinant *Yarrowia lipolytica* microorganism comprises a deletion of fao1, pox1, pox2, pox3, pox4, pox5, and pox6 genes.

7. The recombinant *Yarrowia lipolytica* microorganism of claim 1, wherein the mono- or poly-unsaturated $C_6$-$C_{24}$ fatty alcohol is Z11-16:OH.

8. A method of producing a mono- or poly-unsaturated $C_6$-$C_{24}$ fatty alcohol from an endogenous or exogenous source of saturated $C_6$-$C_{24}$ fatty acid, comprising: cultivating the recombinant *Yarrowia lipolytica* microorganism of claim 1, in a culture medium containing a feedstock that provides a carbon source adequate for the production of the mono- or poly-unsaturated $C_6$-$C_{24}$ fatty alcohol.

9. The method of claim 8, wherein said unsaturated $C_6$-$C_{24}$ fatty alcohol is an insect fatty alcohol.

10. The method of claim 8, wherein said unsaturated $C_6$-$C_{24}$ fatty alcohol is an insect pheromone.

11. The recombinant *Yarrowia lipolytica* microorganism of claim 1, wherein the recombinant *Yarrowia lipolytica* microorganism comprises a deletion of adh1, adh2, adh3, adh4, adh5, adh6, and adh7 genes.

12. The recombinant *Yarrowia lipolytica* microorganism of claim 1, wherein the recombinant *Yarrowia lipolytica* microorganism comprises a deletion of fao1, adh1, adh2, adh3, adh4, adh5, adh6, and adh7 genes.

13. The recombinant *Yarrowia lipolytica* microorganism of claim 1, wherein the recombinant *Yarrowia lipolytica* microorganism comprises a deletion of fao1, adh1, adh2, adh3, adh4, adh5, adh6, adh7, pox1, pox2, pox3, pox4, pox5, and pox6 genes.

* * * * *